US012435047B2

(12) United States Patent
Marugan et al.

(10) Patent No.: US 12,435,047 B2
(45) Date of Patent: Oct. 7, 2025

(54) c-Abl TYROSINE KINASE INHIBITORY COMPOUND EMBODIMENTS AND METHODS OF MAKING AND USING THE SAME

(71) Applicants: The USA, as represented by the Secretary, Dept. of Health and Human Services, Bethesda, MD (US); Pontificia Universidad Católica de Chile, Santiago (CL)

(72) Inventors: Juan J. Marugan, Gaithersburg, MD (US); Marc Ferrer, Potomac, MD (US); Noel T. Southall, Potomac, MD (US); Andres E. Dulcey, Gaithersburg, MD (US); Xin Hu, Frederick, MD (US); Christopher R. Dextras, Frederick, MD (US); Daniel C. Talley, Baltimore, MD (US); Alejandra Alvarez, Santiago (CL); Silvana Zanlungo, Santiago (CL); Rommy M. Von Bernhardi, Santiago (CL)

(73) Assignees: The United States of America, as represented by the Secretary, Department of Health and Human Services, Bethesda, MD (US); Pontifica Universidad Catoclica de Chile, Santiago (CL)

( * ) Notice: Subject to any disclaimer, the term of this patent is extended or adjusted under 35 U.S.C. 154(b) by 0 days.

(21) Appl. No.: 18/128,603

(22) Filed: Mar. 30, 2023

(65) Prior Publication Data

US 2023/0303501 A1 Sep. 28, 2023

Related U.S. Application Data

(62) Division of application No. 16/976,012, filed as application No. PCT/US2019/021434 on Mar. 8, 2019, now Pat. No. 11,649,218.

(Continued)

(51) Int. Cl.

| | |
|---|---|
| ***C07D 243/38*** | (2006.01) |
| ***A61K 31/551*** | (2006.01) |
| ***A61K 31/5513*** | (2006.01) |
| ***A61K 31/553*** | (2006.01) |
| ***A61K 31/554*** | (2006.01) |
| ***A61P 25/08*** | (2006.01) |
| ***A61P 25/28*** | (2006.01) |
| ***A61P 33/06*** | (2006.01) |

(Continued)

(52) U.S. Cl.

CPC ........ *C07D 243/38* (2013.01); *A61K 31/5513* (2013.01); *A61K 31/553* (2013.01); *A61K 31/554* (2013.01); *A61P 25/08* (2018.01); *A61P 25/28* (2018.01); *A61P 33/06* (2018.01); *A61P 35/02* (2018.01); *C07C 201/12* (2013.01); *C07C 227/22* (2013.01); *C07C 319/14* (2013.01); *C07D 267/18* (2013.01); *C07D 267/20* (2013.01); *C07D 281/16* (2013.01); *C07D 401/04* (2013.01); *C07D 403/04* (2013.01); *C07D 413/04* (2013.01); *C07D 413/10* (2013.01); *C07D 413/14* (2013.01); *C07D 417/04* (2013.01); *C07D 471/04* (2013.01); *C07D 487/04* (2013.01); *C07F 5/025* (2013.01); *C07F 7/0812* (2013.01)

(58) Field of Classification Search

CPC .. C07D 243/38; C07D 401/04; C07D 403/04; C07D 409/04; C07D 413/04; C07D 413/10; C07D 413/14; C07D 417/04; A61K 31/551; A61P 25/08; A61P 25/28; A61P 33/06; A61P 35/00; A61P 35/02; A61P 37/00

See application file for complete search history.

(56) References Cited

U.S. PATENT DOCUMENTS 3,773,768 A 11/1973 Howell et al.
3,845,074 A 10/1974 Fresnes et al.

(Continued)

FOREIGN PATENT DOCUMENTS

AU 2015224425 10/2015
CN 105384792 3/2016

(Continued)

OTHER PUBLICATIONS

Abramov et al., "Synthesis of Substituted Dibenzoxazepines and Dibenzothiazepine using of 4-Bromo-5-nitrophthalonitrile," *Heterocycles*, 60(7): 1611-1614, 2003.

(Continued)

*Primary Examiner* — Brenda L Coleman

(74) *Attorney, Agent, or Firm* — Klarquist Sparkman, LLP

(57) ABSTRACT

Disclosed herein are embodiments of a compound that inhibits c-Abl tyrosine kinase (also referred to herein as "c-Abl"). The compound embodiments described herein are novel c-Abl inhibitors that can bind to c-Abl at an allosteric site and inhibit its activity in various pathways. The compound embodiments also are capable of crossing the blood brain barrier and therefore are useful in inhibiting c-Abl activity as it affects pathways and/or proteins in the brain. The compound embodiments described herein are effective therapeutic agents for treating diseases involving c-Abl, such as cancers, motor neuron diseases, and neurodegenerative diseases. Also disclosed herein are embodiments of methods for making and using the c-Abl inhibitory compound embodiments.

19 Claims, 30 Drawing Sheets

Related U.S. Application Data

(60) Provisional application No. 62/641,126, filed on Mar. 9, 2018.

(51) Int. Cl.

| | |
|---|---|
| ***A61P 35/00*** | (2006.01) |
| ***A61P 35/02*** | (2006.01) |
| ***A61P 37/00*** | (2006.01) |
| ***C07C 201/12*** | (2006.01) |
| ***C07C 227/22*** | (2006.01) |
| ***C07C 319/14*** | (2006.01) |
| ***C07D 267/18*** | (2006.01) |
| ***C07D 267/20*** | (2006.01) |
| ***C07D 281/16*** | (2006.01) |
| ***C07D 401/04*** | (2006.01) |
| ***C07D 403/04*** | (2006.01) |
| ***C07D 409/04*** | (2006.01) |
| ***C07D 413/04*** | (2006.01) |
| ***C07D 413/10*** | (2006.01) |
| ***C07D 413/14*** | (2006.01) |
| ***C07D 417/04*** | (2006.01) |
| ***C07D 471/04*** | (2006.01) |
| ***C07D 487/04*** | (2006.01) |
| ***C07F 5/02*** | (2006.01) |
| ***C07F 7/08*** | (2006.01) |

(56) References Cited

U.S. PATENT DOCUMENTS

| | | | | |
|---|---|---|---|---|
| 4,435,391 | A | 3/1984 | Sasahara et al. | |
| 4,610,819 | A | 9/1986 | Lo et al. | |
| 5,017,570 | A | 5/1991 | Noda et al. | |
| 5,173,486 | A | 12/1992 | Monkovic et al. | |
| 5,281,590 | A | 1/1994 | Husa et al. | |
| 7,101,872 | B2 * | 9/2006 | Bachmann | C07D 243/38 514/220 |
| 7,186,713 | B2 * | 3/2007 | Farnet | C12N 9/12 514/220 |
| 7,297,524 | B2 * | 11/2007 | Farnet | C12N 9/88 435/320.1 |
| 7,304,054 | B2 * | 12/2007 | McAlpine | C07D 405/06 514/220 |
| 7,384,935 | B2 * | 6/2008 | Aouidate | C07F 9/5535 514/220 |
| 7,456,169 | B2 * | 11/2008 | Hasvold | C07D 409/12 514/220 |
| 7,521,222 | B2 * | 4/2009 | Zazopoulos | C12N 9/90 435/252.35 |
| 7,655,646 | B2 * | 2/2010 | McAlpine | C07D 401/14 514/220 |
| 7,763,604 | B2 * | 7/2010 | Gourdeau | A61P 35/02 514/220 |
| 8,063,037 | B2 | 11/2011 | Rewinkel et al. | |
| 8,158,623 | B2 * | 4/2012 | Shen | C07D 495/14 549/267 |
| 2004/0235819 | A1 | 11/2004 | Galley et al. | |
| 2006/0079512 | A1 * | 4/2006 | McAlpine | A61P 31/04 514/220 |
| 2009/0029972 | A1 * | 1/2009 | McAlpine | C07D 243/38 435/375 |
| 2009/0062255 | A1 * | 3/2009 | Gourdeau | A61K 31/551 540/577 |
| 2009/0170837 | A1 * | 7/2009 | Gourdeau | C07D 243/38 514/220 |
| 2009/0263886 | A1 * | 10/2009 | Zazopoulos | C12N 15/52 435/252.35 |
| 2015/0175569 | A1 | 6/2015 | Lynch et al. | |

FOREIGN PATENT DOCUMENTS

| | | |
|---|---|---|
| CN | 105949143 | 9/2016 |
| EP | 0 012 385 | 6/1980 |
| EP | 0 218 077 | 4/1987 |
| EP | 0 419 861 | 4/1991 |
| JP | S56166179 | 12/1981 |
| JP | 57002279 | 1/1982 |
| JP | S57120580 | 7/1982 |
| JP | S58206520 | 12/1983 |
| JP | S58225073 | 12/1983 |
| JP | S58225074 | 12/1983 |
| WO | WO 2004/076424 | 9/2004 |
| WO | WO 2008/055068 | 5/2008 |
| WO | WO 2008/112900 | 9/2008 |
| WO | WO 2008/157131 | 12/2008 |
| WO | WO 2009/137462 | 11/2009 |
| WO | WO 2013/006485 | 1/2013 |
| WO | WO 2016/027790 | 2/2016 |

OTHER PUBLICATIONS

Citron, "Alzheimer's disease: strategies for disease modification," *Nature Reviews—Drug Discovery*, vol. 9, pp. 387-399, May 2010.

Hebert et al., "Annual incidence of Alzheimer Disease in the United States Projected to the Years 200 Through 2050," *Alzheimer Disease and Associated Disorders*, 15(4): 169-173, Oct. 2001.

Hurst et al., Metal-Free Synthesis of Dibenzoxazepinones via a One-Pot SNAr and Smiles Rearrangement Process: Orthogonality with Copper-Catalyzed Cyclizations, *Synlett*, 26(11): 1455-1460, Jun. 18, 2015.

International Search Report and Written Opinion issued for International Application No. PCT/US2019/021434 on Apr. 30, 2019.

Jamsheena et al., "Metal-Free Diaryl Etherification of Tertiary Amines by Ortho-C($sp^2$)-H Functionalization for Synthesis of Dibenzoxazepines and ones," *Organic Letters*, 19(24): 6614-6617, Dec. 5, 2017.

Jones et al., "Abl Tyrosine Kinase Promotes Dendrogenesis by Inducing Actin Cytoskeletal Rearrangements in Cooperation with Rho Family Small GTPases in Hippocampal Neurons," *The Journal of Neuroscience*, 24(39): 8510-8521, Sep. 29, 2004.

Katsumata et al., "c-Abl inhibition delays motor neuron degeneration in the G93A mouse, an animal model of amyotrophic lateral sclerosis," *PLOS One*, 7(9): 1-14, Sep. 25, 2012.

Kitching et al., "Copper-Catalyzed Cross-Coupling Interrupted by an Opportunistic Smiles Rearrangement: An Efficient Domino Approach to Dibenzooxazepinones," *Angewandte Chemie*, 51(12): 2925-2929, Feb. 6, 2012.

Lansbury et al., "A century-old debate on protein aggregation and neurodegeneration enters the clinic," *Nature*, vol. 443, pp. 774-779, Oct. 19, 2006.

Lin et al., "Microwave-Assisted Synthesis of Substituted Dibenzo[b,f][1,4]thiazepines, Dibenzo[b,f][1,4]oxazepines, Benzothiazoles and Benzimidazoles," *Journal of Heterocyclic Chemistry*, 51(3): 808-814, Dec. 6, 2013.

Lu et al., "Intramolecular Carbonylation Reactions with Recyclable Palladium-Complexed Dendrimers on Silica: Synthesis of Oxygen, Nitrogen, or Sulfur-Containing Medium Ring Fused Heterocycles," *Journal of the American Chemical Society*, 127(42): 14776-14784, Oct. 1, 2005.

Mayo Clinic "Niemann-Pick," https://www.mayoclinic.org/diseases-conditions/niemann-pick/symptoms-causes/syc-20355887, Jan. 25, 2018.

Moresco et al., "Regulation of neuronal morphogenesis and synaptic function by Abl family kinases," *Current Opinion in Neurobiology*, vol. 13, pp. 535-544, Sep. 10, 2003.

Rhee et al., "Activation of the repulsive receptor Roundabout inhibits N-cadherin-mediated cell adhesion," *Nature Cell Biology*, vol. 4, pp. 798-805, Oct. 23, 2002.

Ross et al., "Re-evaluating the role of BCR/ABL in chronic myelogenous leukemia," *Molecular & Cellular Oncology*, 1(3): e963450-1-e963450-8, Oct. 29, 2014.

(56) References Cited

OTHER PUBLICATIONS

Schlatterer et al., "c-Abl in Neurodegenerative Disease," *J Mol Neurosci*, 45(3): 445-452, Nov. 2011.
Selkoe, "Alzheimer's Disease—Genotypes, Phenotype and Treatments," *Science*, 275(5300): 630-631, Jan. 31, 1997.
Walsh et al., "Aβ Oligomers—a decade of discovery," *Journal of Neurochemistry*, vol. 101, pp. 1172-1184, Jan. 4, 2007.
Yang et al., "Synthesis of dibenzo[b,f][1,4]oxazepin-11(10H)-ones via intramolecular cyclocarbonylation reactions using $PdI_2$/Cytop 292 as the catalytic system," *J. Org. Chem.*, vol. 75, pp. 6297-6299, Aug. 26, 2010.
Zhang et al., "Cu-Catalyzed One-Pot Synthesis of Fused Oxazepinone Derivatives via $sp^2$C-H and O-H Cross-Dehydrogenative Coupling," *Organic Chemistry Frontiers*, 3(7):799-803, Apr. 19, 2016.
Zhou et al., "Access to Different Isomeric Dibenzoxazepinones Through Copper-Catalyzed C-H Etherification and C-N Bond Construction With Controllable Smiles Rearrangement," *Organic Letters*, 18(3): 380-383, Jan. 15, 2016.
Zukerberg et al., Cables Links Cdk5 and c-Abl and Facilitates Cdk5 Tyrosine Phosphorylation, Kinase Upregulation, and Neurite Outgrowth, *Neuron*, vol. 26, pp. 633-646, Jun. 2000.

* cited by examiner c-Abl TYROSINE KINASE INHIBITORY COMPOUND EMBODIMENTS AND METHODS OF MAKING AND USING THE SAME

CROSS REFERENCE TO RELATED APPLICATION

This application is a divisional of U.S. application Ser. No. 16/976,012, filed on Aug. 26, 2020, which is the U.S. National Stage of International Application No. PCT/US2019/021434, filed on Mar. 8, 2019, which was published in English under PCT Article 21(2) which in turn claims the benefit of and priority to the earlier filing date of U.S. Provisional Patent Application No. 62/641,126, filed on Mar. 9, 2018; the entirety of each of these prior applications is incorporated herein by reference.

FIELD

The present disclosure concerns embodiments of a compound that inhibits c-Abl tyrosine kinase, as well as methods of making and using such compounds.

BACKGROUND

Alzheimer's disease (AD) is a complex neurodegenerative disease characterized by the loss of short-term memory, disorientation, and impairments in judgment and reasoning. Presently, AD is the most common cause of dementia in the elderly, and by 2050, the number of people with AD is expected to triple, placing an enormous burden on the health and social care systems. Currently, there is no effective treatment for AD.

The loss of different neuronal populations leading to neuronal dysfunction (reduced connectivity and loss of plasticity), cytoskeletal alterations and abnormal protein phosphorylation are the main hallmarks of neurodegenerative diseases. In particular, the neuropathological hallmarks of AD are neuronal loss in regions related to memory and cognition, neurotransmitter depletion, synaptic alteration and the deposition of abnormal protein aggregates, i.e., amyloid plaques and neurofibrillary tangles (NFT). The major protein component of the plaques is the amyloid-β peptide (Aβ), a 39-42 amino acid peptide that is the product of the proteolytic cleavage of a much larger transmembrane protein, the amyloid precursor protein (APP). NFTs occur intracellularly and are composed of paired helical filaments of hyperphosphorylated tau protein. Aβ toxicity is believed to play a primary role in the development of AD, forming the basis of the amyloid hypothesis. Thus, Aβ toxicity has been the main focus of AD research in recent years. Indeed, the primary approaches for the development of disease modification strategies in AD currently focus on decreasing Aβ levels. A need in the art exists, however, for new therapeutic treatments that can treat or prevent AD and other neurodegenerative diseases.

SUMMARY

Disclosed herein are embodiments of a compound that inhibits c-Abl tyrosine kinase. The structures of these compound embodiments are described herein, along with methods of making the same and composition embodiments comprising the compound. In some embodiments, the compound embodiments are used in a method for treating a disease in a subject. Such methods can comprise administering (i) a therapeutically effective amount of the compound or a stereoisomer, tautomer, pharmaceutically acceptable salt, solvate, or prodrug thereof; or (ii) a therapeutically effective amount of the pharmaceutical composition embodiments disclosed herein to a subject having, or suspected of having, the disease, wherein the disease is a disease involving c-Abl tyrosine kinase. The compounds can be used to treat various diseases associated with c-Abl tyrosine kinase and/or diseases that result from overexpression of c-Abl tyrosine kinase. Representative diseases are discussed herein. In some embodiments, the compound inhibits c-Abl tyrosine kinase by binding to an allosteric site of the c-Abl tyrosine kinase. In some embodiments, the compound binds to a myristate pocket of the c-Abl tyrosine kinase. In additional embodiments, the compound is capable of passing through a blood brain barrier of a subject. In particular embodiments, the compound is

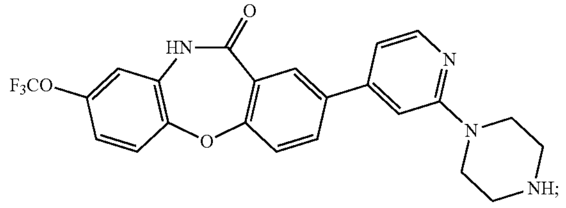

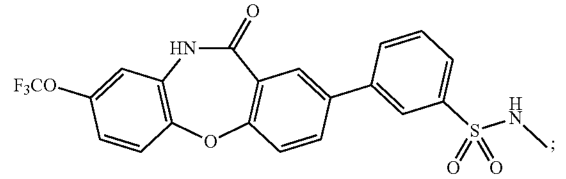

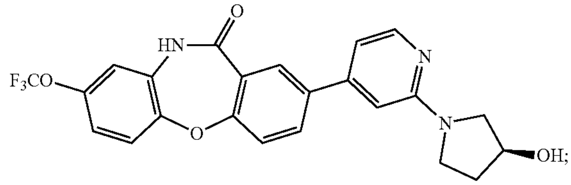

or a stereoisomer, tautomer, pharmaceutically acceptable salt, solvate, or prodrug thereof.

The foregoing and other objects and features of the present disclosure will become more apparent from the following detailed description, which proceeds with reference to the accompanying figures.

BRIEF DESCRIPTION OF THE DRAWINGS

FIGS. 4A and 4B show that both compounds inhibit c-Abl in K562 assays.

FIG. 8A shows results for compound NCGC00373060; FIG. 8B shows results for compound NCGC00373056; FIG. 8C shows results for compound NCGC00355552; FIG. 8D shows results for compound NCGC00355551; and FIG. 8E shows results for compound NCGC00355553.

FIG. 11A shows ThS staining for hippocampus slices from control-, NCGC00373060- and NCGC00373056-treated AD (5×FAD) mice; FIG. 11B shows quantification of the number of amyloid plaques in hippocampus; and FIG. 11C is a Western blot of the Aβ and CTFβ levels in the 5×FAD control and treated mice.

FIG. 12A is a graph showing results from a water maze assay using wild type mice and APP/PSEN1 mice with a vehicle alone; FIG. 12B is a graph showing results from a water maze assay using APP/PSEN1 mice and a vehicle and APP/PSEN1 mice and NCGC00373060; and FIG. 12C summarizes results from using compound NCGC00355551.

FIG. 13A is a graph showing results from a Barnes maze assay using wild type mice and APP/PSEN1 mice with a vehicle alone; and FIG. 13B is a graph showing results from the Barnes maze assay using APP/PSEN1 mice and a vehicle and APP/PSEN1 mice and NCGC00373060.

FIGS. 14A and 14D show staining for hippocampus slices from control and NCGC00373060 treated mice (FIG. 14A) and from control and NCGC00355551 treated mice (FIG. 14D); FIGS. 14B and 14E show quantification of the number of amyloid plaques in cortex for compounds NCGC00373060 and NCGC00355551, respectively; and FIG. 14C shows immunofluorescence results for the GFAP protein of the control and NCGC00373060-treated APP/PSEN1 mice brain slices.

FIG. 19A provides representative images of HeLa TFEB-GFP cells treated with DMSO and NCGC00373060 for 3 hours at 1 and 10 M; FIG. 19B is a graph of the ratio value resulting from the average intensity of nuclear-TFEB-GFP/cytosolic-TFEB-GFP fluorescence; and FIG. 19C is a Western blot.

FIG. 22A shows results using Racine's scale, which confirm that c-Abl inhibition with NCGC00373060 has a significant anticonvulsant effect in TLE mice model extending the time in that the animals reach the epileptic status and FIG. 22B shows the increases in survival rate.

FIGS. 26A-26C are graphs showing results from the MTT viability assay of Example 10, wherein FIG. 26A shows results for NCGC00373060; FIG. 26B shows results for NCGC00508975; and FIG. 26C shows results for Nilotinib.

DETAILED DESCRIPTION

I. Overview of Terms

Figure 1:
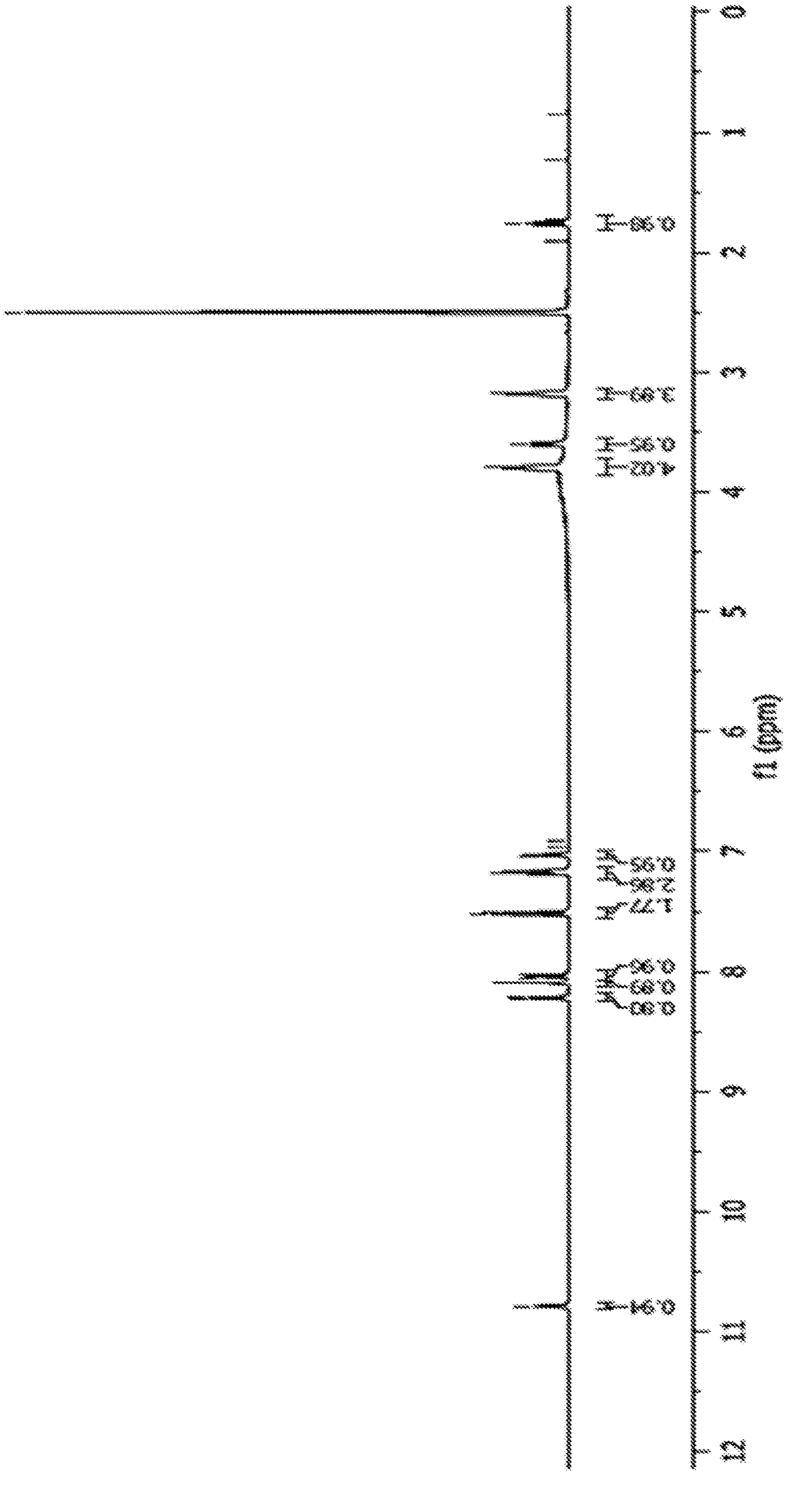
FIG. 1 is a $^{1}$H-NMR spectrum of a representative compound embodiment, NCGC00373060.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Compound embodiments disclosed herein may contain one or more asymmetric elements such as stereogenic centers, stereogenic axes and the like, e.g., asymmetric carbon atoms, so that the chemical conjugates can exist in different stereoisomeric forms. These compound embodiments can be, for example, racemates or optically active forms. For compound embodiments with two or more asymmetric elements, these compound embodiments can additionally be mixtures of diastereomers. For compound embodiments having asymmetric centers, all optical isomers in pure form and mixtures thereof are encompassed by corresponding generic formulas unless context clearly indicates otherwise or an express statement excluding an isomer is provided. In these situations, the single enantiomers, i.e., optically active forms can be obtained by method known to a person of ordinary skill in the art, such as asymmetric synthesis, synthesis from optically pure precursors, or by resolution of the racemates. Resolution of the racemates can also be accomplished, for example, by conventional methods, such as crystallization in the presence of a resolving agent, or chromatography, using, for example a chiral HPLC column. All isomeric forms are contemplated herein regardless of the methods used to obtain them.

All forms (for example solvates, optical isomers, enantiomeric forms, polymorphs, free compound and salts) of an active agent may be employed either alone or in combination. Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (+/−) D and L or R and S are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory To facilitate review of the various embodiments of the disclosure, the following explanations of specific terms and abbreviations are provided. Also, certain functional group terms include a "-" symbol at the beginning of the functional group formula; this symbol is not a part of the functional group, but instead denotes how the functional group connects to the formulas described herein. For example, a functional group with a formula "—OC(O)$R^b$" is attached to an atom of the functionalized compound by the oxygen atom of the functional group that is next to the "-" symbol.

Adjuvant: An excipient that modifies the effect of other agents, typically the active compound.

Adjuvants are often pharmacological and/or immunological agents. An adjuvant may modify the effect of an active compound by increasing a desired neurological response, such as an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight-and branched-chain arrangements, and all stereo and position isomers as well.

Aliphatic-aryl: An aryl group that is or can be coupled to a compound disclosed herein, wherein the aryl group is or becomes coupled to the compound through an aliphatic group.

Aliphatic-heteroaryl: A heteroaryl group that is or can be coupled to a compound disclosed herein, wherein the heteroaryl group is or becomes coupled to the compound through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic (such as —O-alkyl), with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-50}$), such as one to 25 carbon atoms ($C_1$-$_{25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkylaryl/Alkenylaryl/Alkynylaryl: An aryl group that is or can be coupled to a compound disclosed herein, wherein the aryl group is or becomes coupled to the compound through an alkyl, alkenyl, or alkynyl group, respectively.

Alkylheteroaryl/Alkenylheteroaryl/Alkynylheteroaryl: A heteroaryl group that is or can be coupled to a compound disclosed herein, wherein the heteroaryl group is or becomes coupled to the compound through an alkyl, alkenyl, or alkynyl group, respectively.

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or —NHC(O)R$^b$ wherein each of R$^a$ and R$^b$ independently is selected from hydrogen, aliphatic, heteroaliphatic, aromatic, or any combination thereof.

Amine: —NR$^a$R$^b$, wherein each of R$^a$ and R$^b$ independently is selected from hydrogen, aliphatic, heteroaliphatic, aromatic, and any combination thereof. In some embodiments, R$^a$ and R$^b$ can join together to form, with the nitrogen atom to which they are bound, a heterocyclic ring.

Aromatic: A cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Huckel rule (4n+2). The point of attachment to the parent structure typically is through an aromatic portion of the condensed ring system. For example,

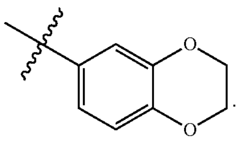 [SMILES: *c1ccc2c(c1)OCCO2]

However, in certain examples, context or express disclosure may indicate that the point of attachment is through a non-aromatic portion of the condensed ring system. For example,

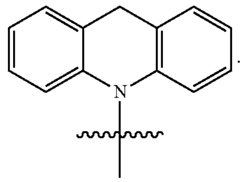 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aromatic, other functional groups, or any combination thereof.

Blood-brain barrier (BBB): The barrier formed by epithelial cells in the capillaries that supply the brain and central nervous system. This barrier selectively allows entry of substances such as water, oxygen, carbon dioxide, and nonionic solutes such as glucose, alcohol, and general anesthetics, while blocking entry of other substances. Some small molecules, such as amino acids, are taken across the barrier by specific transport mechanisms.

Boronic Ester: A functional group comprising a boron atom covalently bound to two oxygen atoms that are in turn bound to aliphatic groups and/or that are bound to one another through an aliphatic group.

Boronic acid: A functional group comprising a boron atom covalently bound to two hydroxyl groups.

c-Abl (Abelson murine leukemia viral oncogene homolog 1): Also known as ABL1, c-Abl is a non-receptor tyrosine kinase found in the cytosol and nucleus of cells. Genetic mutations that result in ABL1 overexpression and/or overactivity are known to lead to cancer in humans, such as chronic myelogenous leukemia (CML). Additionally, signal transduction via c-Abl is associated with neuronal cell death in neurodegenerative disorders, such as Alzheimer's disease (see, e.g., Alvarez et al., *Neurobiol. Dis.,* 17:326-336, 2004; Schlatterer et al., *J. Mol. Neurosci.,* 45:445-452, 2011).

The c-Abl protein includes a myristate binding pocket, which is located at the C terminal domain. Crystal structure of c-Abl with GNF-2 showed that the selective, allosteric small molecule inhibitor binds to the myristate binding pocket of c-Abl, leading to conformational changes in the structural dynamics of the ATP-binding site (Zhang et al., Nature, 463:501-506, 2010). Mutations in the myristate pocket (C464Y, P465S and E505K) interfere with inhibitor binding. Further biochemical and cellular assays in combination 4239-99971-05 E-253-2017*-OUS-03 FILED VIA EFS ON MARCH 30, 2023 with ATP-competitive inhibitors imatinib and nilotinib confirmed the synergistic activity of GNF-5 at the myristate binding site, providing a therapeutically strategy for structure-based design of novel allosteric inhibitors to overcome resistance to either alone.

C-Abl is encoded by the ABL1 gene (NCBI Gene ID NO. 25). An exemplary protein sequence for c-Abl is set forth as NCBI reference sequence NP_005148.2 (accessed Jan. 8, 2018, incorporated by reference herein). An exemplary encoding sequence for human caspase 4 is set forth as NCBI reference sequence NM_005157.5 (accessed Jan. 8, 2018, incorporated by reference herein). Assays for determining if a small molecule inhibits c-Abl activity are known. Non-limiting examples include cell proliferation assays using cancer cells that are BCR-Abl positive and depend on BCR-Abl for growth, such as the leukemia cell line K562. It has been previously reported that allosteric inhibitors of BCR-Abl inhibit proliferation of K562 cells in a dose dependent manner using HTS assays of cell proliferation such as MTT. (Adrian et al. Nature Chem Biol, p95, 2006). In some embodiments described herein, compounds are tested for ability to reduce K562 cell proliferation in an HTS adapted assay which measures cell viability using the reagent CellTiterGlo after 48 hours treatment.

Cancer: A malignant neoplasm that has undergone characteristic anaplasia with loss of differentiation, increased rate of growth, invasion of surrounding tissue, and is capable of metastasis.

Features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

Examples of hematological cancers include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of cancer with solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma, breast cancer or colon cancer.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Residual cancer is cancer that remains in a subject after any form of treatment given to the subject to reduce or eradicate the cancer.

The compound embodiments disclosed herein can be used to treat cancer, such as a hematological cancer or a cancer with a solid tumor, when the cancer is one with increased or upregulated c-Abl expression and/or activity. In several embodiments, administration of a therapeutically effective amount of a disclosed compound embodiment to a subject with or at risk of a cancer (such as a leukemia) delays progression of the cancer, and/or reduces a sign or symptom of the cancer.

Carboxyl: —C(O)OH, or an anion thereof.

Carrier: An excipient that serves as a component capable of delivering a compound described herein. In some embodiments, a carrier can be a suspension aid, solubilizing aid, or aerosolization aid. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical formulations to be administered can contain minor amounts of non-toxic auxiliary substances, such as wetting or emulsifying agents, preservatives, and pH buffering agents and the like, for example sodium acetate or sorbitan monolaurate.

Disease involving c-Abl tyrosine kinase: A disease wherein c-Abl plays a part in the development or predisposition to the disease, such as by being an active component in the biological pathway of the disease, or by being overexpressed in a patient having the disease or that is pre-disposed to the disease, or by being an indirect participant in the biological pathway of the disease (e.g., an activator or suppressor of a direct participant in the disease pathway).

Ester: —C(O)OR$^b$ or —OC(O)R$^b$ wherein R$^b$ is selected from hydrogen, aliphatic, heteroaliphatic, aromatic, or any combination thereof.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled to the compound through a haloaliphatic group.

Haloaliphatic-heteroaryl: A heteroaryl group that is or can be coupled to a compound disclosed herein, wherein the heteroaryl group is or becomes coupled to the compound through a haloaliphatic group.

Haloalkoxy: an alkoxy group wherein one or more hydrogen atoms attached to a carbon atom of the aliphatic group is replaced with a halogen atom. Exemplary haloalkoxy groups include, but are not limited to, $—OCF_3$, $—OCHF_2$, $—OCH_2F$, $—OCH_2CF_3$, $—O(CH_2)_2CF_3$ and the like.

Haloalkyl/Haloalkenyl/Haloalkynyl: An alkyl, alkenyl, or alkynyl group (which can be branched, straight-chain, or cyclic) comprising at least one halogen atom to 20 halogen atoms, such as one to 15 halogen atoms, or one to 5 halogen atoms, which can be selected from, but not limited to bromine, chlorine, fluorine, or iodine.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, silicon, sulfur, selenium, phosphorous, boron, and oxidized forms thereof within the group.

Heteroaliphatic-aryl: An aryl group that is or can be coupled to a compound disclosed herein, wherein the aryl group is or becomes coupled to the compound through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, silicon, selenium, phosphorous, boron, and oxidized forms thereof within the group.

Heteroalkyl-aryl/Heteroalkenyl-aryl/Heteroalkynyl-aryl: An aryl group that is or can be coupled to a compound disclosed herein, wherein the aryl group is or becomes coupled to the compound through a heteroalkyl, heteroalkenyl, or heteroalkynyl group, respectively.

Heteroalkyl-heteroaryl/Heteroalkenyl-heteroaryl/Heteroalkynyl-heteroaryl: A heteroaryl group that is or can be coupled to a compound disclosed herein, wherein the aryl group is or becomes coupled to the compound through a heteroalkyl, heteroalkenyl, or heteroalkynyl group, respectively.

Heteroaryl: An aryl group comprising at least one heteroatom to six heteroatoms, such as one to four heteroatoms, which can be selected from, but not limited to oxygen, nitrogen, sulfur, silicon, selenium, phosphorous, boron, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Heteroaryl groups may be substituted with one or more groups other than hydrogen, such as aliphatic, heteroaliphatic, aryl, heteroaryl, other functional groups, or any combination thereof.

Ketone: —C(O)$R^a$, wherein $R^a$ is selected from aliphatic, aromatic, aliphatic-aromatic, heteroaliphatic-aromatic, heteroaliphatic, and any combination thereof.

Neurodegenerative disorder: An abnormality in the nervous system of a subject, such as a mammal, in which neuronal integrity is threatened. Without being bound by theory, neuronal integrity can be threatened when neuronal cells display decreased survival or when the neurons can no longer propagate a signal. In several embodiments, neurodegenerative diseases are associated with ER stress and protein aggregation, such as accumulation, oligomerization, fibrillization or aggregation, of two or more, hetero- or homomeric, proteins or peptides in the intracellular or extracellular neuronal environment. Non-limiting examples of neurodegenerative disorders associated with ER stress and protein aggregation include Alzheimer's disease, Parkinson's disease, Huntington's disease, and amyotrophic lateral sclerosis (ALS).

Alzheimer's disease (AD) is a progressive brain disorder that occurs gradually and results in memory loss, behavioral and personality changes, and a decline in mental abilities. These losses are related to the death of brain cells and the breakdown of the connections between them. The course of this disease varies from person to person, as does the rate of decline. On average, AD patients live for 8 to 10 years after they are diagnosed, though the disease can last up to 20 years. AD advances by stages, from early, mild forgetfulness to a severe loss of mental function. At first, AD destroys neurons in parts of the brain that control memory, especially in the hippocampus and related structures. As nerve cells in the hippocampus stop functioning properly, short-term memory fails. AD also attacks the cerebral cortex, particularly the areas responsible for language and reasoning.

Parkinson's disease (PD) is an idiopathic, slowly progressive, degenerative CNS disorder characterized by slow and decreased movement, muscular rigidity, resting tremor, and postural instability. The loss of substantia nigra neurons, which project to the caudate nucleus and putamen, results in the depletion of the neurotransmitter dopamine in these areas.

Amyotrophic lateral sclerosis (ALS) is a progressive, usually fatal, neurodegenerative disease caused by the degeneration of motor neurons. The neurons typically affected are located in the lower motor neurons of the brainstem and spinal cord and upper motor neurons in the cerebral cortex. Within 2 to 5 years after clinical onset, the loss of motor neurons leads to progressive atrophy of skeletal muscles, which results in loss of muscular function resulting in paralysis, speech deficits, and death due to respiratory failure. ALS is also known as Lou Gehrig's disease.

Huntington's disease is an autosomal dominant neurodegenerative disease resulting from mutation in the Huntington gene. The mutation is an expansion of a trinucleotide repeat (CAG) in exon 1 of the Huntington gene, resulting in a polyglutamine expansion in the Huntington protein. The resulting gain of function is the basis for the pathological, clinical and cellular sequelae of Huntington's disease. The primary neuro-anatomical affect is found in the caudate nucleus and putamen, including medium spiny neurons.

Clinically, Huntington's disease is characterized by an involuntary choreiform movement disorder, psychiatric and behavioral chances and dementia. The age of onset is usually between 30-50 years of age, although juvenile and late onset cases of Huntington's disease occur. At the cellular level, Huntington's disease is characterized by protein aggregation in the cytoplasm and nucleus of neurons which comprise ubiquitinated terminal fragments of Huntington. (see, e.g., Bence et al., *Science,* 292:1552-1555, 2001; Walter et al., *Mol. Biol. Cell.,* 12:1393-1407, 2001).

Multiple sclerosis is a slowly progressive CNS disease characterized by disseminated patches of demyelination in the brain and spinal cord, resulting in multiple and varied neurological symptoms and signs, usually with remissions and exacerbation. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis is a clinical course of MS that is characterized by clearly defined, acute attacks with full or partial recovery and no disease progression between attacks. Secondary-progressive multiple sclerosis is a clinical course of MS that initially is relapsing-remitting, and then becomes progressive at a variable rate, possibly with an occasional relapse and minor remission. Primary progressive multiple sclerosis presents initially in the progressive form. A clinically isolated syndrome is the first neurologic episode, which is caused by inflammation/demyelination at one or more sites in the CNS.

The compound embodiments disclosed herein can be used to treat neurodegenerative disorders, such as Alzheimer's disease. In several embodiments, administration of a therapeutically effective amount of a disclosed compound embodiment to a subject with or at risk of a neurodegenerative disorder delays progression of the neurodegenerative disorder, and/or reduces a sign or symptom of the neurodegenerative disorder.

Pharmaceutically Acceptable Excipient: A substance, other than an active compound (e.g., a compound described herein), that is included in a formulation of the active compound. As used herein, an excipient may be incorporated within particles of a pharmaceutical formulation, or it may be physically mixed with particles of a pharmaceutical formulation. An excipient also can be in the form of a solution, suspension, emulsion, or the like. An excipient can be used, for example, to dilute an active agent and/or to modify properties of a pharmaceutical formulation. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethylene glycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

Pharmaceutically Acceptable Salt: Pharmaceutically acceptable salts of a compound described herein that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compound embodiments form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

Therapeutically Effective Amount: An amount of a compound sufficient to treat a specified disorder or disease, or to ameliorate or eradicate one or more of its symptoms and/or to prevent the occurrence of the disease or disorder. The amount of a compound which constitutes a "therapeutically effective amount" will vary depending on the compound, the disease state and its severity, the age of the patient to be treated, and the like. The therapeutically effective amount can be determined by a person of ordinary skill in the art.

Prodrug: Compound embodiments disclosed herein that are transformed, most typically in vivo, to yield a biologically active compound, particularly the parent compound, for example, by hydrolysis in the gut or enzymatic conversion. Common examples of prodrug moieties include, but are not limited to, pharmaceutically acceptable ester and amide forms of a compound having an active form bearing a carboxylic acid moiety. Examples of pharmaceutically acceptable esters of the compound embodiments of the present disclosure include, but are not limited to, esters of phosphate groups and carboxylic acids, such as aliphatic esters, particularly alkyl esters (for example $C_{1-6}$alkyl esters). Other prodrug moieties include phosphate esters, such as $—CH_2—O—P(O)(OR^a)_2$ or a salt thereof, wherein $R^a$ is hydrogen or aliphatic (e.g., $C_1$-$_6$alkyl). Acceptable esters also include cycloalkyl esters and arylalkyl esters such as, but not limited to, benzyl. Examples of pharmaceutically acceptable amides of the compound embodiments of this disclosure include, but are not limited to, primary amides, and secondary and tertiary alkyl amides (for example with between one and six carbons). Amides and esters of disclosed exemplary embodiments of compound embodiments according to the present disclosure can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

Subject: Mammals and other animals, such as humans, companion animals (e.g., dogs, cats, rabbits, etc.), utility animals, feed animals and the like; thus, disclosed methods are applicable to both human therapy and veterinary applications.

Sulfonamide: —$SO_2$—$NR^aR^b$ or —$NR^aSO_2R^b$, wherein each of $R^a$ and $R^b$ independently is selected from hydrogen, aliphatic, aromatic, or heteroaliphatic.

Symptom and sign: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting a neurodegenerative disorder or disease.

Treating/Treatment: Treatment of a disease or condition of interest in a subject, particularly a human or mammal having the disease or condition of interest or that may or may not be prone to developing the disease or condition, and includes by way of example, and without limitation:

(i) prophylactic administration to prevent the disease or condition from occurring in a subject, or to ameliorate symptoms associated with the condition if required in particular, when such subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

A person of ordinary skill in the art would recognize that the definitions provided above are not intended to include impermissible substitution patterns (e.g., methyl substituted with five different groups, and the like). Such impermissible substitution patterns are easily recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

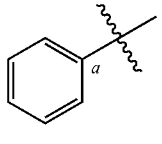 [SMILES: *c1ccccc1]

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein. Any compound embodiment described herein can be deuterated or not deuterated, unless otherwise indicated herein. Suitable positions at which a compound can be deuterated are readily recognized by people of ordinary skill in the art.

II. Introduction

Cytoplasmic tyrosine kinases are important transducers of extracellular signals. C-Abl tyrosine kinase (also referred to herein as "c-Abl") is a ubiquitous non-receptor tyrosine kinase involved in signal transduction. In addition to its classic function in leukemia pathogenesis, c-Abl is also thought to play a role in neuronal development, neurogenesis, neuronal migration, axonal extension, and synaptic plasticity, whereby deregulation of c-Abl could be related to early neuronal dysfunction and cytoskeletal alterations. Mounting evidence points to the role of the Abl tyrosine kinase family as an important player in AD, and thus a potential therapeutic target to delay and ameliorate neurodegeneration.

Disclosed herein are novel compound embodiments that bind to an allosteric site on c-Abl to inhibit c-Abl tyrosine kinase activity. In particular disclosed embodiments, the compound embodiments bind to the myristate pocket of c-Abl to inhibit the c-Abl tyrosine kinase activity. The compound embodiments of the present disclosure also exhibit increased proficiency in crossing the blood brain barrier (or "BBB"), which is at least one feature not shared by conventional compounds used to inhibit c-Abl. The compound embodiments described herein can more effectively bind to c-Abl, particularly in the brain and with increased potency. In particular disclosed embodiments, the compound embodiments of the present disclosure exhibit activity superior to conventional compounds used to treat diseases disclosed herein, such as Imatinib, Nilotinib, GNF-2, and GNF-5.

Also disclosed herein are embodiments of a method for making the compound embodiments as well as methods of using the compound embodiments. Further disclosed are composition embodiments comprising these novel c-Abl inhibitory compounds and method embodiments for targeting c-Abl and treating various diseases associated with c-Abl.

III. Compound Embodiments

Compound embodiments described herein comprise a dibenzoazepinone core (or a reduced, dehydrated, and/or aminated form thereof) and further comprise particular substituents that functionalize the core. The core and corresponding substituents are specifically designed to promote passage of the compound through the blood brain barrier and to promote binding of the compound to c-Abl to thereby inhibit c-Abl tyrosine kinase activity. In particular disclosed embodiments, the compound embodiments have a structure satisfying Formula I below. In some embodiments, the compound can be in the form of a stereoisomer, a tautomer, a pharmaceutically acceptable salt, a prodrug, or a solvate of a compound satisfying Formula I.

Formula I

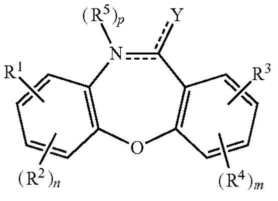

With reference to Formula I, X is oxygen, NR', CR'R", S, SO, or $SO_2$, wherein each R' and R" independently is selected from hydrogen, aliphatic, heteroaliphatic, haloaliphatic, haloheteroaliphatic, aromatic, aliphatic-aromatic, or heteroaliphatic-aromatic; Y is hydrogen, oxygen, NR', NR'R", or CR'R" wherein each R' and R" independently is selected from hydrogen, aliphatic, heteroaliphatic, haloaliphatic, haloheteroaliphatic, aromatic, aliphatic-aromatic, or heteroaliphatic-aromatic; each of $R^1$ and $R^3$, independently, is a functional group and is not hydrogen; each $R^2$, if present (such as when n is an integer selected from 1, 2, or 3), independently is a functional group and is not hydrogen; each $R^4$, if present (such as when n is an integer selected from 1, 2, or 3), independently is a functional group and is not hydrogen; $R^5$, when present (such as when p is 1) is selected from hydrogen, aliphatic, heteroaliphatic, aromatic, aliphatic-aromatic, heteroaliphatic-aromatic, or heteroaliphatic-aromatic; and each of n and m independently is an integer selected from 0 to 3, such as 0, 1, 2, or 3; and p is 0 or 1, wherein when p is 0, then no $R^5$ group is present and therefore the nitrogen atom of Formula I forms a double bond with the carbon atom attached to Y. In embodiments where p is one, $R^5$ is present and thus the nitrogen atom of Formula I forms a single bond with the carbon atom attached to Y.

In some embodiments, the following substituent recitations can apply for Formula I:

X is oxygen, NR', CR'R", S, SO, or $SO_2$, wherein each R' and R" independently is selected from hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl;

Y can be bound to its corresponding carbon atom via a single bond and can be hydrogen or NR'R"; or Y can be bound to its corresponding carbon atom via a double bond and can be oxygen, NR', or CR'R". Each R' and R" independently is selected from hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl. In particular disclosed embodiments, Y is oxygen;

$R^1$ and $R^3$ independently are heteroaliphatic, haloaliphatic, haloheteroaliphatic, aromatic, or boronic acid;

$R^2$ and $R^4$, if present, independently are aliphatic, heteroaliphatic, or halogen;

$R^5$, if present (such as when p is 1 and the nitrogen to which $R^5$ is bound forms a single bond with the carbon atom connected to Y), is hydrogen, alkyl, or heteroalkyl;

n and m are 0 or 1; and p is 0 or 1.

In yet some additional embodiments, the following substituent recitations can apply for Formula I:

X is oxygen, NR', CR'R", S, SO, or $SO_2$, wherein each R' and R" independently is selected from hydrogen, lower alkyl (e.g., methyl, ethyl, propyl, butyl, pentyl, hexyl, heptyl, octyl, nonyl, or decyl), or lower heteroalkyl (e.g., $—CH_2UCH_3$, $—(CH_2)_2UCH_3$, $—(CH_2)_3UCH_3$, or $—(CH_2)_4UCH_3$, wherein U is a heteroatom selected from oxygen, sulfur, $NR^a$ [wherein $R^a$ is hydrogen, aliphatic, heteroaliphatic, or aromatic], silicon, or other heteroatoms described herein);

Y is hydrogen, oxygen, $NH_2$, $NHCH_3$, $N(CH_3)_2$, NH, $NCH_3$, $CH_2$, or $C(CH_3)_2$, wherein when Y is oxygen, NH, $NCH_3$, $CH_2$, or $C(CH_3)_2$, the Y group is bound to the corresponding carbon atom via a double bond;

$R^1$ and $R^3$ independently are alkoxy, thioether, haloalkoxy, haloalkyl, haloalkenyl, haloalkynyl, cyano, aryl, heteroaryl, alkyl-$B(OH)_2$, heteroalkyl-$B(OH)_2$, $—B(OH)_2$, aryl-$(R''')_{n'}$, heteroaryl-$(R''')_{n'}$, wherein each R''' independently is heteroaliphatic, sulfonamide, amine, boronic acid, or hydroxyl, and n' is an integer ranging from 0 to 5, such as 0, 1, 2, 3, 4, or 5;

$R^2$ and $R^4$, if present, independently are alkyl, alkenyl, alkynyl, heteroalkyl, chloro, fluoro, bromo, iodo, or cyano;

$R^5$, if present (such as when p is 1 and the nitrogen to which it is bound forms a single bond with the carbon atom connected to Y), is hydrogen, $CH_3$, or $—(CH_2)_qO(CH_2)_qSi(CH_3)_3$, wherein each q independently is an integer ranging from 0 to 50, such as 0 to 25, or 0 to 10, or 0 to 5.

n and m independently are 0 or 1; and p is 0 or 1.

In an independent embodiment of Formula I, $R^1$ and $R^3$ are not both $—OCH_3$ when $R^5$ is H and when both Y and X are oxygen.

In some embodiments, the compound can have a structure satisfying any one or more of Formulas IIA-IIF, which are illustrated below. In some embodiments, the compound satisfying any one or more of Formulas IIA-IIF can be in the form of a stereoisomer, a tautomer, a pharmaceutically acceptable salt, a prodrug, or a solvate. With reference to any of Formulas IIA-IIF, the illustrated variables can be as recited above for Formula I.

Formula IIA

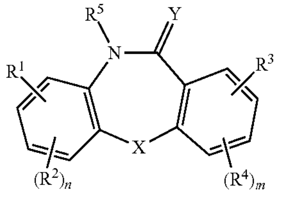

Formula IIB

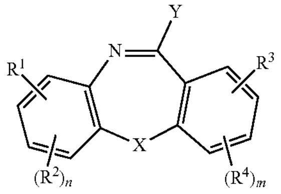

Formula IIC

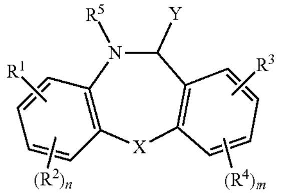

Y = H

Formula IID

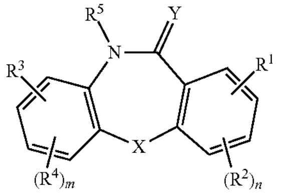

-continued

Formula IIE

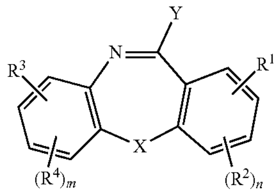

Formula IIF

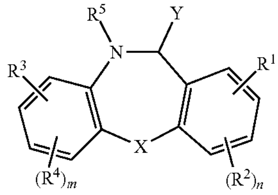

Y = H

In some embodiments, the following substituent recitations can apply for Formulas IIA-IIF, independently:

X is oxygen, NR', CR'R", S, SO, or $SO_2$, wherein each R' and R" independently is selected from hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl;

Y is H (for Formula IIC and IIF); oxygen, NR', or CR'R" (such as in the case of Formula IIA and Formula IID); or $NH_2$ or NR'R" (such as in the case of Formula IIB and Formula IIE. Each R' and R" independently is selected from hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl and in particular disclosed embodiments, Y is oxygen and the compound has a structure satisfying Formula IIA and Formula IID;

$R^1$ is heteroaliphatic, haloaliphatic, or haloheteroaliphatic;

$R^3$ is aromatic, heteroaliphatic, or boronic acid;

each $R^2$ and $R^4$, if present, independently are aliphatic, heteroaliphatic, or halogen;

$R^5$, if present (such as for Formulas IIA, IIC, IID, and IIF), is hydrogen, alkyl, or heteroalkyl;

n and m independently are 0 or 1; and p is0 or 1.

In yet some additional embodiments, the following substituent recitations can apply for Formulas IIA-IIF, independently:

X is oxygen, NR', CR'R", S, SO, or $SO_2$, wherein each R' and R" independently is selected from hydrogen, lower alkyl (e.g., methyl, ethyl, propyl, butyl, pentyl, hexyl, heptyl, octyl, nonyl, or decyl), or lower heteroalkyl (e.g., $—CH_2OCH_3$, $—(CH_2)_2OCH_3$, $—(CH_2)_3OCH_3$, or $—(CH_2)_4OCH_3$);

Y is hydrogen (for Formula IIC and Formula IIF); oxygen, NH, $NCH_3$, $CH_2$, or $C(CH_3)_2$ (for Formula IIA and Formula IID); or $NH_2$, $NHCH_3$, or $N(CH_3)_2$ (for Formula IIB and Formula IIE) and in particular disclosed embodiments, Y is oxygen and the compound has a structure satisfying Formula IIA and Formula IID;

$R^1$ is alkoxy, thioether, haloalkoxy, haloalkyl, haloalkenyl, haloalkynyl, or cyano;

each $R^2$ independently is lower alkyl, cyano, or halogen;

each $R^4$ independently is heteroaliphatic;

$R^3$ is alkoxy, thioether, aryl, heteroaryl, alkyl-$B(OH)_2$, heteroalkyl-$B(OH)_2$, $—B(OH)_2$, aryl-(R'''), heteroaryl-$(R''')_{n'}$, wherein each R''' independently is heteroaliphatic, sulfonamide, amine, boronic acid, or hydroxyl, and n' is an integer ranging from 0 to 5, such as 0, 1, 2, 3, 4, or 5;

$R^5$, if present (such as when the nitrogen to which it is bound forms a single bond with the carbon atom connected to Y), is hydrogen, $CH_3$, or $—(CH_2)_qO(CH_2)_qSi(CH_3)_3$, wherein each q independently is an integer ranging from 0 to 50, such as 0 to 25, or 0 to 10, or 0 to 5.

n and m are 0 or 1; and p is0 or 1.

In some embodiments, the compound can have a structure satisfying any one or more of Formulas IIIA-IIIH, illustrated below. In some embodiments, the compound satisfying any one or more of Formulas IIIA-IIIH can be in the form of a stereoisomer, a tautomer, a pharmaceutically acceptable salt, a prodrug, or a solvate. With reference to any of Formulas IIIA-IIIH, the illustrated variables can be as recited above for Formula I or Formulas IIA-IIF. In particular disclosed embodiments of compounds satisfying any one or more of Formulas IIIA-IIIG, $R^1$ and $R^3$ are not the same.

Formula IIIA

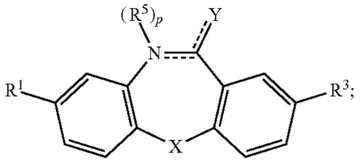

Formula IIIB

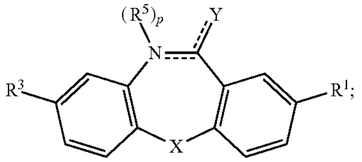

Formula IIIC

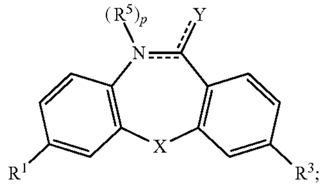

Formula IIID

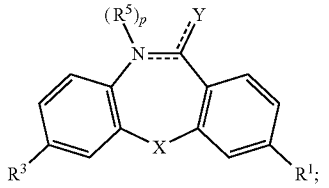

Formula IIIE

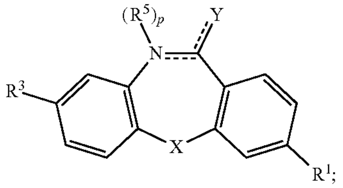

-continued

Formula IIIF

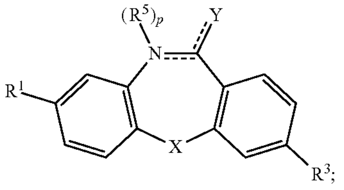

Formula IIIG

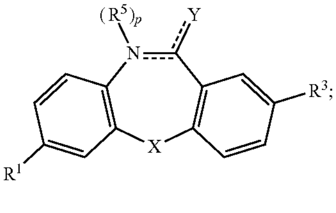

or

Formula IIIH

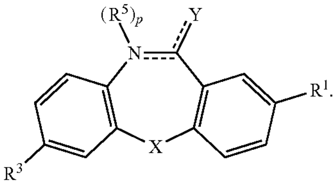

In some embodiments, the following substituent recitations can apply for Formulas IIIA-IIIH, independently:

X is oxygen, NR', CR'R", S, SO, or $SO_2$, wherein each R' and R" independently is selected from hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl;

Y is hydrogen or NR'R" (and is thus bound to the corresponding carbon atom via a single bond) or oxygen, NR', or CR'R" (and thus is bound to the corresponding carbon atom via a double bond), wherein each R' and R" independently is selected from hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl, and in particular disclosed embodiments, Y is oxygen;

$R^1$ is heteroaliphatic, haloaliphatic, or haloheteroaliphatic;

$R^3$ is aromatic, heteroaliphatic, or boronic acid;

$R^5$, if present (such as when the nitrogen to which $R^5$ is bound forms a single bond with the carbon atom connected to Y), is hydrogen, alkyl, or heteroalkyl; and p is0 or 1.

In yet additional embodiments, the compound can have a structure satisfying any one or more of Formulas IVA-IVF, illustrated below. In some embodiments, the compound satisfying any one or more of Formulas IVA-IVF can be in the form of a stereoisomer, a tautomer, a pharmaceutically acceptable salt, a prodrug, or a solvate. With reference to any of Formulas IVA-IVF, the illustrated variables can be as recited above for Formula I or Formulas IIA-IIF and in particular disclosed embodiments, Y is oxygen.

Formula IVA

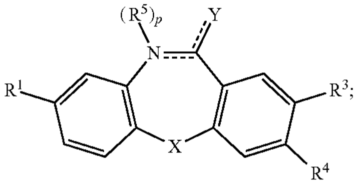

Formula IVB

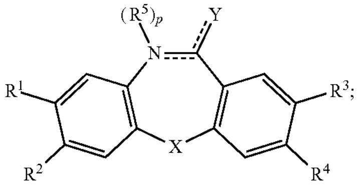

Formula IVC

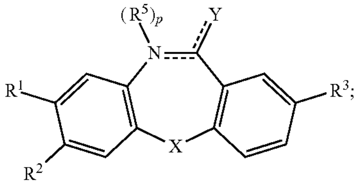

Formula IVD

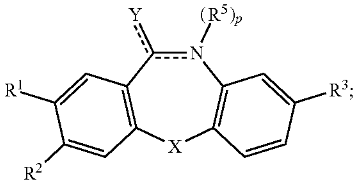

Formula IVE

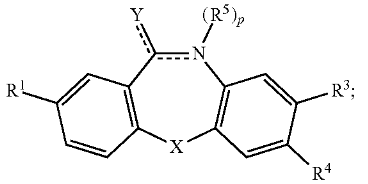

or

Formula IVF

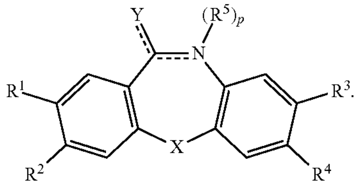

In some embodiments comprising $R^1$ and/or $R^3$ groups wherein $R^1$ and/or $R^3$ are "aromatic" or "aryl-$(R''')_n$", "heteroaryl-$(R''')_n$", the aromatic group or the aryl-$(R''')_n$", heteroaryl-$(R''')_n$" groups can have any of the following structures:

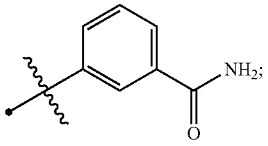

-continued
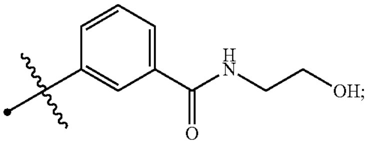
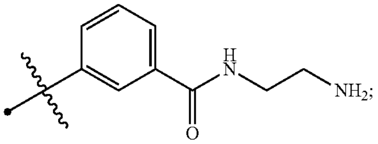
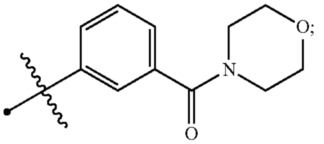
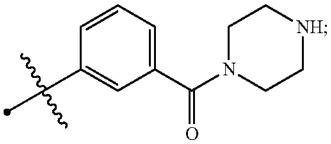
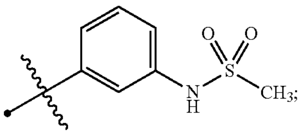
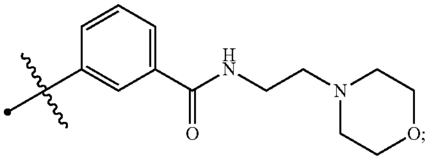
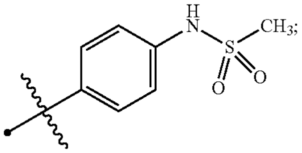
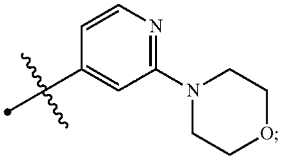
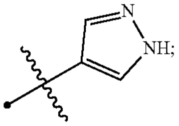
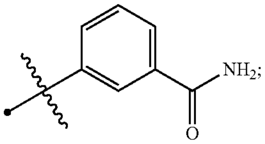
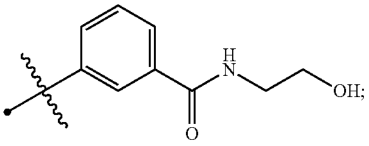
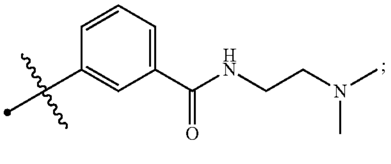
-continued
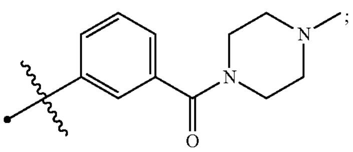
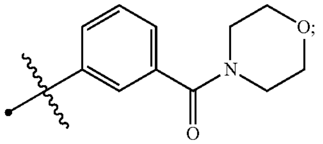
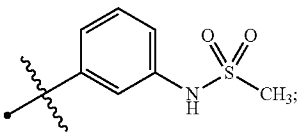
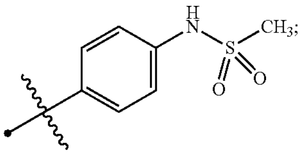
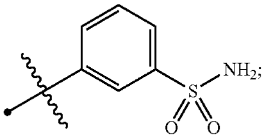
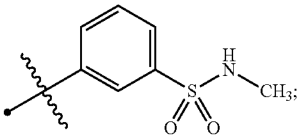
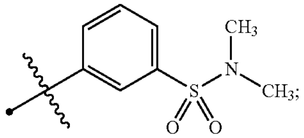
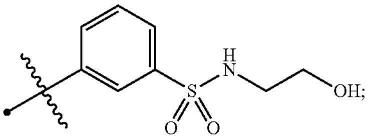
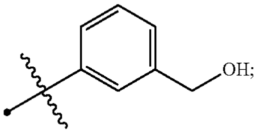
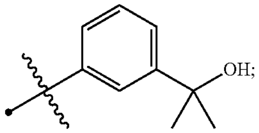
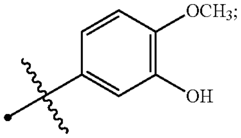
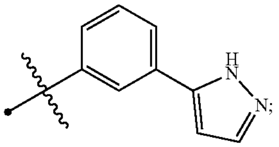
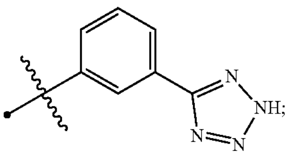
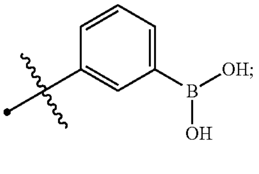

-continued
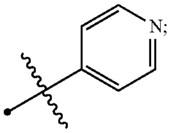
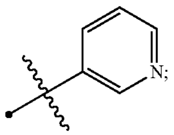
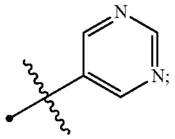
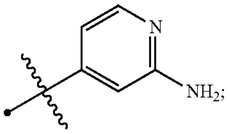
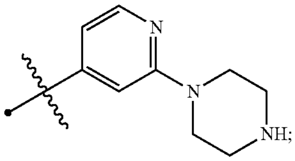
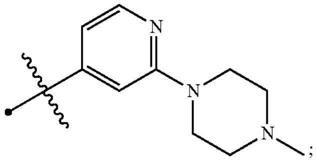
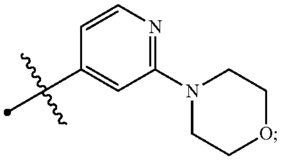
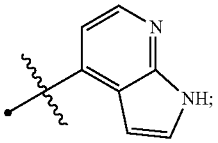
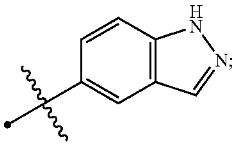
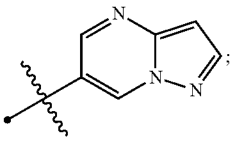
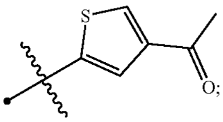
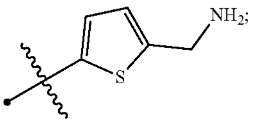
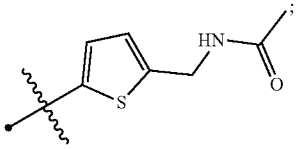
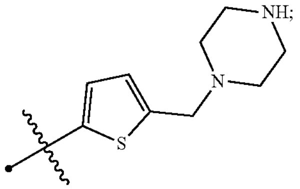
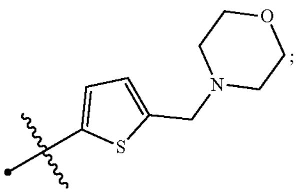
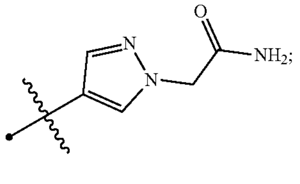
-continued
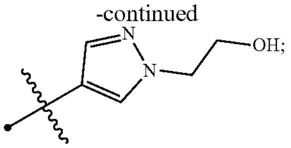
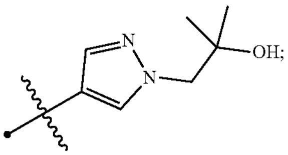
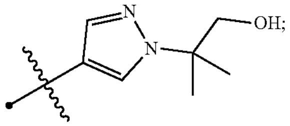
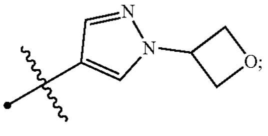
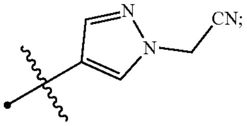
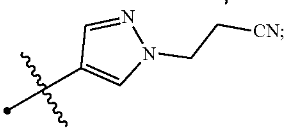
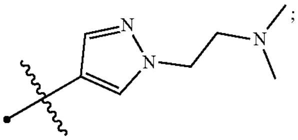
or
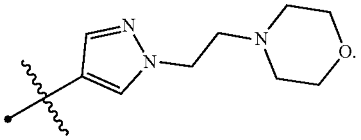
In particular disclosed embodiments, the compound can be selected from any of the structures provided below, including any suitable stereoisomers, tautomers, pharmaceutically acceptable salts, prodrugs, or solvates thereof.
NCGC00354777
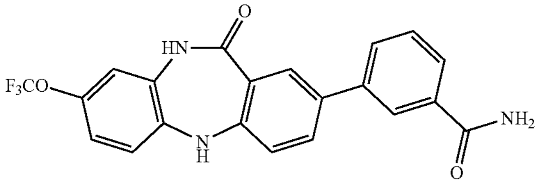
AED007-015
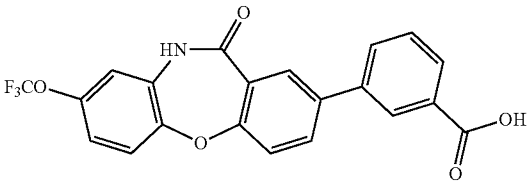
AED005-064
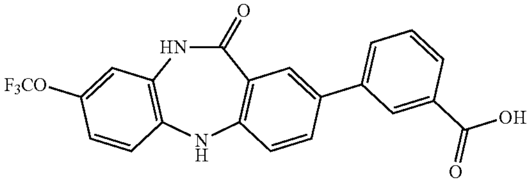

-continued
NCGC00355556
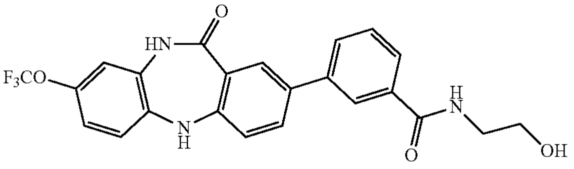
NCGC00355568
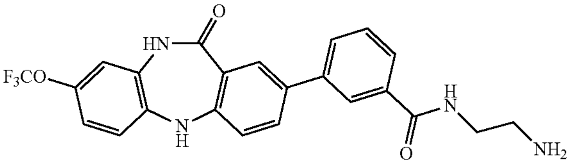
NCGC00355557
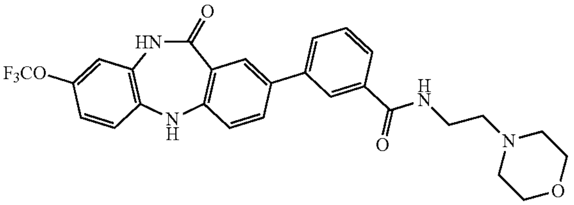
NCGC00355558
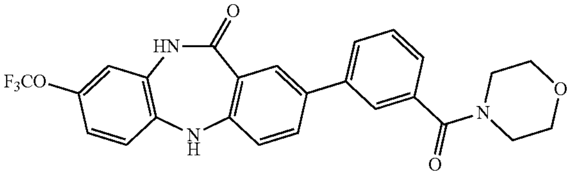
NCGC00355569
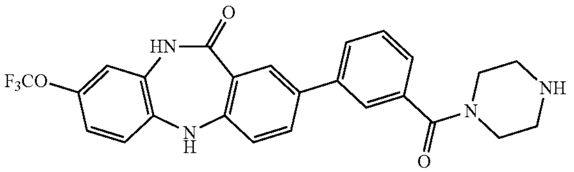
NCGC00355551
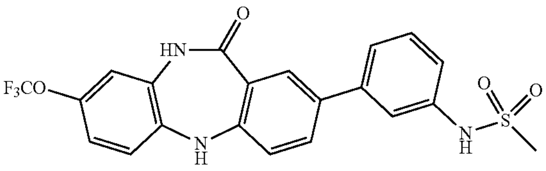
NCGC00355552
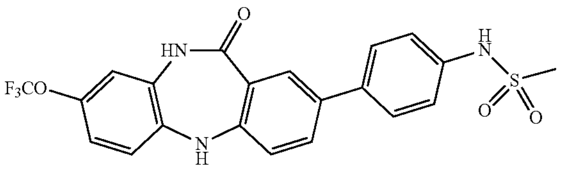
-continued
NCGC00481508
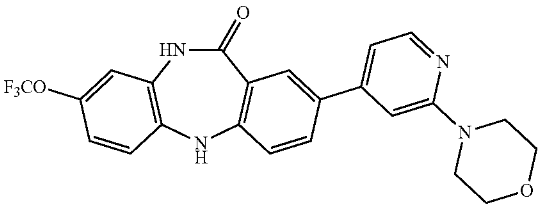
NCGC00355553
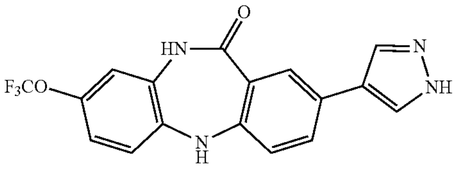
NCGC00356842
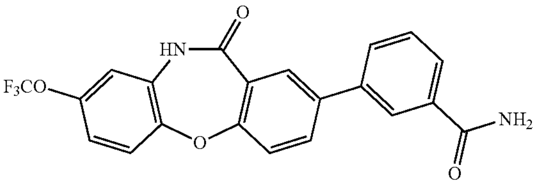
NCGC00356688
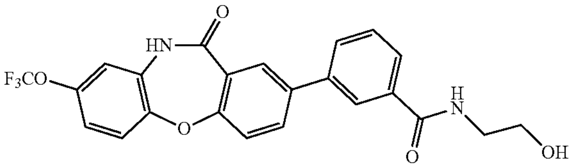
NCGC00356689
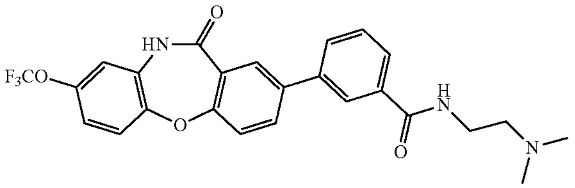
NCGC00356690
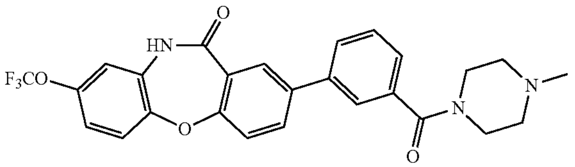
NCGC00356745
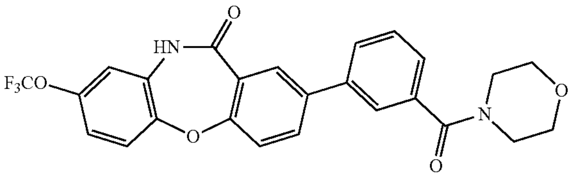

-continued
NCGC00356665
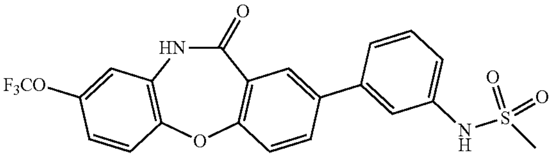
NCGC00356666
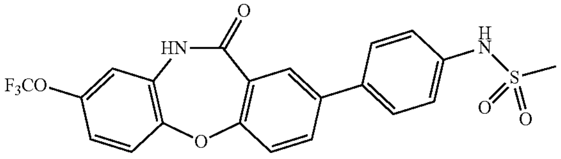
NCGC00371364
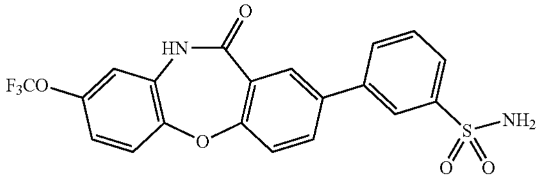
NCGC00373056
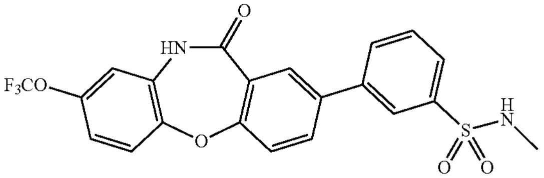
NCGC00373057
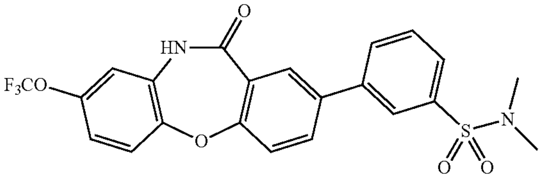
NCGC00373064
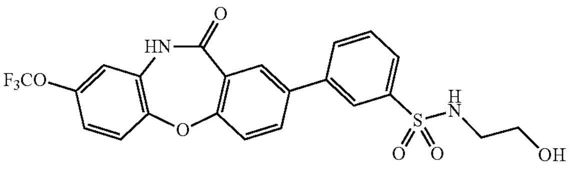
NCGC00415061
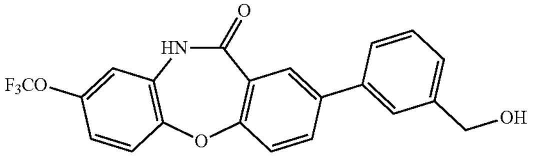
NCGC00411876
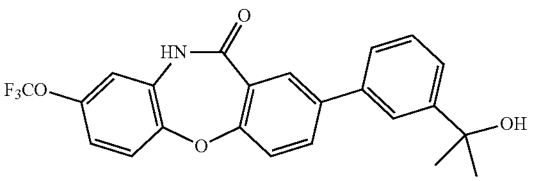
-continued
NCGC00373062
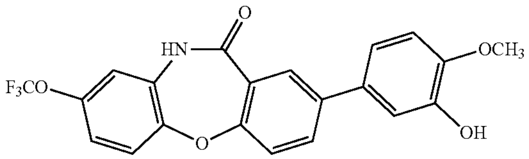
NCGC00411874
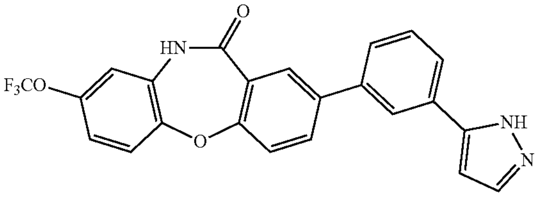
NCGC00420743
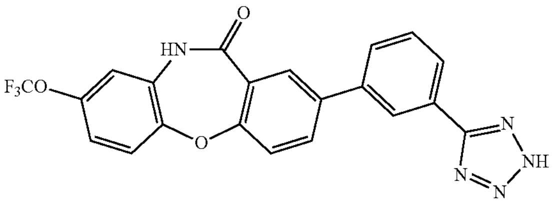
NCGC00415019
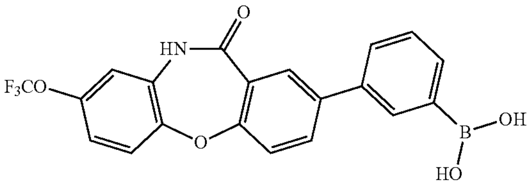
NCGC00371309
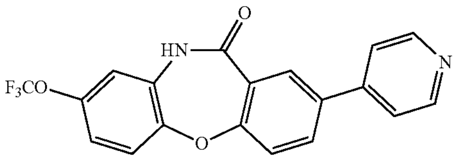
NCGC00371308
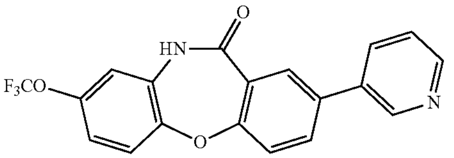
NCGC00371310
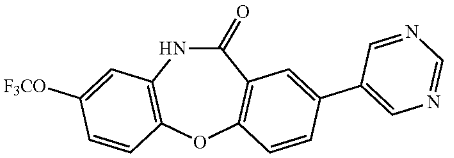
NCGC00373061
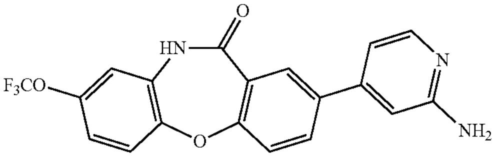

-continued
NCGC00373060
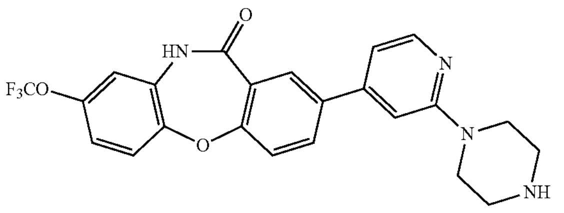
NCGC00373063
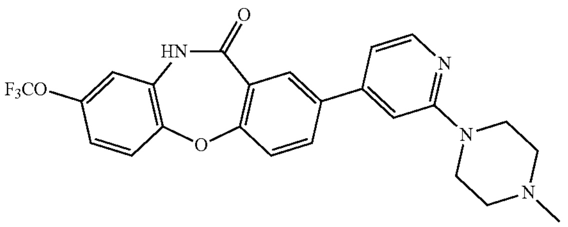
NCGC00411866
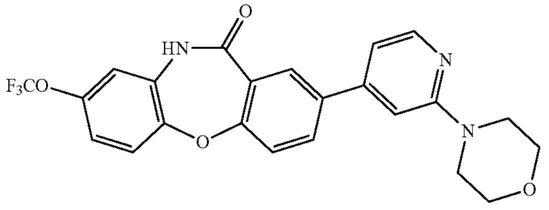
NCGC00373059
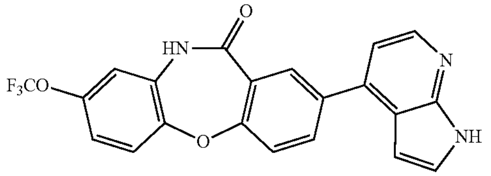
NCGC00373058
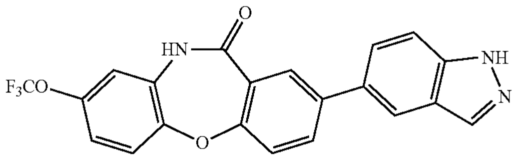
NCGC00409812
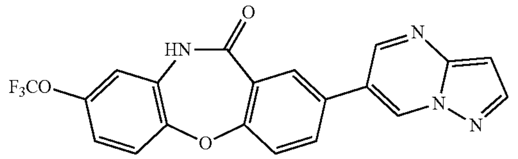
NCGC00388580
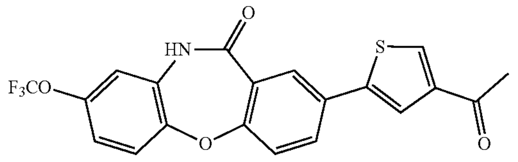
-continued
NCGC00388547
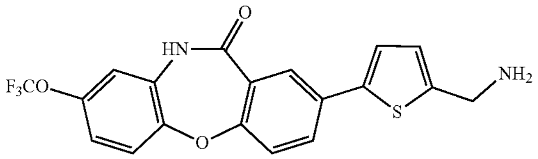
NCGC00388557
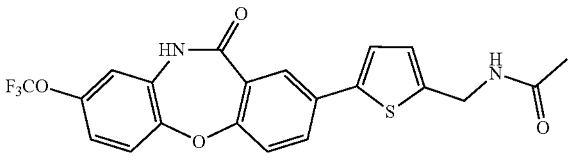
NCGC00388560
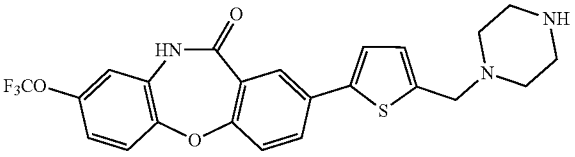
NCGC00388536
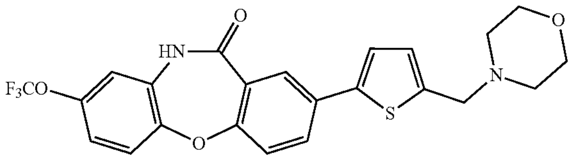
NCGC00387404
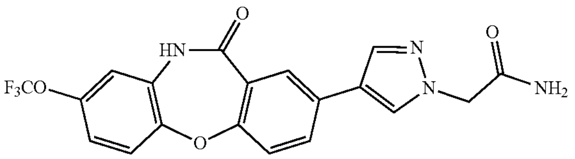
NCGC00387403
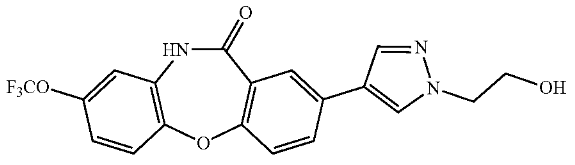
NCGC00387294
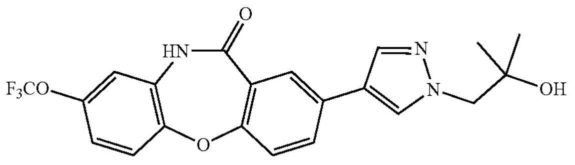
NCGC00387295
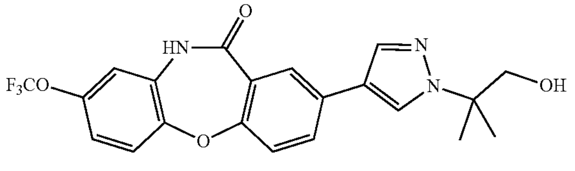

-continued
NCGC00387298
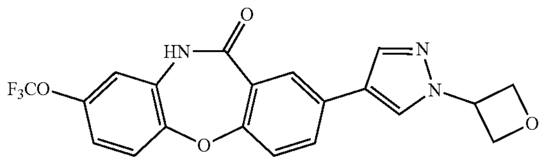
NCGC00388626
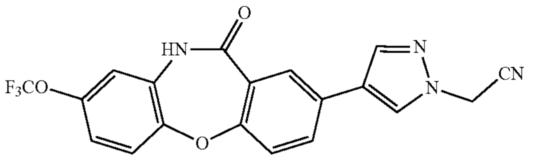
NCGC00387293
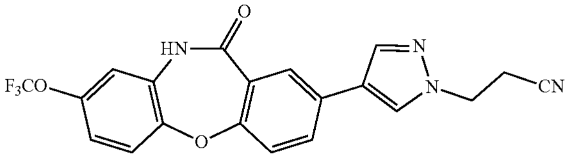
NCGC00387297
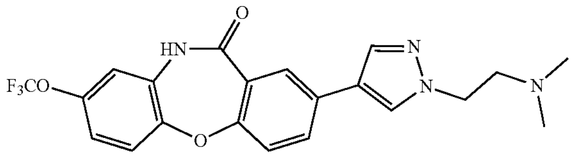
NCGC00387296
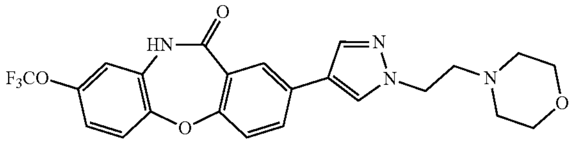
NCGC00390142
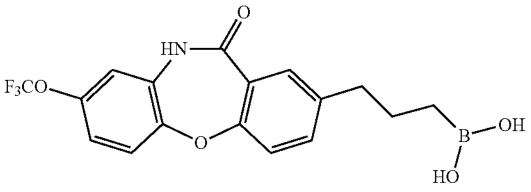
NCGC00390141
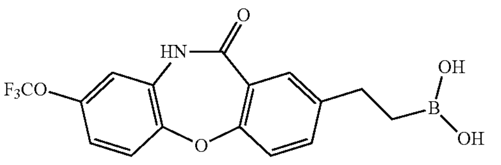
NCGC00387437
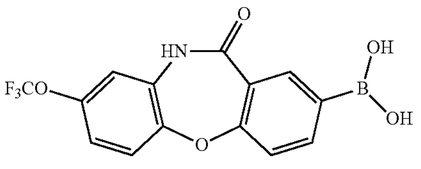
-continued
NCGC00488957
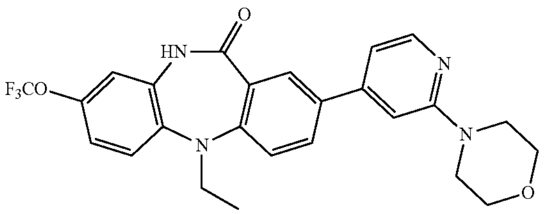
NCGC00488913
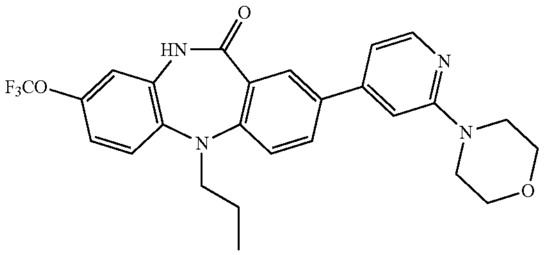
NCGC00488955
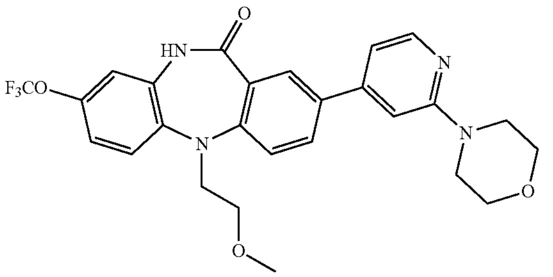
NCGC00384233
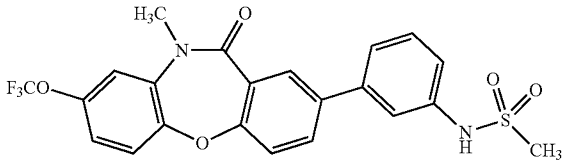
NCGC00494683
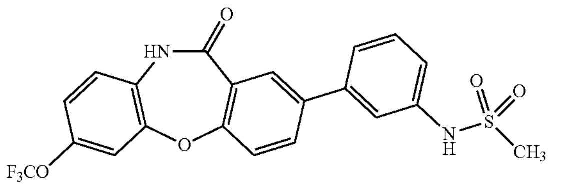
NCGC00494682
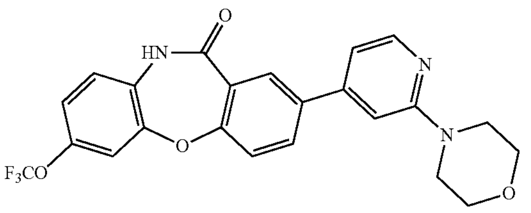

-continued
NCGC00384235
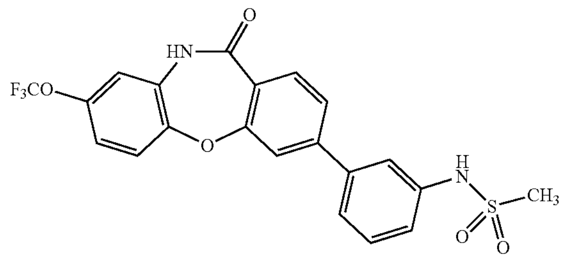
NCGC00384296
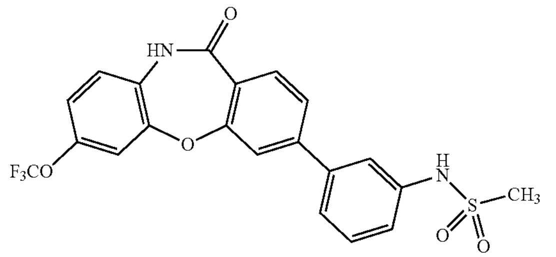
NCGC00384303
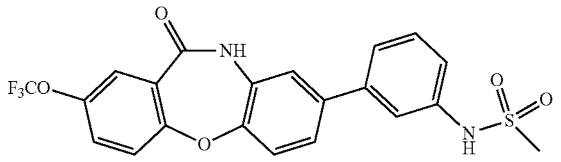
NCGC00384295
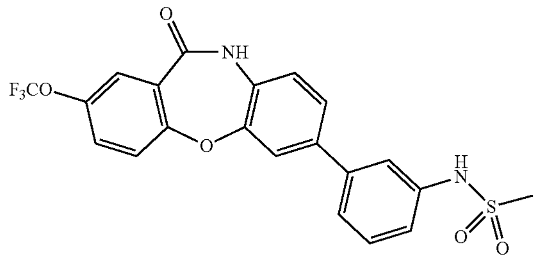
NCGC00384286
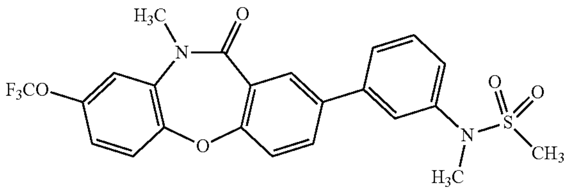
NCGC00371644
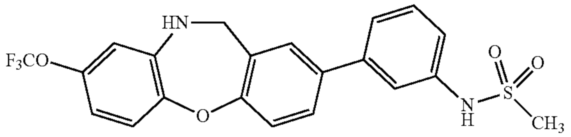
NCGC00373124
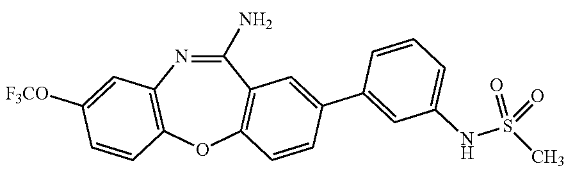
-continued
NCGC00482456
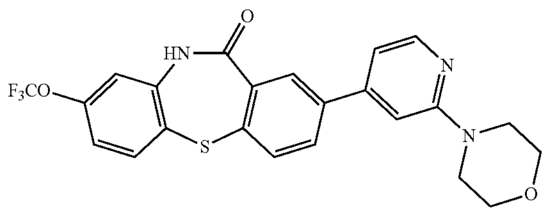
NCGC00481506
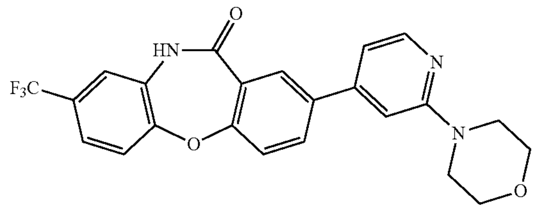
NCGC00481503
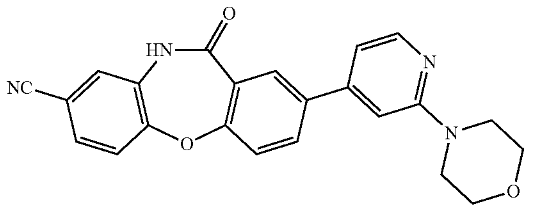
NCGC00481504
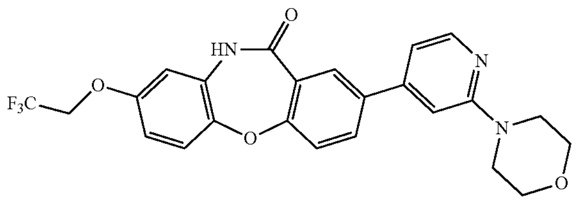
NCGC00481507
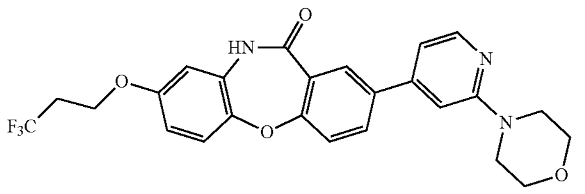
NCGC00482446
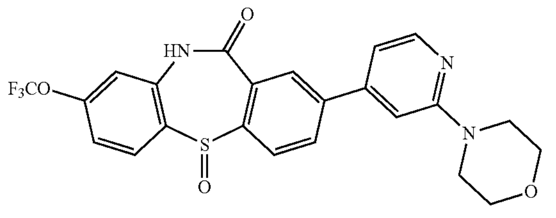
NCGC00483140
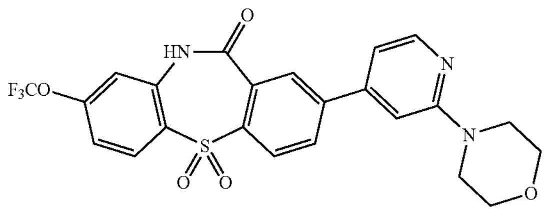

-continued
NCGC00507969
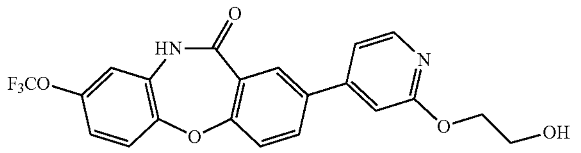
NCGC00496930
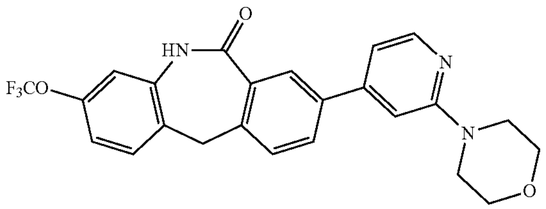
NCGC00532318
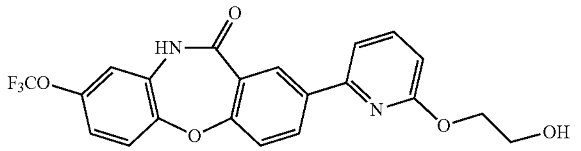
NCGC00508838
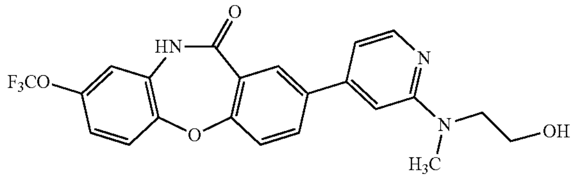
NCGC00532289′
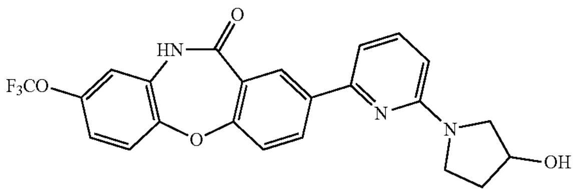
NCGC00508975′
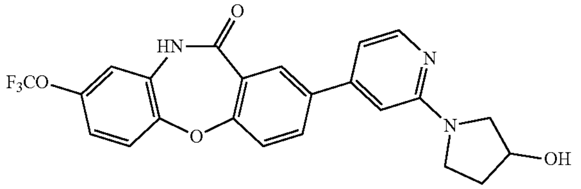
NCGC00532289
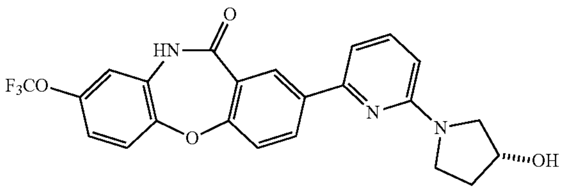
-continued
NCGC00508975
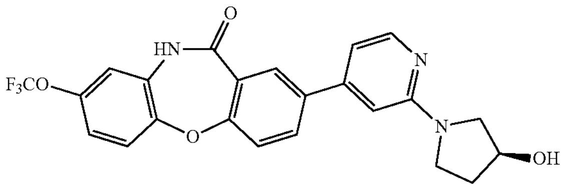
NCGC00508973
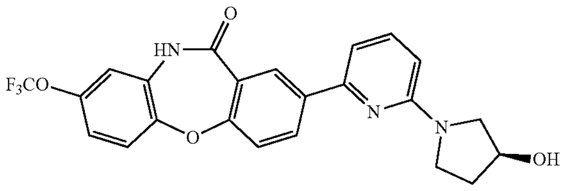
NCGC00507975
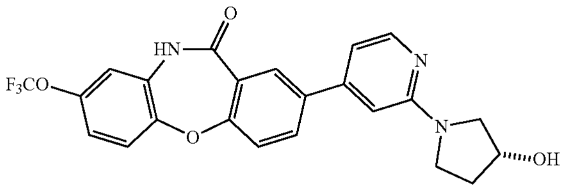
NCGC00508972
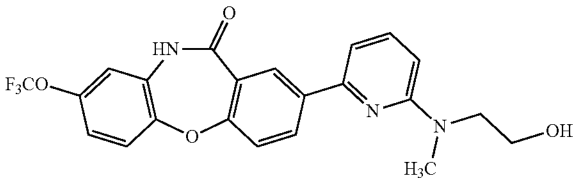
NCGC-xxx01
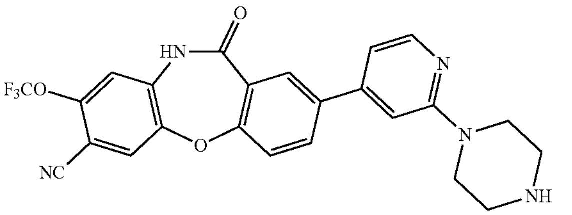
NCGC-xxx02
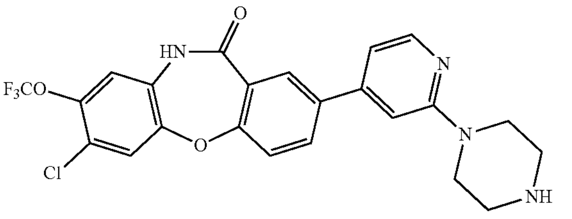
NCGC-xxx03
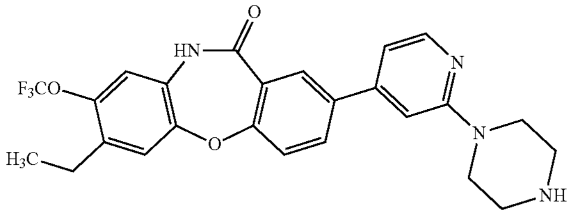

-continued

NCGC-xxx04

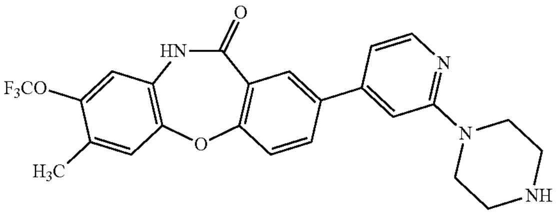

NCGC-xxx05

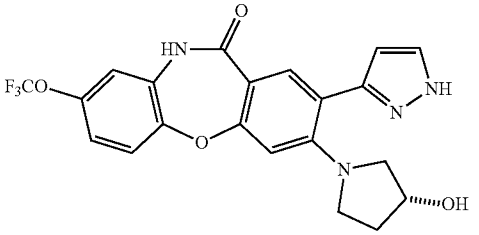

NCGC-xxx06

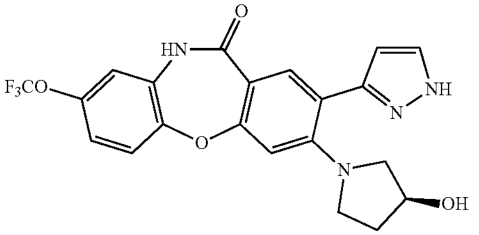

NCGC-xxx07

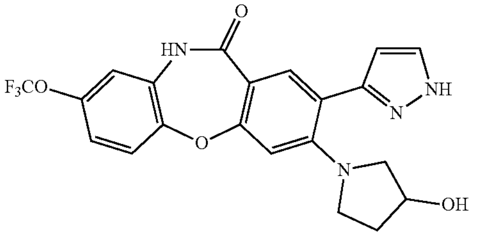

NCGC00488911

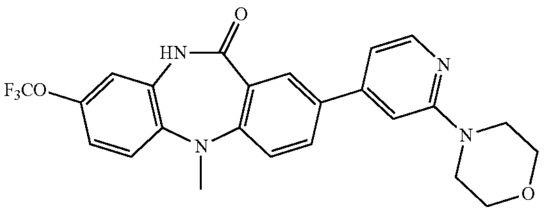

In some embodiments, the compound can be selected from the compounds listed below, including any suitable stereoisomers, tautomers, pharmaceutically acceptable salts, prodrugs, or solvates thereof:

3-(11-oxo-8-(trifluoromethoxy)-10,11-dihydro-5H-dibenzo[b,e][1,4]diazepin-2-yl)benzoic acid;

3-(11-oxo-8-(trifluoromethoxy)-10,11-dihydrodibenzo[b,f][1,4]oxazepin-2-yl)benzoic acid;

3-(11-Oxo-8-(trifluoromethoxy)-10,11-dihydro-5H-dibenzo[b,e][1,4]diazepin-2-yl)benzamide;

N-(2-Hydroxyethyl)-3-(11-oxo-8-(trifluoromethoxy)-10,11-dihydro-5H-dibenzo[b,e][1,4]diazepin-2-yl)benzamide;

N-(2-Aminoethyl)-3-(11-oxo-8-(trifluoromethoxy)-10,11-dihydro-5H-dibenzo[b,e][1,4]diazepin-2-yl)benzamide;

N-(2-Morpholinoethyl)-3-(11-oxo-8-(trifluoromethoxy)-10,11-dihydro-5H-dibenzo[b,e][1,4]diazepin-2-yl)benzamide;

2-(3-(Morpholine-4-carbonyl)phenyl)-8-(trifluoromethoxy)-5,10-dihydro-11H-dibenzo[b,e][1,4]diazepin-11-one;

2-(3-(Piperazine-1-carbonyl)phenyl)-8-(trifluoromethoxy)-5,10-dihydro-11H-dibenzo[b,e][1,4]diazepin-11-one;

N-(3-(11-Oxo-8-(trifluoromethoxy)-10,11-dihydro-5H-dibenzo[b,e][1,4]diazepin-2-yl)phenyl)methanesulfonamide;

N-(4-(11-oxo-8-(trifluoromethoxy)-10,11-dihydro-5H-dibenzo[b,e][1,4]diazepin-2-yl)phenyl)methanesulfonamide;

2-(2-Morpholinopyridin-4-yl)-8-(trifluoromethoxy)-5,10-dihydro-11H-dibenzo[b,e][1,4]diazepin-11-one;

2-(1H-Pyrazol-4-yl)-8-(trifluoromethoxy)-5,10-dihydro-11H-dibenzo[b,e][1,4]diazepin-11-one;

3-(11-Oxo-8-(trifluoromethoxy)-10,11-dihydrodibenzo[b,f][1,4]oxazepin-2-yl)benzamide;

N-(2-Hydroxyethyl)-3-(11-oxo-8-(trifluoromethoxy)-10,11-dihydrodibenzo[b,f][1,4]oxazepin-2-yl)benzamide;

N-(2-(Dimethylamino)ethyl)-3-(11-oxo-8-(trifluoromethoxy)-10,11-dihydrodibenzo[b,f][1,4]oxazepin-2-yl)benzamide;

2-(3-(4-Methylpiperazine-1-carbonyl)phenyl)-8-(trifluoromethoxy)dibenzo[b,f][1,4]oxazepin-11(10H)-one;

2-(3-(Morpholine-4-carbonyl)phenyl)-8-(trifluoromethoxy)dibenzo[b,f][1,4]oxazepin-11(10H)-one;

N-(3-(11-Oxo-8-(trifluoromethoxy)-10,11-dihydrodibenzo[b,f][1,4]oxazepin-2-yl)phenyl)methanesulfonamide;

N-(4-(11-Oxo-8-(trifluoromethoxy)-10,11-dihydrodibenzo[b,f][1,4]oxazepin-2-yl)phenyl)methanesulfonamide;

3-(11-Oxo-8-(trifluoromethoxy)-10,11-dihydrodibenzo[b,f][1,4]oxazepin-2-yl)benzenesulfonamide;

N-Methyl-3-(11-oxo-8-(trifluoromethoxy)-10,11-dihydrodibenzo[b,f][1,4]oxazepin-2-yl)benzenesulfonamide;

N,N-Dimethyl-3-(11-oxo-8-(trifluoromethoxy)-10,11-dihydrodibenzo[b,f][1,4]oxazepin-2-yl)benzenesulfonamide;

N-(2-Hydroxyethyl)-3-(11-oxo-8-(trifluoromethoxy)-10,11-dihydrodibenzo[b,f][1,4]oxazepin-2-yl)benzenesulfonamide;

2-(3-(Hydroxymethyl)phenyl)-8-(trifluoromethoxy)dibenzo[b,f][1,4]oxazepin-11(10H)-one;

2-(3-(2-Hydroxypropan-2-yl)phenyl)-8-(trifluoromethoxy)dibenzo[b,f][1,4]oxazepin-11(10H)-one;

2-(3-Hydroxy-4-methoxyphenyl)-8-(trifluoromethoxy)dibenzo[b,f][1,4]oxazepin-11(10H)-one;

2-(3-(1H-Pyrazol-5-yl)phenyl)-8-(trifluoromethoxy)dibenzo[b,f][1,4]oxazepin-11(10H)-one;

2-(3-(2H-Tetrazol-5-yl)phenyl)-8-(trifluoromethoxy)dibenzo[b,f][1,4]oxazepin-11(10H)-one;

(3-(11-Oxo-8-(trifluoromethoxy)-10,11-dihydrodibenzo[b,f][1,4]oxazepin-2-yl)phenyl)boronic acid;

2-(Pyridin-4-yl)-8-(trifluoromethoxy)dibenzo[b,f][1,4]oxazepin-11(10H)-one;

2-(Pyridin-3-yl)-8-(trifluoromethoxy)dibenzo[b,f][1,4]oxazepin-11(10H)-one;

2-(Pyrimidin-5-yl)-8-(trifluoromethoxy)dibenzo[b,f][1,4]oxazepin-11(10H)-one;
2-(2-Aminopyridin-4-yl)-8-(trifluoromethoxy)dibenzo[b,f][1,4]oxazepin-11(10H)-one;
2-(2-(Piperazin-1-yl)pyridin-4-yl)-8-(trifluoromethoxy)dibenzo[b,f][1,4]oxazepin-11(10H)-one;
2-(2-(4-Methylpiperazin-1-yl)pyridin-4-yl)-8-(trifluoromethoxy)dibenzo[b,f][1,4]oxazepin-11(10H)-one;
2-(2-Morpholinopyridin-4-yl)-8-(trifluoromethoxy)dibenzo[b,f][1,4]oxazepin-11(10H)-one;
2-(1H-Pyrrolo[2,3-b]pyridin-4-yl)-8-(trifluoromethoxy)dibenzo[b,f][1,4]oxazepin-11(10H)-one;
2-(1H-Indazol-5-yl)-8-(trifluoromethoxy)dibenzo[b,f][1,4]oxazepin-11(10H)-one;
2-(pyrazolo[1,5-a]pyrimidin-6-yl)-8-(trifluoromethoxy)dibenzo[b,f][1,4]oxazepin-11(10H)-one;
2-(4-Acetylthiophen-2-yl)-8-(trifluoromethoxy)dibenzo[b,f][1,4]oxazepin-11(10H)-one;
2-(5-(Aminomethyl)thiophen-2-yl)-8-(trifluoromethoxy)dibenzo[b,f][1,4]oxazepin-11(10H)-one;
N-((5-(11-Oxo-8-(trifluoromethoxy)-10,11-dihydrodibenzo[b,f][1,4]oxazepin-2-yl)thiophen-2-yl)methyl)acetamide;
2-(5-(Piperazin-1-ylmethyl)thiophen-2-yl)-8-(trifluoromethoxy)dibenzo[b,f][1,4]oxazepin-11(10H)-one;
2-(5-(Morpholinomethyl)thiophen-2-yl)-8-(trifluoromethoxy)dibenzo[b,f][1,4]oxazepin-11(10H)-one;
2-(4-(11-Oxo-8-(trifluoromethoxy)-10,11-dihydrodibenzo[b,f][1,4]oxazepin-2-yl)-1H-pyrazol-1-yl)acetamide;
2-(1-(2-Hydroxyethyl)-1H-pyrazol-4-yl)-8-(trifluoromethoxy)dibenzo[b,f][1,4]oxazepin-11(10H)-one;
2-(1-(2-Hydroxy-2-methylpropyl)-1H-pyrazol-4-yl)-8-(trifluoromethoxy)dibenzo[b,f][1,4]oxazepin-11(10H)-one;
2-(1-(1-Hydroxy-2-methylpropan-2-yl)-1H-pyrazol-4-yl)-8-(trifluoromethoxy)dibenzo[b,f][1,4]oxazepin-11(10H)-one;
2-(1-(Oxetan-3-yl)-1H-pyrazol-4-yl)-8-(trifluoromethoxy)dibenzo[b,f][1,4]oxazepin-11(10H)-one;
2-(4-(11-Oxo-8-(trifluoromethoxy)-10,11-dihydrodibenzo[b,f][1,4]oxazepin-2-yl)-1H-pyrazol-1-yl)acetonitrile;
3-(4-(11-Oxo-8-(trifluoromethoxy)-10,11-dihydrodibenzo[b,f][1,4]oxazepin-2-yl)-1H-pyrazol-1-yl)propanenitrile;
2-(1-(2-(Dimethylamino)ethyl)-1H-pyrazol-4-yl)-8-(trifluoromethoxy)dibenzo[b,f][1,4]oxazepin-11(10H)-one;
2-(1-(2-Morpholinoethyl)-1H-pyrazol-4-yl)-8-(trifluoromethoxy)dibenzo[b,f][1,4]oxazepin-11(10H)-one;
(3-(11-Oxo-8-(trifluoromethoxy)-10,11-dihydrodibenzo[b,f][1,4]oxazepin-2-yl)propyl)boronic acid;
(2-(11-Oxo-8-(trifluoromethoxy)-10,11-dihydrodibenzo[b,f][1,4]oxazepin-2-yl)ethyl)boronic acid;
(11-Oxo-8-(trifluoromethoxy)-10,11-dihydrodibenzo[b,f][1,4]oxazepin-2-yl)boronic acid;
5-Methyl-2-(2-morpholinopyridin-4-yl)-8-(trifluoromethoxy)-5,10-dihydro-11H dibenzo[b,e][1,4]diazepin-11-one;
5-Ethyl-2-(2-morpholinopyridin-4-yl)-8-(trifluoromethoxy)-5,10-dihydro-11H-dibenzo[b,e][1,4]diazepin-11-one;
2-(2-Morpholinopyridin-4-yl)-5-propyl-8-(trifluoromethoxy)-5,10-dihydro-11H-dibenzo[b,e][1,4]diazepin-11-one;
5-(2-Methoxyethyl)-2-(2-morpholinopyridin-4-yl)-8-(trifluoromethoxy)-5,10-dihydro-11H-dibenzo[b,e][1,4]diazepin-11-one;
N-(3-(11-oxo-7-(trifluoromethoxy)-10,11-dihydrodibenzo[b,f][1,4]oxazepin-2-yl)phenyl)methanesulfonamide;
2-(2-morpholinopyridin-4-yl)-7-(trifluoromethoxy)dibenzo[b,f][1,4]oxazepin-11(10H)-one;
N-(3-(11-Oxo-8-(trifluoromethoxy)-10,11-dihydrodibenzo[b,f][1,4]oxazepin-3-yl)phenyl)methanesulfonamide;
N-(3-(11-oxo-7-(trifluoromethoxy)-10,11-dihydrodibenzo[b,f][1,4]oxazepin-3-yl)phenyl)methanesulfonamide;
N-(3-(11-Oxo-2-(trifluoromethoxy)-10,11-dihydrodibenzo[b,f][1,4]oxazepin-8-yl)phenyl)methanesulfonamide;
N-(3-(11-Oxo-2-(trifluoromethoxy)-10,11-dihydrodibenzo[b,f][1,4]oxazepin-7-yl)phenyl)methanesulfonamide;
N-(3-(10-Methyl-11-oxo-8-(trifluoromethoxy)-10,11-dihydrodibenzo[b,f][1,4]oxazepin-2-yl)phenyl)methanesulfonamide;
N-Methyl-N-(3-(10-methyl-11-oxo-8-(trifluoromethoxy)-10,11-dihydrodibenzo[b,f][1,4]oxazepin-2-yl)phenyl)methanesulfonamide;
N-(3-(8-(Trifluoromethoxy)-10,11-dihydrodibenzo[b,f][1,4]oxazepin-2-yl)phenyl)methanesulfonamide;
N-(3-(11-Amino-8-(trifluoromethoxy)dibenzo[b,f][1,4]oxazepin-2-yl)phenyl)methanesulfonamide;
2-(2-Morpholinopyridin-4-yl)-8-(trifluoromethyl)dibenzo[b,f][1,4]oxazepin-11(10H)-one;
2-(2-Morpholinopyridin-4-yl)-11-oxo-10,11-dihydrodibenzo[b,f][1,4]oxazepine-8-carbonitrile;
2-(2-Morpholinopyridin-4-yl)-8-(2,2,2-trifluoroethoxy)dibenzo[b,f][1,4]oxazepin-11(10H)-one;
2-(2-Morpholinopyridin-4-yl)-8-(3,3,3-trifluoropropoxy)dibenzo[b,f][1,4]oxazepin-11(10H)-one;
2-(2-Morpholinopyridin-4-yl)-8-(trifluoromethoxy)dibenzo[b,f][1,4]thiazepin-11(10H)-one;
2-(2-Morpholinopyridin-4-yl)-8-(trifluoromethoxy)dibenzo[b,f][1,4]thiazepin-11(10H)-one 5-oxide;
2-(2-Morpholinopyridin-4-yl)-8-(trifluoromethoxy)dibenzo[b,f][1,4]thiazepin-11(10H)-one 5,5-dioxide;
8-(2-Morpholinopyridin-4-yl)-3-(trifluoromethoxy)-5,11-dihydro-6H-dibenzo[b,e]azepin-6-one;
2-(2-(2-Hydroxyethoxy)pyridin-4-yl)-8-(trifluoromethoxy)dibenzo[b,f][1,4]oxazepin-11(10H)-one;
2-(6-(2-Hydroxyethoxy)pyridin-2-yl)-8-(trifluoromethoxy)dibenzo[b,f][1,4]oxazepin-11(10H)-one;
2-(2-((2-Hydroxyethyl)(methyl)amino)pyridin-4-yl)-8-(trifluoromethoxy)dibenzo[b,f][1,4]oxazepin-11(10H)-one;
2-(6-((2-Hydroxyethyl)(methyl)amino)pyridin-2-yl)-8-(trifluoromethoxy)dibenzo[b,f][1,4]oxazepin-11(10H)-one;
(R)-2-(2-(3-Hydroxypyrrolidin-1-yl)pyridin-4-yl)-8-(trifluoromethoxy)dibenzo[b,f][1,4]oxazepin-11(10H)-one;
(R)-2-(6-(3-Hydroxypyrrolidin-1-yl)pyridin-2-yl)-8-(trifluoromethoxy)dibenzo[b,f][1,4]oxazepin-11(10H)-one;
(S)-2-(2-(3-Hydroxypyrrolidin-1-yl)pyridin-4-yl)-8-(trifluoromethoxy)dibenzo[b,f][1,4]oxazepin-11(10H)-one;
2-(2-(3-hydroxypyrrolidin-1-yl)pyridin-4-yl)-8-(trifluoromethoxy)dibenzo[b,f][1,4]oxazepin-11(10H)-one;

(S)-2-(6-(3-Hydroxypyrrolidin-1-yl)pyridin-2-yl)-8-(trifluoromethoxy)dibenzo[b,f][1,4]oxazepin-11(10H)-one;

2-(6-(3-hydroxypyrrolidin-1-yl)pyridin-2-yl)-8-(trifluoromethoxy)dibenzo[b,f][1,4]oxazepin-11(10H)-one;

11-oxo-2-(2-(piperazin-1-yl)pyridin-4-yl)-8-(trifluoromethoxy)-10,11-dihydrodibenzo[b,f][1,4]oxazepine-7-carbonitrile;

7-chloro-2-(2-(piperazin-1-yl)pyridin-4-yl)-8-(trifluoromethoxy)dibenzo[b,f][1,4]oxazepin-11(10H)-one;

(S)-3-(3-hydroxypyrrolidin-1-yl)-2-(1H-pyrazol-3-yl)-8-(trifluoromethoxy)dibenzo[b,f][1,4]oxazepin-11(10H)-one;

3-(3-hydroxypyrrolidin-1-yl)-2-(1H-pyrazol-3-yl)-8-(trifluoromethoxy)dibenzo[b,f][1,4]oxazepin-11(10H)-one;

(R)-3-(3-hydroxypyrrolidin-1-yl)-2-(1H-pyrazol-3-yl)-8-(trifluoromethoxy)dibenzo[b,f][1,4]oxazepin-11(10H)-one;

7-methyl-2-(2-(piperazin-1-yl)pyridin-4-yl)-8-(trifluoromethoxy)dibenzo[b,f][1,4]oxazepin-11(10H)-one; or 7-ethyl-2-(2-(piperazin-1-yl)pyridin-4-yl)-8-(trifluoromethoxy)dibenzo[b,f][1,4]oxazepin-11(10H)-one.

Also disclosed herein are embodiments of a composition comprising any one or more of the compound embodiments described above. In some embodiments, the composition can comprise a single compound as described above, or a plurality of compounds wherein each compound in the plurality of compounds is different. In some embodiments, the composition can comprise a pharmaceutically acceptable salt, stereoisomer, tautomer, solvate, or prodrug of the one or more compounds.

Composition embodiments comprising one or more of the compound embodiments disclosed herein typically comprise the compound or plurality of compounds in an amount of from greater than 0% up to 99% total weight percent. In some embodiments, compositions comprising one or more of the compound embodiments disclosed herein comprise from greater than 0 wt % to 95 wt %, such as 0.001 wt % to 95% wt %, or 0.01 wt % to 95 wt %, or 0.1 wt % to 95 wt %, or 1 wt % to 95 wt % of the compound based on the total weight percent of the composition. In some embodiments, compositions comprising one or more of the compound embodiments disclosed herein comprise from greater than 0 wt % to 95 wt %, such as greater than 0 wt % to 90% wt %, or greater than 0 wt % to 85 wt %, or greater than 0 wt % to 80 wt %, or greater than 0 wt % to 75 wt %, or greater than 0 wt % to 70 wt %, or greater than 0 wt % to 65 wt %, or greater than 0 wt % to 60 wt %, or greater than 0 wt % to 55 wt %, or greater than 0 wt % to 50 wt % or lower of the compound based on the total weight percent of the composition. The remaining weight percent of the composition can be made up of any one or more of the other compositional components described below.

Composition embodiments can further comprise a pharmaceutically-acceptable excipient, such as, but not limited to, an adjuvant, a carrier, a stabilizer, or combinations thereof. The composition also can include additional components, such as diluents, fillers, binding agents, moisturizing agents, preservatives, acids, and the like, and any and all combinations thereof. In some embodiments, the composition can further comprise one or more additional compounds, such as therapeutic agents useful for the disorder or condition being treated. Exemplary therapeutic agents (that is, therapeutic agents other than the compound embodiments described herein) that can be used for treating the diseases/conditions described herein include those that would be recognized by a person of ordinary skill in the art, with the benefit of this disclosure, as being suitable for treating such diseases/conditions.

The compound embodiments and/or composition embodiments disclosed herein can be administered in the form of solids, liquids, and/or lotions. Suitable solid forms of administration include, but are not limited to, tablets, capsules, powders, solid dispersions, and the like. Suitable liquid or lotion forms include, but are not limited to, oil-in-water or water-in-oil emulsions, aqueous gel compositions, or liquids or lotions formulated for use as foams, films, sprays, ointments, pessary forms, suppository forms, creams, liposomes or in other forms embedded in a matrix for the slow or controlled release of the compound or the composition to the skin or surface onto which it has been applied or is in contact. In particular disclosed embodiments, a dermal patch can be used to facilitate dosing of the compound or composition.

The compound embodiments and/or compositions disclosed herein may be formulated so as to be suitable for a variety of modes of administration, including, but not limited to, topical, ocular, oral, buccal, systemic, nasal, injection (such as intravenous, intraperitoneal, subcutaneous, intramuscular, or intrathecal), transdermal (e.g., by mixing with a penetrating agent, such as DMSO), rectal, vaginal, etc., or a form suitable for administration by inhalation or insufflation.

For oral or buccal administration, the compound and/or composition may take the form of lozenges, tablets or capsules prepared by conventional means with pharmaceutically acceptable excipients. The tablets or capsules may be coated by methods well known in the art with, for example, sugars, films, or enteric coatings.

Liquid preparations of the compound and/or composition for oral administration may take the form of, for example, elixirs, solutions, syrups or suspensions, or they may be presented as a dry product for constitution with water or other suitable vehicle before use. Preparations for oral administration also may be suitably formulated to give controlled release of the compound or the composition.

For topical administration, the compound and/or the composition can be formulated as solutions, lotions, gels, ointments, creams, suspensions, etc. For transmucosal administration, penetrants appropriate to the barrier to be permeated can be used.

Systemic formulations include those designed for administration by injection, e.g., subcutaneous, intravenous, intramuscular, intrathecal or intraperitoneal injection, as well as those designed for transdermal, transmucosal oral or pulmonary administration. Useful injectable preparations include sterile suspensions, solutions or emulsions of the compound or composition in aqueous or oily vehicles. The composition may also contain formulating agents, such as suspending, stabilizing and/or dispersing agents.

For rectal and vaginal routes of administration, the compound and/or composition may be formulated as solutions (for retention enemas) suppositories or ointments containing conventional suppository bases, such as cocoa butter or other glycerides.

For nasal administration or administration by inhalation or insufflation, the compound and/or composition can be conveniently delivered in the form of an aerosol spray from pressurized packs or a nebulizer with the use of a suitable propellant. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

Also disclosed herein are embodiments of a precursor compound that can be used to make the compound embodiments of the present disclosure. In particular disclosed embodiments, the precursor compound embodiments comprise a functional group that can be converted to a different functional group to provide the compound using a transition metal-mediated coupling reaction, such as the reactions described herein. In some embodiments, the functional group that can be converted to a different functional group is a halogen atom (e.g., bromo, chloro, fluoro, or iodo), a boronic ester (e.g., a pinacol borane, or the like), or a combination thereof. In particular disclosed embodiments, the precursor compound can have a structure satisfying any one or more of Formulas I, IIA-IIF, IIIA-IIIH, and IVA-IVF, wherein at least one of R'or $R^3$ is a halogen atom or a boronic ester.

In particular disclosed embodiments, the precursor compound is selected from the following compounds, including any suitable stereoisomers, tautomers, pharmaceutically acceptable salts, prodrugs, or solvates thereof.

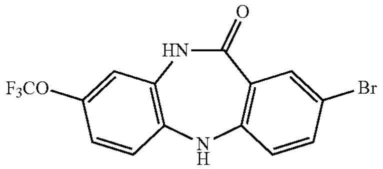

AED007-099

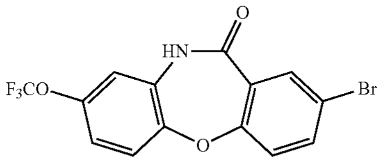

AED013-066

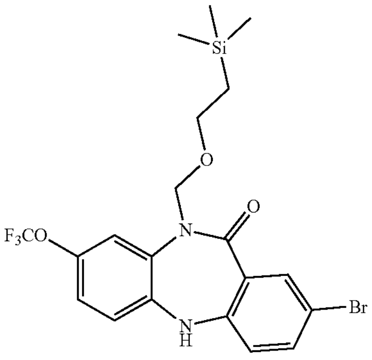

DCT001-056

-continued

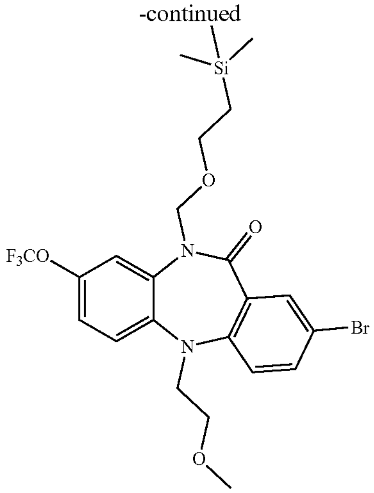

DCT001-061

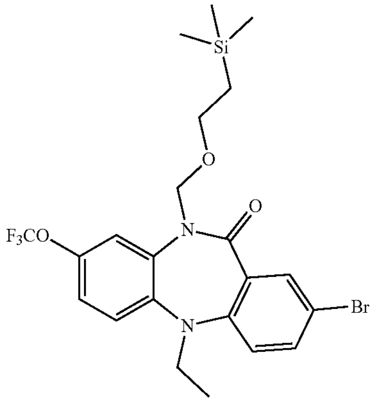

DCT001-064

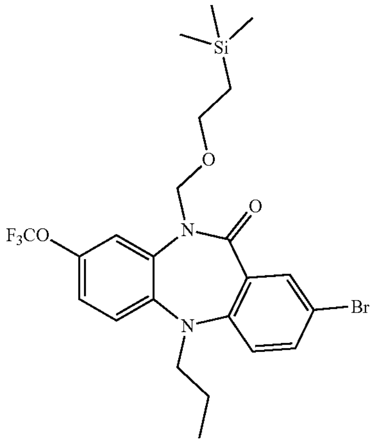

DCT001-048

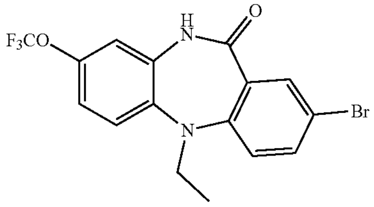

DCT001-068

-continued
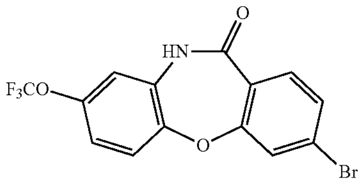
AED011-045
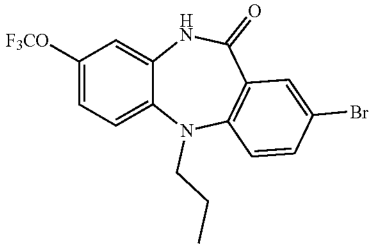
DCT001-055
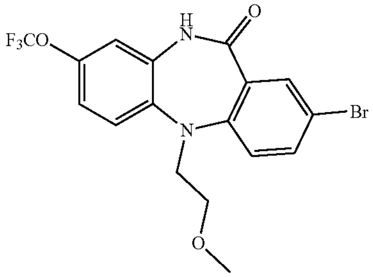
DCT001-062
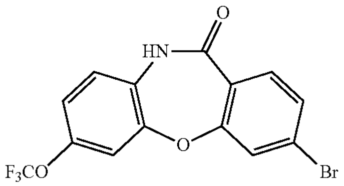
AED012-003
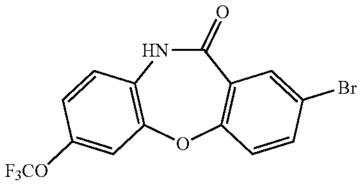
AED018-009
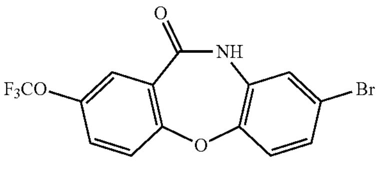
AED012-001
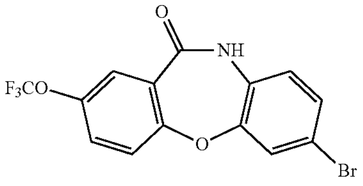
AED012-002
-continued
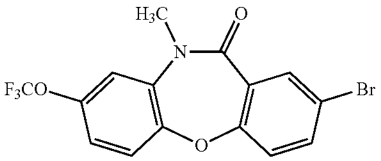
AED011-065
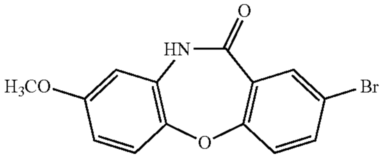
AED011-094
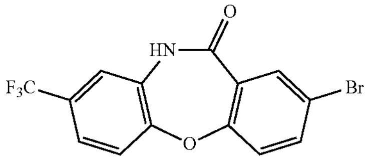
AED014-074
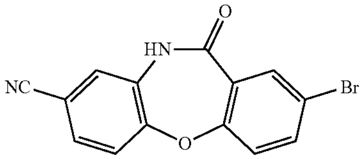
AED015-011
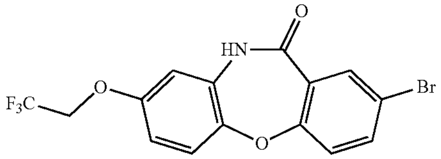
AED015-065
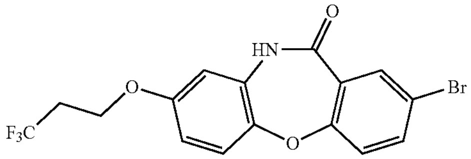
AED015-023
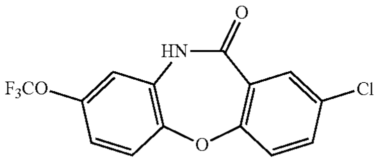
AED015-089
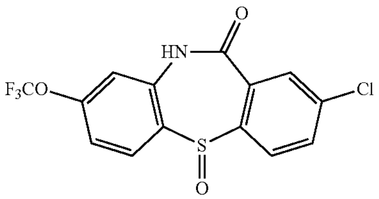
AED015-090

-continued

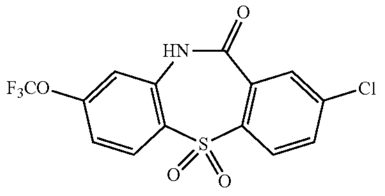

AED015-092

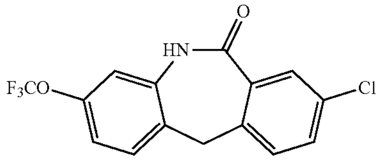

DCT002-021

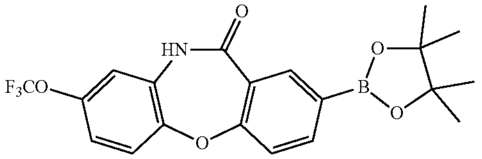

AED020-059

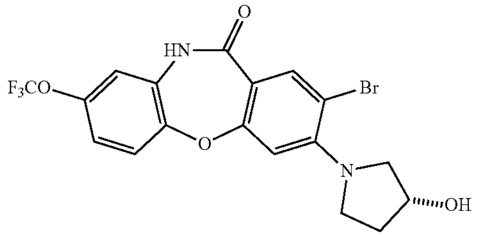

AED000-006

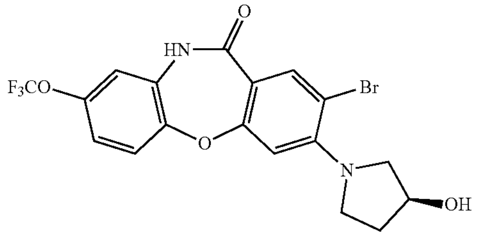

AED000-008

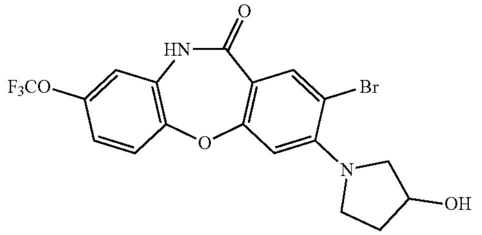

AED000-010

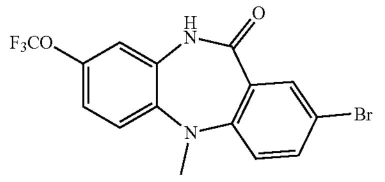

DCT001-018

In some embodiments, the precursor compound can be selected from the compounds listed below, including any suitable stereoisomers, tautomers, pharmaceutically acceptable salts, prodrugs, or solvates thereof:

2-Bromo-8-(trifluoromethoxy)-5,10-dihydro-11H-dibenzo[b,e][1,4]diazepin-11-one;

2-Bromo-8-(trifluoromethoxy)dibenzo[b,f][1,4]oxazepin-11(10H)-one;

2-Bromo-5-methyl-8-(trifluoromethoxy)-5,10-dihydro-11H-dibenzo[b,e][1,4]diazepin-11-one;

2-Bromo-8-(trifluoromethoxy)-10-((2-(trimethylsilyl)ethoxy)methyl)-5,10-dihydro-11H dibenzo[b,e][1,4]diazepin-11-one;

2-Bromo-5-ethyl-8-(trifluoromethoxy)-10-((2-(trimethylsilyl)ethoxy)methyl)-5,10-dihydro-11H-dibenzo[b,e][1,4]diazepin-11-one;

2-Bromo-5-propyl-8-(trifluoromethoxy)-10-((2-(trimethylsilyl)ethoxy)methyl)-5,10-dihydro-11H-dibenzo[b,e][1,4]diazepin-11-one;

2-Bromo-5-(2-methoxyethyl)-8-(trifluoromethoxy)-10-((2-(trimethylsilyl)ethoxy)methyl)-5,10-dihydro-11H-dibenzo[b,e][1,4]diazepin-11-one;

2-Bromo-5-ethyl-8-(trifluoromethoxy)-5,10-dihydro-11H-dibenzo[b,e][1,4]diazepin-11-one;

2-Bromo-5-propyl-8-(trifluoromethoxy)-5,10-dihydro-11H-dibenzo[b,e][1,4]diazepin-11-one;

2-Bromo-5-(2-methoxyethyl)-8-(trifluoromethoxy)-5,10-dihydro-11H-dibenzo[b,e][1,4]diazepin-11-one;

3-Bromo-8-(trifluoromethoxy)dibenzo[b,f][1,4]oxazepin-11(10H)-one;

3-Bromo-7-(trifluoromethoxy)dibenzo[b,f][1,4]oxazepin-11(10H)-one;

2-Bromo-7-(trifluoromethoxy)dibenzo[b,f][1,4]oxazepin-11(10H)-one;

8-Bromo-2-(trifluoromethoxy)dibenzo[b,f][1,4]oxazepin-11(10H)-one;

7-Bromo-2-(trifluoromethoxy)dibenzo[b,f][1,4]oxazepin-11(10H)-one;

2-Bromo-10-methyl-8-(trifluoromethoxy)dibenzo[b,f][1,4]oxazepin-11(10H)-one;

2-Bromo-8-methoxydibenzo[b,f][1,4]oxazepin-11(10H)-one;

2-Bromo-8-(trifluoromethyl)dibenzo[b,f][1,4]oxazepin-11(10H)-one;

2-Bromo-11-oxo-10,11-dihydrodibenzo[b,f][1,4]oxazepine-8-carbonitrile;

2-Bromo-8-(2,2,2-trifluoroethoxy)dibenzo[b,f][1,4]oxazepin-11(10H)-one;

2-Bromo-8-(3,3,3-trifluoropropoxy)dibenzo[b,f][1,4]oxazepin-11(10H)-one;

(S)-2-bromo-3-(3-hydroxypyrrolidin-1-yl)-8-(trifluoromethoxy)dibenzo[b,f][1,4]oxazepin-11(10H)-one;

2-bromo-3-(3-hydroxypyrrolidin-1-yl)-8-(trifluoromethoxy)dibenzo[b,f][1,4]oxazepin-11(10H)-one;

(R)-2-bromo-3-(3-hydroxypyrrolidin-1-yl)-8-(trifluoromethoxy)dibenzo[b,f][1,4]oxazepin-11(10H)-one;

8-Chloro-3-(trifluoromethoxy)-5,11-dihydro-6H-dibenzo[b,e]azepin-6-one;

2-Chloro-8-(trifluoromethoxy)dibenzo[b,f][1,4]thiazepin-11(10H)-one;

2-Chloro-8-(trifluoromethoxy)dibenzo[b,f][1,4]thiazepin-11(10H)-one 5-oxide;

2-Chloro-8-(trifluoromethoxy)dibenzo[b,f][1,4]thiazepin-11(10H)-one 5,5-dioxide;

2-(4,4,5,5-Tetramethyl-1,3,2-dioxaborolan-2-yl)-8-(trifluoromethoxy)dibenzo[b,f][1,4]oxazepin-11(10H)-one;

(S)-2-bromo-3-(3-hydroxypyrrolidin-1-yl)-8-(trifluoromethoxy)dibenzo[b,f][1,4]oxazepin-11(10H)-one;

2-bromo-3-(3-hydroxypyrrolidin-1-yl)-8-(trifluoromethoxy)dibenzo[b,f][1,4]oxazepin-11(10H)-one; and (R)-2-bromo-3-(3-hydroxypyrrolidin-1-yl)-8-(trifluoromethoxy)dibenzo[b,f][1,4]oxazepin-11(10H)-one.

IV. Method of Making Compound Embodiments

Disclosed herein are embodiments of a method for making compound embodiments described herein. In some embodiments, the method comprises coupling two aryl-containing compounds to form a bis-aryl product and then functionalizing and/or cyclizing the bis-aryl product to form a compound comprising a dibenzoazepinone core. In some embodiments, the method can further comprise performing additional modifications to the dibenzoazepinone core to provide a precursor compound, such as chemically modifying functional groups of the core. In yet additional embodiments, the method can further comprise converting the precursor compound to a compound embodiment described herein by coupling a different functional group to the precursor compound such that the functional group replaces whichever of $R^1$ or $R^3$ comprises a boronic ester or halogen. In some embodiments, the precursor compound can first be converted to a compound embodiment, followed by one or more chemical modifications; or the precursor compound can first be chemically modified and then coupled with additional functional groups to provide the compound.

In particular disclosed embodiments, the method can comprise combining two starting compounds that each comprise an aryl ring, such as starting compounds 100 and 102 illustrated in Scheme 1 below.

Scheme 1

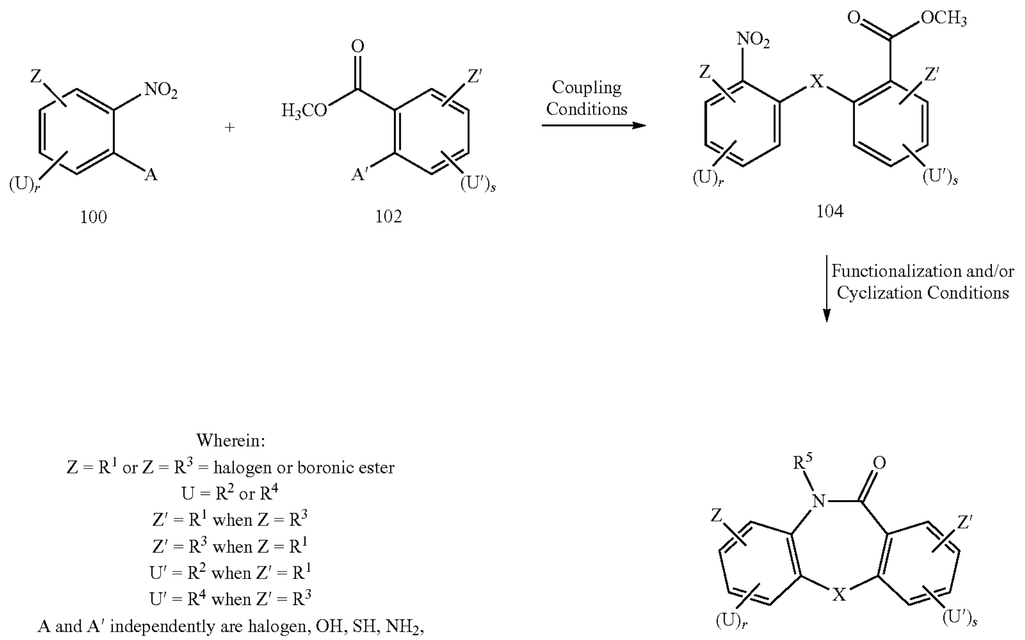

100 102 104 106

Wherein:
Z = $R^1$ or Z = $R^3$ = halogen or boronic ester
U = $R^2$ or $R^4$
Z′ = $R^1$ when Z = $R^3$
Z′ = $R^3$ when Z = $R^1$
U′ = $R^2$ when Z′ = $R^1$
U′ = $R^4$ when Z′ = $R^3$
A and A′ independendently are halogen, OH, SH, $NH_2$, or other heteroatom groups
r = 0 to 3
s = 0 to 3

With reference to Scheme 1, starting compounds 100 and 102 can be coupled together to form bis-aryl product 104 using suitable coupling conditions, such as transition metal-based cross coupling conditions or base-catalyzed coupling conditions. Embodiments of starting compounds 100 and 102 can be made using methods recognized by those of ordinary skill in the art with the benefit of the present disclosure, or they can be purchased from commercial sources. In particular disclosed embodiments, starting compounds 100 and 102 can be coupled using a palladium catalyst (e.g., $CuBr(PPh_3)_3$, $Pd(PPh_3)_4$, or the like) in the presence of a base (e.g., $Cs_2CO_3$, $Na_2CO_3$, or the like) and a solvent (e.g., toluene, dimethoxyethane, or the like); or by using a base (e.g., $K_2CO_3$, $Cs_2CO_3$, or the like) and a solvent (e.g., dimethylformamide). Other suitable transition metals, bases, and solvents can be used and are recognized by those of ordinary skill in the art with the benefit of the present disclosure.

In some embodiments, bis-aryl product 104 can be further functionalized and/or cyclized to form precursor compound 106. In some embodiments, bis-aryl product 104 can first be functionalized and then cyclized. For example, in some embodiments, functionalization steps can involve modifying variable X to be substituted prior to cyclization. In yet additional embodiments, such functionalization steps can be used after cyclization. For example, if X of bis-aryl product 104 is NH, then the NH group can be functionalized using suitable reagents to provide a NR' group, wherein R' is not hydrogen but can be other R' groups recited herein. In another example, bis-aryl product 104 is first cyclized to form an amide group, which can further be functionalized to provide an $R^5$ group that is not hydrogen.

Representative examples of the above-described method embodiments are illustrated in Schemes 2-12.
Scheme 2
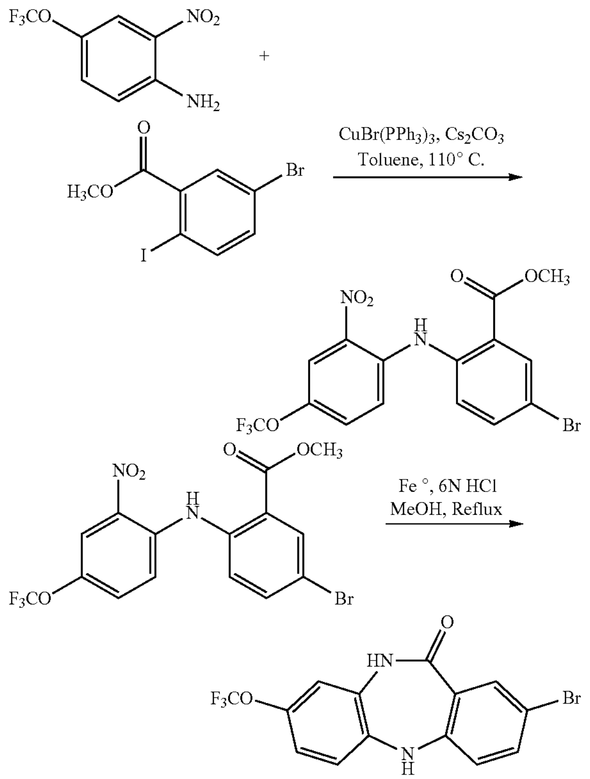
Scheme 3
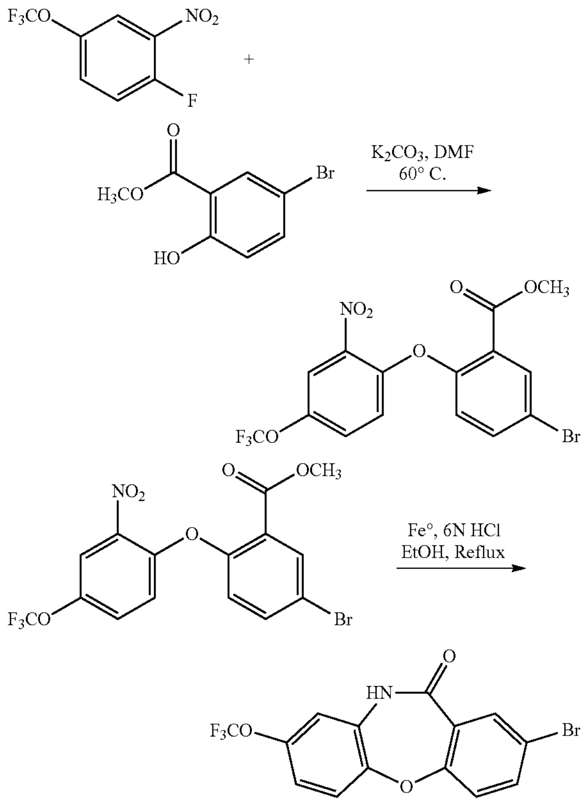
Scheme 4
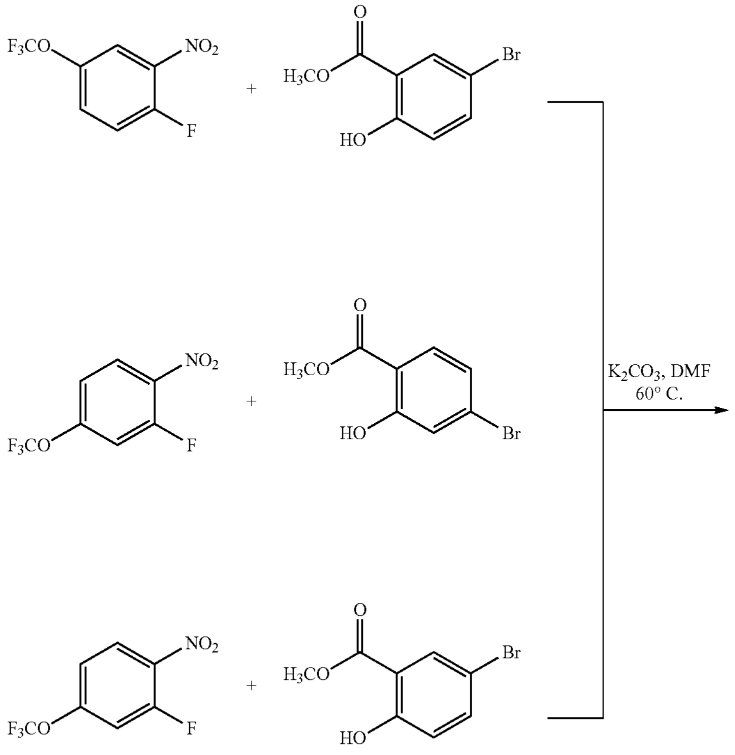

-continued
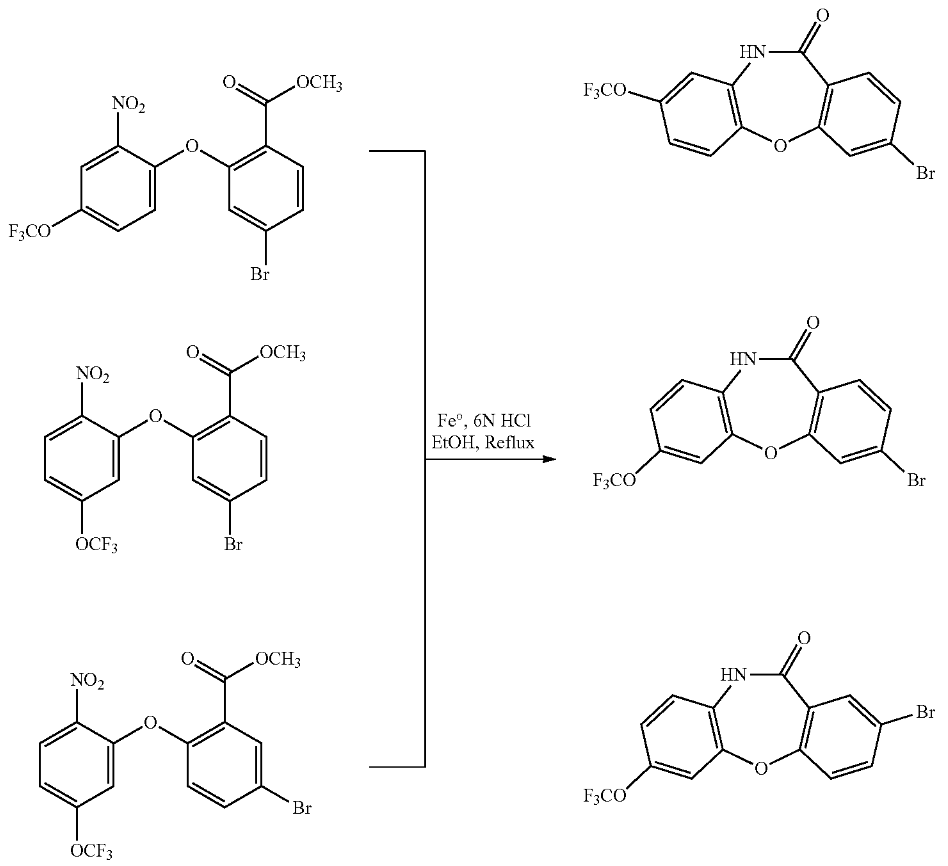
Scheme 5
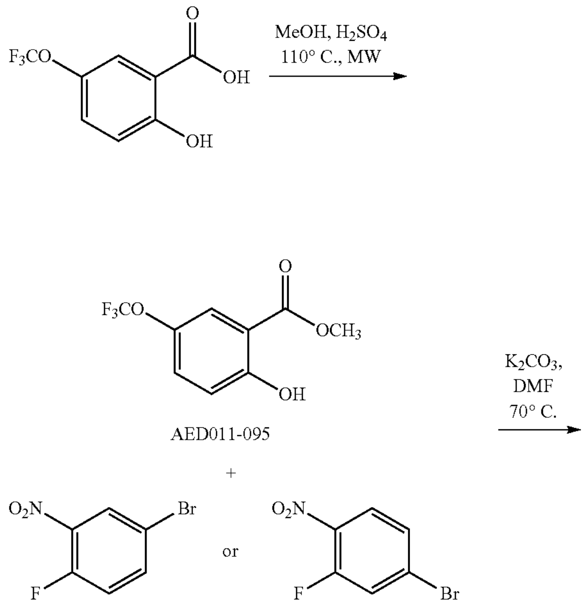
-continued
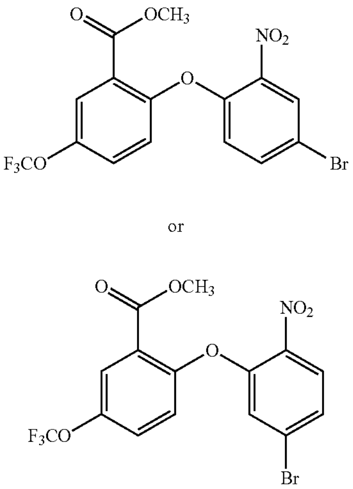

-continued
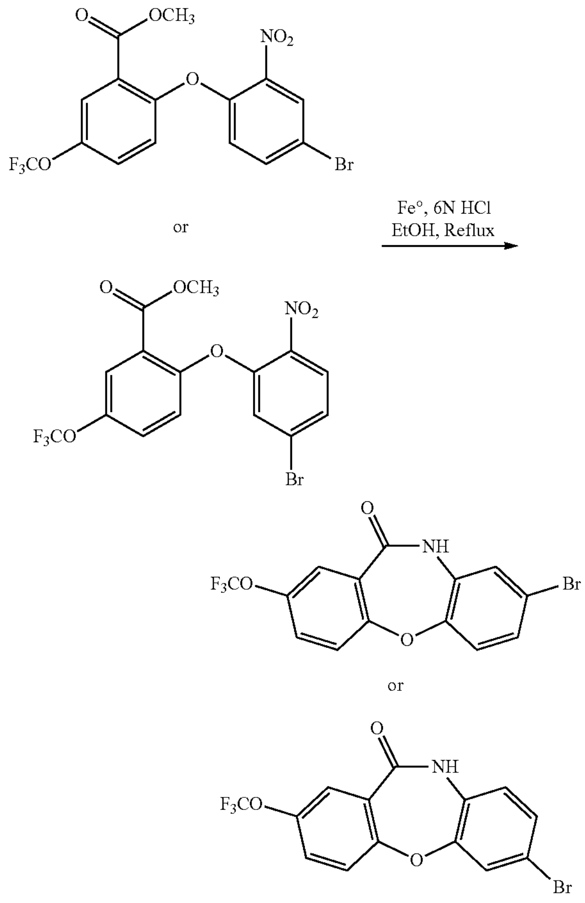
or
or
Scheme 6
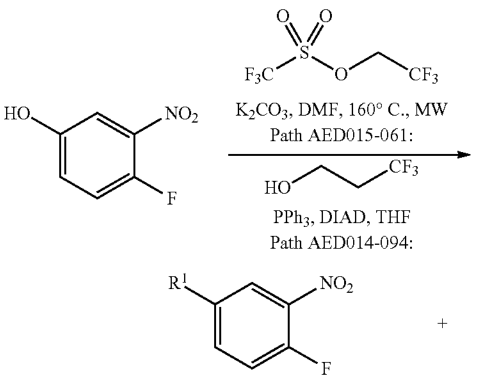
A: $R^1 = OCH_3$
B: $R^1 = CF_3$
C: $R^1 = CN$
AED015-061: $R^1 = OCH_2CF_3$
AED014-094: $R^1 = OCH_2CH_2CF_3$
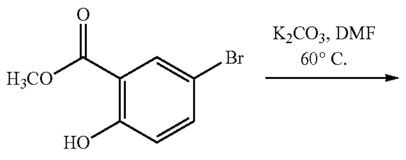
-continued
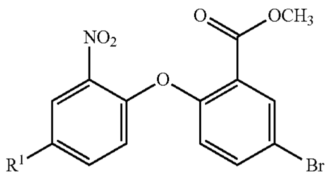
AED011-091: $R^1 = OCH_3$
AED014-072: $R^1 = CF_3$
AED014-095: $R^1 = CN$
AED015-063: $R^1 = OCH_2CF_3$
AED015-004: $R^1 = OCH_2CH_2CF_3$
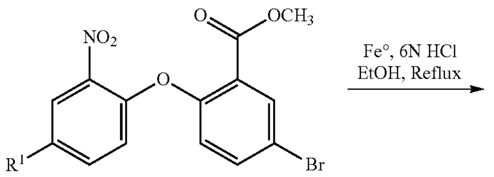
AED011-091: $R^1 = OCH_3$
AED014-072: $R^1 = CF_3$
AED014-095: $R^1 = CN$
AED015-063: $R^1 = OCH_2CF_3$
AED015-004: $R^1 = OCH_2CH_2CF_3$
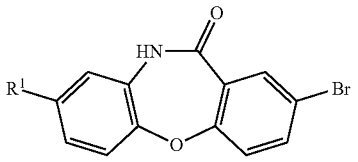
AED011-094: $R^1 = OCH_3$
AED014-074: $R^1 = CF_3$
AED015-011: $R^1 = CN$
AED015-065: $R^1 = OCH_2CF_3$
AED015-023: $R^1 = OCH_2CH_2CF_3$
Scheme 7
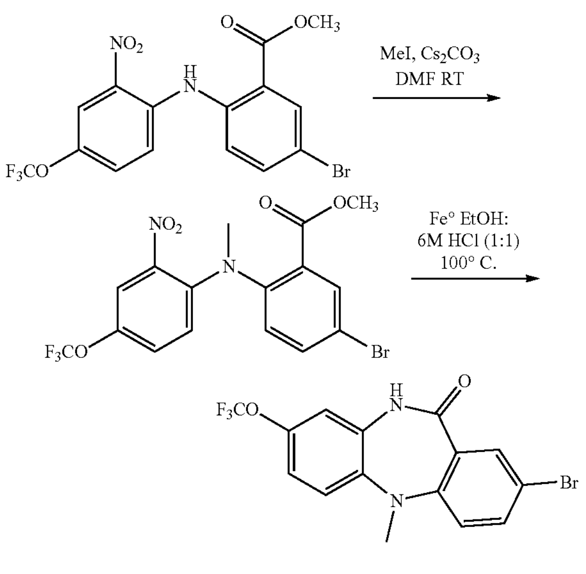

Scheme 8
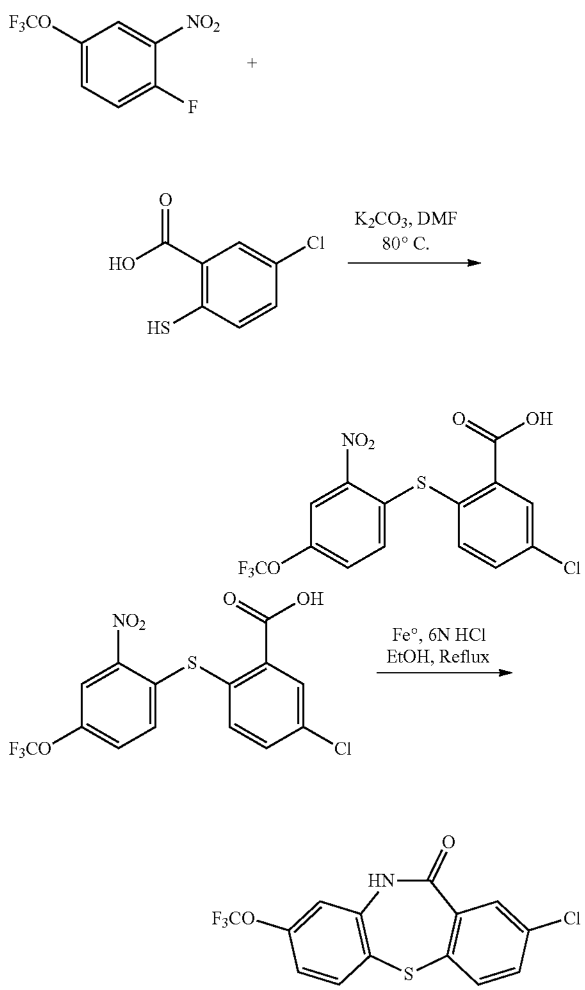
Scheme 9
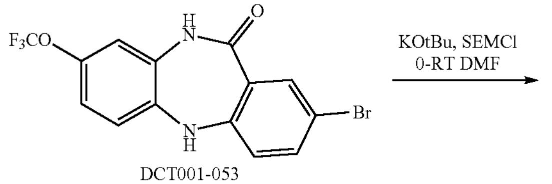
DCT001-053
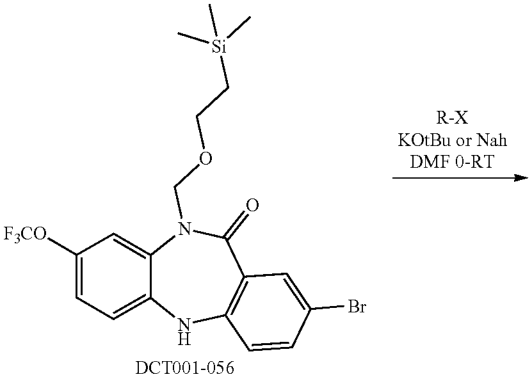
DCT001-056
-continued
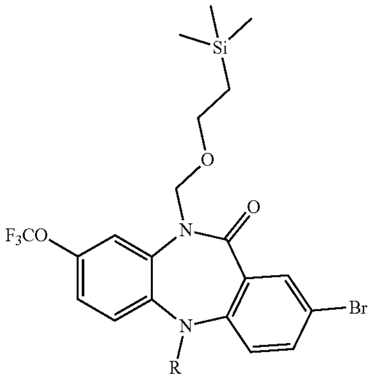
DCT001-064: R = Ethyl
DCT001-048: R = Propyl
DCT001-061: R = $CH_2CH_2OCH_3$
Scheme 10
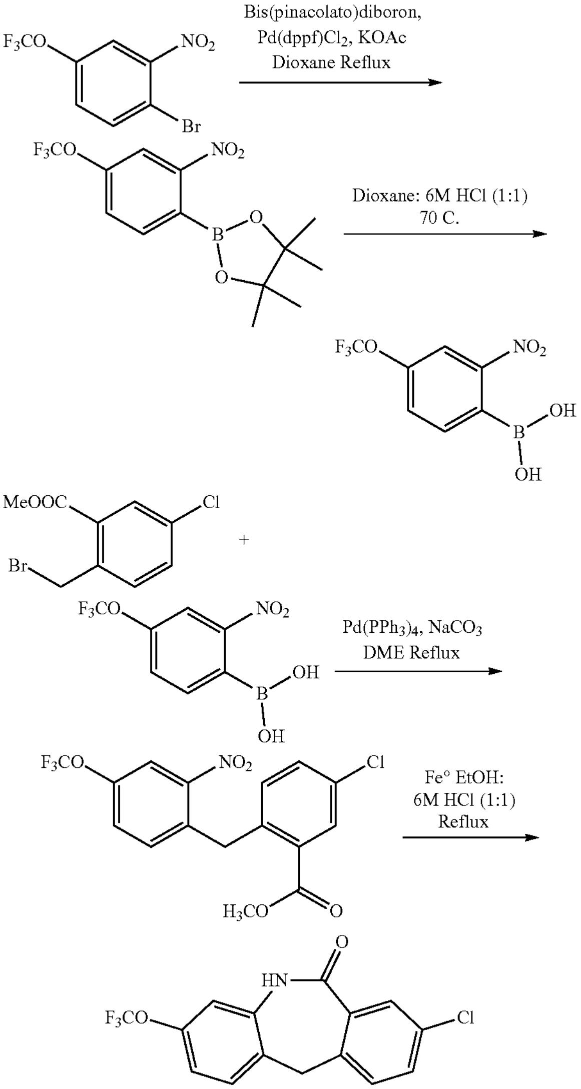

Scheme 11

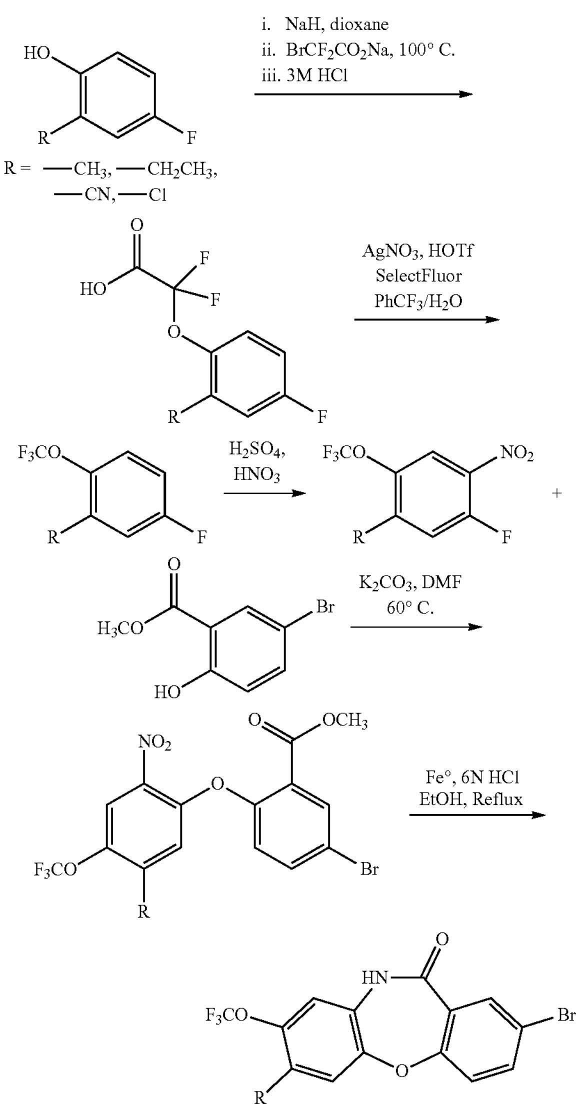

Scheme 12

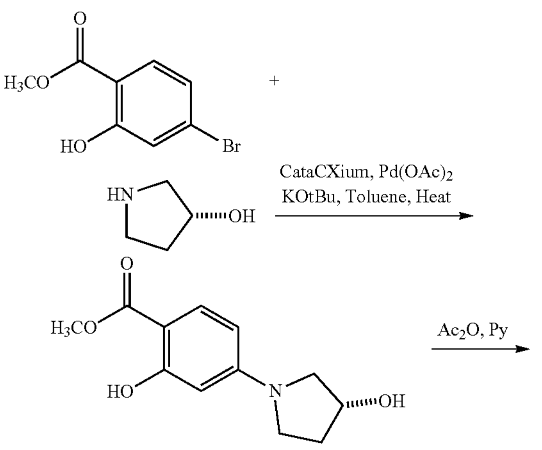

-continued

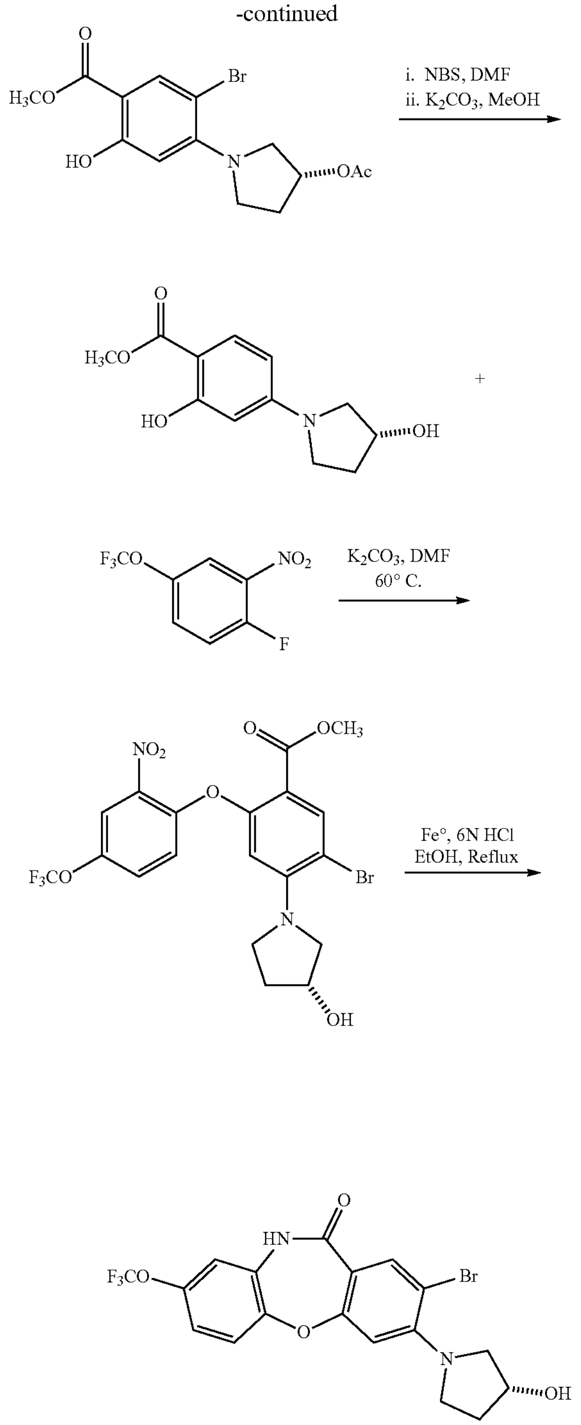

In some embodiments, one or more post-cyclization modifications can be performed on precursor compound 106 to provide structurally-modified versions of the precursor compound. In some embodiments, the post-cyclization modification can comprise modifying a functional group of precursor 106, such as variable X. For example, variable X can be oxidized (e.g., when X is a sulfur atom), functionalized (e.g., when X is an NH group), and the like. Representative embodiments of these types of post-cyclization modifications are illustrate in Schemes 13 and 14.

Scheme 13

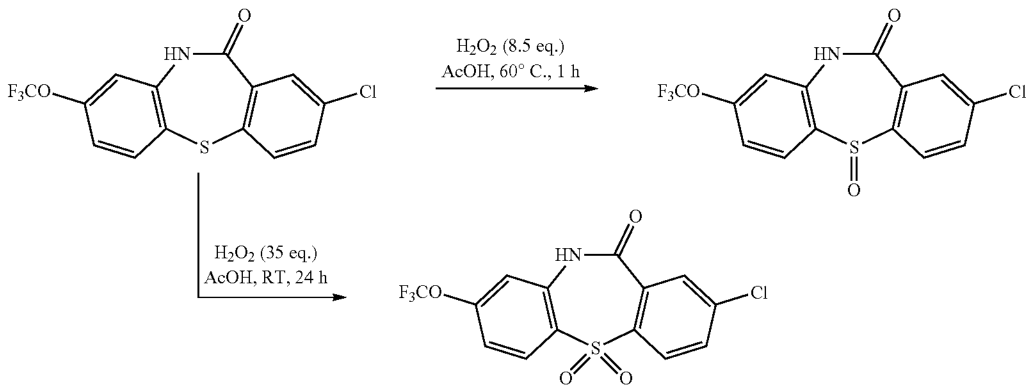

Scheme 14

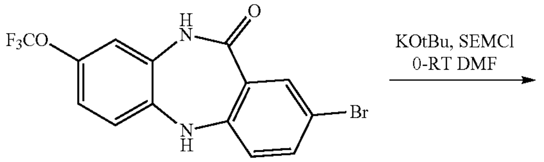

DCT001-053

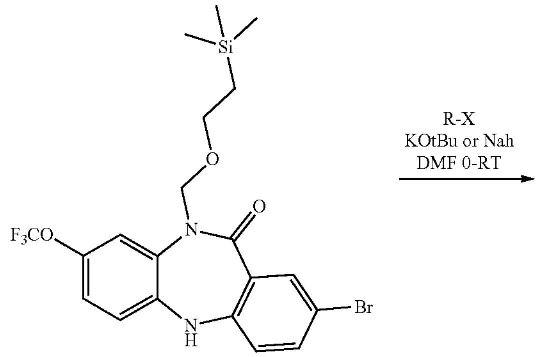

DCT001-056

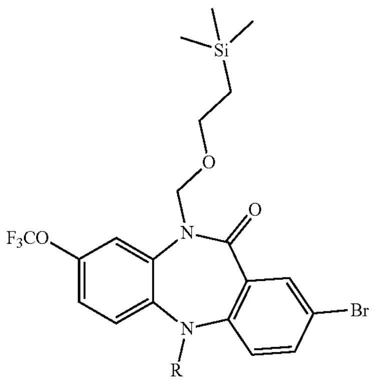

DCT001-064: R = Ethyl
DCT001-048: R = Propyl
DCT001-061: R = $CH_2CH_2OCH_3$

-continued

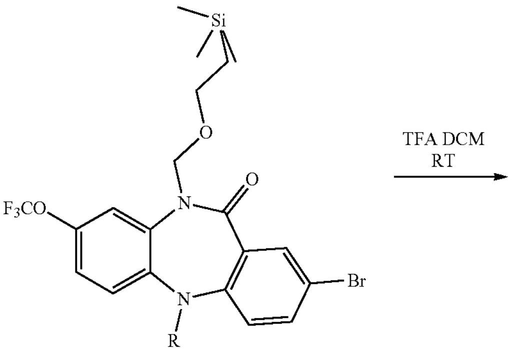

DCT001-064: R = Ethyl
DCT001-048: R = Propyl
DCT001-061: R = $CH_2CH_2OCH_3$

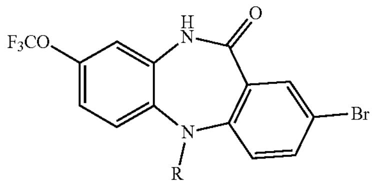

DCT001-068: R = Ethyl
DCT001-055: R = Propyl
DCT001-062: R = $CH_2CH_2OCH_3$

In some embodiments, the post-cyclization modification can comprise a coupling step, wherein the precursor compound 106 illustrated is converted to a functionalized compound, such as compound embodiment 1500 illustrated in Scheme 14, wherein when Z or Z' is $R^3$, $R^3$ is a group other than a halogen or a boronic ester. Compounds having structures satisfying the formula of compound embodiment 1500 also satisfy any one or more of Formulas I, IIA, IID, IIIA-IIIH, and IVA-IVF, and the variables $R^5$ and X are as defined for any of these formulas.

Scheme 15

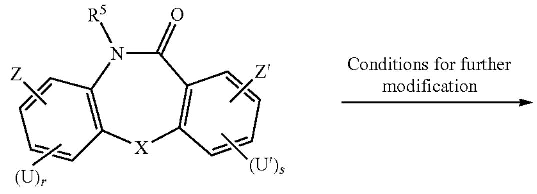

106

Z = $R^1$ or Z = $R^3$ = halogen or boronic ester

U = $R^2$ or $R^4$

Z′ = $R^1$ when Z = $R^3$

Z′ = $R^3$ when Z = $R^1$

U′ = $R^2$ when Z′ = $R^1$

U′ = $R^4$ when Z′ = $R^3$ r = 0 to 3 s = 0 to 3

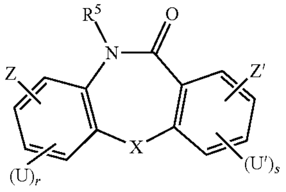

1500

Z = $R^1$ or Z = $R^3$ ≠ halogen or boronic ester

U = $R^2$ or $R^4$

Z′ = $R^1$ when Z = $R^3$

Z′ = $R^3$ when Z = $R^1$

U′ = $R^2$ when Z′ = $R^1$

U′ = $R^4$ when Z′ = $R^3$ r = 0 to 3 s = 0 to 3

In such embodiments, transition metal-mediated coupling conditions can be used to couple precursor compound 106 with a separate coupling partner group, such that a compound embodiment where Z or Z' is an $R^3$ group that is halogen or a boronic ester is converted to a compound embodiment wherein $R^3$ becomes an aromatic group, a boronic acid group, or a heteroaliphatic group, such as any of the groups illustrated in Table 1. The coupling partner groups that can be used to provide certain of the groups illustrated in Table 1 are commercially available and others can be made using methods described in the Examples of the present disclosure. Additional aromatic groups that can be used (and methods for making such aromatic groups) are illustrated in Table 2. The embodiments illustrated in Table 2 can be coupled with compound embodiments wherein Z or Z' is $R^3$ and $R^3$ is a boronic ester.

Table 1: Representative Aromatic, Heteroaliphatic, and Boronic Acid Groups for $R^3$

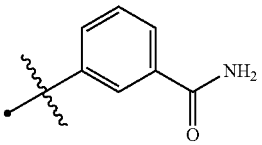

-continued

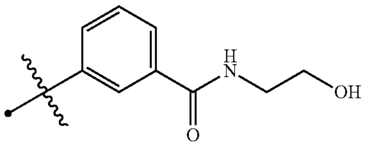

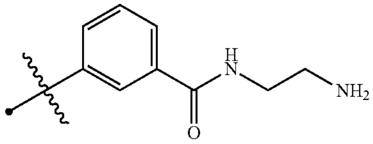

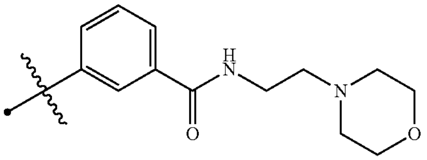

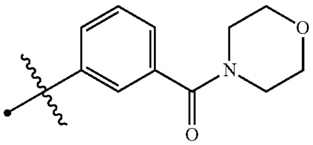

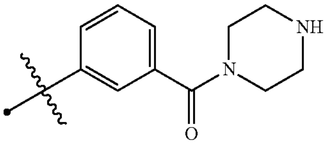

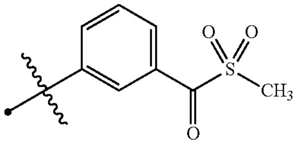

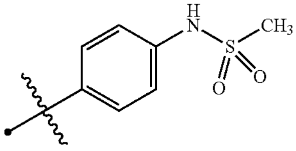

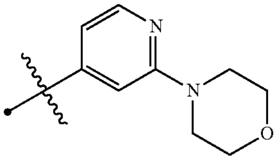

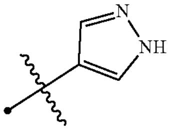

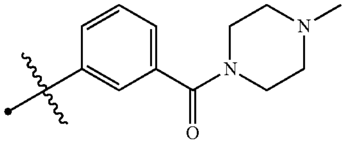

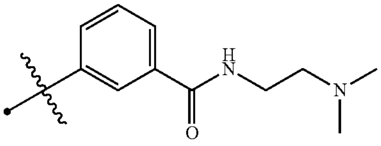

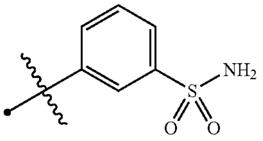

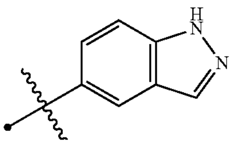

-continued
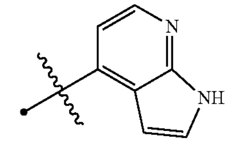
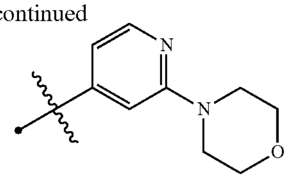
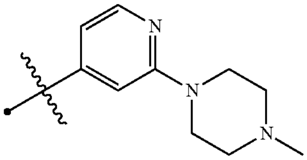
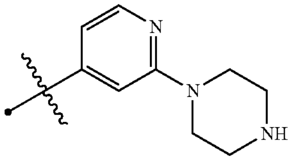
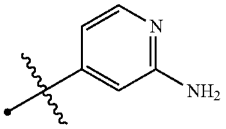
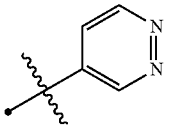
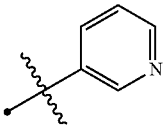
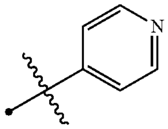
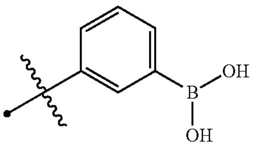
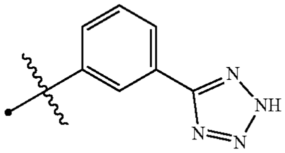
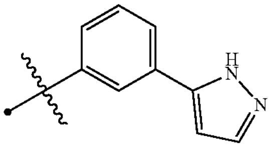
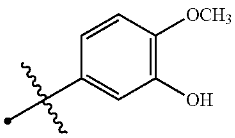
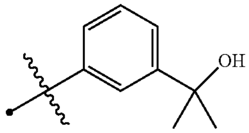
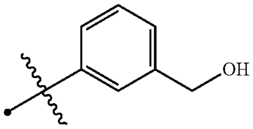
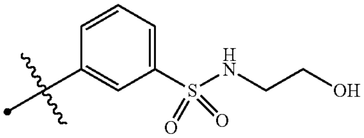
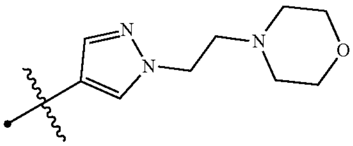
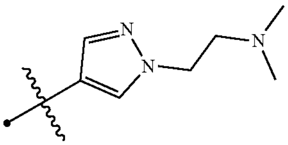
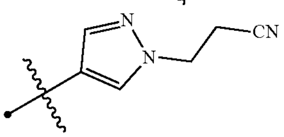
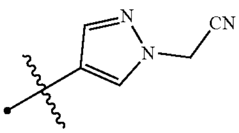
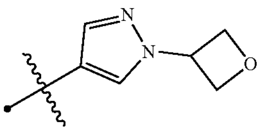
-continued
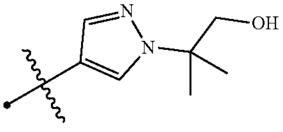
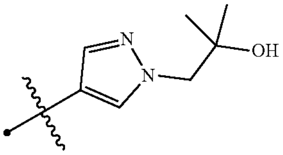
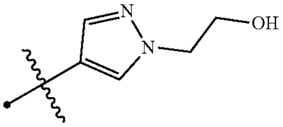
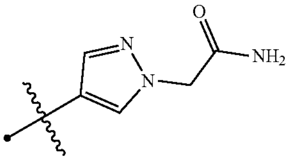
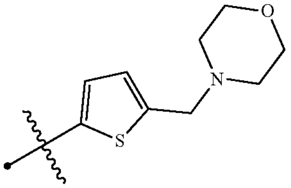
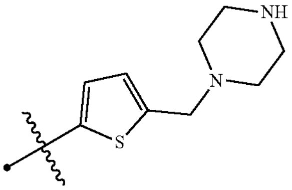
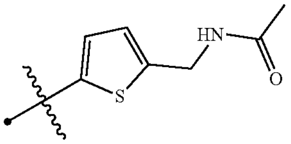
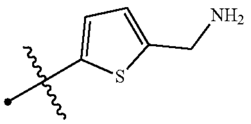
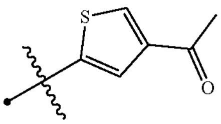
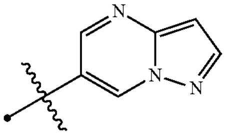
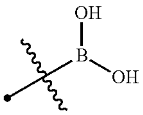
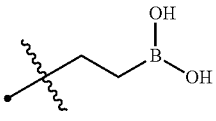
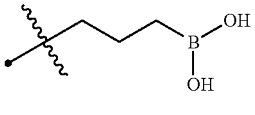

TABLE 2

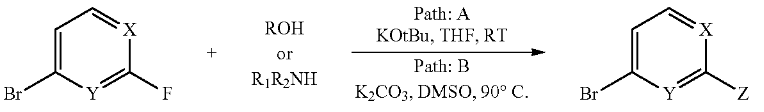

| Cmpd | X | Y | Z |
|---|---|---|---|
| AED020-053 | N | C | 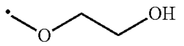 |
| AED020-054 | N | C | 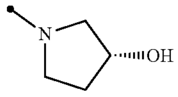 |
| AED020-068 | N | C | 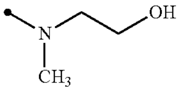 |
| AED020-074 | N | C | 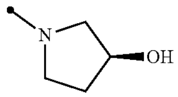 |
| AED020-070 | C | N | 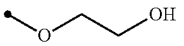 |
| AED020-071 | C | N | 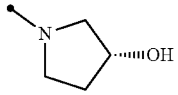 |
| AED020-072 | C | N | 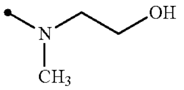 |
| AED020-075 | C | N | 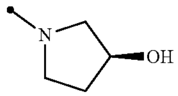 |

In some embodiments, transition metal-based coupling conditions can be used for the method embodiments contemplated by Scheme 15. Suitable conditions and reagents for such couplings are recognized by ordinary people in the art with the benefit of the present disclosure. Solely by way of example, a palladium-containing catalyst (e.g., CuBr $(PPh_3)_3$, $Pd(PPh_3)_4$, $Pd(OAc)_2$, XPhos, Pd(crotyl)Cl, $Pd(dppf)Cl_2$, or the like) can be used with a suitable base (e.g., $Cs_2CO_3$, $Na_2CO_3$, KOAc, or the like) and a solvent (e.g., toluene, dimethoxyethane, dimethylformamide, or the like, including any combinations thereof).

Representative method embodiments for preparing functionalized dibenzoazepinone core-containing compounds using coupling reactions are illustrated below in Schemes 16-24 and Tables 3-5.

Scheme 16

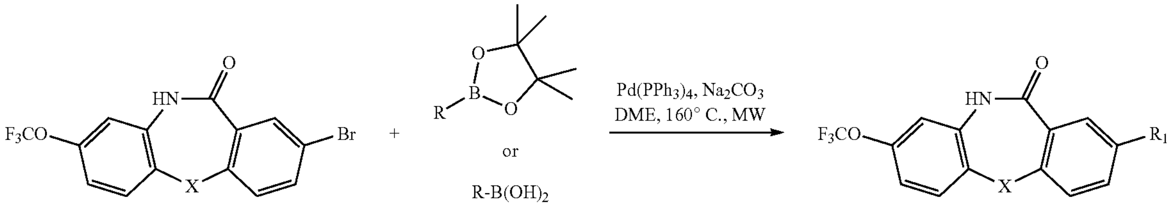

AED007-099 X = NH
AED013-066 X = O

-continued
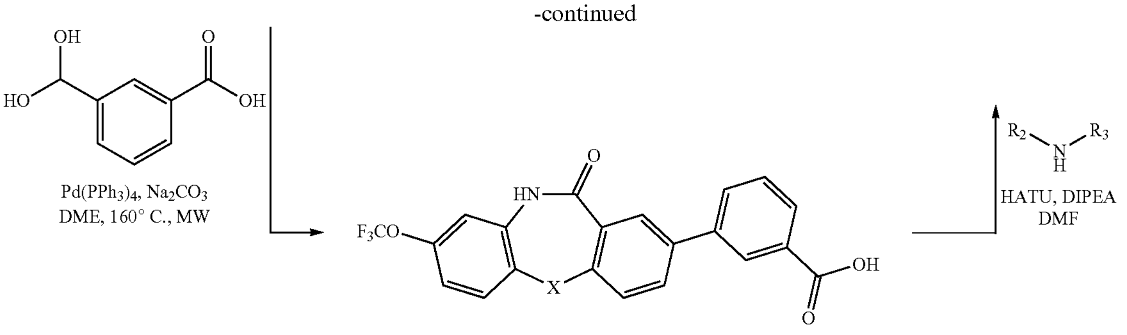
AED005-064 X = NH
AED007-015 X = O
Scheme 17
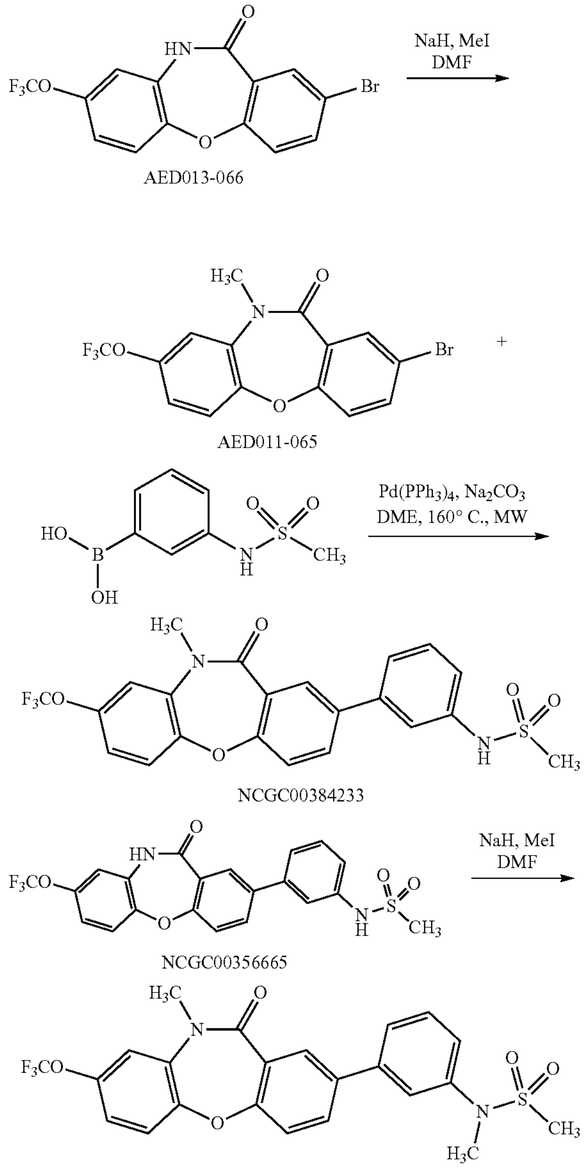
AED013-066
AED011-065
NCGC00384233
NCGC00356665
NCGC00384286
Scheme 18
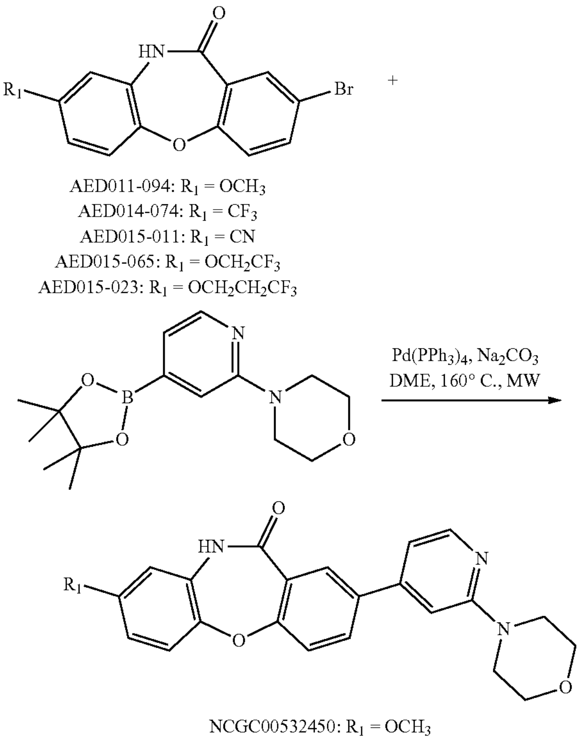
AED011-094: $R_1 = OCH_3$
AED014-074: $R_1 = CF_3$
AED015-011: $R_1 = CN$
AED015-065: $R_1 = OCH_2CF_3$
AED015-023: $R_1 = OCH_2CH_2CF_3$
NCGC00532450: $R_1 = OCH_3$
NCGC00481506: $R_1 = CF_3$
NCGC00481503: $R_1 = CN$
NCGC00481504: $R_1 = OCH_2CF_3$
NCGC00481507: $R_1 = OCH_2CH_2CF_3$
Scheme 19
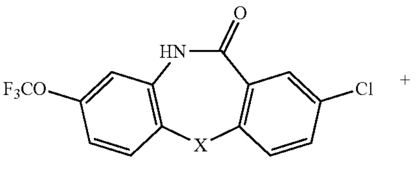
AED015-089: X = S
AED015-090: X = SO
AED015-092: $X = SO_2$ -continued
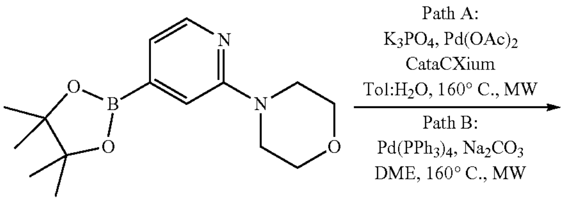
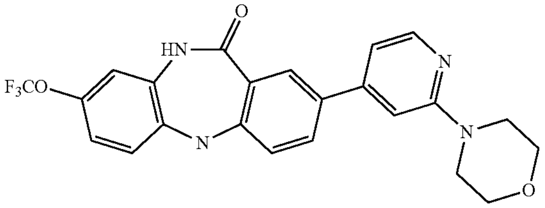
NCGC00496930
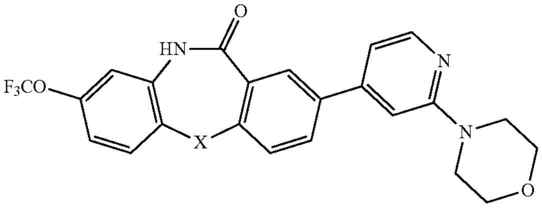
NCGC00482456: X = S, Path A
NCGC00482446: X = SO, Path B
NCGC00483140: X = SO$_2$, Path B
Scheme 20
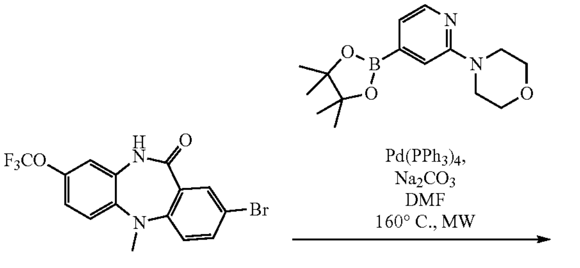
DCT001-018
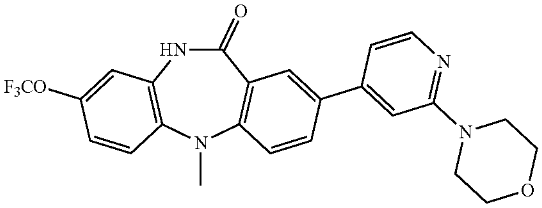
NCGC00488911
Scheme 21
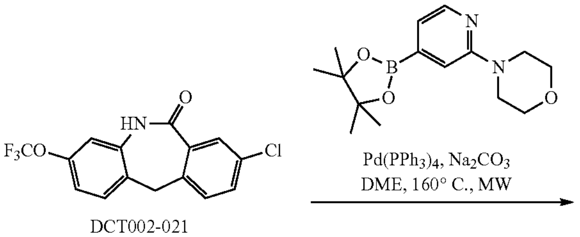
DCT002-021
Scheme 22
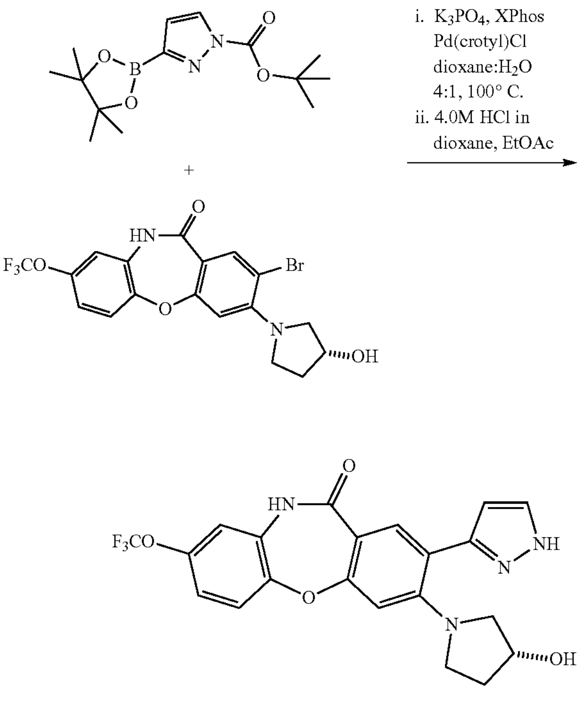
Scheme 23
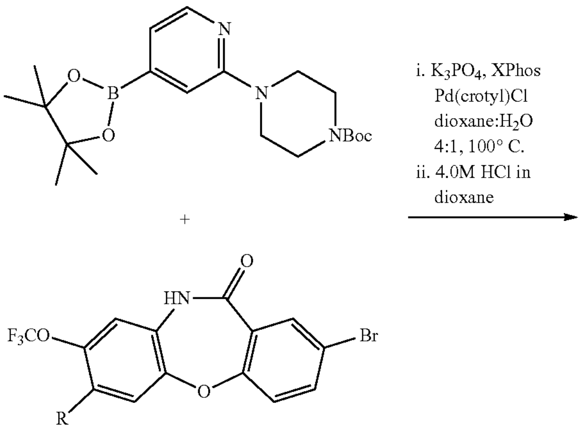

-continued
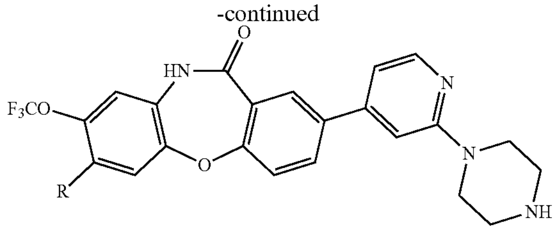
R = $-CH_3$, $-CH_2CH_3$, $-CN$, $-Cl$
Scheme 24
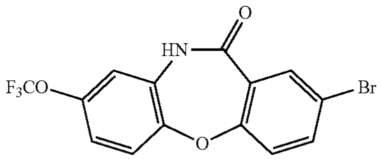
AED013-066
+
-continued
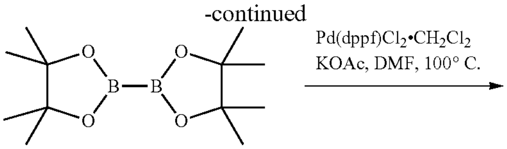
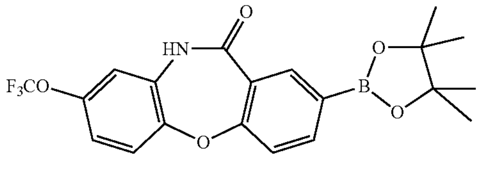
AED020-059
TABLE 3
| Cmpd | $R_1$ | $R_2$ | $R_4$ | $R_5$ |
|---|---|---|---|---|
| NCGC00384235 | $OCF_3$ | H | H | 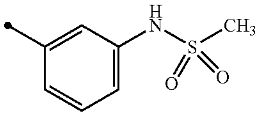 |
| NCGC00384296 | H | $OCF_3$ | H | 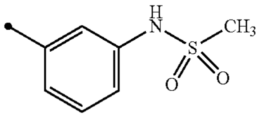 |
| NCGC00494683 | H | $OCF_3$ | 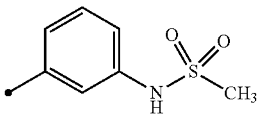 | H |
| NCGC00494682 | H | $OCF_3$ | 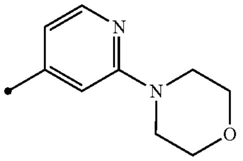 | H |

TABLE 4
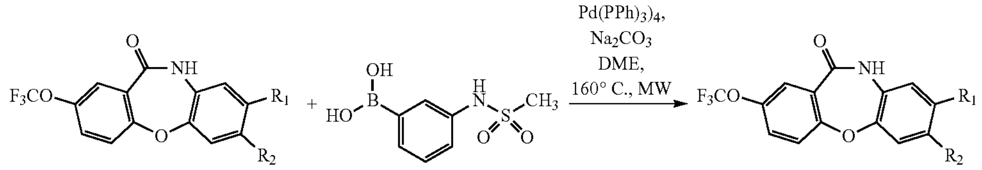
AED012-001: $R_1$ = Br, $R_2$ = H
AED012-002: $R_1$ = H, $R_2$ = Br
| Cmpd | $R_1$ | $R_2$ |
|---|---|---|
| NCGC00384303 | 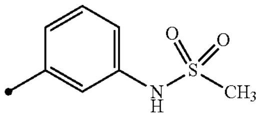 | H |
| NCGC00387403 | H | 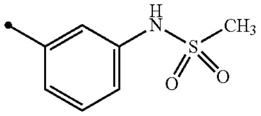 |
TABLE 5
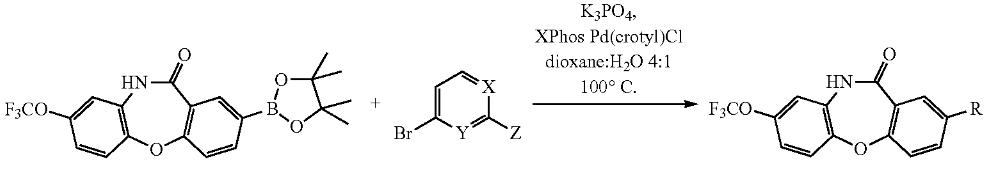
AED020-059
| Cmpd | R |
|---|---|
| NCGC00507969 | 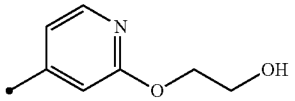 |
| NCGC00508838 | 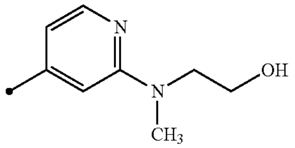 |
| NCGC00507975 | 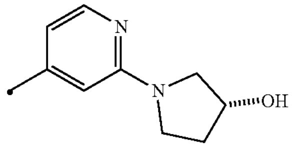 |
| NCGC00508975 | 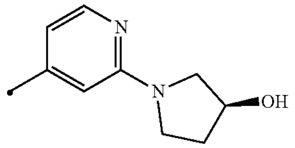 |
| NCGC00532318 | 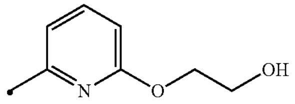 |

TABLE 5-continued

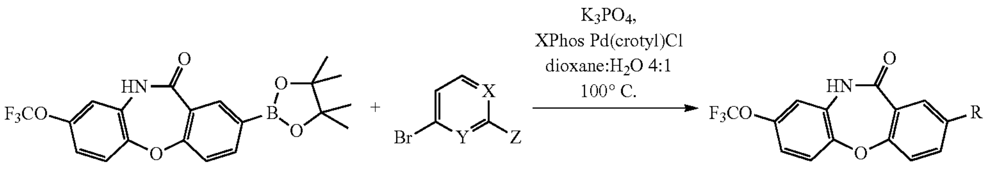

AED020-059

| Cmpd | R |
|---|---|
| NCGC00508972 | 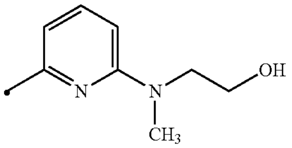 |
| NCGC00532289 | 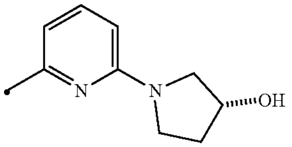 |
| NCGC00508973 | 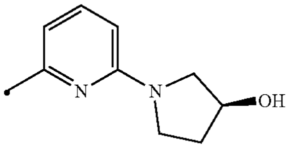 |

In additional embodiments, compound embodiment 1500 can be further modified to convert the illustrated amide group to a different functional group, as illustrated in compound embodiment 2500 shown in Scheme 25. Compounds satisfying the formula 2500 also satisfy Formulas JIB, IIC, IIE, and IIF.

Scheme 25

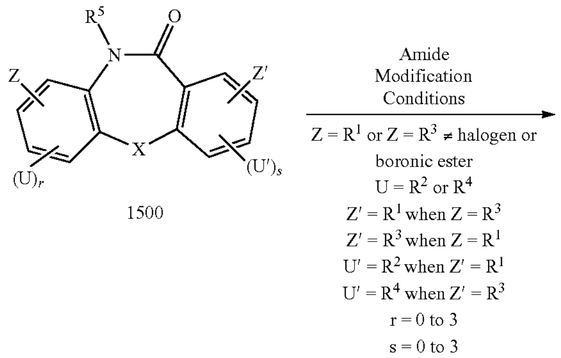

1500

-continued

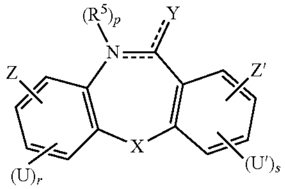

2500

In some such embodiments, the compound embodiment 1500 can be exposed to reagents capable of reducing the carbonyl group of the illustrated amide group, such as borane dimethylsulfide, lithium aluminum hydride, or similar reducing agents. In yet additional embodiments, compound embodiment 1500 can be exposed to reagents capable of converting the carbonyl group of the illustrated amide group to an amine, such as a dehydration reagent (e.g., phosphoryl chloride, thionyl chloride, or the like) and an amine reagent (e.g., $NH_3$, NHR'R", or $NH_2R'$, wherein R' and R" independently are selected from aliphatic, heteroaliphatic, haloaliphatic, haloheteroaliphatic, aromatic, aliphatic-aromatic, or heteroaliphatic-aromatic). Representative methods for making compound embodiments disclosed herein are provided below in Scheme 26. In yet some additional embodiments, the precursor compound 106 can be exposed to similar conditions prior to the coupling step(s) used to make compound embodiment 1500.

Scheme 26

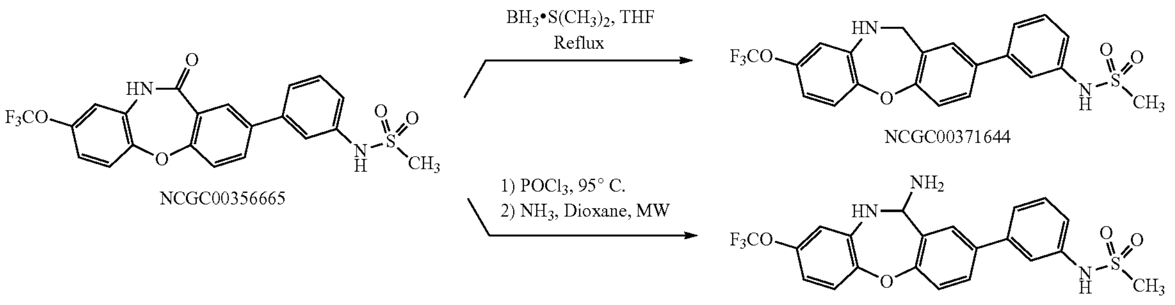

NCGC00356665

NCGC00371644

NCGC00373124

V. Methods of Using Compound Embodiments

Compound embodiments described herein are new c-Abl inhibitors that can be used to treat a disease in which c-Abl tyrosine kinase plays a part. The compounds described herein have unique structures that not only allow them to inhibit c-Abl tyrosine kinase, but that also allow the compounds to pass the blood brain barrier. The compounds also are able to bind to an allosteric site of c-Abl tyrosine kinase. As such, the compounds of the present disclosure exhibit a degree of selectivity for c-Abl that is not achieved by current c-Abl inhibitors.

Because genetic mutations leading to increased c-Abl expression and/or activity can be involved in some cancers, the compound embodiments disclosed herein can be used in treating a subject having, or that may develop, a cancer that arises due to increased c-Abl expression and/or activity because the compound embodiments are able to bind to c-Abl at an allosteric site.

c-Abl also can be active in pathways that result in increasing cell apoptosis. Where cell apoptosis is not desired, such as in neuron death, effectively inhibiting c-Abl is a desirable goal. Because of their ability to pass through the blood brain barrier and their high selectivity for c-Abl, the compound embodiments described herein are able to suppress and/or prevent apoptosis of neurons and as such can be used to treat a subject having, or that may develop, a neurodegenerative disease.

Disclosed herein are embodiments of a method for using the compound embodiments described herein. In some embodiments, the method concerns treating subject having a disease, or that may be prone to developing a disease associated with or involving c-Abl tyrosine kinase. In such embodiments, the method can comprise exposing a subject to a compound embodiment (or any pharmaceutically acceptable salt, prodrug, stereoisomer, tautomer, or solvate of the compound), or a composition thereof. In some embodiments, the method can comprise exposing a sample obtained from a subject to a compound embodiment (or any pharmaceutically acceptable salt, prodrug, stereoisomer, tautomer, or solvate of the compound), or a composition thereof. Samples include, but are not limited to, samples comprising a cell, tissue, blood, urine, or any combination thereof. In some embodiments, the subject or sample can be exposed to the compound embodiment (or any pharmaceutically acceptable salt, prodrug, stereoisomer, tautomer, or solvate of the compound), or a composition thereof by using any of the administration methods described herein.

The dosage used in such method embodiments will depend on certain factors, such as the age, weight, general health, and severity of the condition of the subject being treated, as will be understood by a person of ordinary skill in the art with the benefit of the present disclosure. Dosage also may be tailored to the sex and/or species of the subject. Dosage and frequency of administration may also depend on whether the compound (or a composition thereof, or any pharmaceutically acceptable salt, prodrug, stereoisomer, tautomer, or solvate of the compound) is formulated for treating acute episodes of a disease or for prophylactically treating a disease. Effective dosages can be estimated initially from in vitro assays. For example, an initial dosage for use in subjects can be formulated to achieve a circulating blood or serum concentration, of active compound that is at or above an $IC_{50}$ or $EC_{50}$ of the particular compound as measured in an in vitro assay, such as any of the assays described in the Examples section below. Dosages can be calculated to achieve such circulating blood or serum concentrations taking into account the bioavailability of the particular compound.

Dosage amounts, such as therapeutically effective amounts, of the compound (or a composition thereof, or any pharmaceutically acceptable salt, prodrug, stereoisomer, tautomer, or solvate of the compound) for a subject will typically be in the range of from greater than 0 mg/kg/day (such as 0.0001 mg/kg/day, 0.001 mg/kg/day, or 0.01 mg/kg/day) to 100 mg/kg/day. In some embodiments, the dosage (or therapeutically effective amount) may range from 0.1 mg/kg/day to 30 mg/kg/day, such as 1 mg/kg/day to 10 mg/kg/day.

In additional embodiments, the method concerns inhibiting c-Abl tyrosine kinase. In such embodiments, the method can comprise exposing a subject or a sample to an amount of a compound (or a composition thereof, or any stereoisomer, tautomer, pharmaceutically acceptable salt, prodrug, or solvate of the compound) that is effective to prevent or decrease the activity of c-Abl tyrosine kinase, such as an amount effective to ensure binding of a compound to an allosteric site of c-Abl tyrosine kinase, such as at the myristate pocket. By inhibiting c-Abl tyrosine kinase, it is currently believed that several diseases can be treated. For example, any disease in which c-Abl tyrosine kinase plays a role can be treated due to the decrease in or prevention of c-Abl activity. In some embodiments, the method can comprise treating a subject in need of controlling over-active c-Abl. Exemplary diseases that can be treated using compound embodiments described herein include, but are not limited to, cancers, inflammatory diseases, neurodegenerative diseases, and/or motor neuron diseases, lysosomal storage diseases, and infectious diseases. In particular disclosed embodiments, the disease can be leukemia, glioma, glioblastoma, neuroblastoma, AD, Parkinson's disease, epilepsy, amyotrophic lateral sclerosis, primary lateral sclerosis, Kennedy's syndrome, frontal temporal dementia associated with ALS, spinal muscular atrophy, and the like. Additional disease include lipid storage disorders, such as sphingolipidoses (e.g., Farber disease, Krabbe disease, Fabry disease, Schindler disease, Sandhoff disease, Tay-Sachs disease, Gaucher disease, and Niemann-Pick A and B diseases). Additional diseases include metabolic disorders, such as mucopolysaccharidoses (e.g., Hunter disease and Sanfilippo and Sly syndromes). Yet additional diseases include lipid metabolism diseases, such as lipidoses (e.g., Niemann-Pick C and D diseases). In some embodiments, the disease is bacterial pathogenesis resulting from *Shigella flexneri, Escherichia coli, Helicobacter pylori, Anaplasma phagocytophilum, Salmonella enterica*, and *Plasmodium falciparum*: (malaria), as well as viral pathogenesis resulting from HIV.

Several c-Abl downstream pathways have direct impact on physiological processes, including development and maintenance of the nervous and immune systems and epithelial morphogenesis. Recent studies also indicated that numerous viral and bacterial pathogens highjack Abl signaling for different purposes. Abl kinases are activated to reorganize the host actin cytoskeleton and promote the direct tyrosine phosphorylation of viral surface proteins and injected bacterial type-III and type-IV effector molecules. However, Abl kinases also play other roles in infectious processes of bacteria, viruses, and prions. These activities impact microbial invasion and release from host cells, actin-based motility, pedestal formation, as well as cell-cell dissociation involved in epithelial barrier disruption and other responses. Thus, Abl kinases exhibit important functions in pathological signaling during microbial infections, and therefore present possible therapeutic intervention strategies using compound embodiments disclosed herein.

VI. Examples

Example 1

General Chemistry Methods. All air or moisture sensitive reactions were performed under positive pressure of nitrogen with oven-dried glassware. Anhydrous solvents such as dichloromethane, N,N-dimethylformamide (DMF), acetonitrile (ACN), methanol (MeOH) and triethylamine ($Et_3N$) were purchased from Sigma-Aldrich (St. Louis, MO). Preparative purification was performed on a Waters semi-preparative HPLC system (Waters Corp., Milford, MA). The column used was a Phenomenex Luna C18 (5 micron, 30×75 mm; Phenomenex, Inc., Torrance, CA) at a flow rate of 45.0 mL/min. The mobile phase consisted of acetonitrile and water (each containing 0.1% trifluoroacetic acid). A gradient of 10% to 50% acetonitrile over 8 min was used during the purification. Fraction collection was triggered by UV detection at 220 nM.

Analytical analysis was performed on an Agilent LC/MS (Agilent Technologies, Santa Clara, CA). Method 1: A 7-min gradient of 4% to 100% acetonitrile (containing 0.025% trifluoroacetic acid) in water (containing 0.05% trifluoroacetic acid) was used with an 8-min run time at a flow rate of 1.0 mL/min. Method 2: A 3-min gradient of 4% to 100% acetonitrile (containing 0.025% trifluoroacetic acid) in water (containing 0.05% trifluoroacetic acid) was used with a 4.5-min run time at a flow rate of 1.0 mL/min. A Phenomenex Luna C18 column (3 micron, 3×75 mm) was used at a temperature of 50° C. Purity determination was performed using an Agilent diode array detector for both Method 1 and Method 2. Mass determination was performed using an Agilent 6130 mass spectrometer with electrospray ionization in the positive mode. 1H NMR spectra were recorded on Varian 400 MHz spectrometers (Agilent Technologies, Santa Clara, CA). Chemical shifts are reported in ppm with undeuterated solvent (DMSO at 2.50 ppm) as internal standard for DMSO-d6 solutions. All of the analogs tested in the biological assays have a purity of greater than 95% based on both analytical methods. High resolution mass spectrometry was recorded on Agilent 6210 Time-of-Flight (TOF) LC/MS system. Confirmation of molecular formula was accomplished using electrospray ionization in the positive mode with the Agilent Masshunter software (Version B.02). Starting materials were purchased from Combi-Blocks (San Diego, CA) or Sigma-Aldrich (St. Louis, MO), and were used as received, without further purification.

General Procedure A for the Cross-Coupling of Azepinone Cores with Boronic Acids/Esters:

A mixture of an azepinone core (1.0 eq.) and the corresponding boronic acid/ester (1.1 eq.) was placed in a microwave vial. 1,2-Dimethoxyethane (DME) was added, followed by 2M aqueous $Na_2CO_3$ (4.0 eq.), and the resulting mixture purged with $N_2$ for 2 min, after which was added $Pd(PPh_3)_4$(0.05 eq.), and the mixture purged with $N_2$ for an additional minute. The resulting reaction mixture was heated to 160° C. under microwave irradiation for 1 h. After cooling, the reaction mixture was filtered through celite and the filter cake rinsed generously with EtOAc. The filtrate was concentrated, and the residue taken up in $CH_2Cl_2$, the insoluble salts filtered and the filtrate concentrated. Crude mixture was subjected to purification via standard HPLC conditions using a gradient of 10-100% ACN in $H_2O$ with 0.1% TFA to afford the corresponding azepinone product.

General Procedure B for the carboxylic acid coupling of azepinone cores with amines: HATU (1.1 eq.) was added to a solution of the carboxylic acid (1.0 eq.) in N,N-dimethylformamide (DMF) and allowed to stir for 10 min at RT. The corresponding amine (1.1 eq.) was added and the resulting solution stirred for 20 min before DIPEA (2.5 eq. for free base, 3.5 eq. for salt) was added. The reaction mixture was allowed to stir at RT for 18 hr, or until LC-MS analysis showed completion. Crude mixture was subjected to purification via standard HPLC conditions using a gradient of 10-100% ACN in $H_2O$ with 0.1% TFA to afford the corresponding amide product.

General Procedure C for the cross-coupling of azepinone cores with boronic acids/esters: A mixture of an azepinone core (1.0 eq.), the corresponding boronic acid/ester (2.0 eq.), $K_3PO_4$ (4.0 eq.) and butyldi-1-adamantylphosphine (0.2 eq.) in 16:1 tolune:$H_2O$, was degassed by bubbling $N_2$ through the reaction mixture for 2-3 min. $Pd(OAc)_2$ (0.1 eq.) was then added, degassing continued for 1 min, and then the resulting reaction mixture was heated to 160° C. under MW irradiation for 1 h, after which LC-MS analysis showed completion. The reaction mixture was filtered through celite and the filter cake rinsed generously with EtOAc. The filtrate was concentrated, and the residue taken up in $CH_2Cl_2$, the salts filtered and the filtrate concentrated. Crude mixture was subjected to purification via standard HPLC conditions using a gradient of 10-100% ACN in $H_2O$ with 0.1% TFA to afford the corresponding azepinone product.

General Procedure D for the cross-coupling of azepinone cores with boronic acids/esters: A mixture of an azepinone core (1.0 eq.), the corresponding boronic acid/ester (1.5 eq.), $K_3PO_4$ (2.0 eq. for boronic acids, 4.0 eq. for boronic esters) and XPhos Pd(crotyl)Cl (0.07 eq.) in 4:1 dioxane:$H_2O$ was degassed by bubbling $N_2$ through the reaction mixture for 2 min. The resulting reaction mixture was heated to 100° C. for 30 min, after which LC-MS analysis showed completion. The reaction mixture was concentrated to dryness, and the residue taken up in MeOH/$CH_2Cl_2$, the salts filtered and the filtrate concentrated. Crude mixture was subjected to purification via standard HPLC conditions using a gradient of 10-100% ACN in $H_2O$ with 0.1% TFA to afford the corresponding azepinone product.

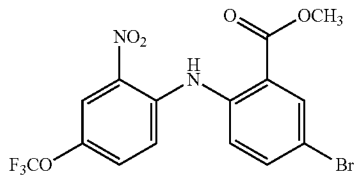

Chemical Formula: $C_{15}H_{10}BrF_3N_2O_5$
Exact Mass: 433.97
Molecular Weight: 435.15

Methyl 5-bromo-2-((2-nitro-4-(trifluoromethoxy)phenyl)amino)benzoate (AED007-096): A mixture of 2-nitro-4-(trifluoromethoxy)aniline (0.651 g, 2.93 mmol), methyl 5-bromo-2-iodobenzoate (1.00 g, 2.93 mmol), $Cs_2CO_3$ (1.43 g, 4.40 mmol) and $CuBr(PPh_3)_3$(0.546 g, 0.587 mmol) were suspended in toluene (15.0 mL). The resulting reaction mixture was heated to 110° C. for 24 h, after which TLC analysis (10% EtOAc in Hex) showed completion. Reaction mixture was filtered through celite and the filtrate concentrated. The crude mixture was recrystallized from EtOH-$H_2O$ to afford methyl 5-bromo-2-((2-nitro-4-(trifluoromethoxy)phenyl)amino)benzoate (818 mg, 64.1% yield) as orange crystals. $^1H$ NMR (400 MHz, DMSO-$d_6$) δ 10.80 (s, 1H), 8.14 (dq, J=2.5, 0.8 Hz, 1H), 8.06 (d, J=2.5 Hz, 1H), 7.74 (dd, J=8.9, 2.5 Hz, 1H), 7.71-7.65 (m, 2H), 7.52 (d, J=8.9 Hz, 1H), 3.89 (s, 3H). $^{19}F$ NMR (376 MHz, DMSO-$d_6$) δ-57.50 (s, 3F). LCMS RT (Method 2)=3.901 min, m/z 436.6 [M+H+].

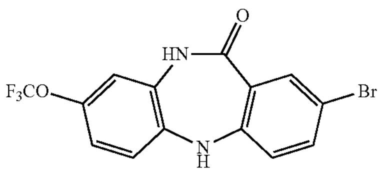

Chemical Formula: $C_{14}H_8BrF_3N_2O_2$
Exact Mass: 371.97
Molecular Weight: 373.13

2-Bromo-8-(trifluoromethoxy)-5,10-dihydro-11H-dibenzo[b,e][1,4]diazepin-11-one (AED007-099): $Fe^0$ powder (523 mg, 9.36 mmol) was added slowly to a suspension of methyl 5-bromo-2-((2-nitro-4-(trifluoromethoxy)phenyl)amino)benzoate (AED007-096) (815 mg, 1.87 mmol) in 6N hydrochloric acid (15.0 mL, 90.0 mmol) and MeOH (15.0 mL). The resulting reaction mixture was heated to reflux for 24 h, after which LC-MS analysis showed completion. Reaction mixture was allowed to cool to RT, concentrated to dryness, taken up in EtOAc, washed with $H_2O$ and brine, dried over $MgSO_4$, filtered and concentrated. Crude material was purified by flash column chromatography: silica gel with a gradient of 10-30% EtOAc in Hex to afford 2-bromo-8-(trifluoromethoxy)-SH-dibenzo[b,e][1,4]diazepin-11(10H)-one (492 mg, 70.4% yield) as a pale yellow solid. $^1H$ NMR (400 MHz, DMSO-$d_6$) δ 10.08 (s, 1H), 8.21 (s, 1H), 7.75 (d, J=2.5 Hz, 1H), 7.52 (dd, J=8.6, 2.5 Hz, 1H), 7.05 (d, J=8.6 Hz, 1H), 7.01-6.91 (m, 3H). $^{19}F$ NMR (376 MHz, DMSO-$d_6$) δ-57.15 (s, 3F). LCMS RT (Method 2)=3.499 min, m/z 769.3 [2M+Na$^+$].

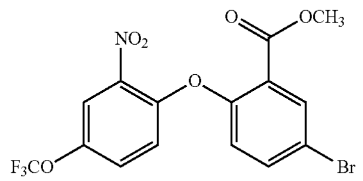

Chemical Formula: $C_{15}H_9BrF_3NO_6$
Exact Mass: 434.96
Molecular Weight: 436.14

Methyl 5-bromo-2-(2-nitro-4-(trifluoromethoxy)phenoxy)benzoate (AED008-074): Methyl 5-bromo-2-hydroxybenzoate (2.00 g, 8.66 mmol) was added to a solution of 1-fluoro-2-nitro-4-(trifluoromethoxy)benzene (1.26 mL, 8.66 mmol) and $K_2CO_3$ (1.56 g, 11.2 mmol) in DMF (12.0 mL). The resulting reaction mixture was stirred at 60° C. overnight, after which LC-MS analysis showed completion. Reaction mixture was allowed to cool to RT and then poured over ice $H_2O$, vigorously stirred for 45 min and insoluble material filtered, washed generously with $H_2O$ and allowed to air dry to afford methyl 5-bromo-2-(2-nitro-4-(trifluoromethoxy)phenoxy)benzoate (3.35 g, 89.0% yield) as a slightly yellow powder, which was used without further purification. $^1H$ NMR (400 MHz, DMSO-$d_6$) δ 8.21 (d, J=2.9 Hz, 1H), 8.07 (d, J=2.6 Hz, 1H), 7.91 (dd, J=8.8, 2.6 Hz, 1H), 7.68 (dd, J=9.2, 3.0 Hz, 1H), 7.32 (d, J=8.7 Hz, 1H), 7.10 (d, J=9.3 Hz, 1H), 3.70 (s, 3H). $^{19}F$ NMR (376 MHz, DMSO-$d_6$) δ-57.53 (s, 3F). LCMS RT (Method 2)=3.722 min, m/z 894.8 [2M+Na$^+$].

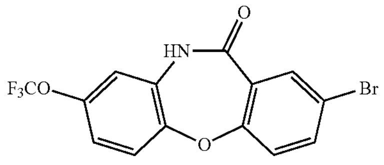

Chemical Formula: $C_{14}H_7BrF_3NO_3$
Exact Mass: 372.96
Molecular Weight: 374.11

2-Bromo-8-(trifluoromethoxy)dibenzo[b,f][1,4]oxazepin-11(10H)-one (AED013-066): 6N Hydrochloric acid (30.0 mL, 180 mmol) was added to a mixture of methyl 5-bromo-2-(2-nitro-4-(trifluoromethoxy)phenoxy)benzoate (AED008-074) (3.40 g, 7.80 mmol) and iron powder (2.18 g, 39.0 mmol) in EtOH (30.0 mL). The resulting reaction mixture was heated to reflux for 24 h, after which LC-MS analysis showed completion. Reaction mixture was allowed to cool to RT and poured over ice $H_2O$, vigorously stirred for 5 min and the insoluble material filtered, rinsed generously with $H_2O$ and allowed to air dry to afford 2-bromo-8-

(trifluoromethoxy)dibenzo[b,f][1,4]oxazepin-11(10H)-one (2.80 g, 96.0% yield) as a lightly tan fluffy solid, which was used without further purification. $^1$H NMR (400 MHz, DMSO-$d_6$) δ 10.76 (s, 1H), 7.84 (d, J=2.5 Hz, 1H), 7.81 (dd, J=8.5, 2.6 Hz, 1H), 7.47 (dd, J=8.2, 1.0 Hz, 1H), 7.35 (d, J=8.5 Hz, 1H), 7.19-7.10 (m, 2H). $^{19}$F NMR (376 MHz, DMSO-$d_6$) δ-57.14 (s, 3F). LCMS RT (Method 2)=3.640 min, m/z 770.1 [2M+$Na^+$].

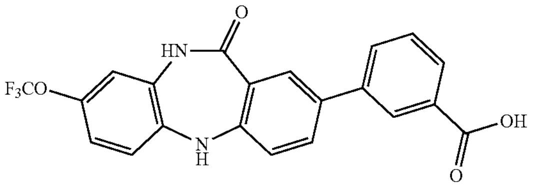

Chemical Formula: $C_{21}H_{12}F_3NO_5$
Exact Mass: 415.07
Molecular Weight: 415.32

3-(11-oxo-8-(trifluoromethoxy)-10,11-dihydro-5H-dibenzo[b,e][1,4]diazepin-2-yl)benzoic acid (AED005-064): A mixture of 2-bromo-8-(trifluoromethoxy)-5H-dibenzo[b,e][1,4]diazepin-11(10H)-one (AED007-099) (100 mg, 0.268 mmol), 3-boronobenzoic acid (44.5 mg, 0.268 mmol), and $Na_2CO_3$ (114 mg, 1.07 mmol) in 1:1 ACN:$H_2O$ (4.00 mL) was degassed for 5 min by bubbling $N_2$ through the reaction mixture. $Pd(PPh_3)_4$(15.5 mg, 0.013 mmol) was then added, and degassing continued for 2 min. The resulting reaction mixture was heated to 160° C. under microwave irradiation for 1 h. After cooling, the reaction mixture was filtered through celite and the filter cake rinsed generously with $H_2O$. The filtrate was acidified to pH ~4 with 1M HCl as the product precipitated. The precipitate was filtered, rinsed generously with $H_2O$, and allowed to air dry to afford 3-(11-oxo-8-(trifluoromethoxy)-10,11-dihydro-5H-dibenzo[b,e][1,4]diazepin-2-yl)benzoic acid (105 mg, 95.0% yield) as an off-white solid, which was used without further purification. $^1$H NMR (400 MHz, DMSO-$d_6$) δ 13.09 (br s, 1H), 10.07 (s, 1H), 8.26 (s, 1H), 8.12 (s, 1H), 7.99 (d, J=2.4 Hz, 1H), 7.89 (dd, J=7.6, 1.6 Hz, 1H), 7.87-7.83 (m, 1H), 7.75 (dd, J=8.4, 2.4 Hz, 1H), 7.66-7.49 (m, 2H), 7.15-7.05 (m, 1H), 6.99 (dd, J=6.2, 2.8 Hz, 2H). $^{19}$F NMR (376 MHz, DMSO-$d_6$) δ-57.14 (s, 3F). LCMS RT (Method 2)=3.301 min, m/z 829.5 [2M'].

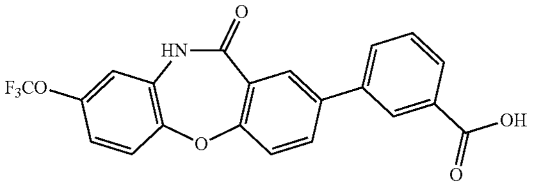

Chemical Formula: $C_{21}H_{12}F_3NO_5$
Exact Mass: 415.07
Molecular Weight: 415.32

3-(11-oxo-8-(trifluoromethoxy)-10,11-dihydrodibenzo[b,f][1,4]oxazepin-2-yl)benzoic acid (AED007-015): A mixture of 2-bromo-8-(trifluoromethoxy)dibenzo[b,f][1,4]oxazepin-11(10H)-one (AED013-066) (250 mg, 0.668 mmol), 3-boronobenzoic acid (111 mg, 0.668 mmol), and $Na_2CO_3$ (283 mg, 2.67 mmol) in 1:1 ACN:$H_2O$ (4.00 mL) was degassed for 5 min by bubbling $N_2$ through the reaction mixture. $Pd(PPh_3)_4$(38.6 mg, 0.033 mmol) was then added and degassing continued for 2 min. The resulting reaction mixture was heated to 160° C. under microwave irradiation for 1 h. After cooling, the reaction mixture was filtered through celite and the filter cake rinsed generously with $H_2O$. The filtrate was acidified to pH ~4 with 1M HCl as the product precipitated. The precipitate was filtered, rinsed generously with $H_2O$, and allowed to air dry to afford 3-(11-oxo-8-(trifluoromethoxy)-10,11-dihydrodibenzo[b,f][1,4]oxazepin-2-yl)benzoic acid (185 mg, 66.7% yield) as an off-white solid, which was used without further purification. $^1$H NMR (400 MHz, DMSO-$d_6$) δ 10.76 (s, 1H), 8.15 (t, J=1.8 Hz, 1H), 8.02 (d, J=2.4 Hz, 1H), 7.97 (dd, J=8.4, 2.5 Hz, 1H), 7.93 (dt, J=7.6, 1.3 Hz, 1H), 7.83 (dt, J=7.8, 1.4 Hz, 1H), 7.58-7.46 (m, 4H), 7.17 (dt, J=8.3, 1.5 Hz, 2H). $^{19}$F NMR (376 MHz, DMSO-$d_6$) δ-57.12 (s, 3F). LCMS RT (Method 2)=3.455 min, m/z 829.5 [$2M^+$].

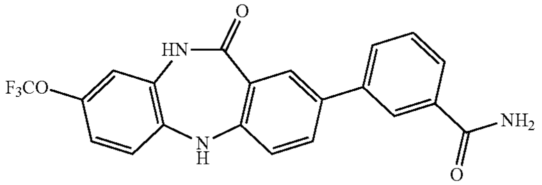

Chemical Formula: $C_{21}H_{14}F_3N_3O_3$
Exact Mass: 413.10
Molecular Weight: 413.36

3-(11-Oxo-8-(trifluoromethoxy)-10,11-dihydro-5H-dibenzo[b,e][1,4]diazepin-2-yl)benzamide (NCGC00354777): Prepared following general Procedure D; 2-bromo-8-(trifluoromethoxy)-5H-dibenzo[b,e][1,4]diazepin-11(10H)-one AED007-099 (40.0 mg, 0.107 mmol), (3-carbamoylphenyl)boronic acid (26.5 mg, 0.161 mmol), $K_3PO_4$ (45.5 mg, 0.214 mmol), XPhos Pd(crotyl)Cl (7.22 mg, 10.7 μmol) in 4:1 dioxane:$H_2O$ (1.25 mL) to afford the title compound (32.0 mg, 56.6% yield). $^1$H NMR (400 MHz, DMSO-$d_6$) δ 10.07 (s, 1H), 8.23 (s, 1H), 8.13-8.07 (m, 2H), 8.04 (d, J=2.4 Hz, 1H), 7.82 (dt, J=7.7, 1.4 Hz, 1H), 7.79-7.71 (m, 2H), 7.51 (t, J=7.7 Hz, 1H), 7.41 (s, 1H), 7.10 (dd, J=9.0, 6.2 Hz, 2H), 7.02-6.95 (m, 2H). $^{19}$F NMR (376 MHz, DMSO-$d_6$) δ-57.15 (s, 3F). LCMS RT (Method 1)=4.917 min, m/z 827.1 [$2M^+$].

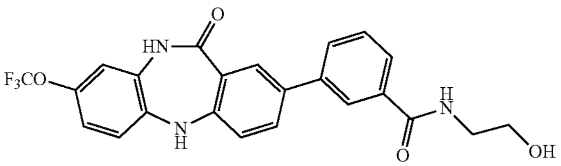

Chemical Formula: $C_{23}H_{18}F_3N_3O_4$
Exact Mass: 457.12
Molecular Weight: 457.41

N-(2-Hydroxyethyl)-3-(11-oxo-8-(trifluoromethoxy)-10,11-dihydro-5H-dibenzo[b,e][1,4]diazepin-2-yl)benzamide (NCGC00355556): Prepared following general Procedure B; HATU (20.2 mg, 0.053 mmol), 3-(11-oxo-8-(trifluoromethoxy)-10,11-dihydro-5H-dibenzo[b,e][1,4]diazepin-2-yl)benzoic acid AED005-064 (20.0 mg, 0.048 mmol), 2-aminoethanol (3.20 μL, 0.053 mmol), DIPEA (21.0 L, 0.121 mmol) in DMF (1.00 mL) to afford the title compound (13.7 mg, 49.6% yield). $^1$H NMR (400 MHz, DMSO-$d_6$) δ

10.07 (s, 1H), 8.57 (t, J=5.6 Hz, 1H), 8.22 (s, 1H), 8.07 (d, J=2.1 Hz, 1H), 8.04 (d, J=2.3 Hz, 1H), 7.83-7.71 (m, 3H), 7.52 (t, J=7.8 Hz, 1H), 7.10 (dd, J=9.0, 7.8 Hz, 2H), 7.03-6.95 (m, 2H), 4.73 (s, 1H), 3.53 (t, J=6.2 Hz, 2H), 3.36 (q, J=6.1 Hz, 2H). $^{19}$F NMR (376 MHz, DMSO-$d_6$) δ-57.14 (s, 3F). LCMS RT (Method 1)=4.817 min, m/z 458.1 [M+H+].

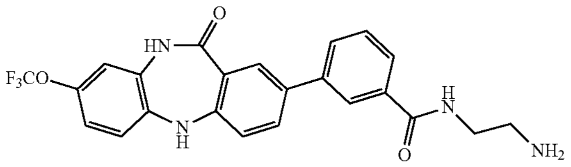

Chemical Formula: $C_{23}H_{19}F_3N_4O_3$
Exact Mass: 456.14
Molecular Weight: 456.43

N-(2-Aminoethyl)-3-(11-oxo-8-(trifluoromethoxy)-10,11-dihydro-5H-dibenzo[b,e][1,4]diazepin-2-yl)benzamide (NCGC00355568): Prepared following general Procedure B; HATU (20.2 mg, 0.053 mmol), 3-(11-oxo-8-(trifluoromethoxy)-10,11-dihydro-5H-dibenzo[b,e][1,4]diazepin-2-yl)benzoic acid AED005-064 (20.0 mg, 0.048 mmol), N-Boc-ethylenediamine (8.41 μL, 0.053 mmol), DIPEA (21.0 L, 0.121 mmol) in DMF (1.00 mL). The reaction mixture was allowed to stir at RT for 18 hr, and then was added $CH_2Cl_2$ (1.00 mL) and trifluoroacetic acid (1.00 mL, 12.9 mmol). The reaction was stirred for 12 h at RT, after which LC-MS showed complete Boc deprotection. The pH of the reaction mixture was adjusted to −10-11 with 1M NaOH and the mixture extracted with $CH_2Cl_2$. The organic layer was washed with brine, dried over $MgSO_4$, filtered and concentrated. Crude mixture was subjected to purification via standard HPLC conditions using a gradient of 10-100% ACN in $H_2O$ with 0.1% TFA to afford the title compound as the TFA salt (14.3 mg, 52.0% yield). $^{1}$H NMR (400 MHz, DMSO-$d_6$) δ 10.08 (s, 1H), 8.73 (t, J=5.6 Hz, 1H), 8.24 (s, 1H), 8.08 (d, J=2.0 Hz, 1H), 8.04 (d, J=2.2 Hz, 1H), 7.84-7.72 (m, 6H), 7.59-7.50 (m, 1H), 7.15-7.05 (m, 2H), 7.03-6.95 (m, 2H), 3.53 (q, J=6.0 Hz, 2H), 3.01 (t, J=6.2 Hz, 2H). $^{19}$F NMR (376 MHz, DMSO-$d_6$) δ-57.14 (s, 3F), −73.45 (s, 3F). LCMS RT (Method 1)=4.390 min, m/z 456.8 [$M^+$].

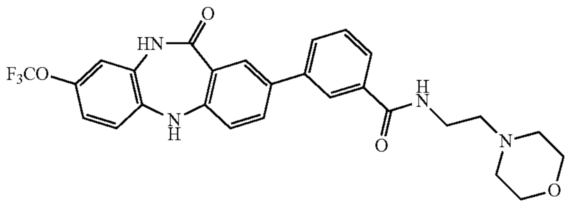

Chemical Formula: $C_{27}H_{25}F_3N_4O_4$
Exact Mass: 526.18
Molecular Weight: 526.52

N-(2-Morpholinoethyl)-3-(11-oxo-8-(trifluoromethoxy)-10,11-dihydro-5H-dibenzo[b,e][1,4]diazepin-2-yl)benzamide (NCGC00355557): Prepared following general Procedure B; HATU (20.2 mg, 0.053 mmol), 3-(11-oxo-8-(trifluoromethoxy)-10,11-dihydro-5H-dibenzo[b,e][1,4]diazepin-2-yl)benzoic acid AED005-064 (20.0 mg, 0.048 mmol), 2-morpholinoethanamine (6.97 μL, 0.053 mmol), DIPEA (21.0 L, 0.121 mmol) in DMF (1.00 mL) to afford the title compound as the TFA salt (12.3 mg, 39.8% yield). $^{1}$H NMR (400 MHz, DMSO-$d_6$) δ 10.08 (s, 1H), 9.56 (s, 1H), 8.84 (s, 1H), 8.25 (s, 1H), 8.08 (s, 1H), 8.03 (d, J=2.2 Hz, 1H), 7.81 (t, J=7.2 Hz, 2H), 7.76 (dd, J=8.3, 2.3 Hz, 1H), 7.57 (t, J=7.8 Hz, 1H), 7.11 (dd, J=10.9, 8.4 Hz, 2H), 6.99 (d, J=8.0 Hz, 2H), 4.01 (d, J=12.9 Hz, 2H), 3.65 (t, J=11.8, 10.8 Hz, 4H), 3.57 (d, J=12.4 Hz, 2H), 3.36 (d, J=10.7 Hz, 2H), 3.15 (d, J=11.0 Hz, 2H). $^{19}$F NMR (376 MHz, DMSO-$d_6$) δ-57.14 (s, 3F), −73.55 (s, 3F). LCMS RT (Method 1)=4.420 min, m/z 527.1 [M+H+].

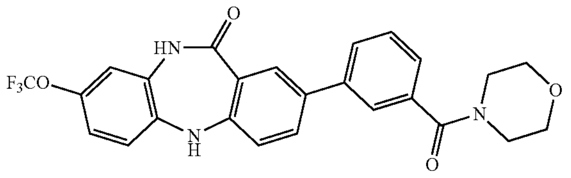

Chemical Formula: $C_{25}H_{20}F_3N_3O_4$
Exact Mass: 483.14
Molecular Weight: 483.45

2-(3-(Morpholine-4-carbonyl)phenyl)-8-(trifluoromethoxy)-5,10-dihydro-11H-dibenzo[b,e][1,4]diazepin-11-one (NCGC00355558): Prepared following general Procedure B; HATU (20.2 mg, 0.053 mmol), 3-(1 1-oxo-8-(trifluoromethoxy)-10,11-dihydro-5H-dibenzo[b,e][1,4]diazepin-2-yl)benzoic acid AED005-064 (20.0 mg, 0.048 mmol), morpholine (4.64 μL, 0.053 mmol), DIPEA (21.0 L, 0.121 mmol) in DMF (1.00 mL) to afford the title compound (11.7 mg, 40.6% yield). $^{1}$H NMR (400 MHz, DMSO-$d_6$) δ 10.04 (s, 1H), 8.21 (s, 1H), 7.98-7.93 (m, 1H), 7.72 (dt, J=8.5, 1.7 Hz, 1H), 7.69-7.63 (m, 1H), 7.58 (q, J=1.5 Hz, 1H), 7.49 (t, J=7.7 Hz, 1H), 7.33 (dt, J=7.6, 1.3 Hz, 1H), 7.11-7.05 (m, 2H), 6.97 (d, J=7.0 Hz, 2H), 3.60 (s, 8H). $^{19}$F NMR (376 MHz, DMSO-$d_6$) δ-57.14 (s, 3F). LCMS RT (Method 1)=5.208 min, m/z 484.1 [M+H+].

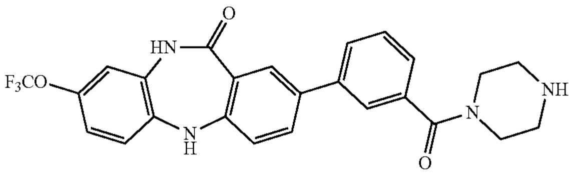

Chemical Formula: $C_{25}H_{21}F_3N_4O_3$
Exact Mass: 482.16
Molecular Weight: 482.46

2-(3-(Piperazine-1-carbonyl)phenyl)-8-(trifluoromethoxy)-5,10-dihydro-11H-dibenzo[b,e][1,4]diazepin-11-one (NCGC00355569): Prepared following general Procedure B; HATU (20.2 mg, 0.053 mmol), 3-(11-oxo-8-(trifluoromethoxy)-10,11-dihydro-5H-dibenzo[b,e][1,4]diazepin-2-yl)benzoic acid AED005-064 (20.0 mg, 0.048 mmol), N-Boc-piperazine (9.89 mg, 0.053 mmol), DIPEA (21.0 L, 0.121 mmol) in DMF (1.00 mL). The reaction mixture was allowed to stir at RT for 18 hr, and then was added $CH_2Cl_2$ (1.00 mL) and trifluoroacetic acid (1.00 mL, 12.9 mmol). The reaction was stirred for 12 h at RT, after which LC-MS showed complete Boc deprotection. The pH of the reaction mixture was adjusted to −10-11 with 1M NaOH and the mixture extracted with $CH_2Cl_2$. The organic layer was washed with brine, dried over $MgSO_4$, filtered and concentrated. Crude mixture was subjected to purification via standard HPLC conditions using a gradient of 10-100% ACN in $H_2O$ with 0.1% TFA to afford the title compound as the TFA salt (10.9 mg, 37.8% yield). $^{1}$H NMR (400 MHz, DMSO-$d_6$) δ 10.06 (s, 1H), 8.79 (s, 2H), 8.24 (s, 1H), 7.99 (d, J=2.4 Hz, 1H), 7.73 (td, J=7.9, 7.3, 1.8 Hz, 2H), 7.66 (s, 1H), 7.53 (t, J=7.7 Hz, 1H), 7.40 (dt, J=7.5, 1.3 Hz, 1H), 7.14-7.05 (m, 2H), 6.99 (d, J=8.0 Hz, 2H), 3.67 (br s, 4H), 3.17 (br s, 4H). $^{19}$F NMR (376 MHz, DMSO-$d_6$) δ-57.14 (s, 3F), −73.45 (s, 3F). LCMS RT (Method 1)=4.351 min, m/z 482.8 [$M^+$].

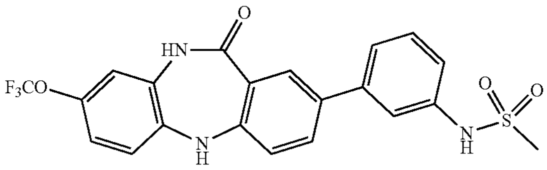

Chemical Formula: $C_{21}H_{16}F_3N_3O_4S$
Exact Mass: 463.08
Molecular Weight: 463.43

N-(3-(11-Oxo-8-(trifluoromethoxy)-10,11-dihydro-SH-dibenzo[b,e][1,4]diazepin-2-yl)phenyl)methanesulfonamide (NCGC00355551): Prepared following general Procedure A; 2-bromo-8-(trifluoromethoxy)-5H-dibenzo[b,e][1,4]diazepin-11(10H)-one AED007-099 (40.0 mg, 0.107 mmol), (3-(methylsulfonamido)phenyl)boronic acid (23.1 mg, 0.107 mmol), 2M $Na_2CO_3$ (212 L, 0.424 mmol), $Pd(PPh_3)_4$(6.19 mg, 5.36 μmol) in DME (4.00 mL) to afford the title compound (32.3 mg, 52.1% yield). $^{1}$H NMR (400 MHz, DMSO-$d_6$) δ 10.05 (s, 1H), 9.78 (s, 1H), 8.22 (s, 1H), 7.92 (d, J=2.3 Hz, 1H), 7.65 (dt, J=8.4, 1.6 Hz, 1H), 7.44-7.35 (m, 2H), 7.33 (dd, J=7.9, 1.5 Hz, 1H), 7.19 (ddd, J=8.0, 2.3, 1.2 Hz, 1H), 7.13-7.05 (m, 2H), 6.98 (d, J=7.0 Hz, 2H), 3.01 (d, J=1.0 Hz, 3H). $^{19}$F NMR (376 MHz, DMSO-$d_6$) δ-57.14 (s, 3F). LCMS RT (Method 1)=5.328 min, m/z 464.0 [M+H+].

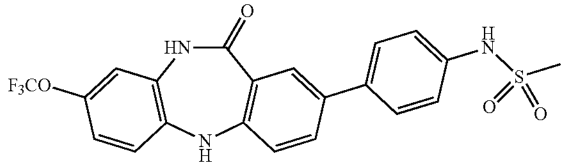

Chemical Formula: $C_{21}H_{16}F_3N_3O_4S$
Exact Mass: 463.08
Molecular Weight: 463.43

N-(4-(11-oxo-8-(trifluoromethoxy)-10,11-dihydro-SH-dibenzo[b,e][1,4]diazepin-2-yl)phenyl)methanesulfonamide (NCGC00355552): Prepared following general Procedure A; 2-bromo-8-(trifluoromethoxy)-SH-dibenzo[b,e][1,4]diazepin-11(10H)-one AED007-099 (40.0 mg, 0.107 mmol), (4-(methylsulfonamido)phenyl)boronic acid (23.1 mg, 0.107 mmol), 2M $Na_2CO_3$ (212 L, 0.424 mmol), $Pd(PPh_3)_4$(6.19 mg, 5.36 μmol) in DME (4.00 mL) to afford the title compound (38.5 mg, 62.2% yield). $^{1}$H NMR (400 MHz, DMSO-$d_6$) δ 10.03 (s, 1H), 9.79 (s, 1H), 8.17 (s, 1H), 7.92 (d, J=2.4 Hz, 1H), 7.66 (dd, J=6.6, 2.0 Hz, 1H), 7.57 (dd, J=7.8, 1.7 Hz, 2H), 7.31-7.23 (m, 2H), 7.12-7.03 (m, 2H), 6.98 (d, J=7.3 Hz, 2H), 3.00 (d, J=1.0 Hz, 3H). $^{19}$F NMR (376 MHz, DMSO-$d_6$) δ-57.14 (s, 3F). LCMS RT (Method 1)=5.213 min, m/z 464.0 [M+H+].

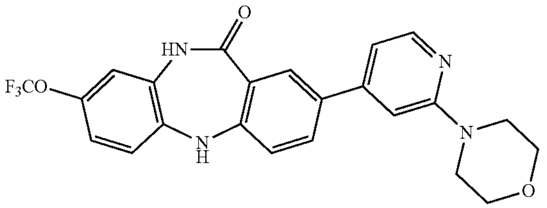

Chemical Formula: $C_{23}H_{19}F_3N_4O_3$
Exact Mass: 456.14
Molecular Weight: 456.43

2-(2-Morpholinopyridin-4-yl)-8-(trifluoromethoxy)-5,10-dihydro-11H-dibenzo[b,e][1,4]diazepin-11-one (NCGC00481508): Prepared following general Procedure A; 2-bromo-8-(trifluoromethoxy)-5H-dibenzo[b,e][1,4]diazepin-11(10H)-one AED007-099 (40.9 mg, 0.110 mmol), 4-(4-(4,4,5,5-tetramethyl-1,3,2-dioxaborolan-2-yl)pyridin-2-yl)morpholine (35.0 mg, 0.121 mmol), 2M $Na_2CO_3$ (219 L, 0.439 mmol), $Pd(PPh_3)_4$(6.34 mg, 5.48 μmol) in DME (4.00 mL) to afford the title compound as the TFA salt (32.8 mg, 65.6% yield). $^{1}$H NMR (400 MHz, DMSO-$d_6$) δ 10.11 (s, 1H), 8.41 (s, 1H), 8.14-8.08 (m, 2H), 7.87 (dd, J=8.6, 2.3 Hz, 1H), 7.19 (s, 1H), 7.15-7.03 (m, 3H), 7.03-6.95 (m, 2H), 3.74 (dd, J=5.9, 3.8 Hz, 4H), 3.59 (d, J=5.0 Hz, 4H). $^{19}$F NMR (376 MHz, DMSO-$d_6$) δ-57.16 (s, 3F), −74.19 (s, 3F). LCMS RT (Method 1)=4.165 min, m/z 457.2 [$M+H^+$].

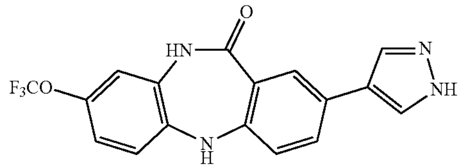

Chemical Formula: $C_{17}H_{11}F_3N_4O_2$
Exact Mass: 360.08
Molecular Weight: 460.30

2-(1H-Pyrazol-4-yl)-8-(trifluoromethoxy)-5,10-dihydro-11H-dibenzo[b,e][1,4]diazepin-11-one (NCGC00355553): Prepared following general Procedure A; 2-bromo-8-(trifluoromethoxy)-5H-dibenzo[b,e][1,4]diazepin-11(10H)-one AED007-099 (40.0 mg, 0.107 mmol), (1H-pyrazol-4-yl) boronic acid, HCl (15.9 mg, 0.107 mmol), 2M $Na_2CO_3$ (219 L, 0.439 mmol), $Pd(PPh_3)_4$(6.34 mg, 5.48 μmol) in DME (4.00 mL) to afford the title compound as the TFA salt (11.8 mg, 28.2% yield). $^{1}$H NMR (400 MHz, DMSO-$d_6$) δ 12.88 (s, 1H), 10.01 (s, 1H), 8.10 (s, 1H), 8.00 (s, 1H), 7.85 (dd, J=2.3, 1.0 Hz, 1H), 7.82 (s, 1H), 7.60 (ddd, J=8.3, 2.3, 1.0

Hz, 1H), 7.10-7.03 (m, 1H), 7.03-6.93 (m, 3H). $^{19}$F NMR (376 MHz, DMSO-$d_6$) δ-57.14 (s, 3F), −74.15 (s, 3F). LCMS RT (Method 1)=4.585 min, m/z 361.1 [M+H$^+$].

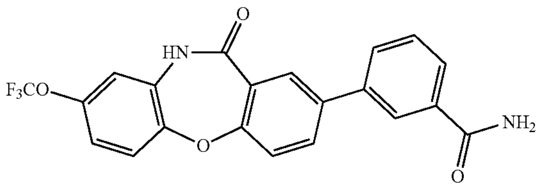

Chemical Formula: $C_{21}H_{13}F_3N_2O_4$
Exact Mass: 414.08
Molecular Weight: 414.34

3-(11-Oxo-8-(trifluoromethoxy)-10,11-dihydrodibenzo[b,f][1,4]oxazepin-2-yl)benzamide (NCGC00356842): Prepared following general Procedure D; 2-bromo-8-(trifluoromethoxy)dibenzo[b,f][1,4]oxazepin-11(10H)-one AED013-066 (40.0 mg, 0.107 mmol), (3-carbamoylphenyl) boronic acid (26.5 mg, 0.161 mmol), $K_3PO_4$ (45.5 mg, 0.214 mmol), XPhos Pd(crotyl)Cl (7.22 mg, 10.7 μmol) in 4:1 dioxane:$H_2O$ (1.25 mL) to afford the title compound (27.5 mg, 62.1% yield). $^1$H NMR (400 MHz, DMSO-$d_6$) δ 10.76 (s, 1H), 8.16 (t, J=1.8 Hz, 1H), 8.13 (s, 1H), 8.09 (d, J=2.4 Hz, 1H), 8.01 (dd, J=8.5, 2.5 Hz, 1H), 7.88 (ddd, J=7.7, 1.7, 1.1 Hz, 1H), 7.82 (ddd, J=7.8, 1.9, 1.1 Hz, 1H), 7.60-7.47 (m, 3H), 7.44 (s, 1H), 7.24-7.13 (m, 2H). $^{19}$F NMR (376 MHz, DMSO-$d_6$) δ-57.13 (s, 3F). LCMS RT (Method 1)=5.148 min, m/z 829.1 [2M$^+$].

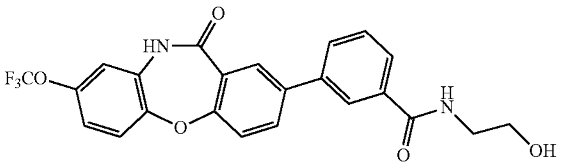

Chemical Formula: $C_{23}H_{17}F_3N_2O_5$
Exact Mass: 458.11
Molecular Weight: 458.39

N-(2-Hydroxyethyl)-3-(11-oxo-8-(trifluoromethoxy)-10,11-dihydrodibenzo[b,f][1,4]oxazepin-2-yl)benzamide (NCGC00356688): Prepared following general Procedure B; HATU (40.3 mg, 0.106 mmol), 3-(11-oxo-8-(trifluoromethoxy)-10,11-dihydrodibenzo[b,f][1,4]oxazepin-2-yl) benzoic acid (AED007-015) (40 mg, 0.096 mmol), 2-aminoethanol (6.39 μL, 0.106 mmol) and DIPEA (42.0 L, 0.241 mmol) in DMF (1.00 mL) to afford the title compound (25.6 mg, 58.0% yield). $^1$H NMR (400 MHz, DMSO-$d_6$) δ 10.76 (s, 1H), 8.61 (t, J=5.6 Hz, 1H), 8.13 (d, J=1.6 Hz, 1H), 8.09 (dd, J=2.5, 1.0 Hz, 1H), 8.01 (ddd, J=8.4, 2.5, 1.0 Hz, 1H), 7.86 (dq, J=7.7, 1.2 Hz, 1H), 7.84-7.78 (m, 1H), 7.60-7.47 (m, 3H), 7.21-7.14 (m, 2H), 4.74 (td, J=5.6, 1.0 Hz, 1H), 3.53 (q, J=6.0 Hz, 2H), 3.36 (q, J=6.1 Hz, 2H). $^{19}$F NMR (376 MHz, DMSO-$d_6$) δ-57.12 (s, 3F). LCMS RT (Method 1)=5.044 min, m/z 458.8 [M$^+$].

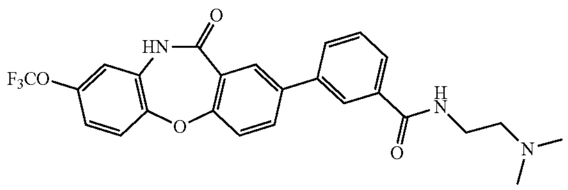

Chemical Formula: $C_{25}H_{22}F_3N_3O_4$
Exact Mass: 485.16
Molecular Weight: 485.46

N-(2-(Dimethylamino)ethyl)-3-(11-oxo-8-(trifluoromethoxy)-10,11-dihydrodibenzo[b,f][1,4]oxazepin-2-yl) benzamide (NCGC00356689): Prepared following general Procedure B; HATU (40.3 mg, 0.106 mmol), 3-(11-oxo-8-(trifluoromethoxy)-10,11-dihydrodibenzo[b,f][1,4]oxazepin-2-yl)benzoic acid (AED007-015) (40 mg, 0.096 mmol), N1,N1-dimethylethane-1,2-diamine (12.0 L, 0.106 mmol) and DIPEA (42.0 L, 0.241 mmol) in DMF (1.00 mL) to afford the title compound as the TFA salt (25.6 mg, 58.0% yield). $^1$H NMR (400 MHz, DMSO-$d_6$) δ 10.78 (s, 1H), 9.40 (s, 1H), 8.86 (t, J=5.7 Hz, 1H), 8.14 (d, J=1.8 Hz, 1H), 8.08 (dd, J=2.5, 0.9 Hz, 1H), 8.00 (ddd, J=8.5, 2.5, 1.0 Hz, 1H), 7.88 (ddd, J=9.4, 7.9, 1.5 Hz, 2H), 7.61 (t, J=7.7 Hz, 1H), 7.55-7.47 (m, 2H), 7.22-7.15 (m, 2H), 3.64 (q, J=5.9 Hz, 2H), 3.27 (t, J=5.5 Hz, 2H), 2.85 (s, 6H). $^{19}$F NMR (376 MHz, DMSO-$d_6$) δ-57.12 (s, 3F), −73.45 (s, 3F). LCMS RT (Method 1)=4.707 min, m/z 485.8 [M$^+$].

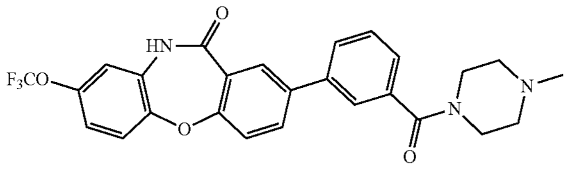

Chemical Formula: $C_{26}H_{22}F_3N_3O_4$
Exact Mass: 497.16
Molecular Weight: 497.47

2-(3-(4-Methylpiperazine-1-carbonyl)phenyl)-8-(trifluoromethoxy)dibenzo[b,f][1,4]oxazepin-11(10H)-one (NCGC00356690): Prepared following general Procedure B; HATU (40.3 mg, 0.106 mmol), 3-(11-oxo-8-(trifluoromethoxy)-10,11-dihydrodibenzo[b,f][1,4]oxazepin-2-yl) benzoic acid (AED007-015) (40 mg, 0.096 mmol), 1-methylpiperazine (12.0 L, 0.106 mmol) and DIPEA (42.0 L, 0.241 mmol) in DMF (1.00 mL) to afford the title compound as the TFA salt (27.0 mg, 45.8% yield). $^1$H NMR (400 MHz, DMSO-$d_6$) δ 10.76 (s, 1H), 9.95 (s, 1H), 8.02 (d, J=2.5 Hz, 1H), 7.97 (dd, J=8.4, 2.5 Hz, 1H), 7.80 (dd, J=7.9, 1.7 Hz, 1H), 7.71 (d, J=1.8 Hz, 1H), 7.58 (t, J=7.7 Hz, 1H), 7.55-7.47 (m, 2H), 7.46 (dd, J=7.6, 1.4 Hz, 1H), 7.21-7.15 (m, 2H), 3.63 (s, 4H), 3.09 (s, 4H), 2.79 (s, 3H). $^{19}$F NMR (376 MHz, DMSO-$d_6$) δ-57.12 (s, 3F), −73.48 (s, 3F). LCMS RT (Method 1)=4.612 min, m/z 497.8 [$M^+$].

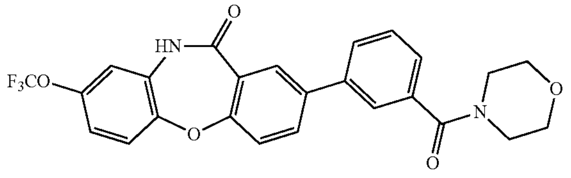

Chemical Formula: $C_{25}H_{19}F_3N_2O_5$
Exact Mass: 484.12
Molecular Weight: 484.43

2-(3-(Morpholine-4-carbonyl)phenyl)-8-(trifluoromethoxy)dibenzo[b,f][1,4]oxazepin-11(10H)-one (NCGC00356745): Prepared following general Procedure B; HATU (40.3 mg, 0.106 mmol), 3-(11-oxo-8-(trifluoromethoxy)-10,11-dihydrodibenzo[b,f][1,4]oxazepin-2-yl) benzoic acid (AED007-015) (40 mg, 0.096 mmol), morpholine (9.27 L, 0.106 mmol) and DIPEA (42.0 L, 0.241 mmol) in DMF (1.00 mL) to afford the title compound (22.3 mg, 47.8% yield). $^1$H NMR (400 MHz, DMSO-$d_6$) δ 10.75 (s, 1H), 8.02 (dd, J=2.5, 0.9 Hz, 1H), 7.97 (ddd, J=8.4, 2.5, 1.0 Hz, 1H), 7.75 (ddt, J=7.7, 2.2, 1.1 Hz, 1H), 7.67 (q, J=1.4 Hz, 1H), 7.59-7.45 (m, 3H), 7.41 (dq, J=7.5, 1.2 Hz, 1H), 7.21-7.13 (m, 2H), 3.62 (s, 6H), 3.45-3.18 (m, 2H). $^{19}$F NMR (376 MHz, DMSO-$d_6$) δ-57.12 (s, 3F). LCMS RT (Method 1)=5.413 min, m/z 484.7 [$M^+$].

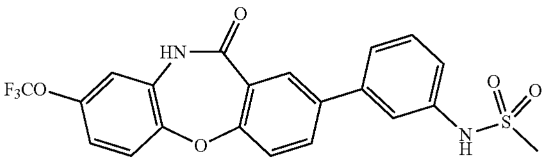

Chemical Formula: $C_{21}H_{15}F_3N_2O_5S$
Exact Mass: 464.07
Molecular Weight: 464.42

N-(3-(11-Oxo-8-(trifluoromethoxy)-10,11-dihydrodibenzo [b,f][1,4]oxazepin-2-yl)phenyl)methanesulfonamide (NCGC00356665): Prepared following general Procedure A; 2-bromo-8-(trifluoromethoxy)dibenzo[b,f][1,4]oxazepin-11(10H)-one AED013-066 (40.0 mg, 0.107 mmol), (3-(methylsulfonamido)phenyl)boronic acid (23.1 mg, 0.107 mmol), 2M $Na_2CO_3$ (212 L, 0.424 mmol), $Pd(PPh_3)_4$(6.19 mg, 5.36 µmol) in DME (4.00 mL) to afford the title compound (24.4 mg, 49.1% yield). $^1$H NMR (400 MHz, DMSO-$d_6$) δ 10.74 (s, 1H), 9.84 (s, 1H), 7.95 (dd, J=2.5, 1.0 Hz, 1H), 7.88 (ddd, J=8.5, 2.6, 1.0 Hz, 1H), 7.54-7.35 (m, 5H), 7.24 (ddt, J=7.8, 2.4, 1.2 Hz, 1H), 7.21-7.13 (m, 2H), 3.03 (d, J=1.0 Hz, 3H).$^{19}$F NMR (376 MHz, DMSO-$d_6$) δ-57.12 (s, 3F). LCMS RT (Method 1)=5.606 min, m/z 465.1 [$M+H^+$].

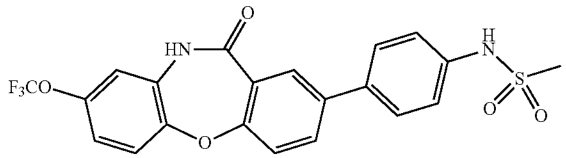

Chemical Formula: $C_{21}H_{16}F_3N_2O_5S$
Exact Mass: 464.07
Molecular Weight: 464.42

N-(4-(11-Oxo-8-(trifluoromethoxy)-10,11-dihydrodibenzo [b,f][1,4]oxazepin-2-yl)phenyl)methanesulfonamide (NCGC00356666): Prepared following general Procedure A; 2-bromo-8-(trifluoromethoxy)dibenzo[b,f][1,4]oxazepin-11(10H)-one AED013-066 (40.0 mg, 0.107 mmol), (4-(methylsulfonamido)phenyl)boronic acid (23.1 mg, 0.107 mmol), 2M $Na_2CO_3$ (212 L, 0.424 mmol), $Pd(PPh_3)_4$(6.19 mg, 5.36 µmol) in DME (4.00 mL) to afford the title compound (28.9 mg, 58.2% yield). $^1$H NMR (400 MHz, DMSO-$d_6$) δ 10.72 (s, 1H), 9.88 (s, 1H), 7.96 (dd, J=2.5, 1.0 Hz, 1H), 7.89 (ddd, J=8.5, 2.5, 1.0 Hz, 1H), 7.68-7.60 (m, 2H), 7.54-7.48 (m, 1H), 7.45 (dd, J=8.4, 1.0 Hz, 1H), 7.34-7.26 (m, 2H), 7.20-7.13 (m, 2H), 3.02 (d, J=1.0 Hz, 3H). $^{19}$F NMR (376 MHz, DMSO-$d_6$) δ-57.12 (s, 3F). LCMS RT (Method 1)=5.540 min, m/z 465.1 [$M+H^+$].

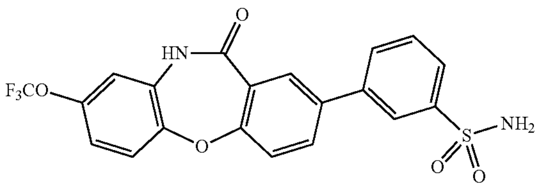

Chemical Formula: $C_{20}H_{13}F_3N_2O_5S$
Exact Mass: 450.05
Molecular Weight: 450.39

3-(11-Oxo-8-(trifluoromethoxy)-10,11-dihydrodibenzo[b,f][1,4]oxazepin-2-yl)benzenesulfonamide (NCGC00371364): Prepared following general Procedure A; 2-bromo-8-(trifluoromethoxy)dibenzo[b,f][1,4]oxazepin-11(10H)-one AED013-066 (40.0 mg, 0.107 mmol), (3-sulfamoylphenyl) boronic acid (21.5 mg, 0.107 mmol), 2M $Na_2CO_3$ (212 L, 0.424 mmol), $Pd(PPh_3)_4$(6.19 mg, 5.36 µmol) in DME (4.00 mL) to afford the title compound (27.3 mg, 56.7% yield). $^1$H NMR (400 MHz, DMSO-$d_6$) δ 10.78 (s, 1H), 8.11 (t, J=1.8 Hz, 1H), 8.08 (d, J=2.5 Hz, 1H), 7.99 (dd, J=8.5, 2.5 Hz, 1H), 7.92 (dt, J=7.8, 1.4 Hz, 1H), 7.83 (dt, J=7.8, 1.3 Hz, 1H), 7.67 (t, J=7.8 Hz, 1H), 7.53 (dd, J=9.1, 7.0 Hz, 2H), 7.42 (s, 2H), 7.21-7.14 (m, 2H). $^{19}$F NMR (376 MHz, DMSO-$d_6$) δ-57.12 (s, 3F). LCMS RT (Method 1)=5.187 min, m/z 451.1 [$M+H^+$].

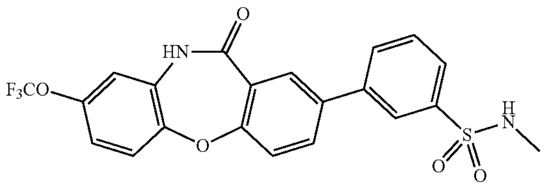

Chemical Formula: $C_{21}H_{15}F_3N_2O_5S$
Exact Mass: 464.07
Molecular Weight: 464.42

N-Methyl-3-(11-oxo-8-(trifluoromethoxy)-10,11-dihydrodibenzo[b,f][1,4]oxazepin-2-yl)benzenesulfonamide (NCGC00373056): Prepared following general Procedure A; 2-bromo-8-(trifluoromethoxy)dibenzo[b,f][1,4]oxazepin-11(10H)-one AED013-066 (40.0 mg, 0.107 mmol), (3-(N-methylsulfamoyl)phenyl)boronic acid (23.0 mg, 0.107 mmol), 2M $Na_2CO_3$ (212 L, 0.424 mmol), $Pd(PPh_3)_4$(6.19 mg, 5.36 μmol) in DME (4.00 mL) to afford the title compound (25.4 mg, 59.7% yield). $^1$H NMR (400 MHz, DMSO-$d_6$) δ 10.79 (s, 1H), 8.06 (d, J=2.5 Hz, 1H), 8.03-7.95 (m, 3H), 7.79 (dt, J=7.8, 1.3 Hz, 1H), 7.71 (t, J=7.7 Hz, 1H), 7.53 (dt, J=8.0, 4.9 Hz, 3H), 7.18 (dddd, J=5.5, 4.3, 2.9, 1.6 Hz, 2H), 2.43 (d, J=5.0 Hz, 3H). $^{19}$F NMR (376 MHz, DMSO-$d_6$) δ-57.13 (s, 3F). LCMS RT (Method 1)=5.726 min, m/z 929.1 [$2M^+$].

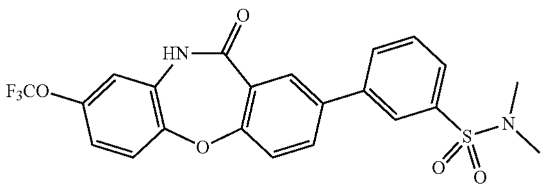

Chemical Formula: $C_{22}H_{17}F_3N_2O_5S$
Exact Mass: 478.08
Molecular Weight: 478.44

N,N-Dimethyl-3-(11-oxo-8-(trifluoromethoxy)-10,11-dihydrodibenzo[b,f][1,4]oxazepin-2-yl)benzenesulfonamide (NCGC00373057): Prepared following general Procedure A; 2-bromo-8-(trifluoromethoxy)dibenzo[b,f][1,4]oxazepin-11(10H)-one AED013-066 (40.0 mg, 0.107 mmol), (3-(N,N-dimethylsulfamoyl)phenyl)boronic acid (24.5 mg, 0.107 mmol), 2M $Na_2CO_3$ (212 L, 0.424 mmol), $Pd(PPh_3)_4$(6.19 mg, 5.36 μmol) in DME (4.00 mL) to afford the title compound (25.5 mg, 49.8% yield). $^1$H NMR (400 MHz, DMSO-$d_6$) δ 10.78 (s, 1H), 8.05-7.99 (m, 3H), 7.94-7.88 (m, 1H), 7.80-7.72 (m, 2H), 7.56-7.52 (m, 1H), 7.51 (s, 1H), 7.22-7.14 (m, 2H), 2.65 (s, 6H). $^{19}$F NMR (376 MHz, DMSO-$d_6$) δ-57.14 (s, 3F). LCMS RT (Method 1)=6.123 min, m/z 957.1 [$2M^+$].

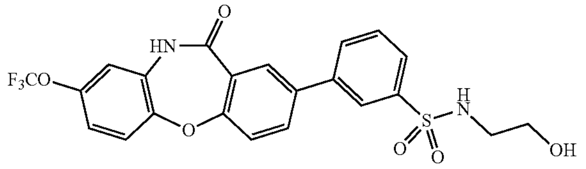

Chemical Formula: $C_{22}H_{17}F_3N_2O_6S$
Exact Mass: 494.08
Molecular Weight: 494.44

N-(2-Hydroxyethyl)-3-(11-oxo-8-(trifluoromethoxy)-10,11-dihydrodibenzo[b,f][1,4]oxazepin-2-yl)benzenesulfonamide (NCGC00373064): Prepared following general Procedure A; 2-bromo-8-(trifluoromethoxy)dibenzo[b,f][1,4]oxazepin-11(10H)-one AED013-066 (40.0 mg, 0.107 mmol), (3-(N-(2-hydroxyethyl)sulfamoyl)phenyl)boronic acid (26.2 mg, 0.107 mmol), 2M $Na_2CO_3$ (212 L, 0.424 mmol), $Pd(PPh_3)_4$(6.19 mg, 5.36 μmol) in DME (4.00 mL) to afford the title compound (30.0 mg, 56.7% yield). $^1$H NMR (400 MHz, DMSO-$d_6$) δ 10.79 (s, 1H), 8.06 (d, J=2.3 Hz, 2H), 8.00 (dd, J=8.4, 2.5 Hz, 1H), 7.98-7.92 (m, 1H), 7.80 (dt, J=7.9, 1.3 Hz, 1H), 7.74-7.65 (m, 2H), 7.54 (d, J=3.7 Hz, 1H), 7.52 (d, J=4.9 Hz, 1H), 7.18 (dddd, J=5.7, 4.6, 3.1, 1.6 Hz, 2H), 4.67 (s, 1H), 3.37 (t, J=6.2 Hz, 2H), 2.81 (q, J=6.2 Hz, 2H). $^{19}$F NMR (376 MHz, DMSO-$d_6$) δ-57.13 (s, 3F). LCMS RT (Method 1)=5.284 min, m/z 989.1 [$2M^+$].

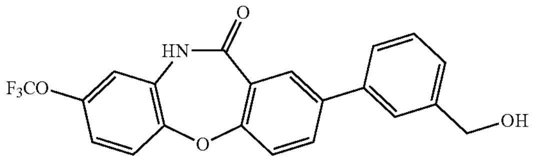

Chemical Formula: $C_{21}H_{15}F_3NO_4$
Exact Mass: 401.09
Molecular Weight: 401.34

2-(3-(Hydroxymethyl)phenyl)-8-(trifluoromethoxy)dibenzo[b,f][1,4]oxazepin-11(10H)-one (NCGC00415061): Prepared following general Procedure D; 2-bromo-8-(trifluoromethoxy)dibenzo[b,f][1,4]oxazepin-11(10H)-one AED013-066 (40.0 mg, 0.107 mmol), (3-(hydroxymethyl)phenyl)boronic acid (24.37 mg, 0.160 mmol), $K_3PO_4$ (45.4 mg, 0.214 mmol), XPhos Pd(crotyl)Cl (7.22 mg, 10.7 μmol) in 4:1 dioxane:$H_2O$ (1.25 mL) to afford the title compound (26.5 mg, 61.8% yield). $^1$H NMR (400 MHz, DMSO-$d_6$) δ

10.74 (s, 1H), 8.00 (d, J=2.4 Hz, 1H), 7.92 (dd, J=8.4, 2.5 Hz, 1H), 7.62-7.59 (m, 1H), 7.54-7.45 (m, 3H), 7.43 (t, J=7.6 Hz, 1H), 7.33 (dt, J=7.5, 1.4 Hz, 1H), 7.19-7.13 (m, 2H), 5.26 (t, J=5.8 Hz, 1H), 4.57 (d, J=5.6 Hz, 2H). $^{19}$F NMR (376 MHz, DMSO-$d_6$) δ -57.12 (s, 3F). LCMS RT (Method 1)=5.130 min, m/z 402.0 [M+H$^+$].

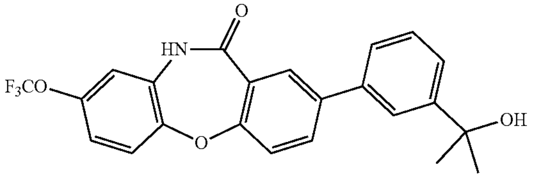

Chemical Formula: $C_{23}H_{18}F_3NO_4$
Exact Mass: 429.12
Molecular Weight: 429.40

2-(3-(2-Hydroxypropan-2-yl)phenyl)-8-(trifluoromethoxy)dibenzo[b,f][1,4]oxazepin-11(10H)-one (NCGC00411876): Prepared following general Procedure A; 2-bromo-8-(trifluoromethoxy)dibenzo[b,f][1,4]oxazepin-11(10H)-one AED013-066 (40.0 mg, 0.107 mmol), (3-(2-hydroxypropan-2-yl)phenyl)boronic acid (21.2 mg, 0.118 mmol), 2M $Na_2CO_3$ (214 μL, 0.428 mmol), $Pd(PPh_3)_4$(6.19 mg, 5.36 μmol) in DME (4.00 mL) to afford the title compound (20.4 mg, 44.4% yield). $^1$H NMR (400 MHz, DMSO-$d_6$) δ 10.74 (s, 1H), 7.99 (d, J=2.4 Hz, 1H), 7.92 (dd, J=8.4, 2.5 Hz, 1H), 7.74 (d, J=1.8 Hz, 1H), 7.54-7.44 (m, 4H), 7.40 (dd, J=8.6, 6.5 Hz, 1H), 7.18 (s, 2H), 5.10 (s, 1H), 1.46 (s, 6H). $^{19}$F NMR (376 MHz, DMSO-$d_6$) δ-57.13 (s, 3F). LCMS RT (Method 1)=6.029 min, m/z 881.2 [2M+Na$^+$].

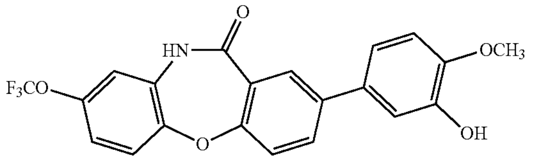

Chemical Formula: $C_{21}H_{14}F_3NO_5$
Exact Mass: 417.08
Molecular Weight: 417.34

2-(3-Hydroxy-4-methoxyphenyl)-8-(trifluoromethoxy)dibenzo[b,f][1,4]oxazepin-11(10H)-one (NCGC00373062): Prepared following general Procedure A; 2-bromo-8-(trifluoromethoxy)dibenzo[b,f][1,4]oxazepin-11(10H)-one AED013-066 (40.0 mg, 0.107 mmol), 2-methoxy-5-(4,4,5,5-tetramethyl-1,3,2-dioxaborolan-2-yl)phenol (26.7 mg, 0.107 mmol), 2M $Na_2CO_3$ (214 L, 0.428 mmol), $Pd(PPh_3)_4$(6.19 mg, 5.36 μmol) in DME (4.00 mL) to afford the title compound (21.7 mg, 48.6% yield). $^1$H NMR (400 MHz, DMSO-$d_6$) δ 10.69 (s, 1H), 9.15 (s, 1H), 7.88 (d, J=2.4 Hz, 1H), 7.81 (dd, J=8.5, 2.5 Hz, 1H), 7.53-7.45 (m, 1H), 7.41 (d, J=8.4 Hz, 1H), 7.20-7.12 (m, 2H), 7.08-7.02 (m, 2H), 7.00 (d, J=9.1 Hz, 1H), 3.80 (s, 3H). $^{19}$F NMR (376 MHz, DMSO-$d_6$) δ-57.13 (s, 3F). LCMS RT (Method 1)=5.820 min, m/z 857.1 [2M+Na$^+$].

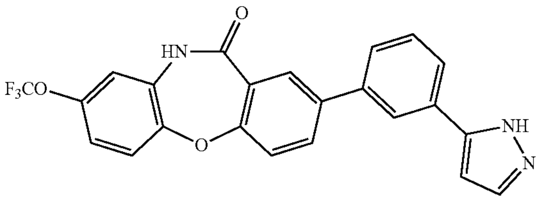

Chemical Formula: $C_{23}H_{14}F_3N_3O_3$
Exact Mass: 437.10
Molecular Weight: 437.38

2-(3-(1H-Pyrazol-5-yl)phenyl)-8-(trifluoromethoxy)dibenzo[b,f][1,4]oxazepin-11(10H)-one (NCGC00411874): Prepared following general Procedure A; 2-bromo-8-(trifluoromethoxy)dibenzo[b,f][1,4]oxazepin-11(10H)-one AED013-066 (40.0 mg, 0.107 mmol), (3-(1H-pyrazol-5-yl)phenyl)boronic acid (22.1 mg, 0.118 mmol), 2M $Na_2CO_3$ (214 μL, 0.428 mmol), $Pd(PPh_3)_4$ (6.19 mg, 5.36 μmol) in DME (4.00 mL) to afford the title compound (24.4 mg, 52.2% yield). $^1$H NMR (400 MHz, DMSO-$d_6$) δ 10.76 (s, 1H), 8.10-8.04 (m, 2H), 8.00 (dd, J=8.4, 2.5 Hz, 1H), 7.82 (d, J=7.6 Hz, 1H), 7.73 (s, 1H), 7.63-7.55 (m, 1H), 7.51 (dd, J=8.9, 7.1 Hz, 3H), 7.22-7.13 (m, 2H), 6.82 (d, J=2.2 Hz, 1H). $^{19}$F NMR (376 MHz, DMSO-$d_6$) δ-57.13 (s, 3F). LCMS RT (Method 1)=5.760 min, m/z 875.2 [2M$^+$].

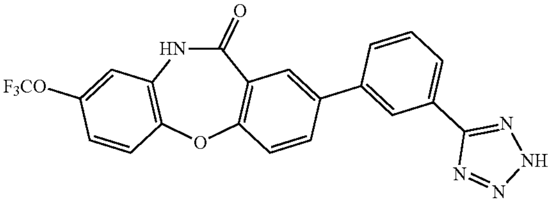

Chemical Formula: $C_{21}H_{12}F_3N_5O_3$
Exact Mass: 439.09
Molecular Weight: 439.35

2-(3-(2H-Tetrazol-5-yl)phenyl)-8-(trifluoromethoxy)dibenzo[b,f][1,4]oxazepin-11(10H)-one (NCGC00420743): Prepared following general Procedure A; 2-bromo-8-(trifluoromethoxy)dibenzo[b,f][1,4]oxazepin-11(10H)-one AED013-066 (40.0 mg, 0.107 mmol), (3-(1H-tetrazol-5-yl)phenyl)boronic acid (22.34 mg, 0.118 mmol), 2M $Na_2CO_3$ (214 μL, 0.428 mmol), $Pd(PPh_3)_4$ (6.19 mg, 5.36 μmol) in DME (4.00 mL) to afford the title compound as the TFA salt (24.4 mg, 52.2% yield). $^1$H NMR (400 MHz, DMSO-$d_6$) δ 10.79 (s, 1H), 8.32 (t, J=1.8 Hz, 1H), 8.13 (d, J=2.5 Hz, 1H), 8.09-8.00 (m, 2H), 7.86 (dt, J=8.1, 1.2 Hz, 1H), 7.69 (t, J=7.8 Hz, 1H), 7.53 (dd, J=9.0, 6.1 Hz, 2H), 7.23-7.15 (m, 2H). $^{19}$F NMR (376 MHz, DMSO-$d_6$) δ-57.12 (s, 3F), −73.44 (s, 3F). LCMS RT (Method 1)=5.593 min, m/z 880.1 [2M+H$^+$].

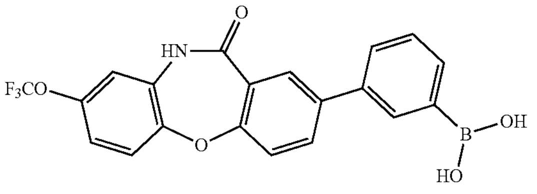

Chemical Formula: $C_{20}H_{13}BF_3NO_5$
Exact Mass: 415.08
Molecular Weight: 415.13

(3-(11-Oxo-8-(trifluoromethoxy)-10,11-dihydrodibenzo[b,f][1,4]oxazepin-2-yl)phenyl)boronic acid (NCGC00415019): Prepared following general Procedure A; 2-bromo-8-(trifluoromethoxy)dibenzo[b,f][1,4]oxazepin-11(10H)-one AED013-066 (40.0 mg, 0.107 mmol), 1,3-phenylenediboronic acid (19.5 mg, 0.118 mmol), 2M $Na_2CO_3$ (214 μL, 0.428 mmol), $Pd(PPh_3)_4$(6.19 mg, 5.36 μmol) in DME (4.00 mL) to afford the title compound (17.4 mg, 39.2% yield). $^1H$ NMR (400 MHz, DMSO-$d_6$) δ 10.74 (s, 1H), 8.18 (s, 2H), 8.11 (s, 1H), 8.05 (d, J=2.4 Hz, 1H), 7.94 (dd, J=8.5, 2.5 Hz, 1H), 7.79 (dt, J=7.4, 1.2 Hz, 1H), 7.70 (ddd, J=7.8, 2.1, 1.2 Hz, 1H), 7.54-7.40 (m, 3H), 7.20-7.14 (m, 2H). $^{19}F$ NMR (376 MHz, DMSO-$d_6$) δ-57.12 (s, 3F). LCMS RT (Method 1)=5.424 min, m/z 831.2

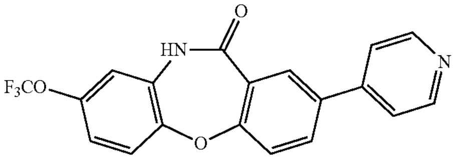

Chemical Formula: $C_{19}H_{11}F_3N_2O_3$
Exact Mass: 372.07
Molecular Weight: 372.30

2-(Pyridin-4-yl)-8-(trifluoromethoxy)dibenzo[b,f][1,4]oxazepin-11(10H)-one (NCGC00371309): Prepared following general Procedure A; 2-bromo-8-(trifluoromethoxy)dibenzo[b,f][1,4]oxazepin-11(10H)-one AED013-066 (40.0 mg, 0.107 mmol), pyridin-4-ylboronic acid (13.1 mg, 0.107 mmol), 2M $Na_2CO_3$ (214 L, 0.428 mmol), $Pd(PPh_3)_4$(6.19 mg, 5.36 μmol) in DME (4.00 mL) to afford the title compound as the TFA salt (24.7 mg, 62.0% yield). $^1H$ NMR (400 MHz, DMSO-$d_6$) δ 10.81 (s, 1H), 8.75 (dd, J=4.8, 2.5 Hz, 2H), 8.22-8.10 (m, 2H), 7.93 (d, J=5.1 Hz, 2H), 7.62-7.49 (m, 2H), 7.19 (t, J=3.4 Hz, 2H). $^{19}F$ NMR (376 MHz, DMSO-$d_6$) δ-57.13 (s, 3F), −74.20 (s, 3F). LCMS RT (Method 1)=4.215 min, m/z 373.1 [M+H$^+$].

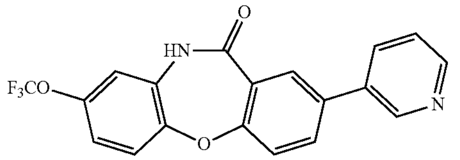

Chemical Formula: $C_{19}H_{11}F_3N_2O_3$
Exact Mass: 372.07
Molecular Weight: 372.30

2-(Pyridin-3-yl)-8-(trifluoromethoxy)dibenzo[b,f][1,4]oxazepin-11(10H)-one (NCGCO00371308): Prepared following general Procedure A; 2-bromo-8-(trifluoromethoxy)dibenzo[b,f][1,4]oxazepin-11(10H)-one AED013-066 (40.0 mg, 0.107 mmol), pyridin-3-ylboronic acid (13.1 mg, 0.107 mmol), 2M $Na_2CO_3$ (214 L, 0.428 mmol), $Pd(PPh_3)_4$(6.19 mg, 5.36 μmol) in DME (4.00 mL) to afford the title compound (24.7 mg, 62.0% yield). $^1H$ NMR (400 MHz, DMSO-$d_6$) δ 10.77 (s, 1H), 8.91 (s, 1H), 8.61 (d, J=4.5 Hz, 1H), 8.14 (dd, J=7.1, 3.4 Hz, 1H), 8.05 (d, J=2.6 Hz, 1H), 8.01 (dd, J=7.5, 4.0 Hz, 1H), 7.53 (dq, J=9.2, 4.9 Hz, 3H), 7.18 (s, 2H). $^{19}F$ NMR (376 MHz, DMSO-$d_6$) δ-57.13 (s, 3F). LCMS RT (Method 1)=4.295 min, m/z 373.1 [M+H$^+$].

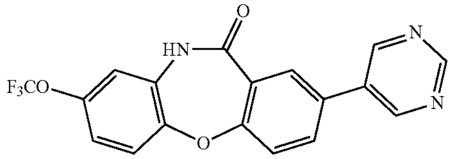

Chemical Formula: $C_{18}H_{10}F_3N_3O_3$
Exact Mass: 373.07
Molecular Weight: 373.29

2-(Pyrimidin-5-yl)-8-(trifluoromethoxy)dibenzo[b,f][1,4]oxazepin-11(10H)-one (NCGC00371310): Prepared following general Procedure A; 2-bromo-8-(trifluoromethoxy)dibenzo[b,f][1,4]oxazepin-11(10H)-one AED013-066 (40.0 mg, 0.107 mmol), pyrimidin-5-ylboronic acid (13.2 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (18.7 mg, 46.9% yield). $^1H$ NMR (400 MHz, DMSO-$d_6$) δ 10.77 (s, 1H), 9.18 (s, 1H), 9.11 (s, 1H), 8.09 (d, J=2.8 Hz, 1H), 8.08-8.01 (m, 1H), 7.58-7.46 (m, 3H), 7.15 (s, 2H). $^{19}F$ NMR (376 MHz, DMSO-$d_6$) δ-57.13 (s, 3F). LCMS RT (Method 1)=4.976 min, m/z 374.1 [M+H$^+$].

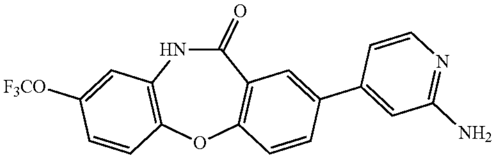

Chemical Formula: $C_{19}H_{12}F_3N_3O_3$
Exact Mass: 387.08
Molecular Weight: 387.32

2-(2-Aminopyridin-4-yl)-8-(trifluoromethoxy)dibenzo[b,f][1,4]oxazepin-11(10H)-one (NCGC00373061): Prepared following general Procedure A; 2-bromo-8-(trifluoromethoxy)dibenzo[b,f][1,4]oxazepin-11(10H)-one AED013-066 (40.0 mg, 0.107 mmol), 4-(4,4,5,5-tetramethyl-1,3,2-dioxaborolan-2-yl)pyridin-2-amine (23.5 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound as the TFA salt (21.9 mg, 40.9% yield). $^1H$ NMR (400 MHz, DMSO-$d_6$) δ 10.83 (s, 1H), 8.12 (d, J=2.4 Hz, 1H), 8.05 (dd, J=8.5, 2.5 Hz, 1H), 8.03-7.99 (m, 1H), 7.75 (s, 2H), 7.58 (d, J=8.5 Hz, 1H), 7.56-7.49 (m, 1H), 7.23-7.15 (m, 4H). $^{19}F$ NMR (376 MHz, DMSO-$d_6$) δ-57.13 (s, 3F), −73.62. LCMS RT (Method 1)=4.263 min, m/z 388.1 [M+H$^+$].

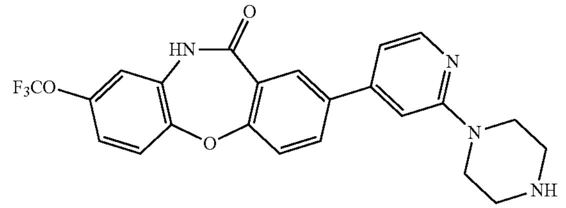

Chemical Formula: $C_{23}H_{19}F_3N_4O_3$
Exact Mass: 456.14
Molecular Weight: 456.43

Figure 2:
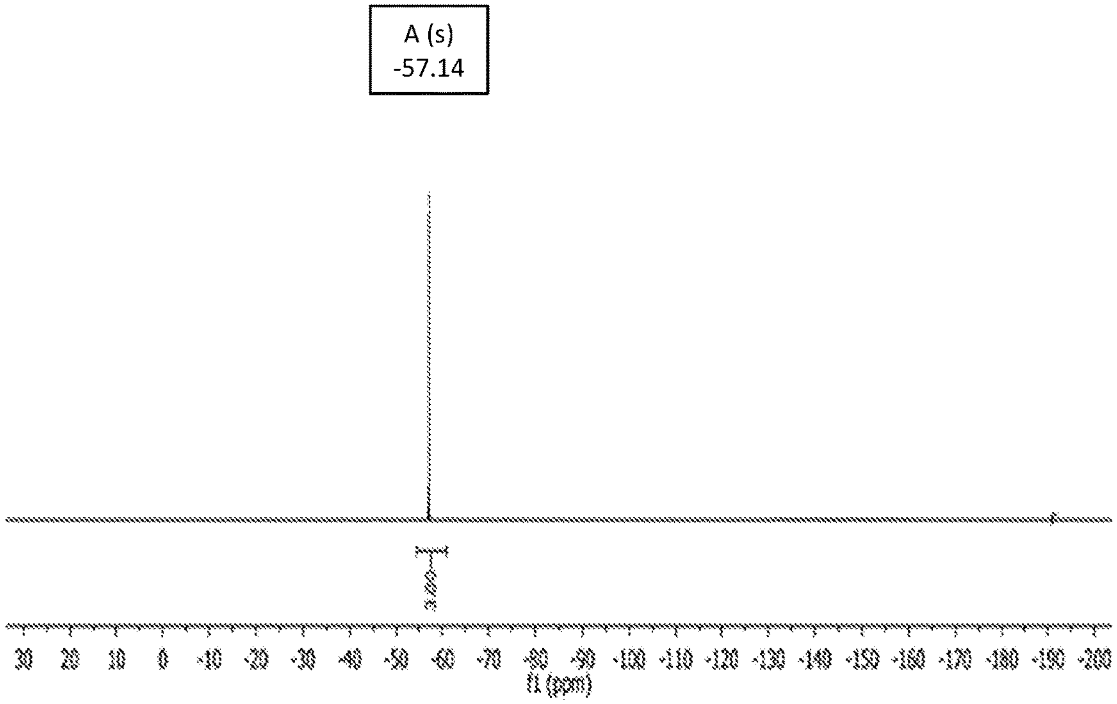
FIG. 2 is a $^{19}$F-NMR spectrum of a representative compound embodiment, NCGC00373060.
Figure 3:
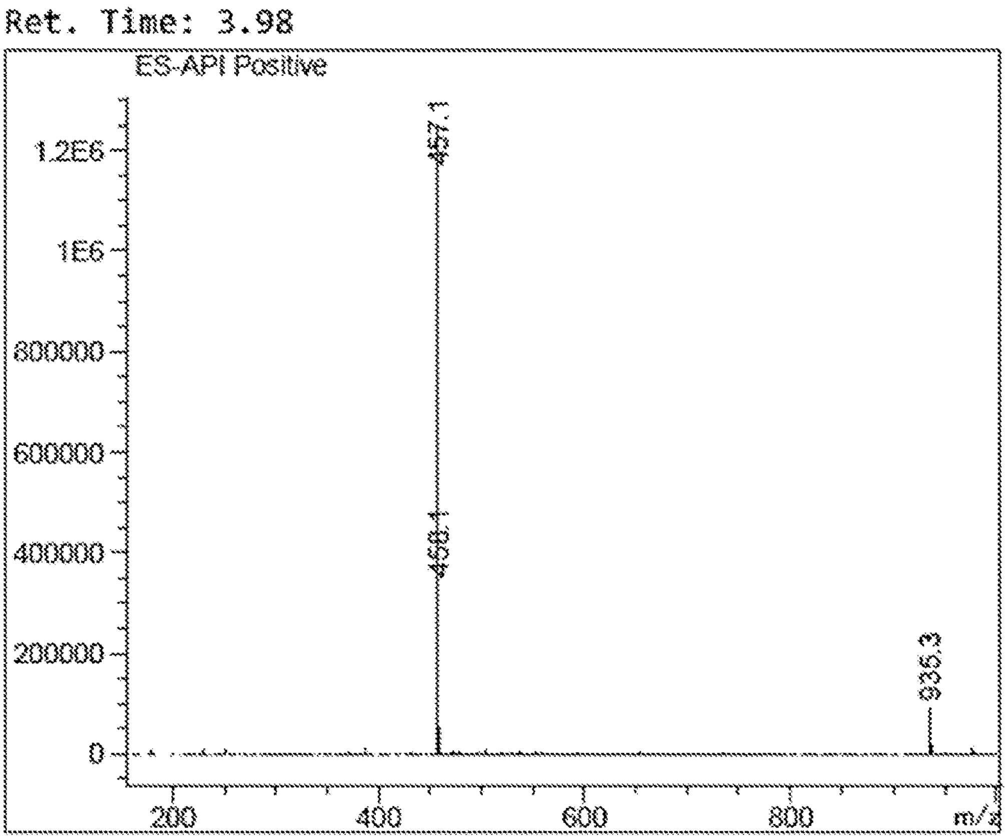
FIG. 3 is a mass spectrum obtained from LC-MS analysis of a representative compound embodiment, NCGC00373060.

2-(2-(Piperazin-1-yl)pyridin-4-yl)-8-(trifluoromethoxy) dibenzo[b,f][1,4]oxazepin-11(10H)-one (NCGC00373060): Prepared following general Procedure A; 2-bromo-8-(trifluoromethoxy)dibenzo[b,f][1,4]oxazepin-11(10H)-one AED013-066 (40.0 mg, 0.107 mmol), (2-(piperazin-1-yl) pyridin-4-yl)boronic acid (22.14 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound as the TFA salt (17.5 mg, 28.7% yield). $^1$H NMR (400 MHz, DMSO-$d_6$) δ 10.79 (s, 1H), 8.74 (s, 2H), 8.22 (d, J=5.3 Hz, 1H), 8.10 (d, J=2.5 Hz, 1H), 8.04 (dd, J=8.4, 2.5 Hz, 1H), 7.53 (d, J=1.2 Hz, 1H), 7.51 (d, J=1.9 Hz, 1H), 7.23-7.14 (m, 3H), 7.04 (dd, J=5.3, 1.4 Hz, 1H), 3.81 (t, J=5.2 Hz, 4H), 3.20 (s, 4H). See FIG. 1. $^{19}$F NMR (376 MHz, DMSO-$d_6$) δ-57.15 (s, 3F), −74.08. See FIG. 2. LCMS RT (Method 1)=4.027 min, m/z 457.1 [M+H$^+$]. See FIG. 3

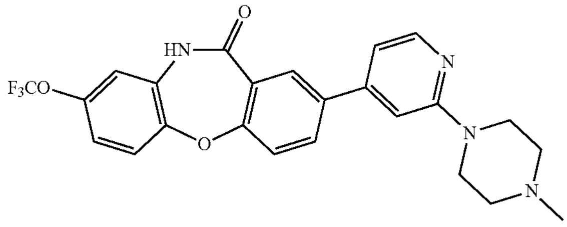

Chemical Formula: $C_{24}H_{21}F_3N_4O_3$
Exact Mass: 470.16
Molecular Weight: 470.45

2-(2-(4-Methylpiperazin-1-yl)pyridin-4-yl)-8-(trifluoromethoxy)dibenzo[b,f][1,4]oxazepin-11(10H)-one (NCGC00373063): Prepared following general Procedure A; 2-bromo-8-(trifluoromethoxy)dibenzo[b,f][1,4]oxazepin-11(10H)-one AED013-066 (40.0 mg, 0.107 mmol), 1-methyl-4-(4-(4,4,5,5-tetramethyl-1,3,2-dioxaborolan-2-yl)pyridin-2-yl)piperazine (32.4 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound as the TFA salt (29.8 mg, 47.7% yield). $^1$H NMR (400 MHz, DMSO-$d_6$) δ 10.79 (s, 1H), 9.71 (s, 1H), 8.23 (d, J=5.3 Hz, 1H), 8.13-8.00 (m, 2H), 7.56-7.48 (m, 2H), 7.23-7.15 (m, 3H), 7.06 (dd, J=5.3, 1.3 Hz, 1H), 4.55 (d, J=13.3 Hz, 2H), 3.51 (d, J=11.3 Hz, 2H), 3.11 (dq, J=22.4, 12.1, 11.5 Hz, 4H), 2.85 (d, J=4.0 Hz, 3H). $^{19}$F NMR (376 MHz, DMSO-$d_6$) δ-57.15 (s, 3F), −74.10. LCMS RT (Method 1)=4.126 min, m/z 471.2 [M+H$^+$].

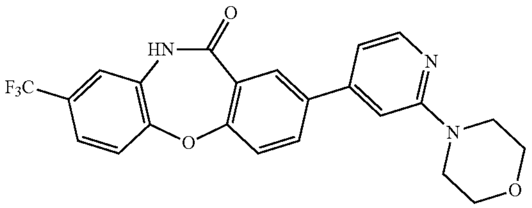

Chemical Formula: $C_{23}H_{18}F_3N_3O_4$
Exact Mass: 457.12
Molecular Weight: 457.41

2-(2-Morpholinopyridin-4-yl)-8-(trifluoromethoxy)dibenzo [b,f][1,4]oxazepin-11(10H)-one (NCGC00411866): Prepared following general Procedure A; 2-bromo-8-(trifluoromethoxy)dibenzo[b,f][1,4]oxazepin-11(10H)-one AED013-066 (40.0 mg, 0.107 mmol), 4-(4-(4,4,5,5-tetramethyl-1,3,2-dioxaborolan-2-yl)pyridin-2-yl)morpholine (34.1 mg, 0.118 mmol), 2M $Na_2CO_3$ (214 μL, 0.428 mmol), $Pd(PPh_3)_4$(6.19 mg, 5.36 μmol) in DME (4.00 mL) to afford the title compound as the TFA salt (34.3 mg, 70.1% yield). $^1$H NMR (400 MHz, DMSO-$d_6$) δ 10.79 (s, 1H), 8.18 (d, J=5.5 Hz, 1H), 8.11 (d, J=2.4 Hz, 1H), 8.06 (dd, J=8.4, 2.5 Hz, 1H), 7.53 (d, J=2.3 Hz, 1H), 7.51 (q, J=1.1 Hz, 1H), 7.18 (ddt, J=8.1, 1.9, 1.0 Hz, 3H), 7.04 (d, J=5.5 Hz, 1H), 3.72 (dd, J=5.8, 3.9 Hz, 4H), 3.56 (t, J=4.8 Hz, 4H). $^{19}$F NMR (376 MHz, DMSO-$d_6$) δ-57.14 (s, 3F), −74.22. LCMS RT (Method 1)=4.381 min, m/z 458.1 [M+H$^+$].

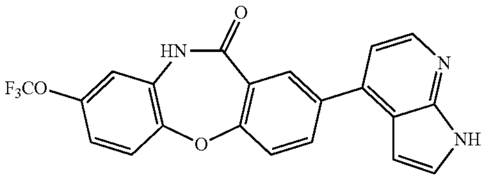

Chemical Formula: $C_{21}H_{12}F_3N_3O_3$
Exact Mass: 411.08
Molecular Weight: 411.34

2-(1H-Pyrrolo[2,3-b]pyridin-4-yl)-8-(trifluoromethoxy) dibenzo[b,f][1,4]oxazepin-11(10H)-one (NCGC00373059): Prepared following general Procedure D; 2-bromo-8-(trifluoromethoxy)dibenzo[b,f][1,4]oxazepin-11(10H)-one AED013-066 (40.0 mg, 0.107 mmol), 4-(4,4,5,5-tetramethyl-1,3,2-dioxaborolan-2-yl)-1H-pyrrolo[2,3-b]pyridine (39.1 mg, 0.160 mmol), $K_3PO_4$ (91.5 mg, 0.428 mmol), XPhos Pd(crotyl)Cl (7.22 mg, 10.7 μmol) in 4:1 dioxane: $H_2O$ (1.25 mL) to afford the title compound as the TFA salt (15.6 mg, 35.5% yield). $^1$H NMR (400 MHz, DMSO-$d_6$) δ 11.88 (s, 1H), 10.77 (s, 1H), 8.30 (d, J=5.0 Hz, 1H), 8.15 (d, J=2.4 Hz, 1H), 8.04 (dd, J=8.4, 2.4 Hz, 1H), 7.61-7.50 (m, 3H), 7.24-7.14 (m, 3H), 6.61 (dd, J=3.5, 1.8 Hz, 1H). $^{19}$F NMR (376 MHz, DMSO-$d_6$) δ-57.12 (s, 3F), −74.13. LCMS RT (Method 1)=4.336 min, m/z 412.0 [M+H$^+$].

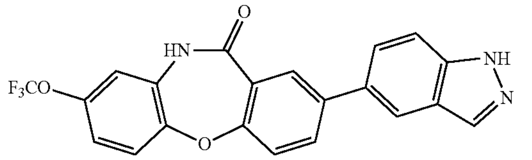

Chemical Formula: $C_{21}H_{12}F_3N_3O_3$
Exact Mass: 411.08
Molecular Weight: 411.34

2-(1H-Indazol-5-yl)-8-(trifluoromethoxy)dibenzo[b,f][1,4]oxazepin-11(10H)-one (NCGC00373058): Prepared following general Procedure A; 2-bromo-8-(trifluoromethoxy)dibenzo[b,f][1,4]oxazepin-11(10H)-one AED013-066 (40.0 mg, 0.107 mmol), 5-(4,4,5,5-tetramethyl-1,3,2-dioxaborolan-2-yl)-1H-indazole (26.1 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (21.3 mg, 48.4% yield). $^1$H NMR (400 MHz, DMSO-$d_6$) δ 13.14 (s, 1H), 10.73 (s, 1H), 8.13 (dd, J=1.5, 0.8 Hz, 1H), 8.06-8.03 (m, 1H), 8.02 (d, J=2.4 Hz, 1H), 7.96 (dd, J=8.4, 2.5 Hz, 1H), 7.65-7.62 (m, 2H), 7.55-7.49 (m, 1H), 7.47 (d, J=8.4 Hz, 1H), 7.21-7.13 (m, 2H). $^{19}$F NMR (376 MHz, DMSO-$d_6$) δ-57.12 (s, 3F). LCMS RT (Method 1)=5.637 min, m/z 412.1 [M+H$^+$].

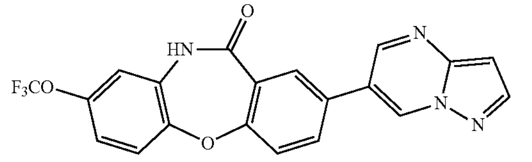

Chemical Formula: $C_{20}H_{11}F_3N_4O_3$
Exact Mass: 412.08
Molecular Weight: 412.33

2-(pyrazolo[1,5-a]pyrimidin-6-yl)-8-(trifluoromethoxy)dibenzo[b,f][1,4]oxazepin-11(10H)-one (NCGC00409812): Prepared following general Procedure D; 2-bromo-8-(trifluoromethoxy)dibenzo[b,f][1,4]oxazepin-11(10H)-one AED013-066 (40.0 mg, 0.107 mmol), 6-(4,4,5,5-tetramethyl-1,3,2-dioxaborolan-2-yl)pyrazolo[1,5-a]pyrimidine (39.3 mg, 0.160 mmol), $K_3PO_4$ (91.5 mg, 0.428 mmol), XPhos Pd(crotyl)Cl (7.22 mg, 10.7 μmol) in 4:1 dioxane: $H_2O$ (1.25 mL) to afford the title compound as the TFA salt (18.9 mg, 42.9% yield). $^1$H NMR (400 MHz, DMSO-$d_6$) δ 10.79 (s, 1H), 9.48 (dd, J=2.3, 0.9 Hz, 1H), 8.90 (d, J=2.3 Hz, 1H), 8.27 (d, J=2.3 Hz, 1H), 8.16 (d, J=2.4 Hz, 1H), 8.10 (dd, J=8.4, 2.5 Hz, 1H), 7.58-7.49 (m, 2H), 7.19 (qdt, J=3.8, 1.9, 0.9 Hz, 2H), 6.78 (dd, J=2.4, 0.9 Hz, 1H). $^{19}$F NMR (376 MHz, DMSO-$d_6$) δ-57.13 (s, 3F), −73.44 (s, 3F). LCMS RT (Method 1)=5.344 min, m/z 413.0 [M+H$^+$].

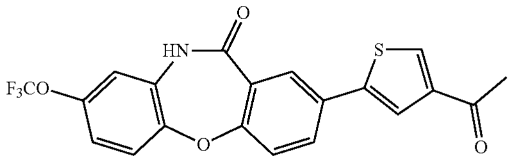

Chemical Formula: $C_{20}H_{12}F_3NO_4S$
Exact Mass: 419.04
Molecular Weight: 419.37

2-(4-Acetylthiophen-2-yl)-8-(trifluoromethoxy)dibenzo[b,f][1,4]oxazepin-11(10H)-one (NCGC00388580): Prepared following general Procedure A; 2-bromo-8-(trifluoromethoxy)dibenzo[b,f][1,4]oxazepin-11(10H)-one AED013-066 (40.0 mg, 0.107 mmol), (4-acetylthiophen-2-yl)boronic acid (20.0 mg, 0.118 mmol), 2M $Na_2CO_3$ (214 μL, 0.428 mmol), $Pd(PPh_3)_4$(6.19 mg, 5.36 μmol) in DME (4.00 mL) to afford the title compound (19.8 mg, 44.5% yield). $^1$H NMR (400 MHz, DMSO-$d_6$) δ 10.78 (s, 1H), 8.48 (d, J=1.4 Hz, 1H), 8.06-7.96 (m, 2H), 7.88 (d, J=1.4 Hz, 1H), 7.54-7.48 (m, 1H), 7.46 (dd, J=8.3, 0.5 Hz, 1H), 7.21-7.13 (m, 2H), 2.52 (s, 3H). $^{19}$F NMR (376 MHz, DMSO-$d_6$) δ-57.13 (s, 3F). LCMS RT (Method 1)=5.927 min, m/z 861.1 [2M+Na$^+$].

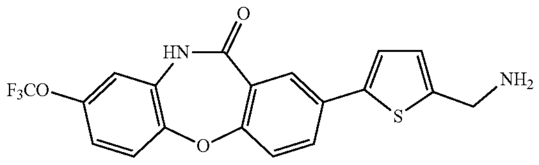

Chemical Formula: $C_{19}H_{13}F_3N_2O_3S$
Exact Mass: 406.06
Molecular Weight: 406.38

2-(5-(Aminomethyl)thiophen-2-yl)-8-(trifluoromethoxy)dibenzo[b,f][1,4]oxazepin-11(10H)-one (NCGC00388547): Prepared following general Procedure A; 2-bromo-8-(trifluoromethoxy)dibenzo[b,f][1,4]oxazepin-11(10H)-one AED013-066 (40.0 mg, 0.107 mmol), (5-(((tert-butoxycarbonyl)amino)methyl)thiophen-2-yl)boronic acid (30.2 mg, 0.118 mmol), 2M $Na_2CO_3$ (214 μL, 0.428 mmol), $Pd(PPh_3)_4$(6.19 mg, 5.36 imol) in DME (4.00 mL). After completion, the reaction mixture was filtered through celite and the filter cake rinsed generously with $CH_2Cl_2$. The filtrate was concentrated, and the residue taken up in $CH_2Cl_2$ (3.00 mL), treated with trifluoroacetic acid (1.00 mL, 13.0 mmol), and the resulting reaction mixture allowed to atir at RT for 3 h, after which LC-MS analysis showed completion. Reaction mixture was concentrated to dryness, residue taken up in $CH_2Cl_2$, the salts filtered, concentrated and the crude residue subjected to purification via standard HPLC conditions using a gradient of 10-100% ACN in $H_2O$ with 0.1% o TFA to afford to afford the title compound as the TFA salt (40.8 mg, 71.9% yield). $^1$H NMR (400 MHz, DMSO-$d_6$) δ 10.76 (s, 1H), 8.14 (s, 3H), 7.97-7.92 (m, 1H), 7.91 (d, J=2.5 Hz, 1H), 7.54-7.48 (m, 2H), 7.46 (dd, J=8.3, 0.5 Hz, 1H), 7.26-7.21 (m, 1H), 7.21-7.14 (m, 2H), 4.26 (s, 2H). $^{19}$F NMR (376 MHz, DMSO-$d_6$) δ-57.14 (s, 3F), −73.45 (s, 3F). LCMS RT (Method 1)=4.422 min m/z 835.1 [2M+Na$^+$].

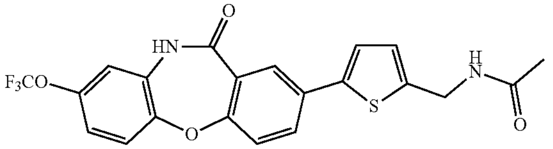

Chemical Formula: $C_{21}H_{15}F_3N_2O_4S$
Exact Mass: 448.07
Molecular Weight: 448.42

N-((5-(11-Oxo-8-(trifluoromethoxy)-10,11-dihydrodibenzo[b,f][1,4]oxazepin-2-yl)thiophen-2-yl)methyl)acetamide (NCGC00388557): Acetyl chloride (20.0 μL, 0.281 mmol) was added to a solution of 2-(5-(aminomethyl)thiophen-2-yl)-8-(trifluoromethoxy)dibenzo[b,f][1,4]oxazepin-11(10H)-one AED012-093 (25.0 mg, 0.062 mmol) and triethylamine (50.0 μL, 0.359 mmol) in $CH_2Cl_2$ (5.00 mL). The resulting reaction mixture was allowed to stir at RT for 1 h, after which LC-MS analysis showed completion. The reaction mixture was concentrated to dryness and the crude residue subjected to purification via standard HPLC conditions using a gradient of 10-100% ACN in $H_2O$ with 0.1% TFA to afford the title compound (17.2 mg, 62.4% yield). $^1H$ NMR (400 MHz, DMSO-$d_6$) δ 10.74 (s, 1H), 8.49 (t, J=5.9 Hz, 1H), 7.92-7.83 (m, 2H), 7.53-7.46 (m, 1H), 7.41 (dd, J=8.2, 0.6 Hz, 1H), 7.36 (d, J=3.6 Hz, 1H), 7.16 (dtd, J=4.9, 2.6, 1.4 Hz, 2H), 6.96 (dt, J=3.6, 0.9 Hz, 1H), 4.40 (d, J=6.1 Hz, 2H), 1.86 (s, 3H). $^{19}F$ NMR (376 MHz, DMSO-$d_6$) δ-57.13 (s, 3F). LCMS RT (Method 1)=5.282 min, m/z 897.1 [$2M^+$].

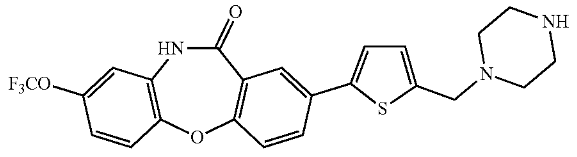

Chemical Formula: $C_{23}H_{20}F_3N_3O_3S$
Exact Mass: 475.12
Molecular Weight: 475.49

2-(5-(Piperazin-1-ylmethyl)thiophen-2-yl)-8-(trifluoromethoxy)dibenzo[b,f][1,4]oxazepin-11(10H)-one (NCGC00388560): Prepared following general Procedure A; 2-bromo-8-(trifluoromethoxy)dibenzo[b,f][1,4]oxazepin-11(10H)-one AED013-066 (40.0 mg, 0.107 mmol), tert-butyl 4-((5-(4,4,5,5-tetramethyl-1,3,2-dioxaborolan-2-yl)thiophen-2-yl)methyl)piperazine-1-carboxylate (48.0 mg, 0.118 mmol), 2M $Na_2CO_3$ (214 μL, 0.428 mmol), $Pd(PPh_3)_4$(6.19 mg, 5.36 μmol) in DME (4.00 mL). After completion, the reaction mixture was filtered through celite and the filter cake rinsed generously with $CH_2Cl_2$. The filtrate was concentrated, and the residue taken up in $CH_2Cl_2$ (3.00 mL), treated with trifluoroacetic acid (1.00 mL, 13.0 mmol), and the resulting reaction mixture allowed to atir at RT for 3 h, after which LC-MS analysis showed completion. Reaction mixture was concentrated to dryness, residue taken up in $CH_2Cl_2$, the salts filtered, concentrated and the crude residue subjected to purification via standard HPLC conditions using a gradient of 10-100% ACN in $H_2O$ with 0.1% TFA to afford to afford the title compound as the TFA salt (29.5 mg, 58.0% yield). $^1H$ NMR (400 MHz, DMSO-$d_6$) δ 10.75 (s, 1H), 8.52 (s, 2H), 7.95-7.86 (m, 2H), 7.55-7.46 (m, 1H), 7.46-7.38 (m, 2H), 7.21-7.14 (m, 2H), 7.03 (d, J=3.6 Hz, 1H), 3.81 (s, 2H), 3.12 (br s, 4H), 2.66 (br s, 4H). $^{19}F$ NMR(376 MHz, DMSO-$d_6$) δ-57.13 (s, 3F), −73.82 (s, 3F). LCMS RT (Method 1)=4.383 min, m/z 876.1 [$M+H^+$].

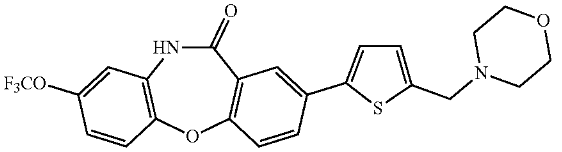

Chemical Formula: $C_{23}H_{19}F_3N_2O_4S$
Exact Mass: 476.10
Molecular Weight: 476.47

2-(5-(Morpholinomethyl)thiophen-2-yl)-8-(trifluoromethoxy)dibenzo[b,f][1,4]oxazepin-11(10H)-one (NCGC00388536): Prepared following general Procedure A; 2-bromo-8-(trifluoromethoxy)dibenzo[b,f][1,4]oxazepin-11(10H)-one AED013-066 (40.0 mg, 0.107 mmol), 4-((5-(4,4,5,5-tetramethyl-1,3,2-dioxaborolan-2-yl)thiophen-2-yl)methyl)morpholine (36.4 mg, 0.118 mmol), 2M $Na_2CO_3$ (214 μL, 0.428 mmol), $Pd(PPh_3)_4$(6.19 mg, 5.36 μmol) in DME (4.00 mL) to afford the title compound as the TFA salt (32.0 mg, 62.8% yield). $^1H$ NMR (400 MHz, DMSO-$d_6$) δ 10.77 (s, 1H), 10.08 (s, 1H), 7.99-7.91 (m, 2H), 7.56 (s, 1H), 7.48 (dd, J=14.3, 9.0 Hz, 2H), 7.31 (s, 1H), 7.18 (ddd, J=6.9, 2.6, 1.5 Hz, 2H), 4.62 (s, 2H), 3.98 (br s, 2H), 3.63 (br s, 4H), 3.12 (br s, 2H). $^{19}F$ NMR (376 MHz, DMSO-$d_6$) δ-57.13 (s, 3F),-73.68 (s, 3F). LCMS RT (Method 1)=4.610 min, m/z 477.1 [$M+H^+$].

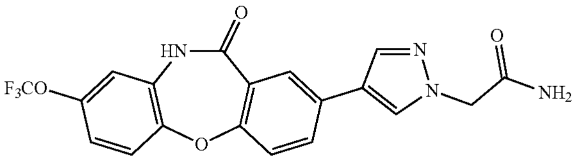

Chemical Formula: $C_{19}H_{13}F_3N_4O_4$
Exact Mass: 418.09
Molecular Weight: 418.33

2-(4-(11-Oxo-8-(trifluoromethoxy)-10,11-dihydrodibenzo[b,f][1,4]oxazepin-2-yl)-1H-pyrazol-1-yl)acetamide (NCGC00387404): Prepared following general Procedure D; 2-bromo-8-(trifluoromethoxy)dibenzo[b,f][1,4]oxazepin-11(10H)-one AED013-066 (40.0 mg, 0.107 mmol), 2-(4-(4,4,5,5-tetramethyl-1,3,2-dioxaborolan-2-yl)-1H-pyrazol-1-yl)acetamide (40.3 mg, 0.160 mmol), $K_3PO4$ (91.5 mg, 0.428 mmol), XPhos Pd(crotyl)Cl (7.22 mg, 10.7 μmol) in 4:1 dioxane:$H_2O$ (1.25 mL) to afford the title compound (21.0 mg, 47.0% yield). $^1H$ NMR (400 MHz, DMSO-$d_6$) δ 10.69 (s, 1H), 8.19 (d, J=0.8 Hz, 1H), 7.93-7.89 (m, 2H), 7.83 (dd, J=8.4, 2.4 Hz, 1H), 7.50 (s, 1H), 7.49-7.44 (m, 1H), 7.37 (d, J=8.4 Hz, 1H), 7.27 (s, 1H), 7.15 (ddt, J=7.7, 1.9, 0.9 Hz, 2H), 4.76 (s, 2H). $^{19}F$ NMR (376

MHz, DMSO-$d_6$) δ-57.13 (s, 3F). LCMS RT (Method 1)=4.687 min, m/z 419.0 [M+H$^+$].

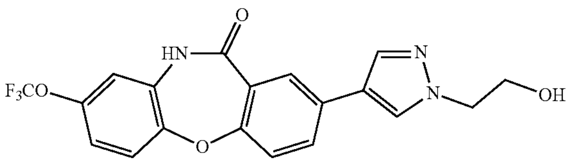

Chemical Formula: $C_{19}H_{14}F_3N_3O_4$
Exact Mass: 405.09
Molecular Weight: 405.33

2-(1-(2-Hydroxyethyl)-1H-pyrazol-4-yl)-8-(trifluoromethoxy)dibenzo[b,f][1,4]oxazepin-11(10H)-one (NCGC00387403): Prepared following general Procedure D; 2-bromo-8-(trifluoromethoxy)dibenzo[b,f][1,4]oxazepin-11(10H)-one AED013-066 (40.0 mg, 0.107 mmol), 2-(4-(4,4,5,5-tetramethyl-1,3,2-dioxaborolan-2-yl)-1H-pyrazol-1-yl)ethan-1-ol (38.2 mg, 0.160 mmol), $K_3PO4$ (91.5 mg, 0.428 mmol), XPhos Pd(crotyl)Cl (7.22 mg, 10.7 μmol) in 4:1 dioxane:$H_2O$ (1.25 mL) to afford the title compound (17.8 mg, 41.1% yield). $^1H$ NMR (400 MHz, DMSO-$d_6$) δ 10.68 (s, 1H), 8.20 (d, J=0.8 Hz, 1H), 7.90 (d, J=2.3 Hz, 1H), 7.89 (d, J=0.8 Hz, 1H), 7.82 (dd, J=8.4, 2.4 Hz, 1H), 7.51-7.43 (m, 1H), 7.36 (d, J=8.4 Hz, 1H), 7.19-7.08 (m, 2H), 4.92 (t, J=5.4 Hz, 1H), 4.15 (t, J=5.6 Hz, 2H), 3.76 (q, J=5.6 Hz, 2H). $^{19}F$ NMR (376 MHz, DMSO-$d_6$) δ-57.13 (s, 3F). LCMS RT (Method 1)=4.873 min, m/z 406.0 [M+H$^+$].

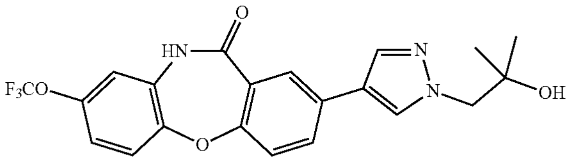

Chemical Formula: $C_{21}H_{18}F_3N_3O_4$
Exact Mass: 433.12
Molecular Weight: 433.39

2-(1-(2-Hydroxy-2-methylpropyl)-JH-pyrazol-4-yl)-8-(trifluoromethoxy)dibenzo[b,f][1,4]oxazepin-11(10H)-one (NCGC00387294): Prepared following general Procedure A; 2-bromo-8-(trifluoromethoxy)dibenzo[b,f][1,4]oxazepin-11(10H)-one AED013-066 (40.0 mg, 0.107 mmol), 2-methyl-1-(4-(4,4,5,5-tetramethyl-1,3,2-dioxaborolan-2-yl)-1H-pyrazol-1-yl)propan-2-ol (28.5 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (20.3 mg, 43.8% yield). $^1H$ NMR (400 MHz, DMSO-$d_6$) δ 10.69 (s, 1H), 8.14 (d, J=0.8 Hz, 1H), 7.93-7.87 (m, 2H), 7.83 (dd, J=8.4, 2.4 Hz, 1H), 7.51-7.44 (m, 1H), 7.36 (d, J=8.4 Hz, 1H), 7.19-7.11 (m, 2H), 4.72 (s, 1H), 4.02 (s, 2H), 1.08 (s, 6H). $^{19}F$ NMR (376 MHz, DMSO-$d_6$) δ-57.13 (s, 3F). LCMS RT (Method 1)=5.910 min, m/z 434.1 [M+H$^+$].

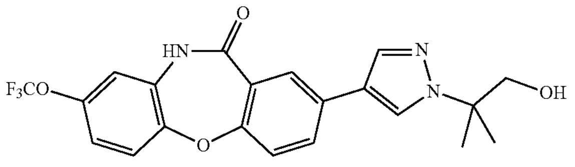

Chemical Formula: $C_{21}H_{18}F_3N_3O_4$
Exact Mass: 433.12
Molecular Weight: 433.39

2-(1-(1-Hydroxy-2-methylpropan-2-yl)-1H-pyrazol-4-yl)-8-(trifluoromethoxy)dibenzo[b,f][1,4]oxazepin-11(10H)-one (NCGC00387295): Prepared following general Procedure A; 2-bromo-8-(trifluoromethoxy)dibenzo[b,f][1,4]oxazepin-11(10H)-one AED013-066 (40.0 mg, 0.107 mmol), 2-methyl-2-(4-(4,4,5,5-tetramethyl-1,3,2-dioxaborolan-2-yl)-1H-pyrazol-1-yl)propan-1-ol (28.5 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (22.4 mg, 48.3% yield). $^1H$ NMR (400 MHz, DMSO-$d_6$) δ 10.66 (s, 1H), 8.26 (d, J=0.8 Hz, 1H), 7.92 (d, J=2.3 Hz, 1H), 7.86 (d, J=0.7 Hz, 1H), 7.83 (dd, J=8.4, 2.4 Hz, 1H), 7.48-7.41 (m, 1H), 7.33 (d, J=8.4 Hz, 1H), 7.17-7.08 (m, 2H), 4.94 (t, J=5.7 Hz, 1H), 3.57 (d, J=5.7 Hz, 2H), 1.46 (s, 6H). $^{19}F$ NMR (376 MHz, DMSO-$d_6$) δ-57.12 (s, 3F). LCMS RT (Method 1)=5.287 min, m/z 434.1 [M+H$^+$].

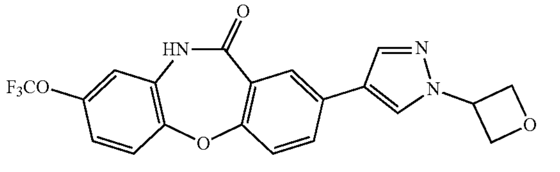

Chemical Formula: $C_{20}H_{14}F_3N_3O_4$
Exact Mass: 417.09
Molecular Weight: 417.34

2-(1-(Oxetan-3-yl)-1H-pyrazol-4-yl)-8-(trifluoromethoxy)dibenzo[b,f][1,4]oxazepin-11(10H)-one (NCGC00387298): Prepared following general Procedure A; 2-bromo-8-(trifluoromethoxy)dibenzo[b,f][1,4]oxazepin-11(10H)-one AED013-066 (40.0 mg, 0.107 mmol), 1-(oxetan-3-yl)-4-(4,4,5,5-tetramethyl-1,3,2-dioxaborolan-2-yl)-1H-pyrazole (26.7 mg, 0.107 mmol), 2M $Na_2CO_3$ (214 L, 0.428 mmol), $Pd(PPh_3)_4$(6.19 mg, 5.36 μmol) in DME (4.00 mL) to afford the title compound (19.8 mg, 44.4% yield). $^1H$ NMR (400 MHz, DMSO-$d_6$) δ 10.70 (s, 1H), 8.45 (d, J=0.8 Hz, 1H), 8.05 (d, J=0.7 Hz, 1H), 7.95 (d, J=2.3 Hz, 1H), 7.86 (dd, J=8.4, 2.4 Hz, 1H), 7.51-7.44 (m, 1H), 7.39 (d, J=8.4 Hz, 1H), 7.16 (tdd, J=3.9, 2.9, 1.9 Hz, 2H), 5.57 (p, J=7.4, 7.4, 6.7, 6.6 Hz, 1H), 4.98-4.87 (m, 4H). $^{19}$F NMR (376 MHz, DMSO-$d_6$) δ-57.13 (s, 3F). LCMS RT (Method 1)=5.190 min, m/z 857.1 [2M+$Na^+$].

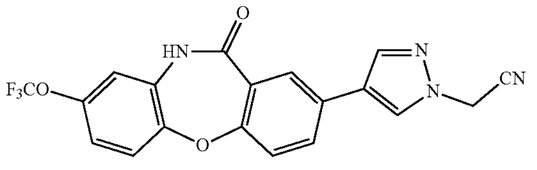

Chemical Formula: $C_{19}H_{11}F_3N_4O_3$
Exact Mass: 400.08
Molecular Weight: 400.32

2-(4-(11-Oxo-8-(trifluoromethoxy)-10,11-dihydrodibenzo[b,f][1,4]oxazepin-2-yl)-1H-pyrazol-1-yl)acetonitrile (NCGC00388626): Prepared following general Procedure A; 2-bromo-8-(trifluoromethoxy)dibenzo[b,f][1,4]oxazepin-11(10H)-one AED013-066 (40.0 mg, 0.107 mmol), 2-(4-(4,4,5,5-tetramethyl-1,3,2-dioxaborolan-2-yl)-1H-pyrazol-1-yl)acetonitrile (24.9 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (19.8 mg, 44.4% yield). $^1$H NMR (400 MHz, DMSO-$d_6$) δ 10.71 (s, 1H), 8.35 (d, J=0.7 Hz, 1H), 8.08 (d, J=0.7 Hz, 1H), 7.93 (d, J=2.4 Hz, 1H), 7.86 (dd, J=8.4, 2.3 Hz, 1H), 7.50-7.45 (m, 1H), 7.40 (d, J=8.4 Hz, 1H), 7.16 (tt, J=3.6, 1.8 Hz, 2H), 5.50 (s, 2H). $^{19}$F NMR (376 MHz, DMSO-$d_6$) δ-57.13 (s, 3F). LCMS RT (Method 1)=5.249 min, m/z 801.2 [$2M^+$].

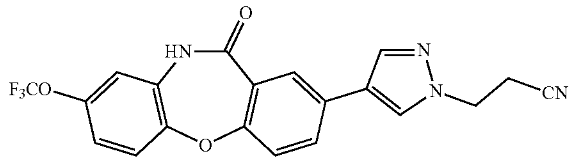

Chemical Formula: $C_{20}H_{13}F_3N_4O_3$
Exact Mass: 414.09
Molecular Weight: 414.34

3-(4-(11-Oxo-8-(trifluoromethoxy)-10,11-dihydrodibenzo[b,f][1,4]oxazepin-2-yl)-1H-pyrazol-1-yl)propanenitrile (NCGC00387293): Prepared following general Procedure A; 2-bromo-8-(trifluoromethoxy)dibenzo[b,f][1,4]oxazepin-11(10H)-one AED013-066 (40.0 mg, 0.107 mmol), 3-(4-(4,4,5,5-tetramethyl-1,3,2-dioxaborolan-2-yl)-1H-pyrazol-1-yl)propanenitrile (26.4 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (17.8 mg, 40.2% yield). $^1$H NMR (400 MHz, DMSO-$d_6$) δ 10.70 (s, 1H), 8.33 (d, J=0.9 Hz, 1H), 7.99 (d, J=0.8 Hz, 1H), 7.92 (d, J=2.3 Hz, 1H), 7.84 (dd, J=8.4, 2.4 Hz, 1H), 7.51-7.44 (m, 1H), 7.39 (d, J=8.5 Hz, 1H), 7.16 (ddt, J=5.2, 2.9, 1.5 Hz, 2H), 4.40 (t, J=6.4 Hz, 2H), 3.10 (t, J=6.4 Hz, 2H). $^{19}$F NMR (376 MHz, DMSO-$d_6$) δ-57.13 (s, 3F). LCMS RT (Method 1)=5.189 min, m/z 829.2 [$2M^+$].

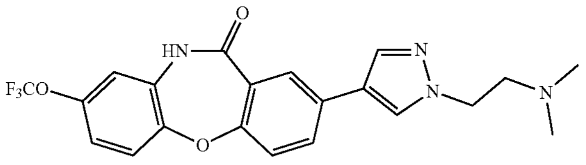

Chemical Formula: $C_{21}H_{19}F_3N_4O_3$
Exact Mass: 432.14
Molecular Weight: 432.40

2-(1-(2-(Dimethylamino)ethyl)-1H-pyrazol-4-yl)-8-(trifluoromethoxy)dibenzo[b,f][1,4]oxazepin-11(10H)-one (NCGC00387297): Prepared following general Procedure A; 2-bromo-8-(trifluoromethoxy)dibenzo[b,f][1,4]oxazepin-11(10H)-one AED013-066 (40.0 mg, 0.107 mmol), N,N-dimethyl-2-(4-(4,4,5,5-tetramethyl-1,3,2-dioxaborolan-2-yl)-1H-pyrazol-1-yl)ethanamine (28.4 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound as the TFA salt (24.7 mg, 53.4% yield). $^1$H NMR (400 MHz, DMSO-$d_6$) δ 10.68 (s, 1H), 9.35 (s, 1H), 8.32 (d, J=0.8 Hz, 1H), 8.02 (d, J=0.8 Hz, 1H), 7.91 (d, J=2.3 Hz, 1H), 7.83 (dd, J=8.4, 2.4 Hz, 1H), 7.49-7.42 (m, 1H), 7.38 (d, J=8.4 Hz, 1H), 7.14 (ddp, J=5.8, 2.2, 1.0 Hz, 2H), 4.51 (t, J=6.1 Hz, 2H), 3.57 (d, J=6.3 Hz, 2H), 2.78 (s, 6H). $^{19}$F NMR (376 MHz, DMSO-$d_6$) δ-57.13 (s, 3F),-73.47 (s, 3F). LCMS RT (Method 1)=4.381 min, m/z 433.1 [M+$H^+$].

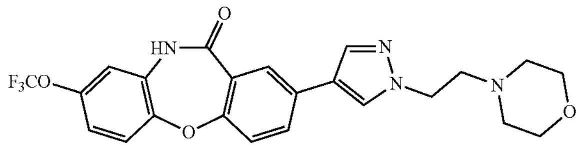

Chemical Formula: $C_{23}H_{21}F_3N_4O_4$
Exact Mass: 474.15
Molecular Weight: 474.44

2-(1-(2-Morpholinoethyl)-1H-pyrazol-4-yl)-8-(trifluoromethoxy)dibenzo[b,f][1,4]oxazepin-11(10H)-one (NCGC00387296): Prepared following general Procedure A; 2-bromo-8-(trifluoromethoxy)dibenzo[b,f][1,4]oxazepin-11(10H)-one AED013-066 (40.0 mg, 0.107 mmol), 4-(2-(4-(4,4,5,5-tetramethyl-1,3,2-dioxaborolan-2-yl)-1H-pyrazol-1-yl)ethyl)morpholine (32.8 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound as the TFA salt (27.5 mg, 54.2% yield). $^1$H NMR (400 MHz, DMSO-$d_6$) δ 10.68 (s, 1H), 9.82 (s, 1H), 8.31 (s, 1H), 8.00 (s, 1H), 7.91 (d, J=2.3 Hz, 1H), 7.82 (dd, J=8.4, 2.4 Hz, 1H), 7.49-7.41 (m, 1H), 7.37 (d, J=8.4 Hz, 1H), 7.14 (ddp, J=4.9, 2.1, 1.0 Hz, 2H), 4.50 (s, 2H), 3.91 (s, 2H), 3.55-3.27 (m, 4H), 3.09 (s, 4H). $^{19}$F NMR (376 MHz, DMSO-$d_6$) δ-57.13 (s, 3F),-73.66 (s, 3F). LCMS RT (Method 1)=4.410 min, m/z 475.2 [M+$H^+$].

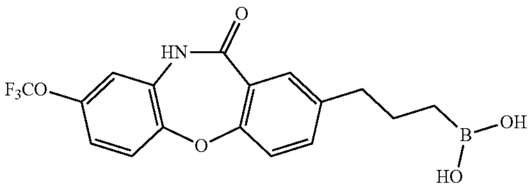

Chemical Formula: $C_{17}H_{15}BF_3NO_5$
Exact Mass: 381.10
Molecular Weight: 381.11

(3-(11-Oxo-8-(trifluoromethoxy)-10,11-dihydrodibenzo[b,f][1,4]oxazepin-2-yl)propyl)boronic acid (NCGC00390142): A mixture of 2-bromo-8-(trifluoromethoxy)dibenzo[b,f][1,4]oxazepin-11(10H)-one AED013-066 (100 mg, 0.267 mmol), allylboronic acid pinacol ester (0.150 mL, 0.802 mmol), $K_3PO_4$ (227 mg, 1.069 mmol) and butyldi-1-adamantylphosphine (9.58 mg, 0.027 mmol) in toluene:$H_2O$ (16:1, 10.7 mL) was degassed by bubbling $N_2$ through the reaction mixture for 5 min. $Pd(OAc)_2$ (3.00 mg, 0.013 mmol) was then added, degassing continued for 2 min, and then the resulting reaction mixture was heated to 160° C. under microwave irradiation for 1 hr, after which LC-MS analysis showed completion. The reaction mixture was allowed to cool to RT, filtered through celite, and the filter cake was rinsed generously with EtOAc. The filtrate was washed with $H_2O$ and brine, dried over $MgSO_4$, filtered and concentrated under reduced pressure. The crude residue was purified by flash column chromatography: silica gel with a gradient of 3-15% EtOAc in Hex to afford 2-allyl-8-(trifluoromethoxy)dibenzo[b,f][1,4]oxazepin-11(10H)-one (80.0 mg, 89.0% yield) as a syrup, which solidified upon standing. LCMS RT (Method 2)=3.770 min, m/z 336.1 [$M^+$]. This allyl intermediate was taken up in THF (2.00 mL) and a 1M solution of borane-THF complex (1.19 mL, 1.19 mmol) added slowly. The mixture was stirred for 2 h at RT, after which LC-MS analysis showed consumption of the allyl intermediate. $H_2O$ (2.00 mL) was added slowly and the mixture stirred for 3 h at RT, after which LC-MS analysis showed completion. Reaction mixture was concentrated to dryness, taken up in EtOAc, washed with $H_2O$, brine, dried over $MgSO_4$, filtered and concentrated. The crude residue was subjected to purification via standard HPLC conditions using a gradient of 10-100% ACN in $H_2O$ with 0.1% TFA to afford the title boronic acid (47.8 mg, 52.6% yield). $^1H$ NMR (400 MHz, DMSO-$d_6$) δ 10.61 (d, J=2.1 Hz, 1H), 7.62-7.53 (m, 1H), 7.51-7.36 (m, 2H), 7.31-7.23 (m, 1H), 7.17-7.09 (m, 2H), 3.38 (t, J=6.4 Hz, 1H), 2.66-2.59 (m, 1H), 2.57-2.50 (m, 3H), 1.74-1.63 (m, 1H), 1.59 (p, J=7.5 Hz, 1H), 0.57 (dd, J=8.6, 7.2 Hz, 1H). $^{19}F$ NMR (376 MHz, DMSO-$d_6$) δ-57.13 (s, 3F). LCMS RT (Method 1)=4.973 min, m/z 381.9 [$M^+$].

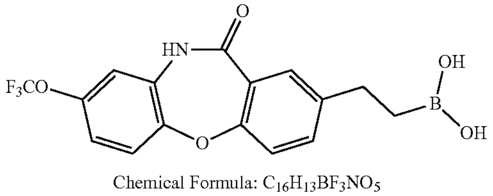

Chemical Formula: $C_{16}H_{13}BF_3NO_5$
Exact Mass: 367.08
Molecular Weight: 367.09

(2-(11-Oxo-8-(trifluoromethoxy)-10,11-dihydrodibenzo[b,f][1,4]oxazepin-2-yl)ethyl)boronic acid (NCGC00390141): A mixture of 2-bromo-8-(trifluoromethoxy)dibenzo[b,f][1,4]oxazepin-11(10H)-one AED013-066 (100 mg, 0.267 mmol), vinylboronic acid pinacol ester (0.136 mL, 0.802 mmol), $K_3PO_4$ (227 mg, 1.07 mmol) and butyldi-1-adamantylphosphine (9.58 mg, 0.027 mmol) in toluene:$H_2O$ (16:1, 4.25 mL) was degassed by bubbling $N_2$ through the reaction mixture for 5 min. $Pd(OAc)_2$ (3.00 mg, 0.013 mmol) was then added, degassing continued for 2 min, and then the resulting reaction mixture was heated to 160° C. under microwave irradiation for 1 hr, after which LC-MS analysis showed completion. The reaction mixture was allowed to cool to RT, filtered through celite, and the filter cake was rinsed generously with EtOAc. The filtrate was washed with $H_2O$ and brine, dried over $MgSO_4$, filtered and concentrated under reduced pressure. Crude residue was purified by flash column chromatography: silica gel with a gradient of 3-15% EtOAc in Hex to afford the intermediate vinyl derivative (60.0 mg, 69.9% yield) as a syrup, which solidified upon standing. LCMS RT (Method 2)=3.684 min, m/z 322.1 [$M^+$]. This vinyl intermediate was taken up in THF (2.00 mL) and a 1M solution of borane-THF complex (0.934 mL, 0.934 mmol) added slowly. The mixture was stirred for 2 h at RT, after which LC-MS analysis showed consumption of the vinyl intermediate. $H_2O$ (2.00 mL) was added slowly and the mixture stirred for 3 h at RT, after which LC-MS analysis showed completion. Reaction mixture was concentrated to dryness, taken up in EtOAc, washed with $H_2O$, brine, dried over $MgSO_4$, filtered and concentrated. The crude residue was subjected to purification via standard HPLC conditions using a gradient of 10-100% ACN in $H_2O$ with 0.1% TFA to afford the title boronic acid (47.8 mg, 52.6% yield). $^1H$ NMR (400 MHz, DMSO-$d_6$) δ 10.60 (d, J=7.1 Hz, 1H), 7.59 (dd, J=12.7, 2.3 Hz, 1H), 7.53 (s, 2H), 7.49-7.40 (m, 2H), 7.26 (dd, J=9.6, 8.2 Hz, 1H), 7.17-7.09 (m, 2H), 2.64 (dd, J=9.2, 7.1 Hz, 2H), 0.93-0.83 (m, 2H). $^{19}F$ NMR (376 MHz, DMSO-$d_6$) δ-57.13 (s, 3F). LCMS RT (Method 1)=4.776 min, m/z 368.0 [$M+H^+$].

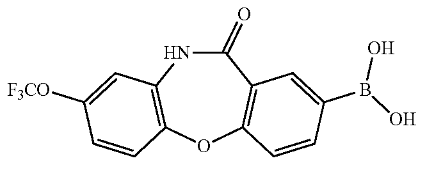

Chemical Formula: $C_{14}H_9BF_3NO_5$
Exact Mass: 339.05
Molecular Weight: 339.03

(11-Oxo-8-(trifluoromethoxy)-10,11-dihydrodibenzo[b,f][1,4]oxazepin-2-yl)boronic acid (NCGC00387437): A mixture of 2-bromo-8-(trifluoromethoxy)dibenzo[b,f][1,4]oxazepin-11(10H)-one AED013-066 (40.0 mg, 0.107 mmol), bis(pinacolato)diboron (54.3 mg, 0.214 mmol), Pd(dppf)C12-$CH_2Cl_2$ (8.73 mg, 10.7 μmol), and KOAc (31.5 mg, 0.321 mmol) in DMF (1.50 mL) was heated to 100° C. for 30 min, after which LC-MS analysis showed formation of both the boronic acid and ester. The reaction mixture was allowed to cool to RT, and then partitioned between EtOAc and $H_2O$. The biphasic mixture was filtered through celite and the filter cake rinsed with EtOAc, the filtrate was separated and the organic phase washed with brine (2×'s), dried over $MgSO_4$, filtered and concentrated. The residue was taken up in 1,4-dioxane (2.00 mL) and 6M HCl (1.00 mL, 6.00 mmol)

added. The resulting reaction mixture was stirred at RT overnight, after which LC-MS analysis showed complete hydrolysis of the boronic ester to the acid. The reaction mixture was diluted with EtOAc and washed with $H_2O$, dried over $MgSO_4$, filtered and concentrated. Residue was subjected to purification via standard HPLC conditions using a gradient of 10-100% ACN in $H_2O$ with 0.1% TFA to afford the title compound (13.9 mg, 38.3% yield). $^1$H NMR (400 MHz, DMSO-$d_6$) δ 10.61 (s, 1H), 8.25 (d, J=1.7 Hz, 1H), 8.22 (s, 2H), 8.00 (dd, J=8.1, 1.8 Hz, 1H), 7.45 (dd, J=8.1, 1.0 Hz, 1H), 7.32 (d, J=8.1 Hz, 1H), 7.18-7.10 (m, 2H). $^{19}$F NMR (376 MHz, DMSO-$d_6$) δ-57.12 (s, 3F). LCMS RT (Method 1)=4.842 min, m/z 340.0 [M+H$^+$].

Exploration about the Dibenzodiazapinone Bridgehead:

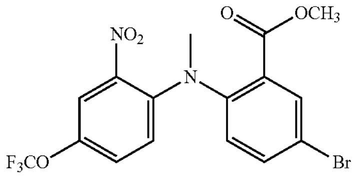

Chemical Formula: $C_{16}H_{12}BrF_3N_2O_5$
Exact Mass: 447.99
Molecular Weight: 449.18

Methyl 5-bromo-2-(methyl(2-nitro-4-(trifluoromethoxy) phenyl)amino)benzoate (DCT001-016): Iodomethane (0.022 mL, 0.345 mmol) was added to a slurry of methyl 5-bromo-2-((2-nitro-4-(trifluoromethoxy)phenyl)amino) benzoate DCT001-012 (0.100 g, 0.230 mmol) and cesium carbonate (0.150 g, 0.460 mmol) in DMF (1.15 mL). The vessel was sealed and stirred at RT for 19 h. The mixture was diluted with DCM (30.0 mL), washed with $H_2O$ (4×25.0 mL) and brine (1×25.0 mL), dried over $MgSO_4$, filtered, and concentrated to give methyl 5-bromo-2-(methyl(2-nitro-4-(trifluoromethoxy)phenyl)amino)benzoate (0.110 g, 90% yield), which was used without further purification. $^1$H NMR (400 MHz, $CDCl_3$) δ 7.84 (d, J=2.4 Hz, 1H), 7.58 (m, 2H), 7.35 (m, 1H), 7.16 (d, J=9.1 Hz, 1H), 7.05 (d, J=8.6 Hz, 1H), 3.63 (s, 3H), 3.34 (s, 3H). $^{19}$F NMR (376 MHz, DMSO-$d_6$) δ-55.75. LCMS RT (Method 1)=3.701 min, m/z 448.9 [M+H$^+$].

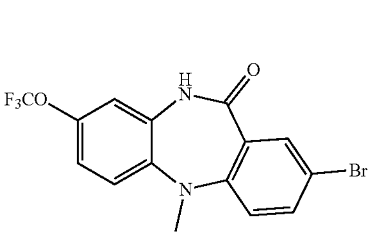

Chemical Formula: $C_{15}H_{10}BrF_3N_2O_2$
Exact Mass: 385.99
Molecular Weight: 387.16

2-Bromo-5-methyl-8-(trifluoromethoxy)-5,10-dihydro-11H-dibenzo[b,e][1,4]diazepin-11-one (DCT001-018): Iron Powder (0.064 g, 1.147 mmol) and a mixture of EtOH (5 mL)/HCl (6M, 5 mL) were added to a reaction vessel containing methyl 5-bromo-2-(methyl(2-nitro-4-(trifluoromethoxy)phenyl)amino)benzoate DCT001-016 (0.103 g, 0.229 mmol) and the mixture was refluxed for 18 hours. The mixture was cooled to RT, poured onto $H_2O$ (50 mL), and extracted with EtOAc (3×30 mL). Combined organic extracts were washed with $H_2O$ (2×30 mL) and brine (1×30 mL), dried over $MgSO_4$, filtered, and concentrated to give a light yellow solid (0.102g). Crude product was purified by flash chromatography: silica gel with a gradient of 0-10% EtOAc in DCM to give 2-bromo-5-methyl-8-(trifluoromethoxy)-5,10-dihydro-11H-dibenzo[b,e][1,4]diazepin-11-one (0.079 g, 89% yield) as a yellow solid. $^1$H NMR (400 MHz, $CDCl_3$) δ 8.06 (s, 1H), 7.95 (d, J=2.5 Hz, 1H), 7.54 (dd, J=8.7, 2.5 Hz, 1H), 7.08 (d, J=8.9 Hz, 1H), 7.04-6.98 (m, 1H), 6.94 (d, J=8.7 Hz, 1H), 6.84 (dd, J=2.7, 0.9 Hz, 1H), 3.31 (d, J=2.2 Hz, 3H). $^{19}$F NMR (376 MHz, Chloroform-d) 6-58.19. LCMS RT (Method 1)=3.620 min, m/z 387.01 [M+H$^+$].

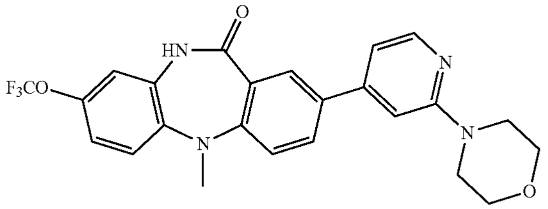

Chemical Formula: $C_{24}H_{21}F_3N_4O_3$
Exact Mass: 470.16
Molecular Weight: 470.45

5-Methyl-2-(2-morpholinopyridin-4-yl)-8-(trifluoromethoxy)-5,10-dihydro-11H dibenzo[b,e][1,4]diazepin-11-one (NCGC00488911): A mixture of 2-bromo-5-methyl-8-(trifluoromethoxy)-5,10-dihydro-11H-dibenzo[b,e][1,4] diazepin-11-one DCT001-018 (0.055 g, 0.142 mmol), 4-(4-(4,4,5,5-tetramethyl-1,3,2-dioxaborolan-2-yl)pyridin-2-yl) morpholine (0.045 g, 0.156 mmol), and sodium carbonate (2M, 0.071 mL, 0.142 mmol) were added to a microwave vial. DMF (1.421 ml) was added and the mixture was purged via $N_2$ bubbling for 5 mins. Tetrakis(triphenylphosphine) palladium(0) (8.21 mg, 7.10 μmol) was added, the mixture was purged for an additional 2 min, and then heated to 160° C. via microwave irradiation for 1 hour. The reaction was cooled to RT, diluted with DCM (20 mL), and filtered through celite. The filtrate was washed with $H_2O$ (4×20 mL) and brine (1×20 mL), dried over $MgSO_4$, filtered, and concentrated to give a pale brown solid. Crude solid was dissolved in DCM, filtered through a 40 μm syringe filter, and concentrated to give a pale yellow solid (0.72g). Crude material was purified via standard HPLC conditions using a gradient of 10-100% ACN in $H_2O$ with 0.1% TFA to give 5-methyl-2-(2-morpholinopyridin-4-yl)-8-(trifluoromethoxy)-5,10-dihydro-11H dibenzo[b,e][1,4]diazepin-11-one (0.053 g, 80% yield) as the TFA salt. $^1$H NMR (400 MHz, DMSO-d6) δ 10.48 (s, 1H), 8.12 (d, J=5.7 Hz, 1H), 8.03-7.91 (m, 2H), 7.34-7.27 (m, 2H), 7.20-7.08 (m, 2H), 7.08-7.00 (m, 2H), 3.71 (s, 3H), 3.56, (m, 8H). $^{19}$F NMR (376 MHz, DMSO-$d_6$) δ-57.55,-74.19. LCMS RT (Method 1)=4.323 min, m/z 471.0 [M+H$^+$].

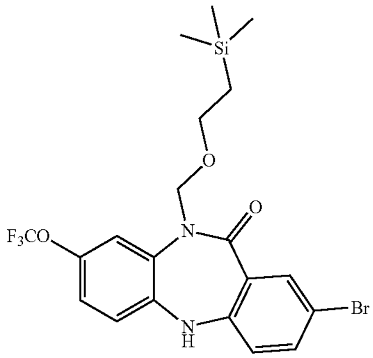

Chemical Formula: $C_{20}H_{22}BrF_3N_2O_3Si$
Exact Mass: 502.05
Molecular Weight: 503.39

2-Bromo-8-(trifluoromethoxy)-10-((2-(trimethylsilyl) ethoxy)methyl)-5,10-dihydro-11H dibenzo[b,e][1,4]diazepin-11-one (DCT001-056): Potassium tert-butoxide (1M in THF, 4.02 ml, 4.02 mmol) was added to a solution of 2-bromo-8-(trifluoromethoxy)-5,10-dihydro-11H-dibenzo [b,e][1,4]diazepin-11-one DCT001-053 (4.02 mmol) in DMF (16 ml) at 0° C. SEM-Cl (0.783 ml, 4.42 mmol) was added dropwise and the reaction mixture was stirred at 0° C. for 15 mins, warmed to RT, and continued for 14 hours. The reaction mixture was diluted with EtOAc (50 mL) and washed with $NH_4Cl$ (1×50 mL), $H_2O$ (2×50 mL), and brine (3×50 mL), dried over $MgSO_4$, filtered, and concentrated to give a yellow oily solid (2.04g). Crude product was purified via flash chromatography: silica gel with a gradient of 75-100% DCM in hexanes to give 2-bromo-8-(trifluoromethoxy)-10-((2-(trimethylsilyl)ethoxy)methyl)-5,10-dihydro-11H dibenzo[b,e][1,4]diazepin-11-one (1.33 g, 66% yield) as a yellow solid. $^1H$ NMR (400 MHz, DMSO-d6) δ 8.31 (s, 1H), 7.70 (d, J=2.4 Hz, 1H), 7.57-7.50 (m, 2H), 7.24-7.12 (m, 2H), 7.04 (d, J=8.6 Hz, 1H), 5.21 (s, 2H), 3.61 (t, J=7.9 Hz, 2H), 0.81 (t, J=7.9 Hz, 2H), −0.08 (s, 9H). $^{19}F$ NMR (376 MHz, DMSO-$d_6$) δ-57.26.

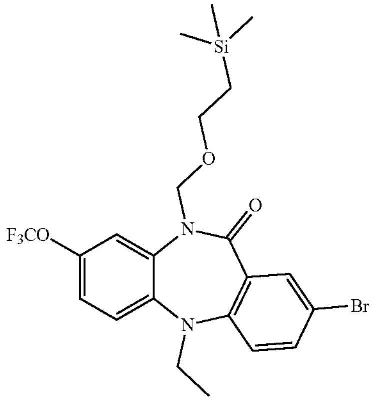

Chemical Formula: $C_{22}H_{26}BrF_3N_2O_3Si$
Exact Mass: 530.08
Molecular Weight: 531.45

2-Bromo-5-ethyl-8-(trifluoromethoxy)-10-((2-(trimethylsilyl)ethoxy)methyl)-5,10-dihydro-11H-dibenzo[b,e][1,4]diazepin-11-one (DCT001-064): Potassium tert-butoxide (1M in THF, 0.219 ml, 0.219 mmol) was added to a solution of 2-bromo-8-(trifluoromethoxy)-10-((2-(trimethylsilyl) ethoxy)methyl)-5,10-dihydro-11H-dibenzo[b,e][1,4]diazepin-11-one DCT001-056 (0.1 g, 0.199 mmol) in DMF (1.419 ml) at 0° C. Iodoethane (0.080 mL, 0.993 mmol) was added and the solution was stirred at 0° C. for 30 mins, warmed to RT, and stirred for 16 hours. The mixture was then quenched with $NH_4Cl$ (20 mL). EtOAc (30 mL) was added and the organic phase was washed with $H_2O$ (4×20 mL), and brine (1×20 mL), dried over $MgSO_4$, filtered, and concentrated to give 2-bromo-5-ethyl-8-(trifluoromethoxy)-10-((2-(trimethylsilyl)ethoxy)methyl)-5,10-dihydro-11H-dibenzo[b,e][1,4]diazepin-11-one (0.101 g, 96% yield) as a yellow oil. $^1H$ NMR (400 MHz, DMSO-$d_6$) δ 7.67-7.56 (m, 3H), 7.35 (d, J=9.0 Hz, 1H), 7.27-7.13 (m, 2H), 5.36 (s, 2H), 3.71 (m, 2H), 3.56 (t, J=8.0 Hz, 2H), 1.09 (t, J=6.9 Hz, 3H), 0.80 (m, 2H), −0.09 (s, 9H). $^{19}F$ NMR (376 MHz, DMSO-$d_6$) δ-57.05

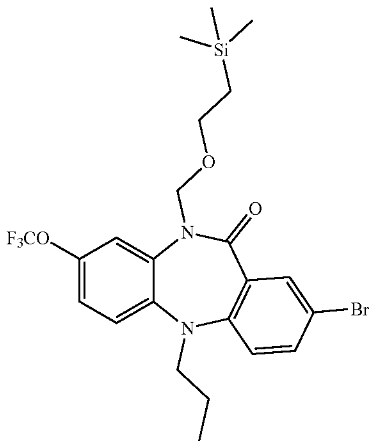

Chemical Formula: $C_{23}H_{28}BrF_3N_2O_3Si$
Exact Mass: 544.10
Molecular Weight: 545.47

2-Bromo-5-propyl-8-(trifluoromethoxy)-10-((2-(trimethylsilyl)ethoxy)methyl)-5,10-dihydro-11H-dibenzo[b,e][1,4] diazepin-11-one (DCT001-048): Sodium hydride (0.024 g, 0.993 mmol) was added to a solution of 2-bromo-8-(trifluoromethoxy)-10-((2-(trimethylsilyl)ethoxy)methyl)-5,10-dihydro-11H-dibenzo[b,e][1,4]diazepin-11-one DCT001-056 (0.100 g, 0.199 mmol) in DMF (1.987 ml) at 0° C. The mixture was stirred at 0° C. for 30 mins, warmed to RT, and stirred for 17 hours. The reaction mixture was quenched with $NH_4Cl$ (30 mL), then diluted with EtOAc (30 mL). The organic phase was washed with $H_2O$ (4×30 mL) and brine (1×30 mL), dried over $MgSO_4$, filtered, and concentrated to give 2-bromo-5-propyl-8-(trifluoromethoxy)-10-((2-(trimethylsilyl)ethoxy)methyl)-5,10-dihydro-11H-dibenzo[b,e] [1,4]diazepin-11-one (0.095 g, 0.174 mmol, 88% yield) as a brown oil. $^1H$ NMR (400 MHz, DMSO-$d_6$) δ 7.68-7.57 (m, 3H), 7.39 (d, J=12 Hz, 1H), 7.25 (m, 1H), 7.23-7.17 (m, 1H), 5.41 (d, J=10.5 Hz, 1H), 5.33 (d, J=10.5 Hz, 1H), 3.73 (dt, J=13.4, 6.8 Hz, 1H), 3.59 (m, 3H), 1.51 (h, J=7.2 Hz, 2H), 0.92-0.78 (m, 5H), −0.07 (s, 9H). $^{19}F$ NMR (376 MHz, DMSO-$d_6$) δ-56.95.002-014

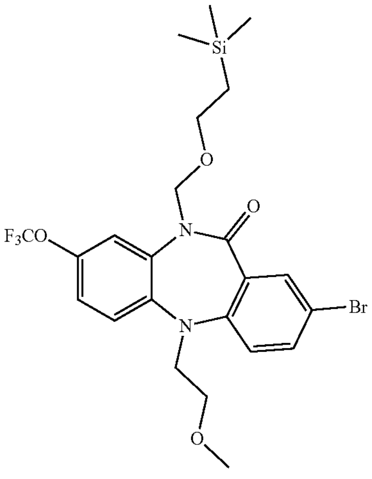

Chemical Formula: $C_{23}H_{28}BrF_3N_2O_4Si$
Exact Mass: 544.10
Molecular Weight: 545.47

2-Bromo-5-(2-methoxyethyl)-8-(trifluoromethoxy)-10-((2-(trimethylsilyl)ethoxy)methyl)-5,10-dihydro-11H-dibenzo [b,e][1,4]diazepin-11-one (DCT001-061): Potassium tert-butoxide (1M in THF, 0.219 ml, 0.219 mmol) was added to a solution of 2-bromo-8-(trifluoromethoxy)-10-((2-(trimethylsilyl)ethoxy)methyl)-5,10-dihydro-11H-dibenzo[b,e][1,4] diazepin-11-one DCT001-056 (0.1 g, 0.199 mmol) in DMF (1.655 ml) at 0° C. 1-Bromo-2-methoxyethane (0.056 ml, 0.596 mmol) was added and the solution was stirred at 0° C. for 30 mins, warmed to RT, and stirred for 18 hours. The reaction mixture was quenched with $NH_4Cl$ (30 mL), then diluted with EtOAc (30 mL).The organic phase was washed with $H_2O$ (4×30 mL), and brine (1×30 mL), dried over $MgSO_4$, filtered, and concentrated to give a yellow oily solid. Crude product was purified by flash chromatography: silica gel with a gradient of 5-10% EtOAc in DCM to give 2-bromo-5-(2-methoxyethyl)-8-(trifl((2-(truoromethoxy)-10-imethylsilyl)ethoxy)methyl)-5,10-dihydro-11H-dibenzo [b,e][1,4]diazepin-11-one (0.057 g, 0.102 mmol, 51.1% yield) as a yellow solid. $^1H$ NMR (400 MHz, DMSO-$d_6$) δ 7.69-7.57 (m, 3H), 7.44 (d, J=9.0 Hz, 1H), 7.25 (dd, J=9.0, 3.6 Hz, 2H), 5.42 (d, J=10.5 Hz, 1H), 5.31 (d, J=10.5 Hz, 1H), 4.00 (m, 2H), 3.84 (m, 1H), 3.61 (t, J=7.9 Hz, 2H), 3.45 (t, J=6.0 Hz, 2H), 3.18 (s, 2H), 0.84 (t, J=7.8 Hz, 2H), −0.06 (s, 9H). $^{19}F$ NMR (376 MHz, DMSO-$d_6$) δ-57.14.

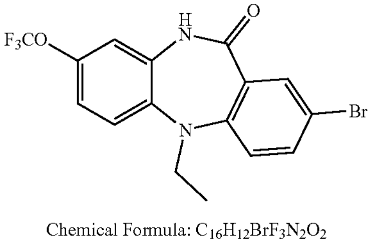

Chemical Formula: $C_{16}H_{12}BrF_3N_2O_2$
Exact Mass: 400.00
Molecular Weight: 401.18

2-Bromo-5-ethyl-8-(trifluoromethoxy)-5,10-dihydro-11H-dibenzo[b,e][1,4]diazepin-11-one (DCT001-068): TFA (0.90 mL) was added to a solution of 2-bromo-5-ethyl-8-(trifluoromethoxy)-10-((2-(trimethylsilyl)ethoxy)methyl)-5,10-dihydro-1I1H-dibenzo[b,e][1,4]diazepin-11-one DCT001-064 (0.101 g, 0.190 mmol) in DCM (3 mL) and the solution was stirred for 14 hours at RT. The reaction mixture was carefully quenched with $NaHCO_3$ (20 mL). DCM (30 mL) was added and the phases were separated. The organic layer was washed with $NaHCO_3$ (20 mL), $H_2O$ (20 mL), and brine (20 mL), dried over $MgSO_4$, filtered, and concentrated to give a yellow oil. Crude material was purified via flash chromatography: silica gel with a gradient of 0-10% EtOAc in DCM to give 2-bromo-5-ethyl-8-(trifluoromethoxy)-5,10-dihydro-11H-dibenzo[b,e][1,4]diazepin-11-one (0.07 g, 0.174 mmol, 92% yield) as a mixture of the free base and the TFA salt. The material was used without further purification. $^1H$ NMR (400 MHz, DMSO-$d_6$) δ 10.46 (bs, 1H), 7.65 (m, 2H), 7.25 (d, J=8.9 Hz, 1H), 7.24-7.14 (m, 1H), 7.15-7.04 (m, 1H), 7.02 (d, J=2.8 Hz, 2H), 3.65 (m, 2H), 1.06 (t, J=7.3 Hz, 3H). $^{19}F$ NMR (376 MHz, DMSO-$d_6$) δ-57.06,-57.09,-74.47. LCMS RT (Method 1)=3.600 min, m/z 400.9 $[M+H^+]$.

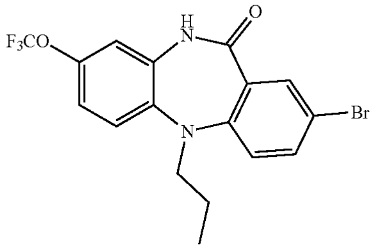

Chemical Formula: $C_{17}H_{14}BrF_3N_2O_2$
Exact Mass: 414.02
Molecular Weight: 415.21

2-Bromo-5-propyl-8-(trifluoromethoxy)-5,10-dihydro-11H-dibenzo[b,e][1,4]diazepin-11-one (DCT001-055): TFA (0.450 mL) was added to a solution of 2-bromo-5-propyl-8-(trifluoromethoxy)-10-((2-(trimethylsilyl)ethoxy) methyl)-5,10-dihydro-1I1H-dibenzo[b,e][1,4]diazepin-11-one (0.095 g, 0.174 mmol) in DCM (3 mL) at RT and the mixture was stirred for 16 hours. The reaction mixture was carefully quenched with $NaHCO_3$ (20 mL). DCM (30 mL) was added and the phases were separated. The organic layer was washed with $NaHCO_3$ (20 mL), $H_{20}$ (20 mL), and brine (20 mL), dried over $MgSO_4$, filtered, and concentrated to give a dark yellow oil. Crude material was purified via flash chromatography: silica gel with a gradient of 0-10% EtOAc in DCM to give 2-bromo-5-propyl-8-(trifluoromethoxy)-5,10-dihydro-11H-dibenzo[b,e][1,4]diazepin-11-one (0.055 g, 0.132 mmol, 76% yield) as a light yellow oily solid, with a small amount of the corresponding TFA salt. $^1H$ NMR (400 MHz, DMSO-$d_6$) δ 10.45 (s, 1H), 7.64 (m, 2H), 7.27 (d, J=8.9 Hz, 1H), 7.24-7.15 (m, 1H), 7.15-7.05 (m, 1H), 7.01 (d, J=2.8 Hz, 2H), 3.65 (m, 2H), 1.45 (h, J=7.1 Hz, 2H), 0.83 (t, J=7.3 Hz, 3H). $^{19}F$ NMR (376 MHz, DMSO-$d_6$) δ-57.06,-57.09,-74.46.

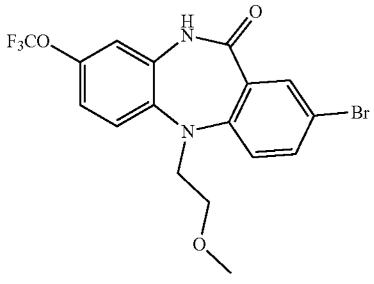

Chemical Formula: $C_{17}H_{14}BrF_3N_2O_3$
Exact Mass: 430.01
Molecular Weight: 431.21

2-Bromo-5-(2-methoxyethyl)-8-(trifluoromethoxy)-5,10-dihydro-11H-dibenzo[b,e][1,4]diazepin-11-one (DCT001-062): TFA (0.600 mL) was added to a solution of 2-bromo-5-(2-methoxyethyl)-8-(trifluoromethoxy)-10-((2-(trimethylsilyl)ethoxy)methyl)-5,10-dihydro-11H-dibenzo [b,e][1,4]diazepin-11-one DCT001-061 (0.057 g, 0.102 mmol) in DCM (3 mL) at RT and the mixture was stirred for 13 hours. The reaction mixture was carefully quenched with $NaHCO_3$ (20 mL). DCM (30 mL) was added and the phases were separated. The organic layer was washed with $NaHCO_3$ (20 mL), $H_2O$ (20 mL), and brine (20 mL), dried over $MgSO_4$, filtered, and concentrated to give a yellow oil. Crude material was purified via flash chromatography: silica gel with a gradient of 5-20% EtOAc in DCM to give 2-bromo-5-(2-methoxyethyl)-8-(trifluoromethoxy)-5,10-dihydro-1I1H-dibenzo[b,e][1,4]diazepin-11-one (0.019 g, 0.044 mmol, 43.4% yield). $^1H$ NMR (400 MHz, DMSO-$d_6$) δ 10.45 (s, 1H), 7.65 (d, J=6.6 Hz, 2H), 7.31 (d, J=8.9 Hz, 1H), 7.20 (d, J=9.1 Hz, 1H), 7.10 (d, J=8.9 Hz, 1H), 7.01 (s, 1H), 3.91 (bd, 2H), 3.40 (t, J=5.8 Hz, 2H), 3.14 (s, 3H). $^{19}F$ NMR (376 MHz, DMSO-$d_6$) δ-57.16. LCMS RT (Method 1)=3.495 min, m/z 430.9 [M+H$^+$].

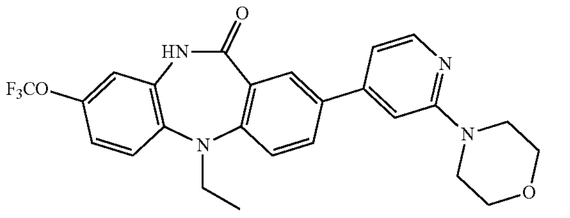

Chemical Formula: $C_{25}H_{23}F_3N_4O_3$
Exact Mass: 484.17
Molecular Weight: 484.48

5-Ethyl-2-(2-morpholinopyridin-4-yl)-8-(trifluoromethoxy)-5,10-dihydro-11H-dibenzo[b,e][1,4]diazepin-11-one (NCGC00488957): A mixture of 2-bromo-5-ethyl-8-(trifluoromethoxy)-5,10-dihydro-11H-dibenzo[b,e][1,4] diazepin-11-one DCT001-068 (0.070 g, 0.174 mmol) in DME (1.85 mL), 4-(4-(4,4,5,5-tetramethyl-1,3,2-dioxaborolan-2-yl)pyridin-2-yl)morpholine (0.056 g, 0.192 mmol), and sodium carbonate (2M, 0.087 ml, 0.174 mmol) were added to a microwave vial. Additional DME (1.745 ml) was added and the mixture was purged via $N_2$ via bubbling for 5 mins. Tetrakis(triphenylphosphine)palladium(0) (10.08 mg, 8.72 μmol) was added, the mixture was purged for an additional 2 min with $N_2$, then heated to 160° C. via microwave irradiation for 1 hour. The reaction mixture was cooled to RT, diluted with DCM (10 mL), and filtered through celite. The filtrate was concentrated to give a dark yellow oil (130mgs) which was purified via standard HPLC conditions using a gradient of 10-100% ACN in $H_2O$ with 0.1% TFA to give 5-ethyl-2-(2-morpholinopyridin-4-yl)-8-(trifluoromethoxy)-5,10-dihydro-11H-dibenzo[b,e][1,4]diazepin-11-one (0.069 g, 81% yield) as the TFA salt. $^1H$ NMR (400 MHz, DMSO-$d_6$) δ 10.47 (s, 1H), 8.10 (d, J=5.7 Hz, 1H), 7.99-7.89 (m, 2H), 7.34-7.25 (m, 2H), 7.18 (s, 1H), 7.15-7.00 (m, 3H), 3.93-3.59 (m, 5H), 3.55 (t, J=4.8 Hz, 5H), 1.11 (t, J=6.9 Hz, 3H). $^{19}F$ NMR (376 MHz, DMSO-$d_6$) δ-57.08,-74.77. LCMS RT (Method 1)=3.4837 min, m/z 485.2 [M+H$^+$].

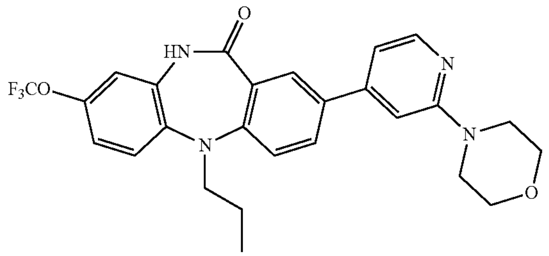

Chemical Formula: $C_{26}H_{25}F_3N_4O_3$
Exact Mass: 498.19
Molecular Weight: 498.51

2-(2-Morpholinopyridin-4-yl)-5-propyl-8-(trifluoromethoxy)-5,10-dihydro-11H-dibenzo[b,e][1,4]diazepin-11-one (NCGC00488913): A mixture of 2-bromo-5-propyl-8-(trifluoromethoxy)-5,10-dihydro-11H-dibenzo[b,e][1,4] diazepin-11-one DCT001-055 (0.0515 g, 0.124 mmol) in DMF (1.24 mL), 4-(4-(4,4,5,5-tetramethyl-1,3,2-dioxaborolan-2-yl)pyridin-2-yl)morpholine (0.040 g, 0.136 mmol), and sodium carbonate (2M, 0.062 ml, 0.124 mmol) were added to a microwave vial under $N_2$. DMF (1.240 ml) was added and the mixture was purged via $N_2$ bubbling for 5 mins. Tetrakis(triphenylphosphine)palladium(0) (7.17 mg, 6.20 μmol) was added, the mixture was purged with $N_2$ for an additional 2 min, then heated to 160° C. via microwave irradiation for 1 hour. The reaction mixture was cooled to RT, diluted with DCM (20 mL), and filtered through celite. The filtrate was then washed with $H_2O$ (4×20 mL) and brine (1×20 mL), dried over $MgSO_4$, filtered, and concentrated to give a pale brown solid (0.055g). Crude material was purified via standard HPLC conditions using a gradient of 10-100% ACN in $H_2O$ with 0.1% TFA to give 2-(2-morpholinopyridin-4-yl)-5-propyl-8-(trifluoromethoxy)-5,10-dihydro-11H-dibenzo[b,e][1,4]diazepin-11-one as the TFA salt. $^1H$ NMR (400 MHz, DMSO-$d_6$) δ 10.48 (s, 1H), 8.14 (d, J=5.6 Hz, 1H), 8.01-7.90 (m, 2H), 7.33 (m, 2H), 7.20-7.09 (m, 2H), 7.08-7.02 (m, 2H), 3.72-3.51 (bm, 10H), 1.53 (h, J=7.1 Hz, 2H), 0.89 (t, J=7.3 Hz, 3H). $^{19}F$ NMR (376 MHz, DMSO-$d_6$) δ-57.06,-74.15. LCMS RT (Method 1)=4.726 min, m/z 499.0 [M+H$^+$].

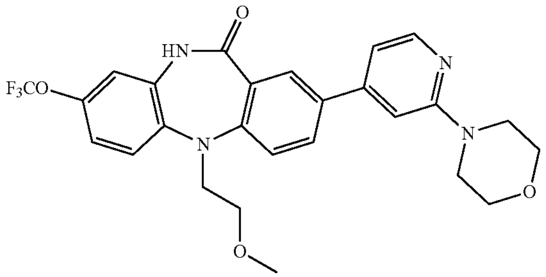

Chemical Formula: $C_{26}H_{25}F_3N_4O_4$
Exact Mass: 514.18
Molecular Weight: 514.51

5-(2-Methoxyethyl)-2-(2-morpholinopyridin-4-yl)-8-(trifluoromethoxy)-5,10-dihydro-11H-dibenzo[b,e][1,4]diazepin-11-one (NCGC00488955): A mixture of 2-bromo-5-(2-methoxyethyl)-8-(trifluoromethoxy)-5,10-dihydro-1I1H-dibenzo[b,e][1,4]diazepin-11-one DCT001-055 (0.018 g, 0.042 mmol) in DMF (1.24 mL), 4-(4-(4,4,5,5-tetramethyl-1,3,2-dioxaborolan-2-yl)pyridin-2-yl)morpholine (0.013 g, 0.046 mmol), and sodium carbonate (2M, 0.021 ml, 0.042 mmol) were added to a microwave vial. DMF (0.417 mL) was added and the mixture was purged via $N_2$ bubbling for 5 mins.

Tetrakis(triphenylphosphine)palladium(0) (2.412 mg, 2.087 μmol) was added, the mixture was purged with $N_2$ for an additional 2 min, then heated to 160° C. via microwave irradiation for 1 hour. The reaction mixture was cooled to RT, diluted with DCM (20 mL), and filtered through celite. The filtrate was concentrate and purified via standard HPLC conditions using a gradient of 10-100% ACN in $H_2O$ with 0.1% TFA to give 5-(2-methoxyethyl)-2-(2-morpholinopyridin-4-yl)-8-(trifluoromethoxy)-5,10-dihydro-11H-dibenzo[b,e][1,4]diazepin-11-one (0.0147 g, 70% yield) as the TFA salt. $^1H$ NMR (400 MHz, DMSO-$d_6$) δ 10.49 (s, 1H), 8.14 (d, J=5.7 Hz, 1H), 8.01-7.91 (m, 2H), 7.38 (dd, J=8.8, 7.1 Hz, 2H), 7.22-7.10 (m, 2H), 7.05 (d, J=2.8 Hz, 2H), 3.93 (m, 2H), 3.76-3.69 (m, 6H), 3.57 (t, J=4.9 Hz, 4H), 3.20 (s, 3H). $^{19}F$ NMR (376 MHz, DMSO-$d_6$) δ-57.05,-74.20. LCMS RT (Method 1)=4.264 min, m/z 515.0 [M+H$^+$].

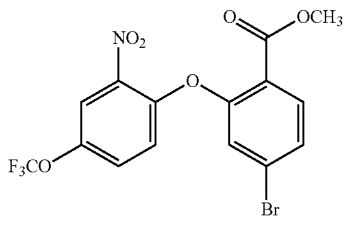

Chemical Formula: $C_{15}H_9BrF_3NO_6$
Exact Mass: 434.96
Molecular Weight: 436.14

Methyl 4-bromo-2-(2-nitro-4-(trifluoromethoxy)phenoxy)benzoate (AED011-030): methyl 4-bromo-2-hydroxybenzoate (0.950 g, 4.11 mmol) was added to a solution of 1-fluoro-2-nitro-4-(trifluoromethoxy)benzene (600 μL, 4.11 mmol) and $K_2CO_3$ (0.739 g, 5.35 mmol) in DMF (12.0 mL). The resulting reaction mixture was stirred at 60° C. overnight, after which LC-MS analysis showed completion. Reaction mixture was allowed to cool to RT and then poured over ice $H_2O$, vigorously stirred for 30 min and insoluble material filtered, washed generously with $H_2O$ and air dried to afford methyl 4-bromo-2-(2-nitro-4-(trifluoromethoxy)phenoxy)benzoate (1.55 g, 86.0% yield) as a slightly yellow powder, which was used without further purification. $^1H$ NMR (400 MHz, DMSO-$d_6$) δ 8.21 (d, J=2.9 Hz, 1H), 7.90 (d, J=8.9 Hz, 1H), 7.72-7.63 (m, 3H), 7.11 (d, J=9.2 Hz, 1H), 3.69 (s, 3H). $^{19}F$ NMR (376 MHz, DMSO-$d_6$) δ-57.51 (s, 3F). LCMS RT (Method 2)=3.719 min, m/z 894.9 [2M+Na$^+$].

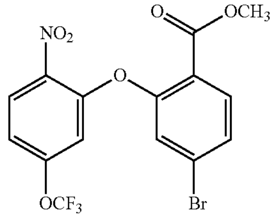

Chemical Formula: $C_{15}H_9BrF_3NO_6$
Exact Mass: 434.96
Molecular Weight: 436.14

Methyl 4-bromo-2-(2-nitro-5-(trifluoromethoxy)phenoxy)benzoate (AED011-098): Methyl 4-bromo-2-hydroxybenzoate (478 mg, 2.07 mmol) was added to a solution of 2-chloro-1-nitro-4-(trifluoromethoxy)benzene (500 mg, 2.07 mmol) and $K_2CO_3$ (372 mg, 2.69 mmol) in DMF (10.0 mL). The resulting reaction mixture was stirred at 70° C. overnight, after which LC-MS analysis showed completion. Reaction mixture was diluted with EtOAc and washed with brine twice, dried over $MgSO_4$, filtered and concentrated. Crude mixture was purified by flash column chromatography: silica gel with a gradient of 3-15% EtOAc in Hex to afford methyl 4-bromo-2-(2-nitro-5-(trifluoromethoxy)phenoxy)benzoate (415 mg, 46.0% yield), which was used without further purification in the next step. $^1H$ NMR (400 MHz, DMSO-$d_6$) δ 8.27 (d, J=9.1 Hz, 1H), 7.92-7.87 (m, 1H), 7.70-7.65 (m, 2H), 7.35 (ddq, J=9.1, 2.6, 1.3 Hz, 1H), 7.02 (dd, J=2.5, 0.7 Hz, 1H), 3.68 (s, 3H). $^{19}F$ NMR (376 MHz, DMSO-$d_6$) δ-56.91 (s, 3F). LCMS RT (Method 2)=3.663 min, m/z 437.9 [M$^+$].

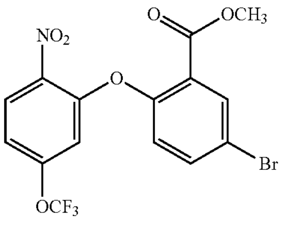

Chemical Formula: $C_{15}H_9BrF_3NO_6$
Exact Mass: 434.96
Molecular Weight: 436.14

Methyl 5-bromo-2-(2-nitro-5-(trifluoromethoxy)phenoxy)benzoate (AED018-008): A mixture of 2-chloro-1-nitro-4-(trifluoromethoxy)benzene (500 mg, 2.07 mmol), methyl 5-bromo-2-hydroxybenzoate (478 mg, 2.07 mmol) and $Cs_2CO_3$ (742 mg, 2.28 mmol) in DMF (10.0 mL) was stirred at 70° C. overnight, after which LC-MS analysis showed completion. Reaction mixture was poured into ice water, stirred for 10 min and extracted with EtOAc (2×'s). The combined organic layers were washed with $H_2O$, brine, dried over $MgSO_4$, filtered and concentrated. Crude mixture was purified by flash column chromatography: silica gel with a gradient of 3-15% EtOAc in Hex to afford methyl 5-bromo-2-(2-nitro-5-(trifluoromethoxy)phenoxy)benzoate (557 mg, 61.7% yield) as a clear oil, which solidified upon standing.

$^1$H NMR (400 MHz, DMSO-$d_6$) δ 8.26 (d, J=9.1 Hz, 1H), 8.07 (d, J=2.6 Hz, 1H), 7.92 (dd, J=8.7, 2.6 Hz, 1H), 7.36-7.29 (m, 2H), 7.00 (dd, J=2.4, 0.7 Hz, 1H), 3.69 (s, 3H). $^{19}$F NMR (376 MHz, DMSO-$d_6$) δ-56.92 (s, 3F). LCMS RT (Method 2)=3.675 min, m/z 437.9 [$M^+$].

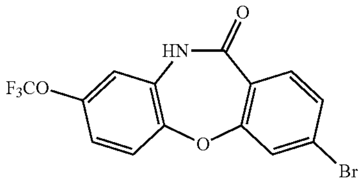

Chemical Formula: $C_{14}H_7BrF_3NO_3$
Exact Mass: 372.96
Molecular Weight: 374.11

3-Bromo-8-(trifluoromethoxy)dibenzo[b,f][1,4]oxazepin-11(10H)-one (AED011-045): 6N HCl (10.0 mL, 60.0 mmol) was added to a mixture of methyl 4-bromo-2-(2-nitro-4-(trifluoromethoxy)phenoxy)benzoate AED011-030 (1.34 g, 3.07 mmol) and $Fe^0$ powder (0.858 g, 15.4 mmol) in EtOH (10.0 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry to afford 3-bromo-8-(trifluoromethoxy)dibenzo[b,f][1,4]oxazepin-11(10H)-one (950 mg, 83.0% yield) as a lightly grayish fluffy solid, which was used without further purification. $^1$H NMR (400 MHz, DMSO-$d_6$) δ 10.73 (s, 1H), 7.76-7.71 (m, 1H), 7.70 (s, 1H), 7.57 (dd, J=8.4, 1.9 Hz, 1H), 7.51 (d, J=8.6 Hz, 1H), 7.19 (dt, J=2.9, 1.0 Hz, 1H), 7.16 (s, 1H). $^{19}$F NMR (376 MHz, DMSO-$d_6$) δ-57.13 (s, 3F). LCMS RT (Method 2)=3.637 min.

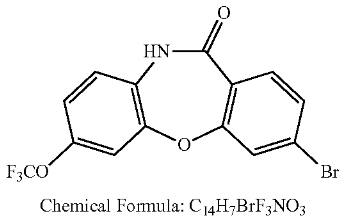

Chemical Formula: $C_{14}H_7BrF_3NO_3$
Exact Mass: 372.96
Molecular Weight: 374.11

3-Bromo-7-(trifluoromethoxy)dibenzo[b,f][1,4]oxazepin-11(10H)-one (AED012-003): 6N HCl (3.00 mL, 18.0 mmol) was added to a mixture of methyl 4-bromo-2-(2-nitro-5-(trifluoromethoxy)phenoxy)benzoate AED011-098 (715 mg, 1.64 mmol) and $Fe^0$ powder (0.458 g, 8.20 mmol) in EtOH (3.00 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry to afford 3-bromo-7-(trifluoromethoxy)dibenzo[b,f][1,4]oxazepin-11(10H)-one (348 mg, 56.7% yield) as a lightly grayish fluffy solid, which was used without further purification. $^1$H NMR (400 MHz, DMSO-$d_6$) δ 10.75 (s, 1H), 7.75 (d, J=1.9 Hz, 1H), 7.71 (d, J=8.3 Hz, 1H), 7.57 (dd, J=8.4, 1.9 Hz, 1H), 7.52 (tt, J=1.6, 0.9 Hz, 1H), 7.27 (q, J=0.7 Hz, 2H). $^{19}$F NMR (376 MHz, DMSO-$d_6$) δ-57.19 (s, 3F). LCMS RT (Method 2)=3.604 min.

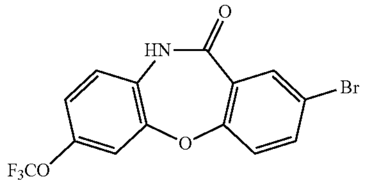

Chemical Formula: $C_{14}H_7BrF_3NO_3$
Exact Mass: 372.96
Molecular Weight: 374.11

2-Bromo-7-(trifluoromethoxy)dibenzo[b,f][1,4]oxazepin-11(10H)-one (AED018-009): 6N HCl (5.00 mL, 30.0 mmol) was added to a mixture of methyl 5-bromo-2-(2-nitro-5-(trifluoromethoxy)phenoxy)benzoate AED018-008 (600 mg, 1.38 mmol) and $Fe^0$ powder (0.384 g, 6.88 mmol) in EtOH (5.00 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry to afford 2-bromo-7-(trifluoromethoxy)dibenzo[b,f][1,4]oxazepin-11(10H)-one (476 mg, 92.0% yield) as a lightly grayish fluffy solid, which was used without further purification. $^1$H NMR (400 MHz, DMSO-$d_6$) δ 10.80 (s, 1H), 7.88-7.81 (m, 2H), 7.50 (tq, J=1.7, 0.9 Hz, 1H), 7.39 (dd, J=8.4, 0.6 Hz, 1H), 7.27 (d, J=1.4 Hz, 2H). $^{19}$F NMR (376 MHz, DMSO-$d_6$) δ-57.23 (s, 3F). LCMS RT (Method 2)=3.559 min.

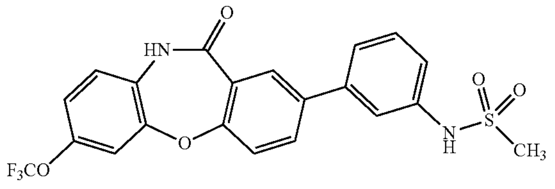

Chemical Formula: $C_{12}H_{15}F_3N_2O_5S$
Exact Mass: 464.07
Molecular Weight: 464.42

N-(3-(11-oxo-7-(trifluoromethoxy)-10,11-dihydrodibenzo[b,f][1,4]oxazepin-2-yl)phenyl)methanesulfonamide (NCGC00494683): Prepared following general Procedure D; 2-bromo-7-(trifluoromethoxy)dibenzo[b,f][1,4]oxazepin-11(10H)-one AED018-009 (25.0 mg, 0.067 mmol), (3-(methylsulfonamido)phenyl)boronic acid (21.6 mg, 0.100 mmol), $K_3PO_4$ (28.4 mg, 0.134 mmol), XPhos Pd(crotyl)Cl (4.50 mg, 6.68 μmol) in 4:1 dioxane:$H_2O$ (1.25 mL) to afford the title compound (12.8 mg, 41.2% yield). $^1$H NMR (400 MHz, DMSO-$d_6$) δ 10.76 (s, 1H), 9.83 (s, 1H), 7.95 (d, J=2.4 Hz, 1H), 7.88 (dd, J=8.4, 2.5 Hz, 1H), 7.55-7.48 (m, 2H), 7.48-7.35 (m, 3H), 7.28 (t, J=1.4 Hz, 2H), 7.24 (ddd, J=7.8, 2.2, 1.2 Hz, 1H), 3.03 (s, 3H). $^{19}$F NMR (376 MHz, DMSO-$d_6$) δ-57.21 (s, 3F). LCMS RT (Method 1)=5.206 min, m/z 465.0 [M+$H^+$].

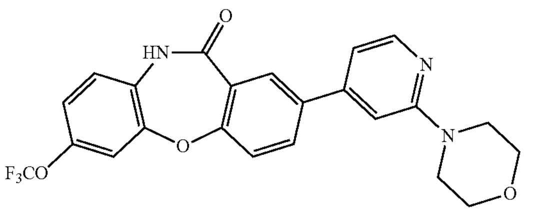

Chemical Formula: $C_{23}H_{18}F_3N_3O_4$
Exact Mass: 457.12
Molecular Weight: 457.41

2-(2-morpholinopyridin-4-yl)-7-(trifluoromethoxy)dibenzo[b,f][1,4]oxazepin-11(10H)-one (NCGC00494682): Prepared following general Procedure D; 2-bromo-7-(trifluoromethoxy)dibenzo[b,f][1,4]oxazepin-11(10H)-one AED018-009 (25.0 mg, 0.067 mmol), 4-(4-(4,4,5,5-tetramethyl-1,3,2-dioxaborolan-2-yl)pyridin-2-yl)morpholine (29.1 mg, 0.100 mmol), $K_3PO_4$ (28.4 mg, 0.134 mmol), XPhos Pd(crotyl)Cl (4.50 mg, 6.68 μmol) in 4:1 dioxane:$H_2O$ (1.25 mL) to afford the title compound as the TFA salt (18.9 mg, 61.8% yield). $^1$H NMR (400 MHz, DMSO-$d_6$) δ 10.81 (s, 1H), 8.17 (d, J=5.5 Hz, 1H), 8.11 (d, J=2.4 Hz, 1H), 8.07 (dd, J=8.4, 2.5 Hz, 1H), 7.58-7.49 (m, 2H), 7.28 (d, J=1.3 Hz, 2H), 7.18 (s, 1H), 7.05 (d, J=5.5 Hz, 1H), 3.72 (dd, J=5.9, 3.8 Hz, 4H), 3.57 (t, J=4.8 Hz, 4H). $^{19}$F NMR (376 MHz, DMSO-$d_6$) δ-57.23 (s, 3F),-74.27 (s, 3F). LCMS RT (Method 1)=4.145 min, m/z 458.0 [M+$H^+$].

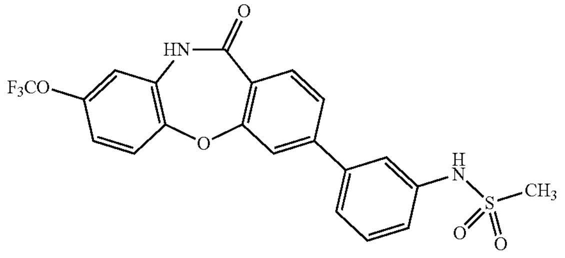

Chemical Formula: $C_{21}H_{15}F_3N_2O_5S$
Exact Mass: 464.07
Molecular Weight: 464.42

N-(3-(11-Oxo-8-(trifluoromethoxy)-10,11-dihydrodibenzo[b,f][1,4]oxazepin-3-yl)phenyl)methanesulfonamide (NCGC00384235): Prepared following general Procedure A; 3-bromo-8-(trifluoromethoxy)dibenzo[b,f][1,4]oxazepin-11(10H)-one AED011-045 (40.0 mg, 0.107 mmol), (3-(methylsulfonamido)phenyl)boronic acid (23.0 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (26.8 mg, 54.0% yield). $^1$H NMR (400 MHz, DMSO-$d_6$) δ 10.66 (s, 1H), 9.86 (s, 1H), 7.85 (d, J=8.1 Hz, 1H), 7.62 (d, J=1.8 Hz, 1H), 7.56 (dd, J=8.1, 1.8 Hz, 1H), 7.54-7.40 (m, 4H), 7.26 (ddt, J=5.4, 3.6, 2.1 Hz, 1H), 7.14 (dtt, J=5.9, 1.9, 1.0 Hz, 2H), 3.02 (s, 3H). $^{19}$F NMR (376 MHz, DMSO-$d_6$) δ-57.13 (s, 3F). LCMS RT (Method 1)=5.464 min, m/z 929.1 [$2M^+$].

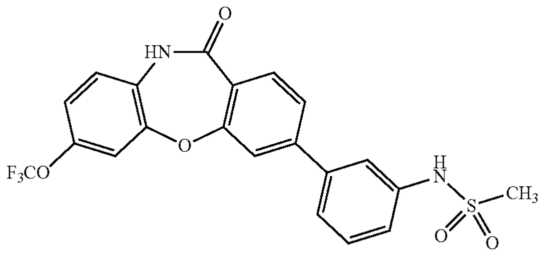

Chemical Formula: $C_{21}H_{15}F_3N_2O_5S$
Exact Mass: 464.07
Molecular Weight: 464.42

N-(3-(11-oxo-7-(trifluoromethoxy)-10,11-dihydrodibenzo[b,f][1,4]oxazepin-3-yl)phenyl)methanesulfonamide (NCGC00384296): Prepared following general Procedure D; 3-bromo-7-(trifluoromethoxy)dibenzo[b,f][1,4]oxazepin-11(10H)-one AED012-003 (40 mg, 0.107 mmol), (3-(methylsulfonamido)phenyl)boronic acid (34.5 mg, 0.160 mmol), $K_3PO_4$ (45.4 mg, 0.214 mmol), XPhos Pd(crotyl)Cl (7.20 mg, 10.7 μmol) in 4:1 dioxane:$H_2O$ (1.25 mL) to afford the title compound (26.5 mg, 53.4% yield). $^1$H NMR (400 MHz, DMSO-$d_6$) δ 10.70 (s, 1H), 9.90 (s, 1H), 7.88 (d, J=8.1 Hz, 1H), 7.69 (d, J=1.8 Hz, 1H), 7.59 (dd, J=8.1, 1.8 Hz, 1H), 7.52 (ddt, J=8.2, 2.4, 1.0 Hz, 2H), 7.50-7.43 (m, 2H), 7.34-7.22 (m, 3H), 3.04 (s, 3H). $^{19}$F NMR (376 MHz, DMSO-$d_6$) δ-57.18 (s, 3F). LCMS RT (Method 1)=5.011 min, m/z 465.0 [M+$H^+$].

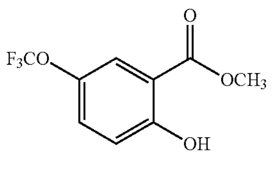

Chemical Formula: $C_9H_7F_3O_4$
Exact Mass: 236.03
Molecular Weight: 236.15

Methyl 2-hydroxy-5-(trifluoromethoxy)benzoate (AED011-095): A mixture of 2-hydroxy-5-(trifluoromethoxy)benzoic acid (300 mg, 1.35 mmol) and a few drops of concentrated $H_2SO_4$ was heated to 120° C. for 1 h under microwave irradiation, after which LC-MS analysis showed completion. Reaction mixture was concentrated to dryness to afford methyl 2-hydroxy-5-(trifluoromethoxy)benzoate (319 mg, 100% yield) as a white solid, which was used without further purification. $^1$H NMR (400 MHz, DMSO-$d_6$) δ 10.57 (s, 1H), 7.65 (d, J=3.2 Hz, 1H), 7.54 (dt, J=9.4, 3.0 Hz, 1H), 7.10 (d, J=9.1 Hz, 1H), 3.89 (s, 3H). $^{19}$F NMR (376 MHz, DMSO-$d_6$) δ-57.17 (s, 3F). LCMS RT (Method 2)=3.507 min.

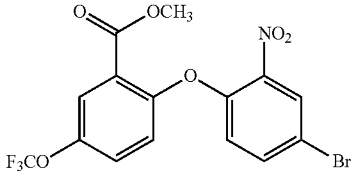

Chemical Formula: $C_{15}H_9BrF_3NO_6$
Exact Mass: 434.96
Molecular Weight 436.14

Methyl 2-(4-bromo-2-nitrophenoxy)-5-(trifluoromethoxy) benzoate (AED011-097): A mixture of methyl 2-hydroxy-5-(trifluoromethoxy)benzoate AED011-095 (155 mg, 0.656 mmol), 4-bromo-1-fluoro-2-nitrobenzene (0.082 mL, 0.656 mmol) and $K_2CO_3$ (118 mg, 0.853 mmol) in DMF (5.00 mL) was stirred at 70° C. overnight, after which LC-MS analysis showed completion. Reaction mixture was diluted with EtOAc and washed twice with brine, dried over $MgSO_4$, filtered and concentrated to afford methyl 2-(4-bromo-2-nitrophenoxy)-5-(trifluoromethoxy)benzoate (162 mg, 56.6% yield), which was used without further purification in the next step. $^1$H NMR (400 MHz, DMSO-$d_6$) δ 8.32 (d, J=2.5 Hz, 1H), 7.87 (dt, J=3.0, 1.0 Hz, 1H), 7.82 (dd, J=8.9, 2.5 Hz, 1H), 7.77-7.71 (m, 1H), 7.44 (d, J=9.0 Hz, 1H), 6.98 (d, J=8.9 Hz, 1H), 3.73 (s, 3H). $^{19}$F NMR (376 MHz, DMSO-$d_6$) δ-57.22 (s, 3F). LCMS RT (Method 2)=3.857 min, m/z 436.0 [$M^+$].

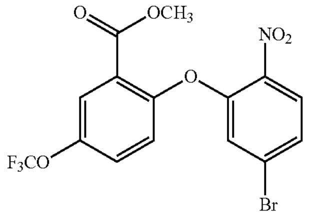

Chemical Formula: $C_{15}H_9BrF_3NO_6$
Exact Mass: 434.96
Molecular Weight: 436.14

Methyl 2-(5-bromo-2-nitrophenoxy)-5-(trifluoromethoxy) benzoate (AED011-099): A mixture of methyl 2-hydroxy-5-(trifluoromethoxy)benzoate AED011-095 (155 mg, 0.656 mmol), 4-bromo-2-fluoro-1-nitrobenzene (144 mg, 0.656 mmol) and $K_2CO_3$ (118 mg, 0.853 mmol) in DMF (5.00 mL) was stirred at 70° C. overnight, after which LC-MS analysis showed completion. Reaction mixture was diluted with EtOAc and washed twice with brine, dried over $MgSO_4$, filtered and concentrated to afford methyl 2-(5-bromo-2-nitrophenoxy)-5-(trifluoromethoxy)benzoate (189 mg, 66.0% yield), which was used without further purification in the next step. $^1$H NMR (400 MHz, DMSO-$d_6$) δ 8.06 (d, J=8.7 Hz, 1H), 7.87 (dt, J=2.9, 0.9 Hz, 1H), 7.74 (ddt, J=9.0, 3.0, 0.9 Hz, 1H), 7.58 (dd, J=8.7, 2.0 Hz, 1H), 7.45 (d, J=9.0 Hz, 1H), 7.26 (d, J=2.0 Hz, 1H), 3.73 (s, 3H). $^{19}$F NMR (376 MHz, DMSO-$d_6$) δ-57.17 (s, 3F). LCMS RT (Method 2)=3.837 min, m/z 458.9 [$M+Na^+$].

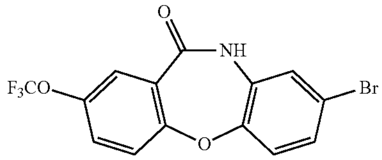

Chemical Formula: $C_{14}H_7BrF_3NO_3$
Exact Mass: 372.96
Molecular Weight: 374.11

8-Bromo-2-(trifluoromethoxy)dibenzo[b,f][1,4]oxazepin-11(10H)-one (AED012-001): 6N hydrochloric acid (2.00 mL, 12.0 mmol) was added to a mixture of methyl 2-(4-bromo-2-nitrophenoxy)-5-(trifluoromethoxy)benzoate AED011-097 (160 mg, 0.367 mmol) and $Fe^0$ powder (102 mg, 1.83 mmol) in EtOH (2.00 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry to afford 8-bromo-2-(trifluoromethoxy)dibenzo[b,f][1,4]oxazepin-11(10H)-one (77.0 mg, 56.1% yield) as an off-white solid, which was used without further purification. $^1$H NMR (400 MHz, DMSO-$d_6$) δ 10.80 (s, 1H), 7.71-7.63 (m, 2H), 7.57-7.48 (m, 1H), 7.37-7.32 (m, 3H). $^{19}$F NMR (376 MHz, DMSO-$d_6$) δ-57.28 (s, 3F). LCMS RT (Method 2)=3.581 min, m/z 770.9 [$2M+Na^+$].

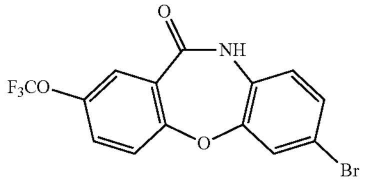

Chemical Formula: $C_{14}H_7BrF_3NO_3$
Exact Mass: 372.96
Molecular Weight: 374.11

7-Bromo-2-(trifluoromethoxy)dibenzo[b,f][1,4]oxazepin-11(10H)-one (AED012-002): 6N hydrochloric acid (2.00 mL, 12.0 mmol) was added to a mixture of methyl 2-(5-bromo-2-nitrophenoxy)-5-(trifluoromethoxy)benzoate AED011-099 (189 mg, 0.433 mmol) and $Fe^0$ powder (121 mg, 2.17 mmol) in EtOH (2.00 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with water and allowed to air dry to afford 7-bromo-2-(trifluoromethoxy)dibenzo[b,f][1,4]oxazepin-11(10H)-one (83.0 mg, 51.2% yield) as a tan solid, which was used without further purification. $^1$H NMR (400 MHz, DMSO-$d_6$) δ 10.82 (s, 1H), 7.74-7.63 (m, 3H), 7.55 (dd, J=8.7, 0.5 Hz, 1H), 7.43

(dd, J=8.5, 2.2 Hz, 1H), 7.13 (d, J=8.6 Hz, 1H). $^{19}$F NMR (376 MHz, DMSO-$d_6$) δ-57.27 (s, 3F). LCMS RT (Method 2)=3.601 min, m/z 374.9 [$M^+$].

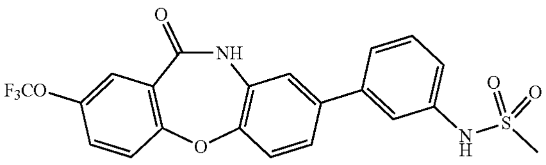

Chemical Formula: $C_{21}H_{15}F_3N_2O_5S$
Exact Mass: 464.07
Molecular Weight: 464.42

N-(3-(11-Oxo-2-(trifluoromethoxy)-10,11-dihydrodibenzo[b,f][1,4]oxazepin-8-yl)phenyl)methanesulfonamide (NCGC00384303): Prepared following general Procedure D; 8-bromo-2-(trifluoromethoxy)dibenzo[b,f][1,4]oxazepin-11(10H)-one AED012-001 (40.0 mg, 0.107 mmol), (3-(methylsulfonamido)phenyl)boronic acid (34.5 mg, 0.160 mmol), $K_3PO_4$ (45.4 mg, 0.214 mmol), XPhos Pd(crotyl)Cl (7.22 mg, 10.7 μmol) in 4:1 dioxane:$H_2O$ (1.25 mL) to afford the title compound (38.7 mg, 78.0% yield). $^1$H NMR (400 MHz, DMSO-$d_6$) δ 10.84 (s, 1H), 9.88 (s, 1H), 7.71-7.65 (m, 2H), 7.57-7.52 (m, 1H), 7.49-7.36 (m, 5H), 7.30 (ddd, J=7.7, 1.9, 1.1 Hz, 1H), 7.21 (ddd, J=8.0, 2.2, 1.0 Hz, 1H), 3.03 (s, 3H). $^{19}$F NMR (376 MHz, DMSO-$d_6$) δ-57.26 (s, 3F). LCMS RT (Method 1)=5.233 min, m/z 465.0 [$M+H^+$].

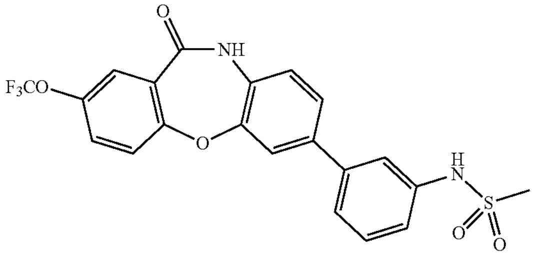

Chemical Formula: $C_{21}H_{15}F_3N_2O_5S$
Exact Mass: 464.07
Molecular Weight: 464.42

N-(3-(11-Oxo-2-(trifluoromethoxy)-10,11-dihydrodibenzo[b,f][1,4]oxazepin-7-yl)phenyl)methanesulfonamide (NCGC00384295): Prepared following general Procedure A; 7-bromo-2-(trifluoromethoxy)dibenzo[b,f][1,4]oxazepin-11(10H)-one AED012-002 (40.0 mg, 0.107 mmol), (3-(methylsulfonamido)phenyl)boronic acid (23.0 mg, 0.107 mmol), 2M $Na_2CO_3$ (214 μL, 0.428 mmol), $Pd(PPh_3)_4$(6.19 mg, 5.36 μmol) in DME (4.00 mL) to afford the title compound (19.3 mg, 38.9% yield). $^1$H NMR (400 MHz, DMSO-$d_6$) δ 10.84 (s, 1H), 9.82 (s, 1H), 7.71-7.66 (m, 2H), 7.64 (d, J=2.1 Hz, 1H), 7.60-7.55 (m, 1H), 7.47 (dd, J=8.3, 2.1 Hz, 1H), 7.45-7.36 (m, 3H), 7.27 (d, J=8.3 Hz, 1H), 7.21 (dt, J=7.7, 1.8 Hz, 1H), 3.02 (s, 3H). $^{19}$F NMR (376 MHz, DMSO-$d_6$) δ-57.27 (s, 3F). LCMS RT (Method 1)=5.452 min, m/z 929.1 [$2M^+$].

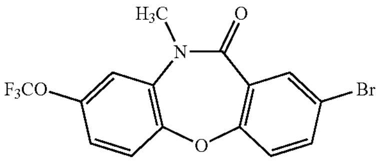

Chemical Formula: $C_{15}H_9BrF_3NO_3$
Exact Mass: 386.97
Molecular Weight: 388.14

2-Bromo-10-methyl-8-(trifluoromethoxy)dibenzo[b,f][1,4]oxazepin-11(10H)-one (AED011-065): A 60% dispersion in mineral oil of NaH (50.0 mg, 1.25 mmol) was added in portions to a solution of 2-bromo-8-(trifluoromethoxy)dibenzo[b,f][1,4]oxazepin-11(10H)-one AED013-066 (200 mg, 0.535 mmol) in DMF (5.00 mL) at RT. After stirring for 5 min, was added $CH_3I$ (0.100 mL, 1.60 mmol) and the resulting reaction mixture allowed to stir for 2 h at RT, after which LC-MS analysis showed completion. Reaction mixture was diluted with $H_2O$ and extracted with $CH_2Cl_2$ (2×'s). The combined organic layers were washed with saturated Na2S2$O_3$, brine, dried over $MgSO_4$, filtered and concentrated. Crude Residue was purified by flash column chromatography: silica gel with a gradient of 3-10% EtOAc in Hex to afford 2-bromo-10-methyl-8-(trifluoromethoxy)dibenzo[b,f][1,4]oxazepin-11(10H)-one (180 mg, 87.0% yield) as an off-white solid. $^1$H NMR (400 MHz, DMSO-$d_6$) δ 7.87-7.76 (m, 2H), 7.59-7.50 (m, 2H), 7.38 (d, J=8.5 Hz, 1H), 7.28 (ddd, J=8.9, 2.8, 1.2 Hz, 1H), 3.49 (s, 3H). $^{19}$F NMR (376 MHz, DMSO-$d_6$) δ-57.13 (s, 3F). LCMS RT (Method 2)=3.893 min, m/z 388.0 [$M^+$].

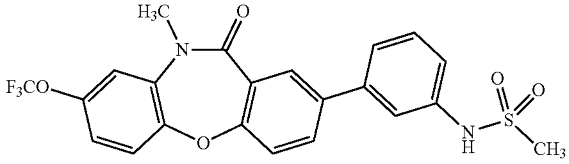

Chemical Formula: $C_{22}H_{17}F_3N_2O_5S$
Exact Mass: 478.08
Molecular Weight: 478.44

N-(3-(10-Methyl-11-oxo-8-(trifluoromethoxy)-10,11-dihydrodibenzo[b,f][1,4]oxazepin-2-yl)phenyl)methanesulfonamide (NCGC00384233): Prepared following general Procedure A; 2-bromo-10-methyl-8-(trifluoromethoxy)dibenzo[b,f][1,4]oxazepin-11(10H)-one AED011-065 (40.0 mg, 0.103 mmol), (3-(methylsulfonamido)phenyl)boronic acid (22.2 mg, 0.103 mmol), 2M $Na_2CO_3$ (214 μL, 0.428 mmol), $Pd(PPh_3)_4$(6.19 mg, 5.36 μmol) in DME (4.00 mL) to afford the title compound (23.0 mg, 46.6% yield). $^1$H NMR (400 MHz, DMSO-$d_6$) δ 9.85 (s, 1H), 7.92 (d, J=2.4 Hz, 1H), 7.85 (dd, J=8.4, 2.5 Hz, 1H), 7.60-7.47 (m, 3H), 7.48-7.34 (m, 3H), 7.33-7.19 (m, 2H), 3.53 (s, 3H), 3.02 (s, 3H). $^{19}$F NMR (376 MHz, DMSO-$d_6$) δ-57.12 (s, 3F). LCMS RT (Method 1)=5.932 min, m/z 957.2 [$2M^+$].

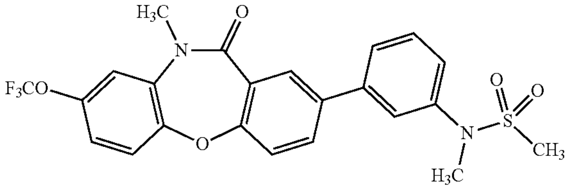

Chemical Formula: $C_{23}H_{19}F_3N_2O_5S$
Exact Mass: 492.10
Molecular Weight: 492.47

N-Methyl-N-(3-(10-methyl-11-oxo-8-(trifluoromethoxy)-10,11-dihydrodibenzo[b,f][1,4]oxazepin-2-yl)phenyl)methanesulfonamide (NCGC00384286): A 60% dispersion in mineral oil of NaH (50.0 mg, 1.25 mmol) was added in portions to a solution of N-(3-(11-oxo-8-(trifluoromethoxy)-10,11-dihydrodibenzo[b,f][1,4]oxazepin-2-yl)phenyl)methanesulfonamide AED007-012 (50.0 mg, 0.108 mmol) in DMF (5.00 mL) at RT. After stirring for 5 min, was added $CH_3I$ (0.100 mL, 1.60 mmol) and the resulting reaction mixture allowed to stir at RT for 2 h, after which LC-MS analysis showed completion. Reaction mixture was diluted with $H_2O$ and extracted with EtOAc. The combined organic layers were washed with saturated $Na_2S2O_3$, brine, dried over $MgSO_4$, filtered and concentrated. Crude mixture was subjected to purification via standard HPLC conditions using a gradient of 10-100% ACN in $H_2O$ with 0.1% TFA to afford N-methyl-N-(3-(10-methyl-11-oxo-8-(trifluoromethoxy)-10,11-dihydrodibenzo[b,f][1,4]oxazepin-2-yl)phenyl)methanesulfonamide (24.0 mg, 45.3% yield).). $^1H$ NMR (400 MHz, DMSO-$d_6$) δ 7.98 (d, J=2.4 Hz, 1H), 7.91 (dd, J=8.4, 2.5 Hz, 1H), 7.66 (t, J=1.9 Hz, 1H), 7.62-7.54 (m, 3H), 7.50 (dd, J=8.2, 6.9 Hz, 2H), 7.42 (ddd, J=7.9, 2.2, 1.1 Hz, 1H), 7.28 (ddt, J=8.8, 2.3, 1.1 Hz, 1H), 3.53 (s, 3H), 3.29 (s, 3H), 2.96 (s, 3H). $^{19}F$ NMR (376 MHz, DMSO-$d_6$) δ-57.13 (s, 3F). LCMS RT (Method 1)=6.176 min, m/z 985.2 [$2M^+$].

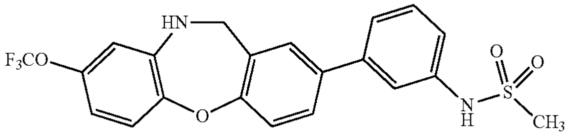

Chemical Formula: $C_{21}H_{17}F_3N_2O_4S$
Exact Mass: 450.09
Molecular Weight: 450.43

N-(3-(8-(Trifluoromethoxy)-10,11-dihydrodibenzo[b,f][1,4]oxazepin-2-yl)phenyl)methanesulfonamide (NCGC00371644): A 2M THF solution $BH_3$—$S(CH_3)_2$ complex (0.100 mL, 0.200 mmol) was added to a solution of N-(3-(11-oxo-8-(trifluoromethoxy)-10,11-dihydrodibenzo[b,f][1,4]oxazepin-2-yl)phenyl)methanesulfonamide AED007-012 (25.0 mg, 0.054 mmol) in THF (2.00 mL). The resulting reaction mixture was heated to reflux for 1 h, after which LC-MS analysis showed completion. Reaction mixture was allowed to cool to RT, and quenched by slow addition of MeOH, followed by 3M HCl. The mixture was concentrated to dryness and the residue was subjected to purification via standard HPLC conditions using a gradient of 10-100% ACN in $H_2O$ with 0.1% TFA to afford. LCMS RT (Method 1)=6.016 min, m/z 451.1 [$M+H^+$].

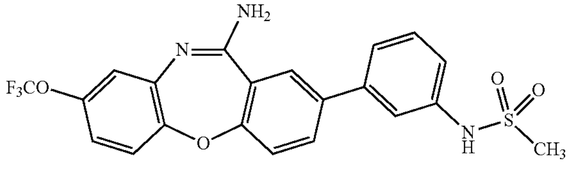

Chemical Formula: $C_{21}H_{16}F_3N_3O_4S$
Exact Mass: 463.08
Molecular Weight: 463.43

N-(3-(11-Amino-8-(trifluoromethoxy)dibenzo[b,f][1,4]oxazepin-2-yl)phenyl)methanesulfonamide (NCGC00373124): A solution of N-(3-(11-oxo-8-(trifluoromethoxy)-10,11-dihydrodibenzo[b,f][1,4]oxazepin-2-yl)phenyl)methanesulfonamide AED007-012 (80.0 mg, 0.172 mmol) in $POCl_3$ (4.00 mL, 42.9 mmol) was heated to 95° C. overnight, after which LC-MS analysis showed completion. Reaction mixture was concentrated under reduced pressure, and the residue taken up in EtOAc, washed with brine, dried over $MgSO_4$, filtered and concentrated to afford the intermediate imidoyl chloride N-(3-(11-chloro-8-(trifluoromethoxy)dibenzo[b,f][1,4]oxazepin-2-yl)phenyl)methanesulfonamide (80.0 mg, 96% yield), which was used in the next step without further purification. LCMS RT (Method 2)=3.726 min, m/z 483.0 [$M+H^+$].

The intermediate imidoyl chloride was taken up in 0.5 M $NH_3$ in dioxane (15.0 mL, 7.50 mmol), and heated to 100° C. under microwave irradiation for 1 h, after which LC-MS analysis showed completion. Reaction mixture was concentrated under reduced pressure and residue was subjected to purification via standard HPLC conditions using a gradient of 10-100% ACN in $H_2O$ with 0.1% TFA to afford the title compound as the TFA salt (23.5 mg, 30.6% yield). $^1H$ NMR (400 MHz, DMSO-$d_6$) δ 9.88 (s, 1H), 9.06 (br s, 3H), 7.99 (d, J=8.6 Hz, 1H), 7.93 (d, J=2.3 Hz, 1H), 7.60 (d, J=8.4 Hz, 1H), 7.53 (d, J=8.7 Hz, 1H), 7.50-7.42 (m, 4H), 7.29-7.17 (m, 2H), 3.03 (s, 3H). $^{19}F$ NMR (376 MHz, DMSO-$d_6$) δ-57.15 (s, 3F),-73-87 (s, 3F). LCMS RT (Method 1)=4.512 min, m/z 464.0 [$M+H^+$].

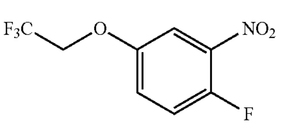

Chemical Formula: $C_8H_5F_4NO_3$
Exact Mass: 239.02
Molecular Weight: 239.13

1-Fluoro-2-nitro-4-(2,2,2-trifluoroethoxy)benzene (AED015-061): To a mixture of 4-fluoro-3-nitrophenol (1.00 g, 6.37 mmol) and $K_2CO_3$ (1.76 g, 12.7 mmol) in DMF (10.0 mL) was added 2,2,2-trifluoroethyl trifluoromethanesulfonate (0.963 mL, 6.68 mmol). The resulting reaction mixture was heated to 160° C. under microwave irradiation for 30 min, after which TLC analysis (20% EtOAc in Hex) showed completion. Reaction mixture was taken up in EtOAc, washed with $H_2O$, brine (2×'s), dried over $MgSO_4$, filtered and concentrated. Crude residue was purified by flash column chromatography: silica gel with a gradient of 3-15% EtOAc in Hex to afford 1-fluoro-2-nitro-4-(2,2,2-trifluoroethoxy)benzene (1.07 g, 70.3% yield) as a gold syrup, which solidified upon standing. $^1H$ NMR (400 MHz, DMSO-$d_6$) δ 7.84 (dd, J=5.9, 3.2 Hz, 1H), 7.61 (dd, J=10.7, 9.2 Hz, 1H), 7.54 (ddd, J=9.3, 3.8, 3.2 Hz, 1H), 4.92 (q, J=8.8 Hz, 2H). $^{19}$F NMR (376 MHz, DMSO-$d_6$) δ-72.57 (t, J=8.7 Hz, 3F),-127.72 (ddd, J=10.3, 5.8, 3.7 Hz, 1F). LCMS RT (Method 2)=3.477 min.

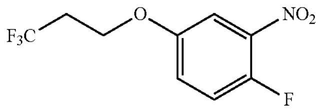

Chemical Formula: $C_9H_7F_4NO_3$
Exact Mass: 253.04
Molecular Weight: 253.15

1-Fluoro-2-nitro-4-(3,3,3-trifluoropropoxy)benzene (AED014-094): A solution of DIAD (0.743 mL, 3.82 mmol) in THF (2.00 mL) was added slowly to a solution of 4-fluoro-3-nitrophenol (500 mg, 3.18 mmol), 3,3,3-trifluoropropan-1-ol (0.310 mL, 3.50 mmol) and $PPh_3$ (1.00 g, 3.82 mmol) in THF (10.0 mL). The resulting reaction mixture was allowed to stir at RT overnight, after which TLC (20% EtOAc in Hex) and LC-MS analysis showed product formation. Reaction mixture was concentrated under reduced pressure and residue purified by flash column chromatography: silica gel with a gradient of 5-20% EtOAc in Hex to afford 1-fluoro-2-nitro-4-(3,3,3-trifluoropropoxy)benzene (322 mg, 40.0% yield) as a clear golden oil. $^1$H NMR (400 MHz, DMSO-$d_6$) δ 7.68 (dd, J=6.0, 3.2 Hz, 1H), 7.54 (dd, J=10.9, 9.2 Hz, 1H), 7.42 (dt, J=9.3, 3.5 Hz, 1H), 4.31 (t, J=5.9 Hz, 2H), 2.81 (qt, J=11.4, 5.9 Hz, 2H). $^{19}$F NMR (376 MHz, DMSO-$d_6$) δ-63.06 (t, J=11.2 Hz, 3F),-129.28 (ddd, J=10.3, 6.0, 3.6 Hz, 1F). LCMS RT (Method 2)=3.491 min.

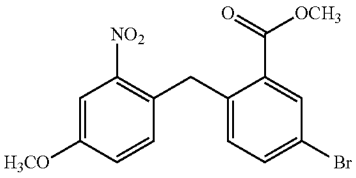

Chemical Formula: $C_{15}H_{12}BrNO_6$
Exact Mass: 380.98
Molecular Weight: 382.17

Methyl 5-bromo-2-(4-methoxy-2-nitrophenoxy)benzoate (AED011-091): Methyl 5-bromo-2-hydroxybenzoate (405 mg, 1.75 mmol) was added to a solution of 1-fluoro-4-methoxy-2-nitrobenzene (300 mg, 1.75 mmol) and $K_2CO_3$ (315 mg, 2.28 mmol) in DMF (6.00 mL). The resulting reaction mixture was stirred at 100° C. for 4 h, after which LC-MS analysis showed completion. Reaction mixture was poured into ice $H_2O$, stirred for 10 min and extracted with EtOAc (2×'s). The combined organic layers were washed with $H_2O$, brine, dried over $MgSO_4$, filtered and concentrated. Crude residue was purified by flash column chromatography: silica gel with a gradient of 3-15% EtOAc in Hex to afford methyl 5-bromo-2-(4-methoxy-2-nitrophenoxy) benzoate (315 mg, 47.0% yield) as golden syrup, which solidified upon standing. $^1$H NMR (400 MHz, DMSO-$d_6$) δ 7.98 (d, J=2.6 Hz, 1H), 7.77 (dd, J=8.8, 2.6 Hz, 1H), 7.64 (d, J=3.1 Hz, 1H), 7.30 (dd, J=9.2, 3.1 Hz, 1H), 7.14 (d, J=9.1 Hz, 1H), 6.97 (d, J=8.8 Hz, 1H), 3.84 (s, 3H), 3.76 (s, 3H). LCMS RT (Method 2)=3.729 min, m/z 787.0 [2M+$Na^+$].

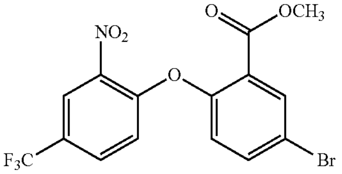

Chemical Formula: $C_{15}H_9BrF_3NO_5$
Exact Mass: 418.96
Molecular Weight: 420.14

Methyl 5-bromo-2-(2-nitro-4-(trifluoromethyl)phenoxy) benzoate (AED014-072): 1-Fluoro-2-nitro-4-(trifluoromethyl)benzene (0.303 mL, 2.16 mmol) was added to a solution of methyl 5-bromo-2-hydroxybenzoate (500 mg, 2.16 mmol) and $K_2CO_3$ (389 mg, 2.81 mmol) in DMF (10.0 mL). The resulting reaction mixture was stirred at 70° C. overnight, after which LC-MS analysis showed completion. Reaction mixture was allowed to cool to RT and then poured over ice $H_2O$, vigorously stirred for 45 min and allowed to stand overnight, after which insoluble material was filtered, washed generously with $H_2O$ and air dried to afford methyl 5-bromo-2-(2-nitro-4-(trifluoromethyl)phenoxy)benzoate (820 mg, 90.0% yield) as a slightly yellow powder, which was used without further purification. $^1$H NMR (400 MHz, DMSO-$d_6$) δ 8.49 (dd, J=2.3, 0.8 Hz, 1H), 8.12 (d, J=2.6 Hz, 1H), 8.01-7.91 (m, 2H), 7.43 (d, J=8.7 Hz, 1H), 7.08 (dd, J=8.8, 0.9 Hz, 1H), 3.68 (s, 3H). $^{19}$F NMR (376 MHz, DMSO-$d_6$) δ-63.63 (s, 3F). LCMS RT (Method 2)=3.749 min, m/z 862.9 [2M+$Na^+$].

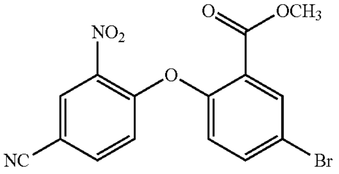

Chemical Formula: $C_{15}H_9BrN_2O_5$
Exact Mass: 375.97
Molecular Weight: 377.15

Methyl 5-bromo-2-(4-cyano-2-nitrophenoxy)benzoate (AED014-095): Methyl 5-bromo-2-hydroxybenzoate (500 mg, 2.16 mmol) was added to a solution of 4-fluoro-3-nitrobenzonitrile (359 mg, 2.16 mmol) and $K_2CO_3$ (389 mg, 2.81 mmol) in DMF (10.0 mL). The resulting reaction mixture was stirred at 80° C. overnight, after which LC-MS analysis showed completion. Reaction mixture was allowed to cool to RT and then poured over ice $H_2O$, vigorously stirred for 45 min and insoluble material filtered, washed generously with $H_2O$ and air dried to afford methyl 5-bromo-2-(4-cyano-2-nitrophenoxy)benzoate (780 mg, 96.0% yield) as a slightly yellow powder, which was used without further purification. $^1$H NMR (400 MHz, DMSO-$d_6$) δ 8.68 (d, J=2.0 Hz, 1H), 8.12 (d, J=2.5 Hz, 1H), 8.03 (dd, J=8.8, 2.1 Hz, 1H), 7.98 (dd, J=8.7, 2.6 Hz, 1H), 7.43 (d, J=8.7 Hz, 1H), 7.05 (d, J=8.8 Hz, 1H), 3.68 (s, 3H). LCMS RT (Method 2)=3.539 min, m/z 377.0 [M$^+$].

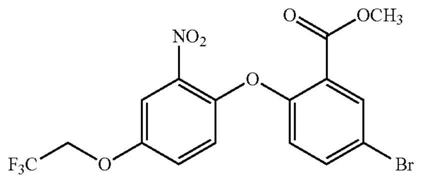

Chemical Formula: $C_{16}H_{11}BrF_3NO_6$
Exact Mass: 448.97
Molecular Weight: 450.16

Methyl 5-bromo-2-(2-nitro-4-(2,2,2-trifluoroethoxy)phenoxy)benzoate (AED015-063): A mixture of methyl 5-bromo-2-hydroxybenzoate (500 mg, 2.16 mmol), $K_2CO_3$ (389 mg, 2.81 mmol) and 1-fluoro-2-nitro-4-(2,2,2-trifluoroethoxy)benzene AED015-061 (517 mg, 2.16 mmol) in DMF (10.0 mL), was stirred at 80° C. overnight, after which LC-MS analysis showed completion. Reaction mixture was allowed to cool to RT and then poured over ice $H_2O$, vigorously stirred for 45 min and insoluble material filtered, washed generously $H_2O$ water and air dried to afford methyl 5-bromo-2-(2-nitro-4-(2,2,2-trifluoroethoxy)phenoxy)benzoate (820 mg, 84.0% yield), as a slightly yellow powder, which was used without further purification. $^1H$ NMR (400 MHz, DMSO-$d_6$) δ 8.00 (d, J=2.6 Hz, 1H), 7.86-7.77 (m, 2H), 7.41 (dd, J=9.2, 3.2 Hz, 1H), 7.13 (d, J=9.2 Hz, 1H), 7.06 (d, J=8.8 Hz, 1H), 4.90 (q, J=8.8 Hz, 2H), 3.74 (s, 3H). $^{19}F$ NMR (376 MHz, DMSO-$d_6$) δ-72.57 (t, J=8.8 Hz, 3F). LCMS RT (Method 2)=3.793 min.

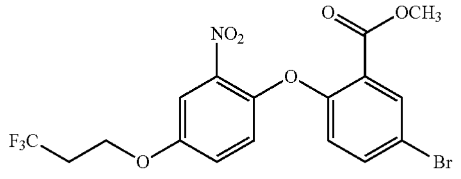

Chemical Formula: $C_{17}H_{13}BrF_3NO_6$
Exact Mass: 462.99
Molecular Weight: 464.19

Methyl 5-bromo-2-(2-nitro-4-(3,3,3-trifluoropropoxy)phenoxy)benzoate (AED015-004): Methyl 5-bromo-2-hydroxybenzoate (294 mg, 1.27 mmol) was added to a solution of 1-fluoro-2-nitro-4-(3,3,3-trifluoropropoxy)benzene AED014-094 (322 mg, 1.27 mmol) and $K_2CO_3$ (229 mg, 1.65 mmol) in DMF (10.0 mL). The resulting reaction mixture was stirred at 80° C. overnight, after which LC-MS analysis showed completion. Reaction mixture was diluted with EtOAc, washed with $H_2O$ and brine, dried over $MgSO_4$, filtered and concentrated. Crude product was purified by flash column chromatography: silica gel with a gradient of 10-20% EtOAc in Hex to afford methyl 5-bromo- 2-(2-nitro-4-(3,3,3-trifluoropropoxy)phenoxy)benzoate (350 mg, 59.3% yield) as a light gold syrup. $^1H$ NMR (400 MHz, DMSO-$d_6$) δ 7.99 (d, J=2.6 Hz, 1H), 7.78 (dd, J=8.8, 2.6 Hz, 1H), 7.68 (d, J=3.1 Hz, 1H), 7.31 (dd, J=9.2, 3.1 Hz, 1H), 7.12 (d, J=9.1 Hz, 1H), 7.01 (d, J=8.8 Hz, 1H), 4.31 (t, J=5.9 Hz, 2H), 3.75 (s, 3H), 2.82 (qt, J=11.4, 5.9 Hz, 2H). $^{19}F$ NMR (376 MHz, DMSO-$d_6$) δ-63.04 (t, J=11.2 Hz, 3F). LCMS RT (Method 2)=3.740 min, m/z 950.8 [2M+Na$^+$].

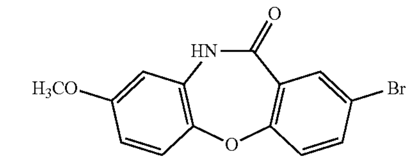

Chemical Formula: $C_{14}H_{10}BrNO_3$
Exact Mass: 318.98
Molecular Weight: 320.14

2-Bromo-8-methoxydibenzo[b,f][1,4]oxazepin-11(10H)-one (AED011-094): 6N Hydrochloric acid (5.00 mL, 30.0 mmol) was added to a mixture of methyl 5-bromo-2-(4-methoxy-2-nitrophenoxy)benzoate AED011-091 (310 mg, 0.811 mmol) and $Fe^0$ powder (226 mg, 4.06 mmol) in EtOH (5.00 mL). The resulting reaction mixture was heated to reflux for 18 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry to afford 2-bromo-8-methoxydibenzo[b,f][1,4]oxazepin-11(10H)-one (234 mg, 90.0% yield) as a lightly grayish fluffy solid, which was used without further purification. $^1H$ NMR (400 MHz, DMSO-$d_6$) δ 10.59 (s, 1H), 7.83 (d, J=2.6 Hz, 1H), 7.79 (dd, J=8.6, 2.6 Hz, 1H), 7.31 (d, J=8.6 Hz, 1H), 7.28-7.22 (m, 1H), 6.74-6.66 (m, 2H), 3.70 (s, 3H). LCMS RT (Method 2)=3.337 min, m/z 663.0 [2M+Na$^+$].

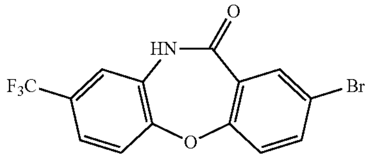

Chemical Formula: $C_{14}H_7BrF_3NO_2$
Exact Mass: 356.96
Molecular Weight: 358.11

2-Bromo-8-(trifluoromethyl)dibenzo[b,f][1,4]oxazepin-11(10H)-one (AED014-074): 6N Hydrochloric acid (10.0 mL, 60.0 mmol) was added to a mixture of methyl 5-bromo-2-(2-nitro-4-(trifluoromethyl)phenoxy)benzoate AED014-072 (810 mg, 1.93 mmol) and $Fe^0$ powder (538 mg, 9.64 mmol) in EtOH (10.0 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry to afford 2-bromo-8-(trifluoromethyl)dibenzo[b,f][1,4]oxazepin-11(10H)-one (646 mg, 94.0% yield) as an off-white fluffy solid, which was used without further purification. $^1H$ NMR (400 MHz, DMSO-$d_6$) δ 10.84 (s, 1H), 7.90-7.81 (m, 2H), 7.62-7.49 (m, 3H), 7.40 (d, J=8.5

Hz, 1H). $^{19}$F NMR (376 MHz, DMSO-$d_6$) δ-60.92 (s, 3F). LCMS RT (Method 2)=3.595 min.

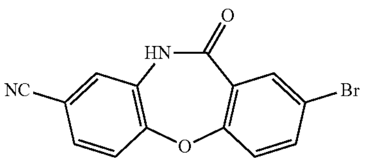

Chemical Formula: $C_{14}H_7BrN_2O_2$
Exact Mass: 313.97
Molecular Weight: 315.13

2-Bromo-11-oxo-10,11-dihydrodibenzo[b,f][1,4]oxazepine-8-carbonitrile (AED015-011): 6N Hydrochloric acid (10.0 mL, 60.0 mmol) was added to a mixture of methyl 5-bromo-2-(4-cyano-2-nitrophenoxy)benzoate AED014-095 (600 mg, 1.59 mmol) and $Fe^0$ powder (444 mg, 7.95 mmol) in EtOH (15.0 mL). The resulting reaction mixture was heated to reflux for 24 h, after which LC-MS analysis showed completion. Reaction mixture was allowed to cool to RT and poured over ice $H_2O$, vigorously stirred for 5 min, and insoluble material filtered, rinsed generously with $H_2O$ and allowed to air dry to afford 2-bromo-11-oxo-10,11-dihydrodibenzo[b,f][1,4]oxazepine-8-carbonitrile (233 mg, 46.5% yield) as an off-white fluffy solid, which was used without further purification. $^1$H NMR (400 MHz, DMSO-$d_6$) δ 10.88 (s, 1H), 7.87 (q, J=2.4 Hz, 1H), 7.84 (dd, J=3.7, 2.6 Hz, 1H), 7.67 (dd, J=8.4, 2.0 Hz, 1H), 7.64-7.54 (m, 2H), 7.39 (d, J=8.4 Hz, 1H). LCMS RT (Method 2)=3.364 min.

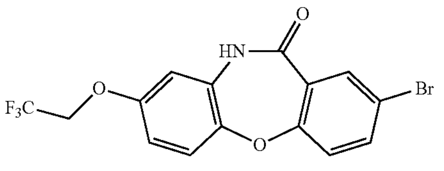

Chemical Formula: $C_{15}H_9BrF_3NO_3$
Exact Mass: 386.97
Molecular Weight: 388.14

2-Bromo-8-(2,2,2-trifluoroethoxy)dibenzo[b,f][1,4]oxazepin-11(10H)-one (AED015-065): 6N Hydrochloric acid (15.0 mL, 90.0 mmol) was added to a mixture of methyl 5-bromo-2-(2-nitro-4-(2,2,2-trifluoroethoxy)phenoxy)benzoate AED015-063 (800 mg, 1.78 mmol) and $Fe^0$ powder (496 mg, 8.89 mmol) in EtOH (15.0 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry to afford 2-bromo-8-(2,2,2-trifluoroethoxy)dibenzo[b,f][1,4]oxazepin-11(10H)-one (640 mg, 93.0% yield) as a tan fluffy solid, which was used without further purification. $^1$H NMR (400 MHz, DMSO-$d_6$) δ 10.66 (s, 1H), 7.84 (d, J=2.5 Hz, 1H), 7.80 (dd, J=8.6, 2.6 Hz, 1H), 7.32 (dd, J=8.7, 1.0 Hz, 2H), 6.86 (dd, J=8.9, 3.1 Hz, 1H), 6.80 (d, J=3.0 Hz, 1H), 4.72 (q, J=8.9 Hz, 2H). $^{19}$F NMR (376 MHz, DMSO-$d_6$) δ -72.62 (t, J=8.8 Hz, 3F). LCMS RT (Method 2)=3.635 min, m/z 389.9 [M+H$^+$].

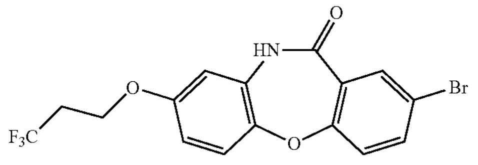

Chemical Formula: $C_{16}H_{11}BrF_3NO_3$
Exact Mass: 400.99
Molecular Weight: 402.17

2-Bromo-8-(3,3,3-trifluoropropoxy)dibenzo[b,f][1,4]oxazepin-11(10H)-one (AED015-023): 6N Hydrochloric acid (10.0 mL, 60.0 mmol) was added to a mixture of methyl 5-bromo-2-(2-nitro-4-(3,3,3-trifluoropropoxy)phenoxy) benzoate AED015-004 (350 mg, 0.754 mmol) and $Fe^0$ powder (211 mg, 3.77 mmol) in EtOH (15.0 mL). The resulting reaction mixture was heated to reflux for 24 h, after which LC-MS analysis showed completion. Reaction mixture was allowed to cool to RT and poured over ice $H_2O$, vigorously stirred for 5 min and insoluble material filtered, rinsed generously with $H_2O$ and allowed to air dry. Crude residue was purified by flash column chromatography: silica gel with a gradient of 10-30% EtOAc in Hex to afford 2-bromo-8-(3,3,3-trifluoropropoxy)dibenzo[b,f][1,4]oxazepin-11(10H)-one (160 mg, 52.8% yield) as an off-white solid. $^1$H NMR (400 MHz, DMSO-$d_6$) δ 10.58 (s, 1H), 7.84 (d, J=2.6 Hz, 1H), 7.79 (dd, J=8.6, 2.6 Hz, 1H), 7.31 (d, J=8.6 Hz, 1H), 7.27 (dd, J=8.6, 0.5 Hz, 1H), 6.79-6.68 (m, 2H), 4.15 (t, J=5.9 Hz, 2H), 2.76 (qt, J=11.4, 5.9 Hz, 2H). $^{19}$F NMR (376 MHz, DMSO-$d_6$) δ-63.07 (t, J=11.4 Hz, 3F). LCMS RT (Method 2)=3.629 min, m/z 827.9 [2M+Na$^+$].

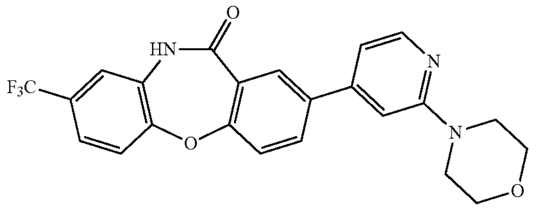

Chemical Formula: $C_{23}H_{18}F_3N_3O_3$
Exact Mass: 441.13
Molecular Weight: 441.41

2-(2-Morpholinopyridin-4-yl)-8-(trifluoromethyl)dibenzo [b,f][1,4]oxazepin-11(10H)-one (NCGC00481506): Prepared following general Procedure A; 2-bromo-8-(trifluoromethyl)dibenzo[b,f][1,4]oxazepin-11(10H)-one AED014-074 (39.3 mg, 0.110 mmol), 4-(4-(4,4,5,5-tetramethyl-1,3,2-dioxaborolan-2-yl)pyridin-2-yl)morpholine (35.0 mg, 0.121 mmol), 2M $Na_2CO_3$ (219 L, 0.439 mmol), $Pd(PPh_3)_4$(6.34 mg, 5.48 μmol) in DME (4.00 mL) to afford the title compound as the TFA salt (32.3 mg, 66.7% yield). $^1$H NMR (400 MHz, DMSO-$d_6$) δ 10.84 (s, 1H), 8.18 (d, J=5.5 Hz, 1H), 8.11 (d, J=2.4 Hz, 1H), 8.06 (dd, J=8.4, 2.5 Hz, 1H), 7.62 (d, J=8.3 Hz, 1H), 7.54 (dt, J=11.3, 2.4 Hz, 3H), 7.11 (s, 1H), 7.01 (d, J=5.4 Hz, 1H), 3.72 (dd, J=5.8, 3.8 Hz, 4H), 3.54 (t, J=4.8 Hz, 4H). $^{19}F$ NMR (376 MHz, DMSO-$d_6$) δ-60.87 (s, 3F),-73.94 (s, 3F). LCMS RT (Method 1)=4.317 min, m/z 442.2 [M+$H^+$].

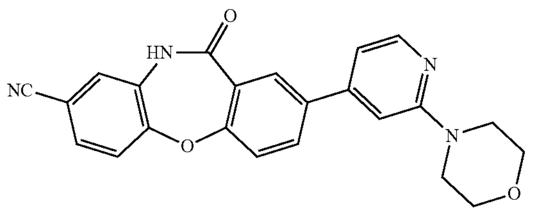

Chemical Formula: $C_{23}H_{18}N_4O_3$
Exact Mass: 398.14
Molecular Weight: 398.42

2-(2-Morpholinopyridin-4-yl)-11-oxo-10,11-dihydrodibenzo[b,f][1,4]oxazepine-8-carbonitrile (NCGC00481503): Prepared following general Procedure A; 2-bromo-11-oxo-10,11-dihydrodibenzo[b,f][1,4]oxazepine-8-carbonitrile AED015-011 (34.6 mg, 0.110 mmol), 4-(4-(4,4,5,5-tetramethyl-1,3,2-dioxaborolan-2-yl)pyridin-2-yl)morpholine (35.0 mg, 0.121 mmol), 2M $Na_2CO_3$ (219 L, 0.439 mmol), $Pd(PPh_3)_4$(6.34 mg, 5.48 μmol) in DME (4.00 mL) to afford the title compound as the TFA salt (19.8 mg, 45.3% yield). $^1H$ NMR (400 MHz, DMSO-$d_6$) δ 10.89 (s, 1H), 8.18 (d, J=5.5 Hz, 1H), 8.11 (d, J=2.5 Hz, 1H), 8.07 (dd, J=8.5, 2.5 Hz, 1H), 7.68 (dd, J=8.4, 2.0 Hz, 1H), 7.64-7.56 (m, 2H), 7.54 (d, J=8.4 Hz, 1H), 7.14 (s, 1H), 7.03 (d, J=5.4 Hz, 1H), 3.72 (dd, J=5.8, 3.9 Hz, 4H), 3.55 (t, J=4.8 Hz, 4H). $^{19}F$ NMR (376 MHz, DMSO-$d_6$) δ-74.11 (s, 3F). LCMS RT (Method 1)=3.660 min, m/z 399.2 [M+$H^+$].

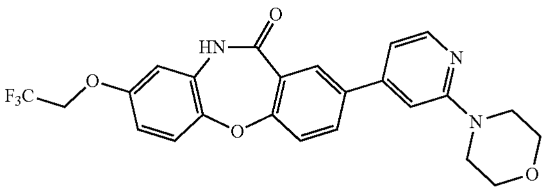

Chemical Formula: $C_{24}H_{20}F_3N_3O_4$
Exact Mass: 471.14
Molecular Weight: 471.44

2-(2-Morpholinopyridin-4-yl)-8-(2,2,2-trifluoroethoxy)dibenzo[b,f][1,4]oxazepin-11(10H)-one (NCGC00481504): Prepared following general Procedure A; 2-bromo-8-(2,2,2-trifluoroethoxy)dibenzo[b,f][1,4]oxazepin-11(10H)-one AED015-065 (42.6 mg, 0.110 mmol), 4-(4-(4,4,5,5-tetramethyl-1,3,2-dioxaborolan-2-yl)pyridin-2-yl)morpholine (35.0 mg, 0.121 mmol), 2M $Na_2CO_3$ (219 L, 0.439 mmol), $Pd(PPh_3)_4$(6.34 mg, 5.48 μmol) in DME (4.00 mL) to afford the title compound as the TFA salt (27.0 mg, 52.2% yield). $^1H$ NMR (400 MHz, DMSO-$d_6$) δ 10.66 (s, 1H), 8.17 (d, J=5.6 Hz, 1H), 8.11 (d, J=2.5 Hz, 1H), 8.04 (dd, J=8.5, 2.5 Hz, 1H), 7.47 (d, J=8.4 Hz, 1H), 7.35 (d, J=8.9 Hz, 1H), 7.20 (s, 1H), 7.06 (d, J=5.6 Hz, 1H), 6.87 (dd, J=8.9, 3.0 Hz, 1H), 6.81 (d, J=3.0 Hz, 1H), 4.72 (q, J=8.9 Hz, 2H), 3.73 (dd, J=5.7, 4.0 Hz, 4H), 3.58 (t, J=4.8 Hz, 4H). $^{19}F$ NMR (376 MHz, DMSO-$d_6$) δ-72.61 (t, J=8.9 Hz, 3F),-74.34 (s, 3F). LCMS RT (Method 1)=4.306 min, m/z 471.7 [$M^+$].

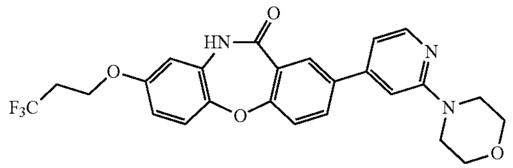

Chemical Formula: $C_{25}H_{22}F_3N_3O_4$
Exact Mass: 485.16
Molecular Weight: 485.46

2-(2-Morpholinopyridin-4-yl)-8-(3,3,3-trifluoropropoxy)dibenzo[b,f][1,4]oxazepin-11(10H)-one (NCGC00481507): Prepared following general Procedure A; 2-bromo-8-(3,3,3-trifluoropropoxy)dibenzo[b,f][1,4]oxazepin-11(10H)-one AED015-023 (44.1 mg, 0.110 mmol), 4-(4-(4,4,5,5-tetramethyl-1,3,2-dioxaborolan-2-yl)pyridin-2-yl)morpholine (35.0 mg, 0.121 mmol), 2M $Na_2CO_3$ (219 L, 0.439 mmol), $Pd(PPh_3)_4$(6.34 mg, 5.48 μmol) in DME (4.00 mL) to afford the title compound as the TFA salt (27.0 mg, 52.2% yield). $^1H$ NMR (400 MHz, DMSO-$d_6$) δ 10.59 (s, 1H), 8.16 (d, J=5.6 Hz, 1H), 8.10 (d, J=2.4 Hz, 1H), 8.04 (dd, J=8.5, 2.5 Hz, 1H), 7.46 (d, J=8.4 Hz, 1H), 7.30 (d, J=8.6 Hz, 1H), 7.19 (s, 1H), 7.06 (d, J=5.6 Hz, 1H), 6.80-6.71 (m, 2H), 4.15 (t, J=5.9 Hz, 2H), 3.76-3.69 (m, 3H), 3.57 (t, J=4.9 Hz, 4H), 2.78 (tq, J=11.3, 5.7 Hz, 2H). $^{19}F$ NMR (376 MHz, DMSO-$d_6$) δ-63.05 (t, J=11.3 Hz, 3F),-74.31 (s, 3F). LCMS RT (Method 1)=4.412 min, m/z 485.7 [$M^+$].

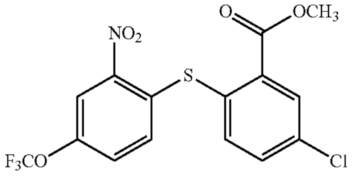

Chemical Formula: $C_{14}H_7ClF_3NO_5S$
Exact Mass: 392.97
Molecular Weight: 393.72

5-Chloro-2-((2-nitro-4-(trifluoromethoxy)phenyl)thio)benzoic acid (AED015-085): 5-chloro-2-mercaptobenzoic acid (500 mg, 2.65 mmol) was added to a solution of 1-fluoro-2-nitro-4-(trifluoromethoxy)benzene (0.387 mL, 2.65 mmol) and $K_2CO_3$ (476 mg, 3.45 mmol) in DMF (10.0 mL). The resulting reaction mixture was stirred at 80° C. overnight, after which LC-MS analysis showed completion. Reaction mixture was allowed to cool to RT and then poured over ice $H_2O$, vigorously stirred for 45 min and insoluble material filtered, washed generously with $H_2O$ and air dried to afford 5-chloro-2-((2-nitro-4-(trifluoromethoxy)phenyl)thio)benzoic acid (900 mg, 86.0% yield) as a yellow powder, which was used without further purification. $^1H$ NMR (400 MHz, DMSO-$d_6$) δ 13.71 (s, 1H), 8.24 (dt, J=2.7, 0.9 Hz, 1H), 7.93 (d, J=2.4 Hz, 1H), 7.70 (ddq, J=8.9, 2.9, 1.0 Hz, 1H), 7.66 (dd, J=8.5, 2.5 Hz, 1H), 7.39 (d, J=8.5 Hz, 1H), 7.35 (d, J=8.9 Hz, 1H). $^{19}F$ NMR (376 MHz, DMSO-$d_6$) δ-57.18 (s, 3F). LCMS RT (Method 2)=3.622 min.

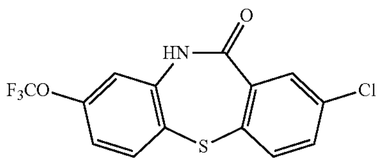

Chemical Formula: $C_{14}H_7ClF_3NO_2S$
Exact Mass: 344.98
Molecular Weight: 345.72

2-Chloro-8-(trifluoromethoxy)dibenzo[b,f][1,4]thiazepin-11(10H)-one (AED015-089): 6N Hydrochloric acid (15.0 mL, 90.0 mmol) was added to a mixture of 5-chloro-2-((2-nitro-4-(trifluoromethoxy)phenyl)thio)benzoic acid AED015-085 (900 mg, 2.29 mmol) and $Fe^0$ powder (638 mg, 11.4 mmol) in EtOH (15.0 mL). The resulting reaction mixture was heated to reflux for 24 h, after which LC-MS analysis showed completion. Reaction mixture was allowed to cool to RT, poured over ice $H_2O$, vigorously stirred for 5 min and insoluble material filtered, rinsed generously with $H_2O$ and allowed to air dry to afford 2-chloro-8-(trifluoromethoxy)dibenzo[b,f][1,4]thiazepin-11(10H)-one (735 mg, 93.0% yield) as a cream colored solid, which was used without further purification. $^1H$ NMR (400 MHz, DMSO-$d_6$) δ 10.96 (s, 1H), 7.71 (s, 1H), 7.70-7.66 (m, 1H), 7.60-7.56 (m, 2H), 7.23-7.14 (m, 2H). $^{19}F$ NMR (376 MHz, DMSO-$d_6$) δ-56.85 (s, 3F). LCMS RT (Method 2)=3.664 min.

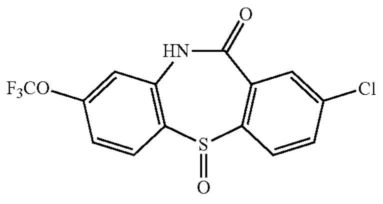

Chemical Formula: $C_{14}H_7ClF_3NO_3S$
Exact Mass: 360.98
Molecular Weight: 361.72

2-Chloro-8-(trifluoromethoxy)dibenzo[b,f][1,4]thiazepin-11(10H)-one 5-oxide (AED015-090): To a stirred solution of 2-chloro-8-(trifluoromethoxy)dibenzo[b,f][1,4]thiazepin-11(10H)-one AED015-089 (200 mg, 0.578 mmol) in AcOH (5.00 mL) was added $H_2O_2$(30 wt. % in $H_2O$) (0.500 mL, 4.89 mmol). The resulting reaction mixture was stirred at 60° C. for 1 h, after which LC-MS analysis showed complete conversion to the sulfoxide product without any apparent sulfone formation. Reaction mixture was allowed to cool to RT, poured over ice $H_2O$, stirred for 10 min, filtered, rinsed with $H_2O$, and allowed to air dry to afford 2-chloro-8-(trifluoromethoxy)dibenzo[b,f][1,4]thiazepin-11(10H)-one 5-oxide (195 mg, 93.0% yield) as an off-white solid, which was used without further purification. $^1H$ NMR (400 MHz, DMSO-$d_6$) δ 11.20 (s, 1H), 7.90 (dd, J=8.4, 2.2 Hz, 1H), 7.80 (d, J=2.2 Hz, 1H), 7.76-7.69 (m, 2H), 7.51-7.43 (m, 1H), 7.27 (dt, J=1.9, 1.0 Hz, 1H). $^{19}F$ NMR (376 MHz, DMSO-$d_6$) δ-56.85 (s, 3F). LCMS RT (Method 2)=3.372 min.

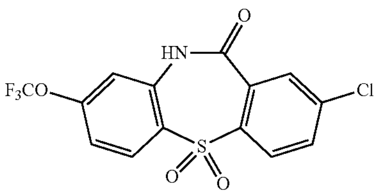

Chemical Formula: $C_{14}H_7ClF_3NO_4S$
Exact Mass: 376.97
Molecular Weight: 377.72

2-Chloro-8-(trifluoromethoxy)dibenzo[b,f][1,4]thiazepin-11(10H)-one 5,5-dioxide (AED015-092): To a stirred solution of 2-chloro-8-(trifluoromethoxy)dibenzo[b,f][1,4]thiazepin-11(10H)-one AED015-089 (200 mg, 0.578 mmol) in AcOH (20.0 mL) was added $H_2O_2$(30 wt. % in $H_2O$) (2.00 mL, 19.6 mmol). The resulting reaction mixture was stirred at RT overnight, after which LC-MS analysis showed complete conversion to the sulfone product. Reaction mixture was concentrated to half volume, poured over ice $H_2O$, stirred for 10 min, filtered, rinsed with $H_2O$, and allowed to air dry to afford 2-chloro-8-(trifluoromethoxy)dibenzo[b,f][1,4]thiazepin-11(10H)-one 5,5-dioxide (175 mg, 80.0% yield) as a white solid, which was used without further purification. $^1H$ NMR (400 MHz, DMSO-$d_6$) δ 11.68 (s, 1H), 8.09 (d, J=8.8 Hz, 1H), 8.01-7.96 (m, 2H), 7.96-7.91 (m, 1H), 7.42 (ddq, J=8.8, 2.2, 1.1 Hz, 1H), 7.36 (dt, J=2.2, 1.0 Hz, 1H). $^{19}F$ NMR (376 MHz, DMSO-$d_6$) δ-56.70 (s, 3F). LCMS RT (Method 2)=3.422 min. m/z 778.8 [2M+$Na^+$].

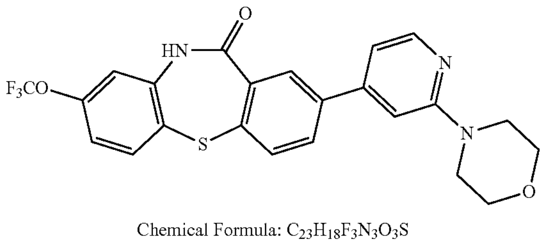

Chemical Formula: $C_{23}H_{18}F_3N_3O_3S$
Exact Mass: 473.10
Molecular Weight: 473.47

2-(2-Morpholinopyridin-4-yl)-8-(trifluoromethoxy)dibenzo[b,f][1,4]thiazepin-11(10H)-one (NCGC00482456): Prepared following general Procedure C; 2-chloro-8-(trifluoromethoxy)dibenzo[b,f][1,4]thiazepin-11(10H)-one AED015-089 (40 mg, 0.116 mmol), 4-(4-(4,4,5,5-tetramethyl-1,3,2-dioxaborolan-2-yl)pyridin-2-yl)morpholine (67.1 mg, 0.231 mmol), $K_3PO_4$ (98.0 mg, 0.463 mmol), butyldi-1-adamantylphosphine (8.30 mg, 0.023 mmol), and $Pd(OAc)_2$ (2.60 mg, 0.012 mmol) in 16:1 tolune:$H_2O$ (4.25 mL) to afford the title compound as the TFA salt (19.0 mg, 34.7% yield). $^1H$ NMR (400 MHz, DMSO-$d_6$) δ 10.95 (s, 1H), 8.17 (d, J=5.4 Hz, 1H), 8.03 (d, J=2.2 Hz, 1H), 7.91 (dd, J=8.1, 2.2 Hz, 1H), 7.72 (d, J=8.4 Hz, 1H), 7.67 (d, J=8.1 Hz, 1H), 7.24-7.14 (m, 3H), 7.03 (d, J=5.5 Hz, 1H), 3.71 (dd, J=5.8, 3.9 Hz, 4H), 3.55 (t, J=4.9 Hz, 4H). $^{19}F$ NMR (376 MHz, DMSO-$d_6$) δ-56.86 (s, 3F),-74.26 (s, 3F). LCMS RT (Method 1)=4.446 min, m/z 474.1 [M+H$^+$].

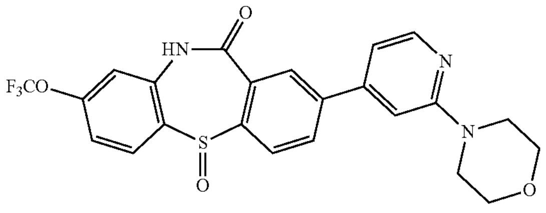

Chemical Formula: $C_{23}H_{18}F_3N_3O_4S$
Exact Mass: 489.10
Molecular Weight: 489.47

2-(2-Morpholinopyridin-4-yl)-8-(trifluoromethoxy)dibenzo[b,f][1,4]thiazepin-11(10H)-one 5-oxide (NCGC00482446): Prepared following general Procedure A; 2-chloro-8-(trifluoromethoxy)dibenzo[b,f][1,4]thiazepin-11(10H)-one 5-oxide AED015-090 (40.0 mg, 0.111 mmol), 4-(4-(4,4,5,5-tetramethyl-1,3,2-dioxaborolan-2-yl)pyridin-2-yl)morpholine (35.3 mg, 0.122 mmol), 2M $Na_2CO_3$ (221 L, 0.442 mmol), $Pd(PPh_3)_4$(6.39 mg, 5.53 μmol) in DME (4.00 mL) to afford the title compound as the TFA salt (20.0 mg, 37.0% yield). $^1H$ NMR (400 MHz, DMSO-$d_6$) δ 11.20 (s, 1H), 8.25-8.17 (m, 2H), 8.13 (d, J=1.9 Hz, 1H), 7.83 (d, J=8.2 Hz, 1H), 7.74 (d, J=8.7 Hz, 1H), 7.48 (ddd, J=8.7, 2.5, 1.2 Hz, 1H), 7.28 (dd, J=2.3, 1.0 Hz, 1H), 7.18 (s, 1H), 7.05 (d, J=5.1 Hz, 1H), 3.75-3.67 (m, 4H), 3.55 (t, J=4.9 Hz, 4H). $^{19}F$ NMR (376 MHz, DMSO-$d_6$) δ-56.85 (s, 3F),-74.30 (s, 3F). LCMS RT (Method 1)=3.982 min, m/z 490.1 [M+H$^+$].

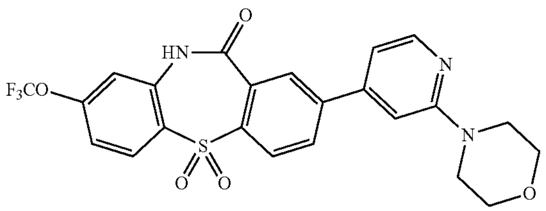

Chemical Formula: $C_{23}H_{18}F_3N_3O_5S$
Exact Mass: 505.09
Molecular Weight: 505.47

2-(2-Morpholinopyridin-4-yl)-8-(trifluoromethoxy)dibenzo[b,f][1,4]thiazepin-11(10H)-one 5,5-dioxide (NCGC00483140): Prepared following general Procedure A; 2-chloro-8-(trifluoromethoxy)dibenzo[b,f][1,4]thiazepin-11(10H)-one 5,5-dioxide AED015-092 (40.0 mg, 0.106 mmol), 4-(4-(4,4,5,5-tetramethyl-1,3,2-dioxaborolan-2-yl)pyridin-2-yl)morpholine (33.8 mg, 0.116 mmol), 2M $Na_2CO_3$ (212 L, 0.424 mmol), $Pd(PPh_3)_4$(5.29 mg, 5.29 μmol) in DME (4.00 mL) to afford the title compound as the TFA salt (24.0 mg, 44.8% yield). $^1H$ NMR (400 MHz, DMSO-$d_6$) δ 11.69 (s, 1H), 8.28 (d, J=1.9 Hz, 1H), 8.26-8.19 (m, 2H), 8.11 (d, J=8.8 Hz, 1H), 8.07 (d, J=8.1 Hz, 1H), 7.43 (ddq, J=8.8, 2.2, 1.1 Hz, 1H), 7.37 (dd, J=2.3, 1.1 Hz, 1H), 7.23 (s, 1H), 7.09 (dd, J=5.5, 1.4 Hz, 1H), 3.72 (dd, J=5.8, 3.9 Hz, 4H), 3.57 (t, J=4.9 Hz, 4H). $^{19}F$ NMR (376 MHz, DMSO-$d_6$) δ-56.70 (s, 3F),-74.49 (s, 3F). LCMS RT (Method 1)=4.194 min, m/z 506.1 [M+H$^+$].

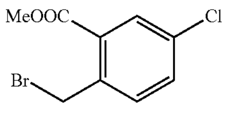

Chemical Formula: $C_9H_8BrClO_2$
Exact Mass: 261.94
Molecular Weight: 263.52

Methyl 2-(bromomethyl)-5-chlorobenzoate (DCT001-010): AIBN (0.044 g, 0.271 mmol) was added to a mixture of methyl 5-chloro-2-methylbenzoate (1 g, 5.42 mmol) and NBS (0.964 g, 5.42 mmol) in $CCl_4$ (24.62 ml). The vessel was sealed and heated to reflux for 16 hours, then cooled to RT and filtered. The filtrate was concentrated and purified via flash chromatography: silica gel with a gradient of 10-50% DCM in hexanes to give methyl 2-(bromomethyl)-5-chlorobenzoate (1.0607 g, 4.03 mmol, 74.3% yield) as a colorless liquid. $^1H$ NMR (400 MHz, DMSO-$d_6$) δ 7.86 (d, J=2.3 Hz, 1H), 7.73-7.59 (m, 2H), 4.99 (s, 2H), 3.88 (s, 3H). LCMS RT (Method 1)=3.499 min, m/z 183 [M−Br$^-$]$^+$.

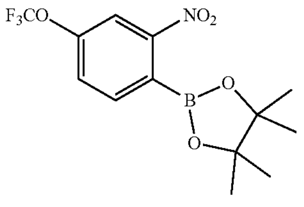

Chemical Formula: $C_{13}H_{15}BF_3O_5$
Exact Mass: 333.10
Molecular Weight: 333.07

4,4,5,5-Tetramethyl-2-(2-nitro-4-(trifluoromethoxy)phenyl)-1,3,2-dioxaborolane (DCT001-081): 4,4,4',4',5,5,5',5'-Octamethyl-2,2'-bi(1,3,2-dioxaborolane) (1.332 g, 5.24 mmol), 1-bromo-2-nitro-4-(trifluoromethoxy)benzene (1 g, 3.50 mmol), and potassium acetate (1.029 g, 10.49 mmol) were added to a reaction vessel. Dioxane (13.99 ml) was added and the slurry was purged via $N_2$ bubbling for 3 mins, after which [1,1'-Bis(diphenylphosphino)ferrocene]dichloropalladium(II) (0.128 g, 0.175 mmol) wad added. The reaction vessel was sealed, the mixture was refluxed for 15 hours, then cooled to RT, and filtered through celite. Crude product was purified via flash chromatography: silica gel with a gradient of 60-90% DCM in hexanes to give 4,4,5,5-tetramethyl-2-(2-nitro-4-(trifluoromethoxy)phenyl)-1,3,2-dioxaborolane (0.897 g, 2.69 mmol, 77% yield) as a brown liquid. 1H NMR (400 MHz, $CDCl_3$) δ 8.01 (dd, J=2.2, 1.1 Hz, 1H), 7.61 (d, J=8.1 Hz, 1H), 7.52 (dd, J=8.1, 2.0, 1H), 1.42 (s, 12H). $^{19}$F NMR (376 MHz, $CDCl_3$) δ−58.00. LCMS RT (Method 1)=3.702 min.

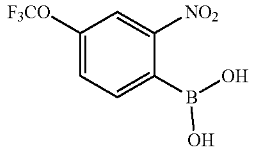

Chemical Formula: $C_7H_5BF_3O_5$
Exact Mass: 251.02
Molecular Weight: 250.92

(2-Nitro-4-(trifluoromethoxy)phenyl)boronic acid (DCT002-014): 1,4-Dioxane (5 ml) and 6M HCl (5.00 ml) were added to 4,4,5,5-tetramethyl-2-(2-nitro-4-(trifluoromethoxy)phenyl)-1,3,2-dioxaborolane DCT001-081 (0.6 g, 1.801 mmol). The reaction vessel was sealed and the mixture was heated to 70° C. for 16 hours, then cooled to RT and concentrated. $H_2O$ (5 mL) was added to the resulting oily solid and the slurry was stirred for 5 mins at RT. Solids were collected via vacuum filtration, washed with additional $H_2O$ (2×5 mL), and dried to give (2-nitro-4-(trifluoromethoxy)phenyl)boronic acid (0.261 g, 0.832 mmol, 46.2% yield) as a brown solid which was used without further purification. $^1$H NMR (400 MHz, DMSO-$d_6$) δ 8.33 (bs, 2H), 8.11 (d, J=1.9, 1H), 7.83-7.78 (m, 1H), 7.71 (d, J=8.1 Hz, 1H). $^{19}$F NMR (376 MHz, DMSO-$d_6$) δ 57.11 LCMS RT (Method 1)=2.832 min.

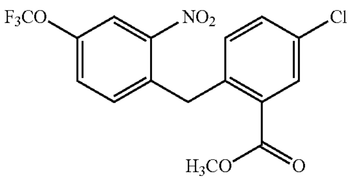

Chemical Formula: $C_{16}H_{11}ClF_3NO_5$
Exact Mass: 389.03
Molecular Weight: 389.71

Methyl 5-chloro-2-(2-nitro-4-(trifluoromethoxy)benzyl) benzoate (DCT002-016): (2-Nitro-4-(trifluoromethoxy)phenyl)boronic acid DCT002-014 (0.26 g, 1.036 mmol) was added to reaction vessel containing methyl 2-(bromomethyl)-5-chlorobenzoate (0.273 g, 1.036 mmol) in DME (10.4 mL), and sodium carbonate (2M, 0.329 g, 3.11 mmol). The mixture was purged via N2 bubbling for 5 min, after which tetrakis(triphenylphosphine)palladium(0) (0.060 g, 0.052 mmol) was added. The mixture was purged with $N_2$ for another 2 min, sealed, and heated to 120° C. for 15 hours. The reaction mixture was cooled to RT and filtered through celite. The filtrate was concentrated and purified via flash chromatography: silica gel with a gradient of 60-100% DCM in hexanes to give methyl 5-chloro-2-(2-nitro-4-(trifluoromethoxy)benzyl)benzoate (0.088 g, 22% yield) as a pale yellow solid. $^1$H NMR (400 MHz, DMSO-$d_6$) δ8.10-8.04 (bs, 1H), 7.89 (d, J=2.4 Hz, 1H), 7.71-7.60 (m, 2H), 7.33-7.27 (m, 1H), 7.23 (d, J=8.7 Hz, 1H), 4.54 (s, 2H), 3.73 (s, 3H). LCMS RT (Method 1)=3.435 min.

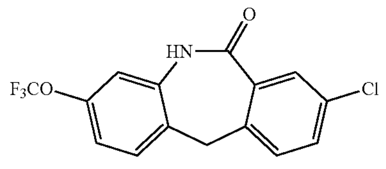

Chemical Formula: $C_{15}H_9ClF_3NO_2$
Exact Mass: 327.03
Molecular Weight: 327.69

8-Chloro-3-(trifluoromethoxy)-5,11-dihydro-6H-dibenzo[b,e]azepin-6-one (DCT002-021): Iron powder (0.062 g, 1.103 mmol) was added to a solution of methyl 5-chloro-2-(2-nitro-4-(trifluoromethoxy)benzyl)benzoate DCT002-016 (0.086 g, 0.221 mmol) in ethanol (2 ml)/6M HCl (2.000 ml) in a round bottom flask and the mixture was refluxed overnight. The reaction mixture was cooled to RT, neutralized with $NaHCO_3$ (10 mL), and extracted with DCM (3x15 mL). Combined organic phases were washed with $NaHCO_3$ (1×20 mL) and brine (1×20 mL), dried over $MgSO_4$, filtered, and concentrated to give an off-white solid (0.035 g). Crude material was purified via flash chromatography: silica gel with a gradient of 0-15% EtOAc in DCM to give 8-chloro-3-(trifluoromethoxy)-5,11-dihydro-6H-dibenzo[b,e]azepin-6-one (0.056 g, 0.171 mmol, 77% yield) as an off white solid. $^1$H NMR (400 MHz, DMSO-$d_6$) δ 10.68 (s, 1H), 7.64 (d, J=2.2 Hz, 1H), 7.55 (m, 1H), 7.43 (m, 2H), 7.10-7.03 (m, 2H), 3.99 (s, 2H). $^{19}$F NMR (376 MHz, DMSO-$d_6$) δ-56.90. LCMS RT (Method 1)=3.464 min, m/z 328.0 [M+$H^+$].

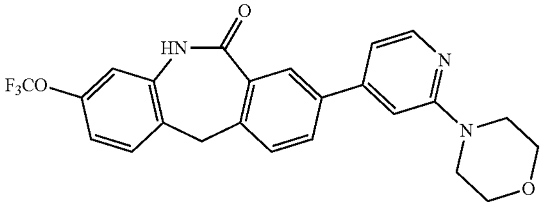

Chemical Formula: $C_{24}H_{20}F_3N_3O_3$
Exact Mass: 455.15
Molecular Weight: 455.14

8-(2-Morpholinopyridin-4-yl)-3-(trifluoromethoxy)-5,11-dihydro-6H-dibenzo[b,e]azepin-6-one (NCGC00496930): A mixture of 8-chloro-3-(trifluoromethoxy)-5,11-dihydro-6H-dibenzo[b,e]azepin-6-one DCT002-021 (0.034 g, 0.104 mmol) in DMF (1.038 ml), 4-(4-(4,4,5,5-tetramethyl-1,3,2-dioxaborolan-2-yl)pyridin-2-yl)morpholine (0.033 g, 0.114 mmol), and sodium carbonate (2M, 0.052 ml, 0.104 mmol) were added to a microwave vial. The mixture was purged via $N_2$ bubbling for 5 mins.

Tetrakis(triphenylphosphine)palladium(0) (6.00 mg, 5.19 μmol) was added, the mixture was purged with $N_2$ for an additional 2 min, and heated to 160° C. via microwave irradiation for 2 hours. Crude product was purified via standard HPLC conditions using a gradient of 10-100% ACN in $H_2O$ with 0.1% TFA to give 8-(2-morpholinopyridin-4-yl)-3-(trifluoromethoxy)-5,11-dihydro-6H-dibenzo[b,e]azepin-6-one (0.032 g, 69% yield) as the TFA salt. $^1$H NMR (400 MHz, DMSO-$d_6$) δ 10.68 (s, 1H), 8.14 (d, J=5.5 Hz, 1H), 8.03 (d, J=2.1 Hz, 1H), 7.94-7.87 (m, 1H), 7.51 (dd, J=15.8, 8.5 Hz, 2H), 7.17-7.05 (m, 3H), 7.02 (s, 1H), 4.01 (s, 2H), 3.70 (bm, 4H), 3.54 (bm, 4H). $^{19}$F NMR (376

MHz, DMSO-$d_6$) δ-56.89,-74.17. LCMS RT (Method 1)=4.403 min, m/z 456.1 [M+$H^+$].

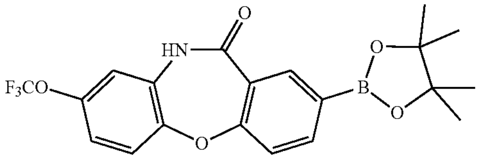

Chemical Formula: $C_{20}H_{19}BF_3NO_5$
Exact Mass: 421.13
Molecular Weight: 421.18

2-(4,4,5,5-Tetramethyl-1,3,2-dioxaborolan-2-yl)-8-(trifluoromethoxy)dibenzo[b,f][1,4]oxazepin-11(10H)-one (AED020-059): A mixture of 2-bromo-8-(trifluoromethoxy) dibenzo[b,f][1,4]oxazepin-11(10H)-one AED013-066 (1.50 g, 4.01 mmol), bis(pinacolato)diboron (2.04 g, 8.02 mmol), Pd(dppf)$C1_2$—$CH_2Cl_2$ (0.327 g, 0.401 mmol), and potassium acetate (1.18 g, 12.0 mmol) in DMF (30.0 mL) was heated to 100° C. for 45 min, after which LC-MS analysis showed formation of mostly ester, with less than 10% acid. The reaction mixture was allowed to cool to RT, poured over ice $H_2O$, vigorously stirred for 20 min, and insoluble material filtered, rinsed with $H_2O$ and air dried. The crude solid was taken up in EtOAc, and filtered through celite. The filtrate was treated with SiliaMetS Thiol metal scavenger (4.00 g @loading of 1.31 mmol/g) and allowed to stir at RT overnight. The mixture was filtered through celite and the filtrate concentrated to dryness. Solid residue was triturated in hexanes for 15 min, and the solid filtered, rinsed with hexanes and dried under vacuum to afford the title compound (1.45 g, 3.44 mmol, 86% yield) as a slightly tan solid, which was used without further purification. $^1H$ NMR (400 MHz, DMSO-$d_6$) δ 10.68 (s, 1H), 8.10 (d, J=1.7 Hz, 1H), 7.88 (dd, J=8.1, 1.7 Hz, 1H), 7.48 (dt, J=9.1, 1.4 Hz, 1H), 7.38 (d, J=8.0 Hz, 1H), 7.19-7.10 (m, 2H), 1.29 (s, 12H). $^{19}F$ NMR (376 MHz, DMSO-$d_6$) δ-57.13 (s, 3F). LCMS RT (Method 2)=3.891 min. m/z 865.2 [2M+$Na^+$].

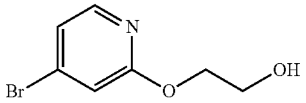

Chemical Formula: $C_7H_8BrNO_2$
Exact Mass: 216.97
Molecular Weight: 218.05

2-((4-Bromopyridin-2-yl)oxy)ethan-1-ol (AED020-053): A 1.0M THF solution of KOtBu (6.82 mL, 6.82 mmol) was added slowly to a solution of 4-bromo-2-fluoropyridine (0.584 mL, 5.68 mmol) and ethylene glycol (0.951 mL, 17.1 mmol). The resulting reaction mixture was stirred at RT for 24 h, after which LC-MS analysis showed product formation. Reaction was quenched by addition of saturated $NH_4Cl$ solution, diluted with EtOAc, washed with $H_2O$, brine, dried over $MgSO_4$, filtered and concentrated. Crude residue was purified by flash column chromatography: silica gel with a gradient of 20-50% EtOAc in Hex to afford the title compound (560 mg, 2.57 mmol, 45.2% yield) as a clear syrup. $^1H$ NMR (400 MHz, DMSO-$d_6$) δ 8.06 (d, J=5.5 Hz, 1H), 7.21 (dd, J=5.5, 1.6 Hz, 1H), 7.11 (d, J=1.6 Hz, 1H), 4.81 (s, 1H), 4.27 (t, J=5.0 Hz, 2H), 3.69 (t, J=5.3 Hz, 2H). LCMS RT (Method 2)=2.567 min. m/z 219.9 [M+$H^+$].

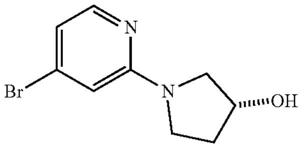

Chemical Formula: $C_9H_{11}BrN_2O$
Exact Mass: 242.01
Molecular Weight: 243.10

(R)-1-(4-Bromopyridin-2-yl)pyrrolidin-3-ol (AED020-054): A solution of 4-bromo-2-fluoropyridine (0.584 mL, 5.68 mmol), (R)-pyrrolidin-3-ol (0.551 mL, 6.82 mmol) and potassium carbonate (2.36 g, 17.1 mmol) in DMSO (10.0 mL) was heated to 90° C. for 5 h, after which LC-MS analysis showed product formation. Reaction mixture was poured over ice $H_2O$, vigorously stirred for 30 min, and insoluble material filtered, rinsed generously with $H_2O$, and allowed to air dry to afford the title compound (1.04 g, 4.28 mmol, 75% yield) as a white powder, which was used without further purification. $^1H$ NMR (400 MHz, DMSO-$d_6$) δ 7.93 (d, J=5.4 Hz, 1H), 6.71 (dd, J=5.4, 1.7 Hz, 1H), 6.62 (d, J=1.6 Hz, 1H), 4.96 (s, 1H), 4.37 (tt, J=4.7, 2.5 Hz, 1H), 3.43 (ddd, J=13.9, 10.2, 5.7 Hz, 3H), 3.28 (d, J=11.3 Hz, 1H), 2.00 (dtd, J=13.3, 8.7, 4.6 Hz, 1H), 1.88 (dddd, J=13.8, 6.8, 3.9, 1.2 Hz, 1H). LCMS RT (Method 2)=1.323 min. m/z 245.0 [M+$H^+$].

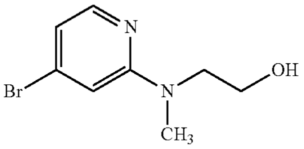

Chemical Formula: $C_8H_{11}BrN_2O$
Exact Mass: 230.01
Molecular Weight: 231.09

2-((4-Bromopyridin-2-yl)(methyl)amino)ethan-1-ol (AED020-068): A solution of 4-bromo-2-fluoropyridine (0.584 mL, 5.68 mmol), 2-(methylamino)ethan-1-ol (0.548 mL, 6.82 mmol) and potassium carbonate (2.36 g, 17.1 mmol) in DMSO (10.0 mL) was heated to 90° C. for 5 h, after which LC-MS analysis showed product formation. Reaction mixture was diluted with EtOAc, washed with $H_2O$, brine, dried over $MgSO_4$, filtered and concentrated. Crude residue was purified by flash column chromatography: silica gel with a gradient of 25-65% EtOAc in Hex to afford the title compound (1.05 g, 4.54 mmol, 80% yield) as a clear syrup. $^1H$ NMR (400 MHz, DMSO-$d_6$) δ 7.92 (dd, J=5.3, 0.5 Hz, 1H), 6.80 (d, J=1.6 Hz, 1H), 6.72 (dd, J=5.3, 1.6 Hz, 1H), 4.67 (s, 1H), 3.54 (q, J=4.8, 3.9 Hz, 4H), 3.01 (d, J=0.9 Hz, 3H). LCMS RT (Method 2)=2.147 min. m/z 233.0 [M+$H^+$].

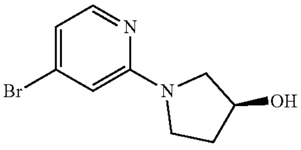

Chemical Formula: $C_9H_{11}BrN_2O$
Exact Mass: 242.01
Molecular Weight: 243.10

(S)-1-(4-Bromopyridin-2-yl)pyrrolidin-3-ol (AED020-074): A solution of 4-bromo-2-fluoropyridine (0.491 mL, 4.78 mmol), (S)-pyrrolidin-3-ol (0.464 mL, 5.74 mmol) and potassium carbonate (1.98 g, 14.4 mmol) in DMSO (10.0 mL) was heated to 90° C. for 5 h, after which LC-MS analysis showed product formation. Reaction mixture was poured over ice $H_2O$, vigorously stirred for 30 min, and insoluble material filtered, rinsed generously with $H_2O$, and allowed to air dry to afford the title compound (774 mg, 3.18 mmol, 66.6% yield) as a white powder, which was used without further purification. $^1H$ NMR (400 MHz, DMSO-$d_6$) δ 7.93 (d, J=5.3 Hz, 1H), 6.71 (dd, J=5.4, 1.7 Hz, 1H), 6.62 (d, J=1.6 Hz, 1H), 4.95 (d, J=3.7 Hz, 1H), 4.36 (dq, J=5.2, 2.0 Hz, 1H), 3.43 (ddd, J=13.8, 10.1, 5.7 Hz, 3H), 3.28 (d, J=11.3 Hz, 1H), 2.00 (dtd, J=13.3, 8.8, 4.6 Hz, 1H), 1.96-1.82 (m, 1H). LCMS RT (Method 2)=1.994 min. m/z 245.0 [M+H$^+$].

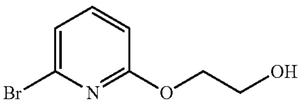

Chemical Formula: $C_7H_8BrNO_2$
Exact Mass: 216.97
Molecular Weight: 218.05

2-((6-Bromopyridin-2-yl)oxy)ethan-1-ol (AED020-070): A 1.0M THF solution of KOtBu (6.82 mL, 6.82 mmol) was added slowly to a solution of 2-bromo-6-fluoropyridine (1.00 g, 5.68 mmol) and ethylene glycol (0.951 mL, 17.1 mmol). The resulting reaction mixture was stirred at RT for 24 h, after which LC-MS analysis showed product formation. Reaction was quenched by addition of saturated $NH_4Cl$ solution, diluted with EtOAc, washed with $H_2O$, brine, dried over $MgSO_4$, filtered and concentrated. Crude residue was purified by flash column chromatography: silica gel with a gradient of 20-40% EtOAc in Hex to afford the title compound (648 mg, 2.97 mmol, 52.3% yield) as a clear oil. $^1H$ NMR (400 MHz, DMSO-$d_6$) δ 7.65 (dd, J=8.2, 7.5 Hz, 1H), 7.21 (dd, J=7.5, 0.6 Hz, 1H), 6.86 (dd, J=8.2, 0.7 Hz, 1H), 4.78 (s, 1H), 4.27-4.20 (m, 2H), 3.73-3.66 (m, 2H). LCMS RT (Method 2)=3.131 min. m/z 219.9 [M+H$^+$].

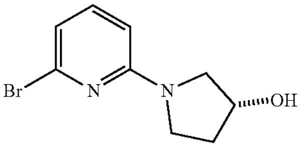

Chemical Formula: $C_9H_{11}BrN_2O$
Exact Mass: 242.01
Molecular Weight: 243.10

(R)-1-(6-Bromopyridin-2-yl)pyrrolidin-3-ol (AED020-071): A solution of 2-bromo-6-fluoropyridine (1.00 g, 5.68 mmol), (R)-pyrrolidin-3-ol (0.551 mL, 6.82 mmol) and potassium carbonate (2.36 g, 17.1 mmol) in DMSO (10.0 mL) was heated to 90° C. for 5 h, after which LC-MS analysis showed product formation. Reaction mixture was poured over $H_2O$, and extracted twice with EtOAc. The combined organic layers were washed with $H_2O$, brine, dried over $MgSO_4$, filtered and concentrated. Crude residue was purified by flash column chromatography: silica gel with a gradient of 20-55% EtOAc in Hex to afford the title compound (1.14 g, 4.69 mmol, 83% yield) as a clear oil. $^1H$ NMR (400 MHz, DMSO-$d_6$) δ 7.37 (dd, J=8.3, 7.4 Hz, 1H), 6.67 (dd, J=7.4, 0.6 Hz, 1H), 6.40 (dd, J=8.4, 0.6 Hz, 1H), 4.95 (s, 1H), 4.37 (tt, J=4.7, 2.4 Hz, 1H), 3.47-3.35 (m, 3H), 3.26 (d, J=11.3 Hz, 1H), 2.07-1.95 (m, 1H), 1.92-1.84 (m, 1H). LCMS RT (Method 2)=3.428 min. m/z 245.0 [M+H$^+$].

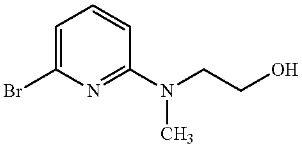

Chemical Formula: $C_7H_{11}BrN_2O$
Exact Mass: 230.01
Molecular Weight: 231.09

2-((6-Bromopyridin-2-yl)(methyl)amino)ethan-1-ol (AED020-072): A solution of 2-bromo-6-fluoropyridine (1.00 g, 5.68 mmol), 2-(methylamino)ethan-1-ol (0.548 mL, 6.82 mmol) and potassium carbonate (2.36 g, 17.1 mmol) in DMSO (10.0 mL) was heated to 90° C. for 5 h, after which LC-MS analysis showed product formation. Reaction mixture was poured over $H_2O$, and extracted twice with EtOAc. The combined organic layers were washed with $H_2O$, brine, dried over $MgSO_4$, filtered and concentrated. Crude residue was purified by flash column chromatography: silica gel with a gradient of 20-50% EtOAc in Hex to afford the title compound (1.13 g, 4.89 mmol, 86% yield) as a clear oil. $^1H$ NMR (400 MHz, DMSO-$d_6$) δ 7.37 (dd, J=8.4, 7.4 Hz, 1H), 6.71-6.64 (m, 1H), 6.63-6.56 (m, 1H), 4.69 (s, 1H), 3.59-3.47 (m, 5H), 3.00 (s, 3H). LCMS RT (Method 2)=3.288 min. m/z 233.0 [M+H$^+$].

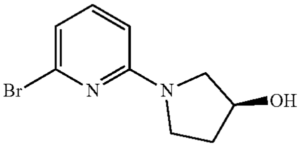

Chemical Formula: $C_9H_{11}BrN_2O$
Exact Mass: 242.01
Molecular Weight: 243.10

(S)-1-(6-Bromopyridin-2-yl)pyrrolidin-3-ol (AED020-075): A solution of 2-bromo-6-fluoropyridine (842 mg, 4.78 mmol), (S)-pyrrolidin-3-ol (0.464 mL, 5.74 mmol) and potassium carbonate (1.98 g, 14.4 mmol) in DMSO (10.0 mL) was heated to 90° C. for 5 h, after which LC-MS analysis showed product formation. Reaction mixture was poured over $H_2O$, and extracted twice with EtOAc. The combined organic layers were washed with $H_2O$, brine, dried over $MgSO_4$, filtered and concentrated. Crude residue was purified by flash column chromatography: silica gel with a gradient of 20-55% EtOAc in Hex to afford the title compound (1.15 g, 4.73 mmol, 99% yield) as a clear oil. $^1$H NMR (400 MHz, DMSO-$d_6$) δ 7.37 (dd, J=8.3, 7.4 Hz, 1H), 6.67 (dd, J=7.4, 0.6 Hz, 1H), 6.40 (dd, J=8.3, 0.6 Hz, 1H), 4.96 (d, J=3.5 Hz, 1H), 4.37 (dq, J=5.0, 2.4 Hz, 1H), 3.47-3.35 (m, 3H), 3.26 (d, J=11.3 Hz, 1H), 2.00 (dtd, J=13.3, 8.8, 4.6 Hz, 1H), 1.93-1.82 (m, 1H). LCMS RT (Method 2)=2.993 min. m/z 245.0 [M+H$^+$].

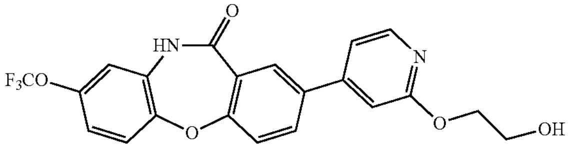

Chemical Formula: $C_{21}H_{15}F_3N_2O_5$
Exact Mass: 432.09
Molecular Weight: 432.36

2-(2-(2-Hydroxyethoxy)pyridin-4-yl)-8-(trifluoromethoxy)dibenzo[b,f][1,4]oxazepin-11(10H)-one (NCGC00507969): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), 2-((4-bromopyridin-2-yl)oxy)ethan-1-ol AED020-053 (18.8 mg, 0.086 mmol), $K_3PO_4$ (73.3 mg, 0.345 mmol), XPhos Pd(crotyl)Cl (5.82 mg, 8.63 μmol) in 4:1 dioxane:$H_2O$ (2.50 mL) to afford the title compound (17.3 mg, 46.3% yield). $^1$H NMR (400 MHz, DMSO-$d_6$) δ 10.78 (s, 1H), 8.22 (dd, J=5.4, 0.7 Hz, 1H), 8.09-8.02 (m, 2H), 7.52 (t, J=2.2 Hz, 1H), 7.51 (s, 1H), 7.29 (dd, J=5.4, 1.6 Hz, 1H), 7.18 (dddt, J=5.2, 2.9, 2.0, 1.0 Hz, 2H), 7.09 (dd, J=1.6, 0.7 Hz, 1H), 4.82 (t, J=5.5 Hz, 1H), 4.31 (dd, J=5.8, 4.6 Hz, 2H), 3.73 (q, J=5.3 Hz, 2H). $^{19}$F NMR (376 MHz, DMSO-$d_6$) δ-57.13 (s, 3F). LCMS RT (Method 1)=4.960 min, m/z 888.1

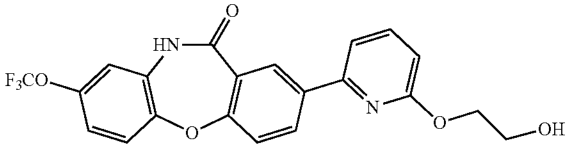

Chemical Formula: $C_{21}H_{15}F_3N_2O_5$
Exact Mass: 432.09
Molecular Weight: 432.36

2-(6-(2-Hydroxyethoxy)pyridin-2-yl)-8-(trifluoromethoxy)dibenzo[b,f][1,4]oxazepin-11(10H)-one (NCGC00532318): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), 2-((6-bromopyridin-2-yl)oxy)ethan-1-ol AED020-070 (18.8 mg, 0.086 mmol), $K_3PO_4$ (73.3 mg, 0.345 mmol), XPhos Pd(crotyl)Cl (5.82 mg, 8.63 μmol) in 4:1 dioxane:$H_2O$ (2.50 mL) to afford the title compound (15.0 mg, 40.2% yield). $^1$H NMR (400 MHz, DMSO-$d_6$) δ 10.74 (s, 1H), 8.43 (d, J=2.4 Hz, 1H), 8.31 (dd, J=8.5, 2.4 Hz, 1H), 7.80 (dd, J=8.2, 7.5 Hz, 1H), 7.56 (dd, J=7.5, 0.7 Hz, 1H), 7.53-7.46 (m, 2H), 7.23-7.11 (m, 2H), 6.81 (dd, J=8.2, 0.6 Hz, 1H), 4.85 (t, J=5.5 Hz, 1H), 4.38 (dd, J=5.7, 4.7 Hz, 2H), 3.76 (q, J=5.3 Hz, 2H). $^{19}$F NMR (376 MHz, DMSO-$d_6$) δ-57.13 (s, 3F). LCMS RT (Method 1)=5.483 min, m/z 887.1

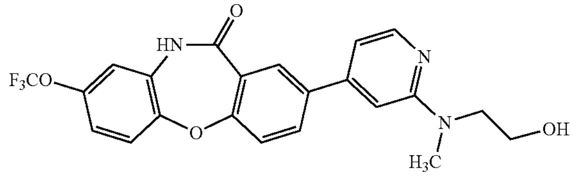

Chemical Formula: $C_{22}H_{18}F_3N_3O_4$
Exact Mass: 445.12
Molecular Weight: 445.40

2-(2-((2-Hydroxyethyl)(methyl)amino)pyridin-4-yl)-8-(trifluoromethoxy)dibenzo[b,f][1,4]oxazepin-11(10H)-one (NCGC00508838): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), 2-((4-bromopyridin-2-yl)(methyl)amino)ethan-1-ol AED020-068 (19.9 mg, 0.086 mmol), $K_3PO_4$ (73.3 mg, 0.345 mmol), XPhos Pd(crotyl)Cl (5.82 mg, 8.63 μmol) in 4:1 dioxane:$H_2O$ (2.50 mL) to afford the title compound (17.8 mg, 46.3% yield). $^1$H NMR (400 MHz, DMSO-$d_6$) δ 10.82 (s, 1H), 8.18-8.00 (m, 3H), 7.54 (dd, J=12.1, 8.5 Hz, 2H), 7.19 (d, J=8.2 Hz, 2H), 7.06 (s, 2H), 3.72 (d, J=5.7 Hz, 2H), 3.64 (t, J=5.4 Hz, 2H), 3.19 (s, 3H), 3.01 (s, 1H). $^{19}$F NMR (376 MHz, DMSO-$d_6$) δ-57.13 (s, 3F). LCMS RT (Method 1)=4.206 min, m/z 446.2 [M+H$^+$].

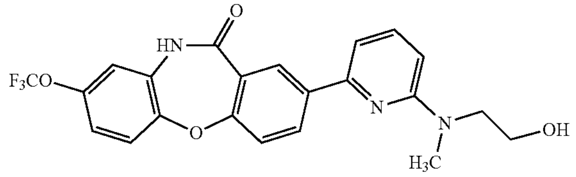

Chemical Formula: $C_{22}H_{18}F_3N_3O_4$
Exact Mass: 445.12
Molecular Weight: 445.40

2-(6-((2-Hydroxyethyl)(methyl)amino)pyridin-2-yl)-8-(trifluoromethoxy)dibenzo[b,f][1,4]oxazepin-11(10H)-one (NCGC00508972): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), 2-((6-bromopyridin-2-yl)(methyl)amino)ethan-1-ol AED020-072 (19.9 mg, 0.086 mmol), $K_3PO_4$ (73.3 mg, 0.345 mmol), XPhos Pd(crotyl)Cl (5.82 mg, 8.63 μmol) in 4:1 dioxane:$H_2O$ (2.50 mL) to afford the title compound (16.3 mg, 42.4% yield). $^1$H NMR (400 MHz, DMSO-$d_6$) δ 10.70 (s, 1H), 8.38 (d, J=2.3 Hz, 1H), 8.26 (dd, J=8.5, 2.4 Hz, 1H), 7.57 (dd, J=8.5, 7.4 Hz, 1H), 7.52-7.47 (m, 1H), 7.45 (d, J=8.5 Hz, 1H), 7.16 (d, J=7.2 Hz, 2H), 7.11 (d, J=7.4 Hz, 1H), 6.63 (d, J=8.5 Hz, 1H), 3.63 (dt, J=8.2, 4.6 Hz, 4H), 3.11 (s, 3H). $^{19}$F NMR (376 MHz, DMSO-$d_6$) δ-57.12 (s, 3F). LCMS RT (Method 1)=4.450 min, m/z 446.2 [M+H$^+$].

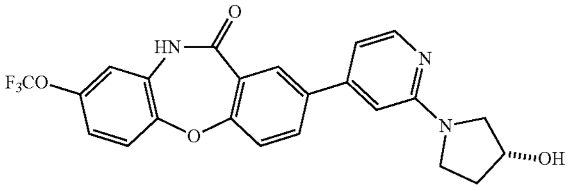

Chemical Formula: $C_{23}H_{18}F_3N_3O_4$
Exact Mass: 457.12
Molecular Weight: 457.41

(R)-2-(2-(3-Hydroxypyrrolidin-1-yl)pyridin-4-yl)-8-(trifluoromethoxy)dibenzo[b,f][1,4]oxazepin-11(10H)-one (NCGC00507975): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), (R)-1-(4-bromopyridin-2-yl)pyrrolidin-3-ol AED020-054 (21.0 mg, 0.086 mmol), $K_3PO4$ (73.3 mg, 0.345 mmol), XPhos Pd(crotyl)Cl (5.82 mg, 8.63 μmol) in 4:1 dioxane:$H_2O$ (2.50 mL) to afford the title compound (18.0 mg, 45.6% yield). $^1H$ NMR (400 MHz, DMSO-$d_6$) δ 10.83 (s, 1H), 8.18 (d, J=2.4 Hz, 1H), 8.15 (dd, J=8.5, 2.5 Hz, 1H), 8.06 (d, J=6.8 Hz, 1H), 7.57 (d, J=8.4 Hz, 1H), 7.55-7.49 (m, 1H), 7.23-7.16 (m, 2H), 7.13 (s, 2H), 5.19 (s, 1H), 4.51-4.45 (m, 1H), 3.70-3.61 (m, 3H), 3.48 (d, J=11.6 Hz, 1H), 2.08 (ddt, J=12.9, 8.6, 4.2 Hz, 1H), 2.00 (d, J=8.2 Hz, 1H). $^{19}F$ NMR (376 MHz, DMSO-$d_6$) δ-57.15 (s, 3F). LCMS RT (Method 1)=4.198 min, m/z 458.1 [M+H$^+$].

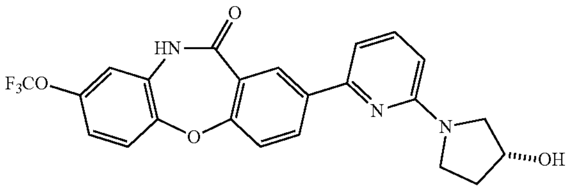

Chemical Formula: $C_{23}H_{18}F_3N_3O_4$
Exact Mass: 457.12
Molecular Weight: 457.41

(R)-2-(6-(3-Hydroxypyrrolidin-1-yl)pyridin-2-yl)-8-(trifluoromethoxy)dibenzo[b,f][1,4]oxazepin-11(10H)-one (NCGC00532289): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), (R)-1-(6-bromopyridin-2-yl)pyrrolidin-3-ol AED020-071 (21.0 mg, 0.086 mmol), $K_3PO4$ (73.3 mg, 0.345 mmol), XPhos Pd(crotyl)Cl (5.82 mg, 8.63 μmol) in 4:1 dioxane:$H_2O$ (2.50 mL) to afford the title compound (21.0 mg, 53.2% yield). $^1H$ NMR (400 MHz, DMSO-$d_6$) δ 10.71 (s, 1H), 8.41 (d, J=2.3 Hz, 1H), 8.27 (dd, J=8.5, 2.4 Hz, 1H), 7.59 (t, J=7.9 Hz, 1H), 7.53-7.48 (m, 1H), 7.45 (d, J=8.5 Hz, 1H), 7.17 (d, J=6.6 Hz, 2H), 7.12 (d, J=7.4 Hz, 1H), 6.46 (d, J=8.4 Hz, 1H), 4.41 (dt, J=5.0, 2.3 Hz, 1H), 3.61-3.47 (m, 3H), 3.41 (d, J=11.2 Hz, 1H), 2.05 (dtd, J=13.1, 8.5, 4.5 Hz, 1H), 1.93 (dd, J=10.3, 6.1 Hz, 1H). $^{19}F$ NMR (376 MHz, DMSO-$d_6$) δ-57.13 (s, 3F). LCMS RT (Method 1)=4.292 min, m/z 458.2 [M+H$^+$].

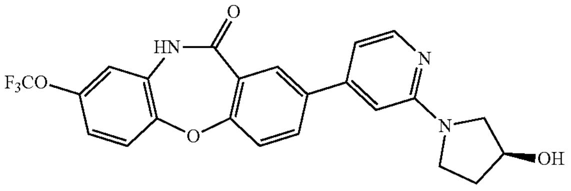

Chemical Formula: $C_{23}H_{18}F_3N_3O_4$
Exact Mass: 457.12
Molecular Weight: 457.41

(S)-2-(2-(3-Hydroxypyrrolidin-1-yl)pyridin-4-yl)-8-(trifluoromethoxy)dibenzo[b,f][1,4]oxazepin-11(10H)-one (NCGC00508975): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), (S)-1-(4-bromopyridin-2-yl)pyrrolidin-3-ol AED020-074 (21.0 mg, 0.086 mmol), $K_3PO_4$ (73.3 mg, 0.345 mmol), XPhos Pd(crotyl)Cl (5.82 mg, 8.63 μmol) in 4:1 dioxane:$H_2O$ (2.50 mL) to afford the title compound (20.0 mg, 50.6% yield). $^1H$ NMR (400 MHz, DMSO-$d_6$) δ 10.83 (s, 1H), 8.18 (s, 1H), 8.16-8.11 (m, 1H), 8.06 (d, J=6.5 Hz, 1H), 7.57 (d, J=8.4 Hz, 1H), 7.55-7.49 (m, 1H), 7.19 (d, J=8.2 Hz, 2H), 7.12 (s, 2H), 4.47 (s, 1H), 3.65 (d, J=9.5 Hz, 4H), 2.08 (dd, J=8.8, 4.4 Hz, 1H), 1.99 (s, 1H). $^{19}F$ NMR (376 MHz, DMSO-$d_6$) δ-57.14 (s, 3F). LCMS RT (Method 1)=4.196 min, m/z 458.2 [M+H$^+$].

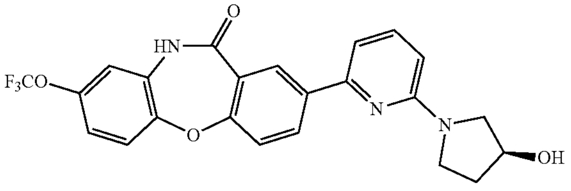

Chemical Formula: $C_{23}H_{18}F_3N_3O_4$
Exact Mass: 457.12
Molecular Weight: 457.41

(S)-2-(6-(3-Hydroxypyrrolidin-1-yl)pyridin-2-yl)-8-(trifluoromethoxy)dibenzo[b,f][1,4]oxazepin-11(10H)-one (NCGC00508973): Prepared following general Procedure D; 2-(4,4,5,5-tetramethyl-1,3,2-dioxaborolan-2-yl)-8-(trifluoromethoxy)dibenzo[b,f][1,4]oxazepin-11(10H)-one AED020-059 (40.0 mg, 0.095 mmol), (S)-1-(6-bromopyridin-2-yl)pyrrolidin-3-ol AED020-075 (21.0 mg, 0.086 mmol), $K_3PO_4$ (73.3 mg, 0.345 mmol), XPhos Pd(crotyl)Cl (5.82 mg, 8.63 μmol) in 4:1 dioxane:$H_2O$ (2.50 mL) to afford the title compound (22.5 mg, 57.0% yield). $^1H$ NMR (400 MHz, DMSO-$d_6$) δ 10.71 (s, 1H), 8.42 (d, J=2.3 Hz, 1H), 8.27 (dd, J=8.5, 2.4 Hz, 1H), 7.59 (t, J=7.9 Hz, 1H), 7.54-7.48 (m, 1H), 7.45 (d, J=8.5 Hz, 1H), 7.16 (d, J=6.9 Hz, 2H), 7.12 (d, J=7.4 Hz, 1H), 6.46 (d, J=8.4 Hz, 1H), 4.41 (dp, J=5.1, 2.8 Hz, 1H), 3.54 (qd, J=9.8, 8.5, 5.8 Hz, 3H), 3.41 (d, J=11.1 Hz, 1H), 2.99 (s, 1H), 2.05 (dtd, J=13.1, 8.6, 4.7 Hz, 1H), 1.97-1.87 (m, 1H). $^{19}F$ NMR (376 MHz, DMSO-$d_6$) δ-57.13 (s, 3F). LCMS RT (Method 1)=4.368 min, m/z 458.2 [M+H$^+$].

Example 2

Figure 4A:
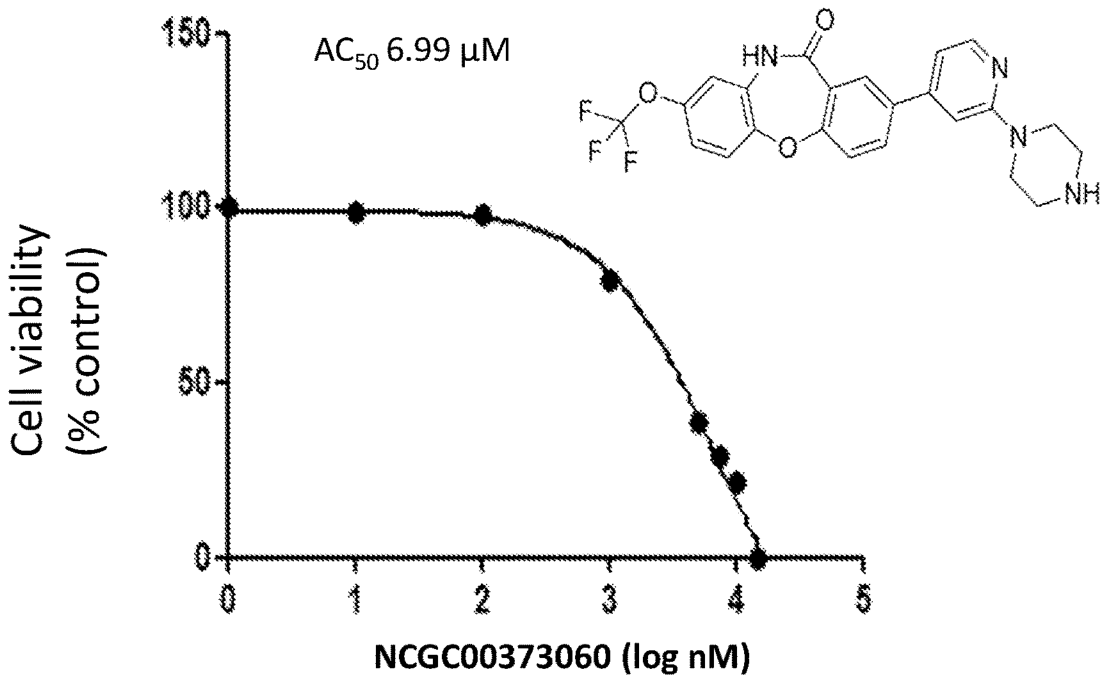
FIGS. 4A and 4B show the chemical structure and activity of two compound embodiments, NCGC00373060 (FIG. 4A) and NCGC00373056 (FIG. 4B), in K562 assays.
Figure 4B:
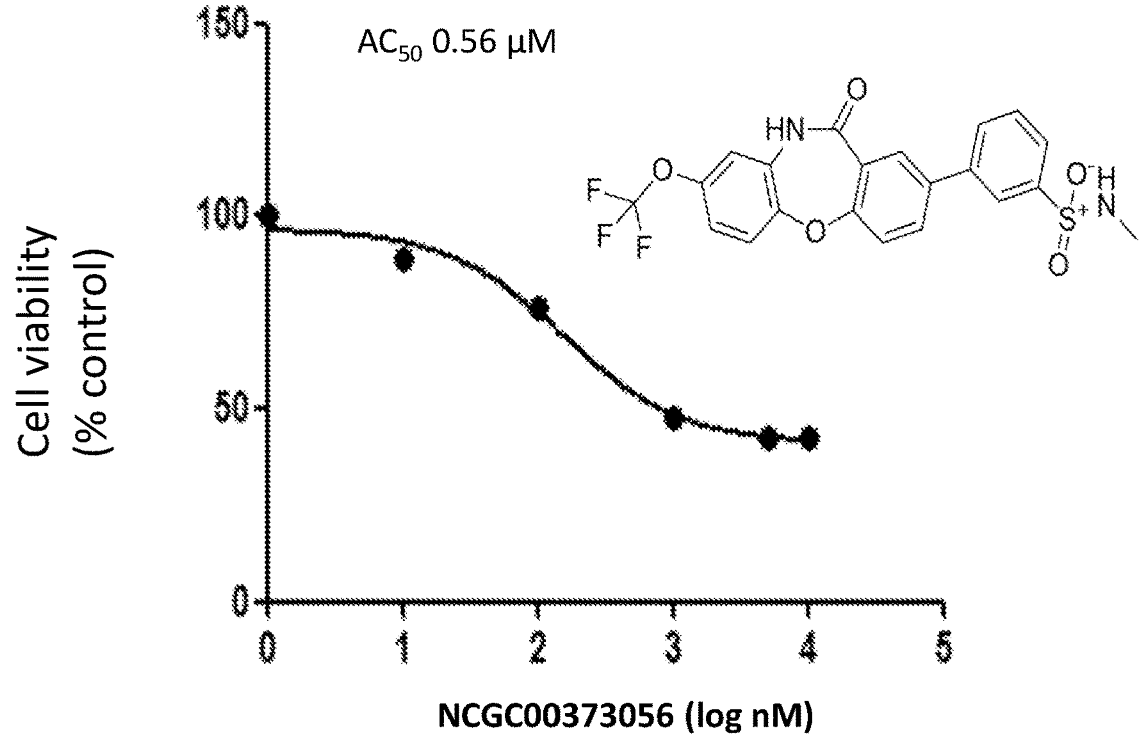
Figure 5A:
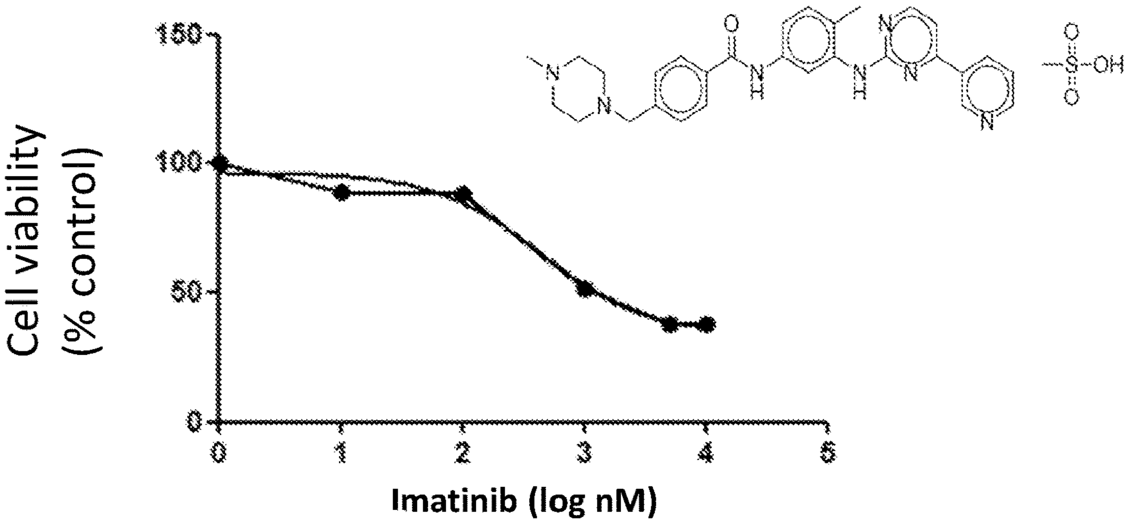
FIGS. 5A-5C show the chemical structure and activity of three known c-Abl inhibitors, Imatinib (FIG. 5A), GNF-2 (FIG. 5B), and GNF-5 (FIG. 5C).
Figure 5B:
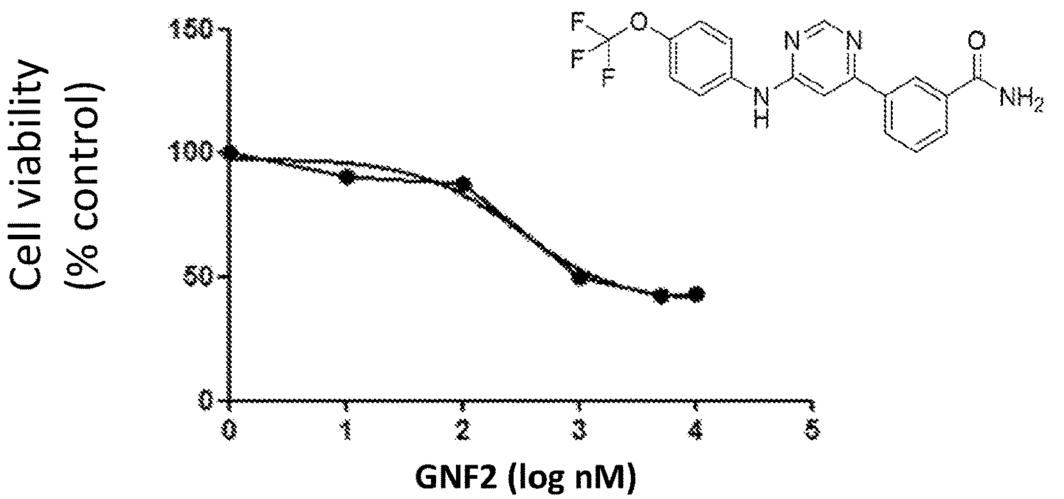
Figure 5C:
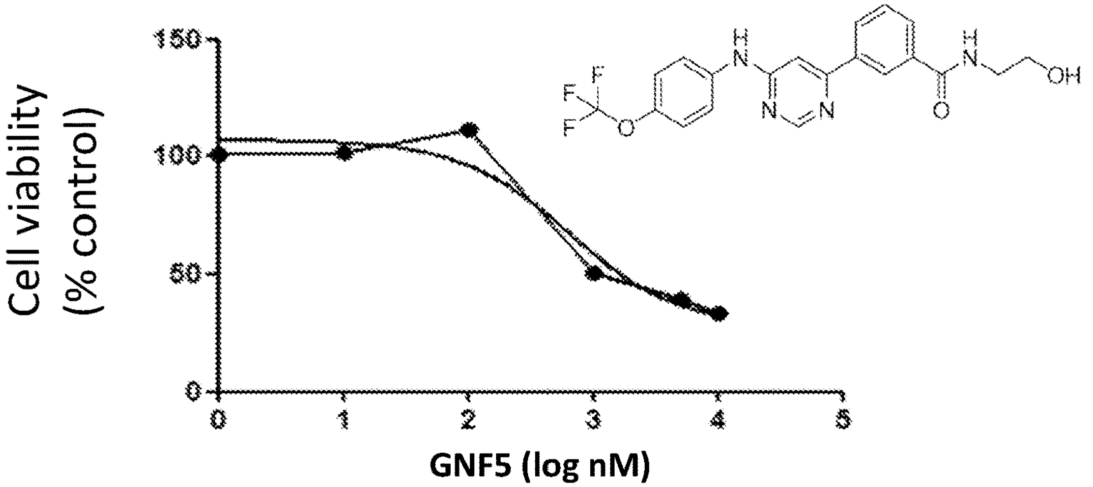
Figure 6A:
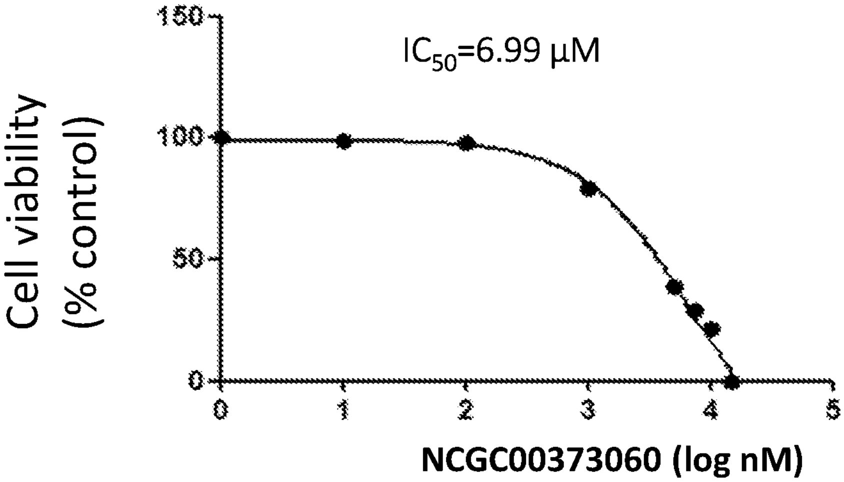
FIGS. 6A-6C show the c-Abl inhibitory activity of NCGC00373060 using three different assays, wherein the $IC_{50}$ values were determined.
Figure 6B:
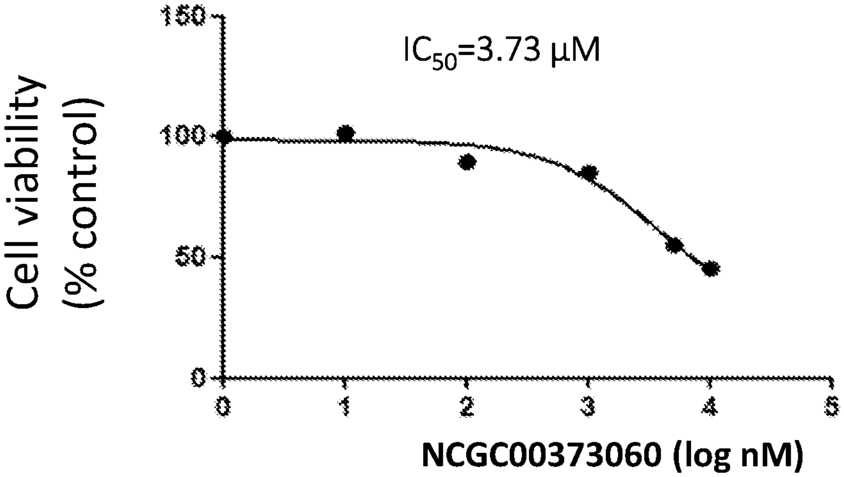
Figure 6C:
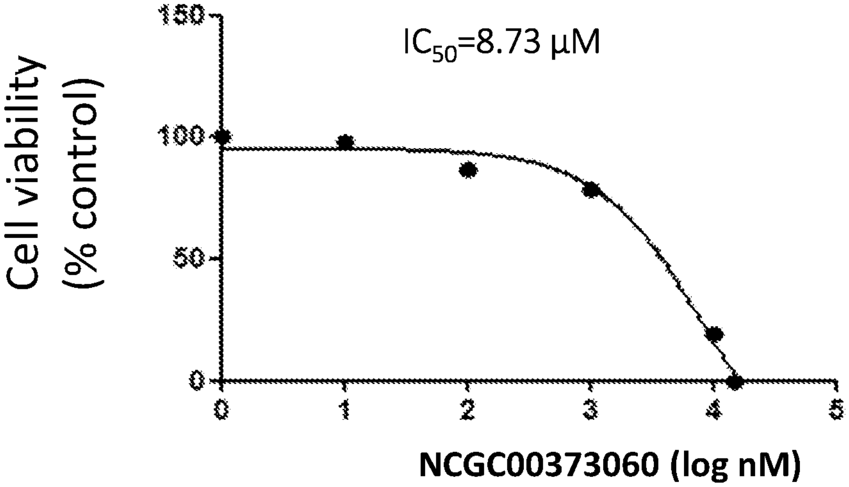
Figure 7A:
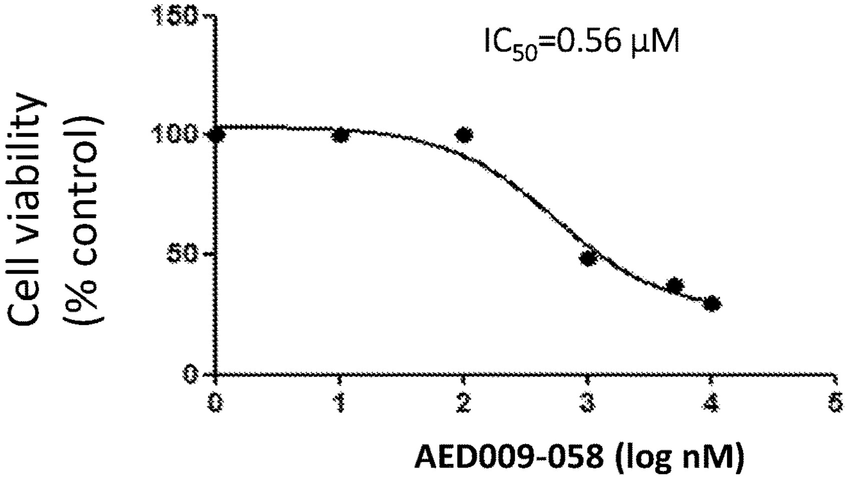
FIGS. 7A-7C show the c-Abl inhibitory activity of NCGC00373056 using three different assays, wherein the $IC_{50}$ values were determined.
Figure 7B:
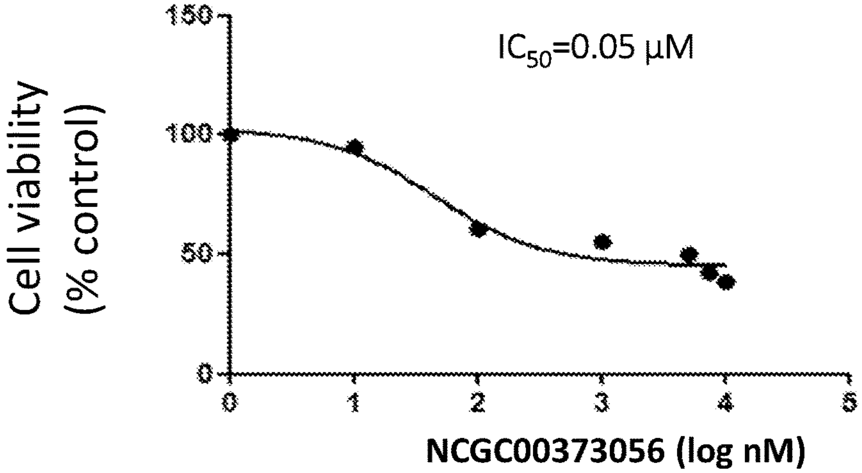
Figure 7C:
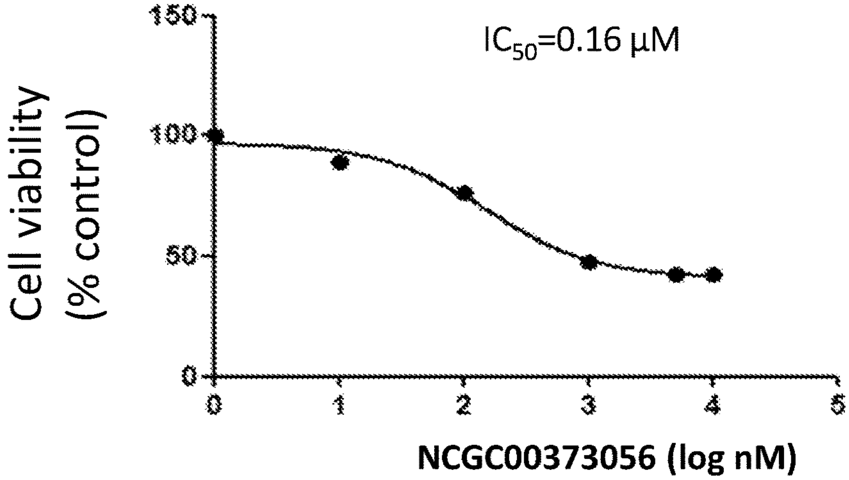

In this example, the ability of two compound embodiments described here, NCGC00373060 and NCGC00373056, to induce cell death in the CML (K562) cell line was evaluated. The leukemia cells were incubated with different concentrations of the compounds for 48 hours, and the cell proliferation inhibition was evaluated by the MTT assay. FIGS. 4A and 4B show that NCGC00373060 and NCGC00373056 are able to induce cell death in this cell line. As such, these compounds inhibit the BCR-ABL, fusion protein that includes the kinase domain of c-Abl, confirming that NCGC00373060 and NCGC00373056 are c-Abl inhibitors. These compound embodiments present an $AC_{50}$ that is superior to compounds like Imatinib, GNF-2 and GNF-5 (see FIGS. 5A-5C). The activity of NCGC00373060 and NCGC00373056 determined in different assays provides $AC_{50}$ values of 5 μM for NCGC00373060 and 0.5 μM for NCGC00373056 (FIGS. 6A-6C and 7A-7C, respectively). The leukemia cells were incubated with different concentrations of each compound embodiment for 48 hours, and the cell proliferation inhibition was evaluated by the MTT assay.

Example 3

Figure 8A:
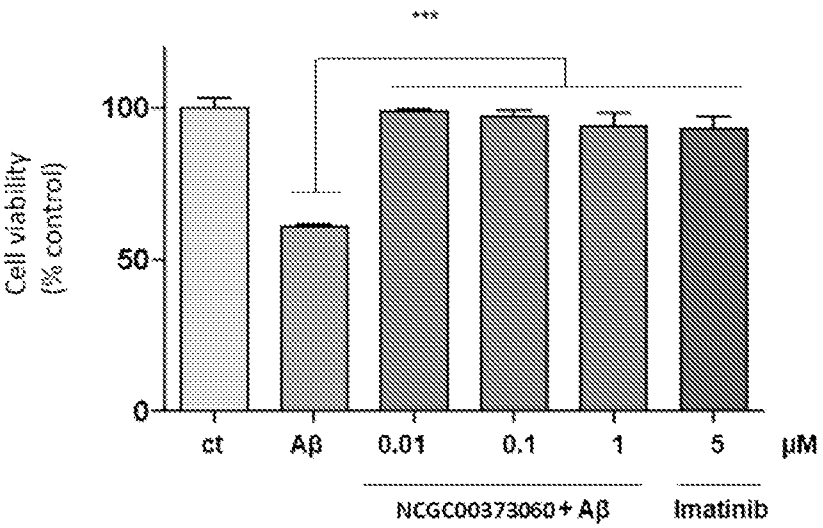
FIGS. 8A-8E show results obtained from evaluating compound activity in protecting hippocampal neurons against Aβ toxicity.
Figure 8B:
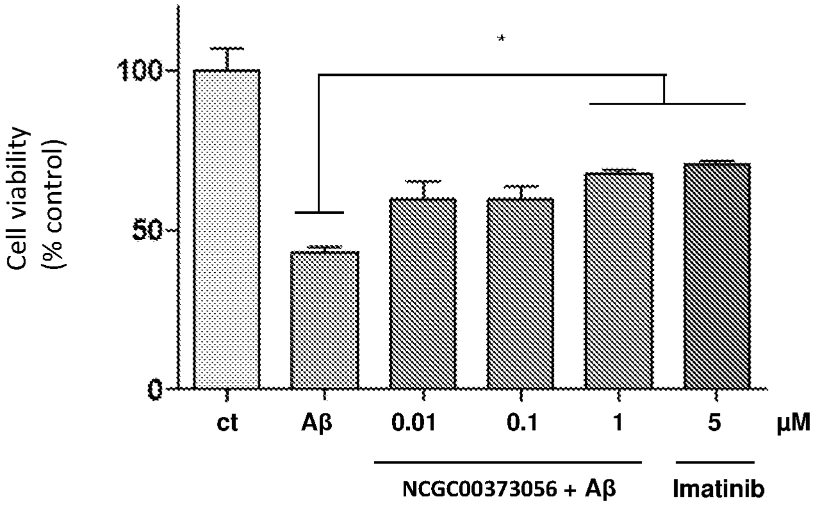
Figure 8C:
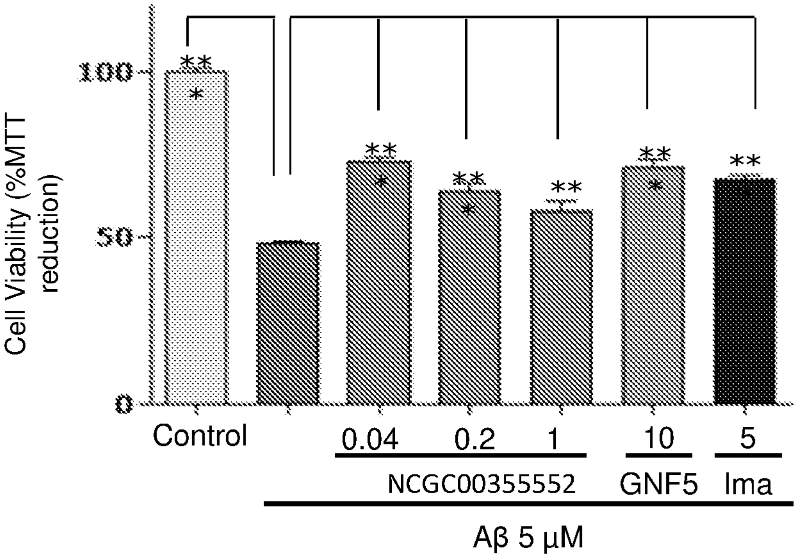
Figure 8D:
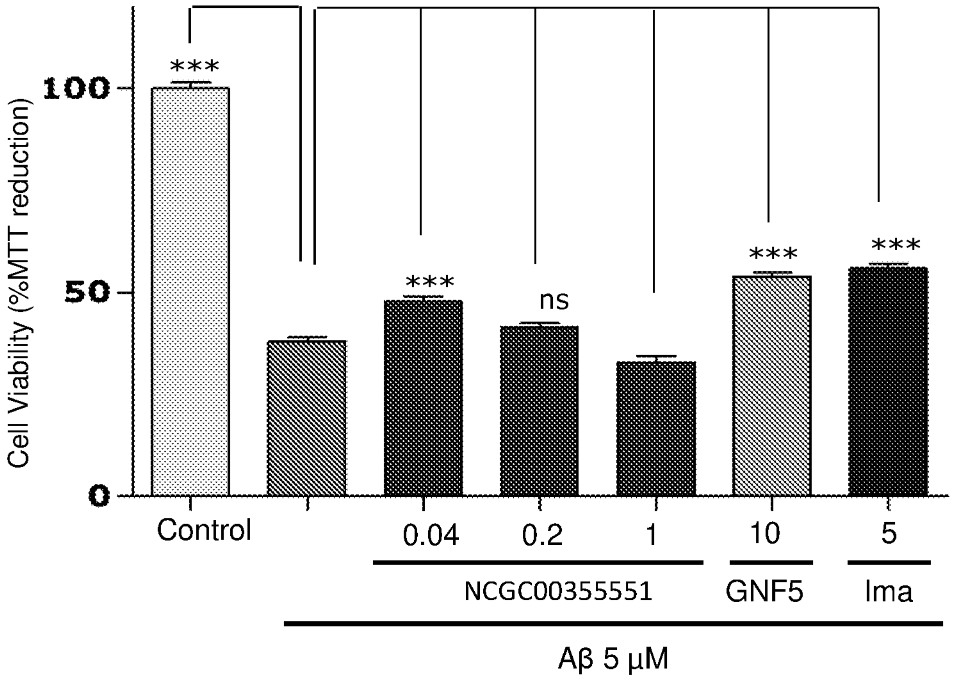
Figure 8E:
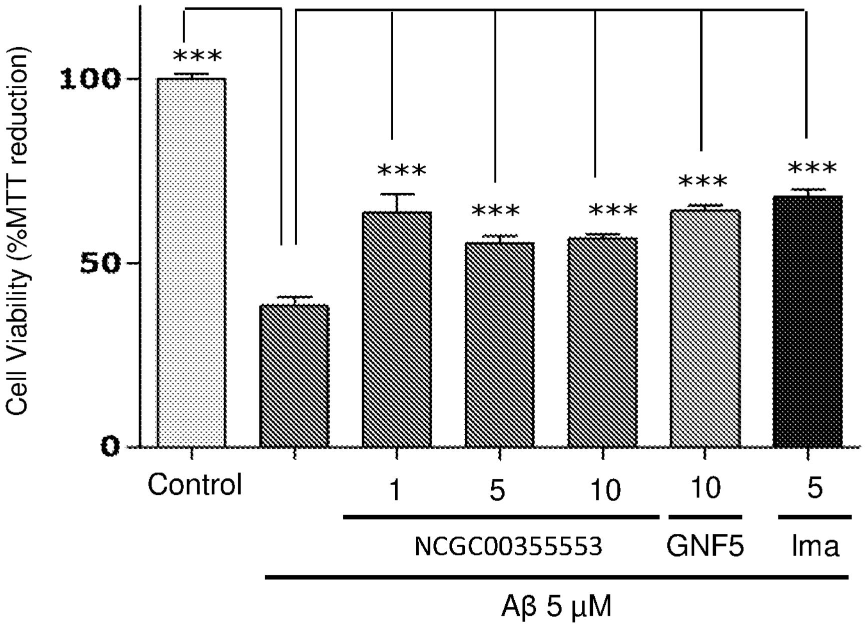

Compound embodiments NCGC00373060 and NCGC00373056 also conferred neuroprotection against Aβ fibrils. FIGS. 8A and 8B show that NCGC00373060 (FIG. 8A) and NCGC00373056 (FIG. 8B) at 0.01, 0.1 and 1 μM protect neurons against the Aβ toxicity followed by MTT assays. Additional data from other compounds are provided by FIGS. 8C-8E. Neurons were incubated with 5 μM Aβ peptide in presence of the different compound concentrations for 24 hours and cell viability was evaluated by the MTT assay. Results from additional compounds are provided by FIG. 8C.

Figure 9A:
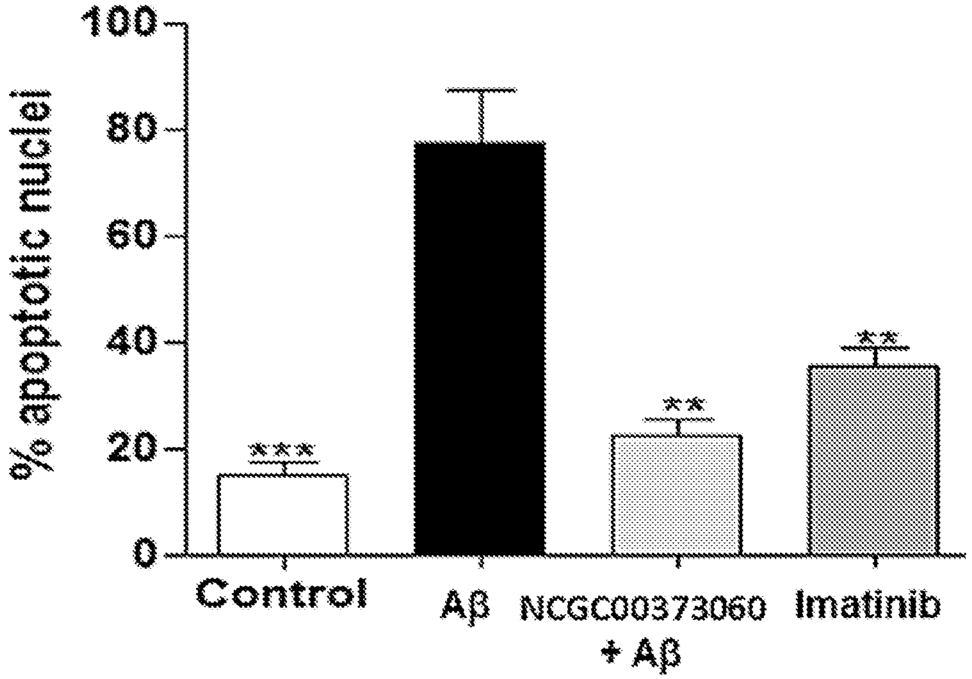
FIGS. 9A-9C show that compound embodiments NCGC00373060 (FIG. 9A), NCGC00373056 (FIG. 9B), and NCGC00355553 (FIG. 9C) prevent increases in apoptotic nuclei induced by Aβ fibrils.
Figure 9B:
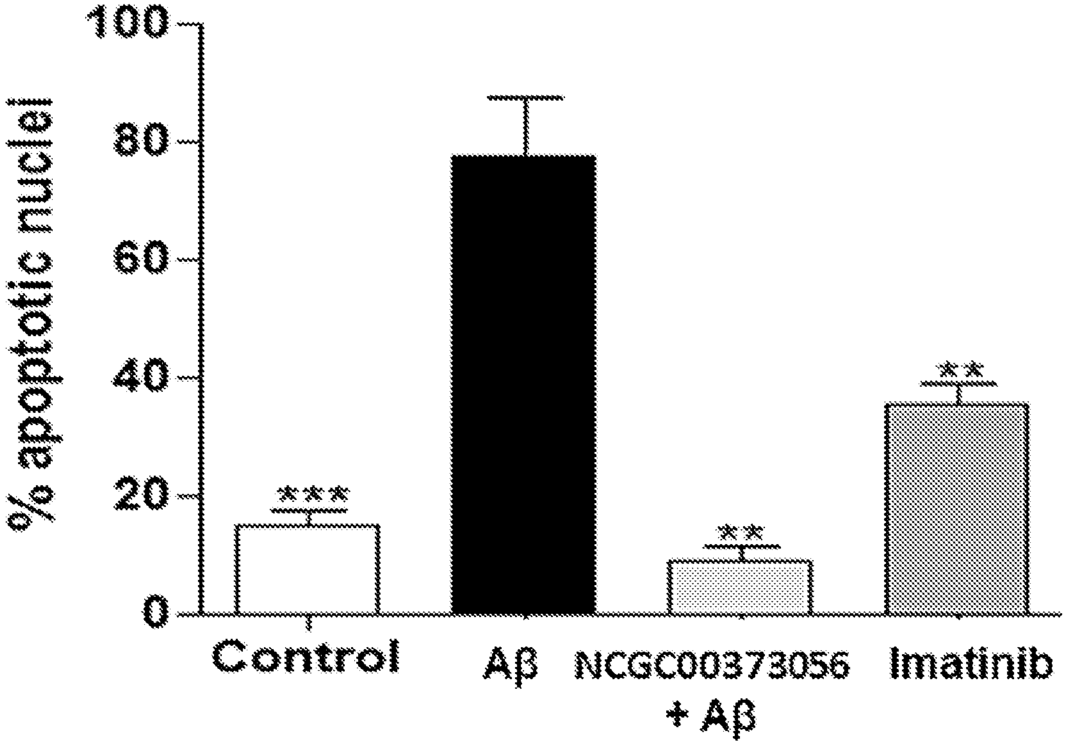
Figure 9C:
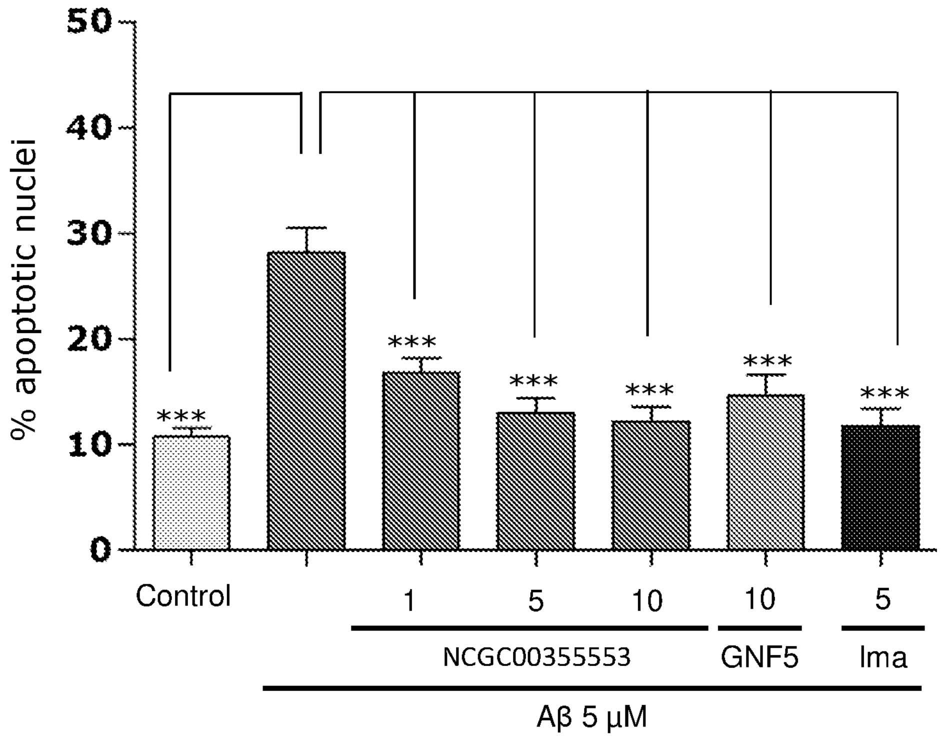

Also, a prevention of the increases in apoptotic nuclei induced by Aβ fibrils by NCGC00373060 and NCGC00373056 was observed (FIGS. 9A and 9B, respectively, wherein *<0.0001, <0.005, and *<0.01). Additional results from another compound embodiment, NCGC00355553, are provided by FIG. 9C. Apoptotic nuclei were evaluated by Hoescht staining.

Figure 10A:
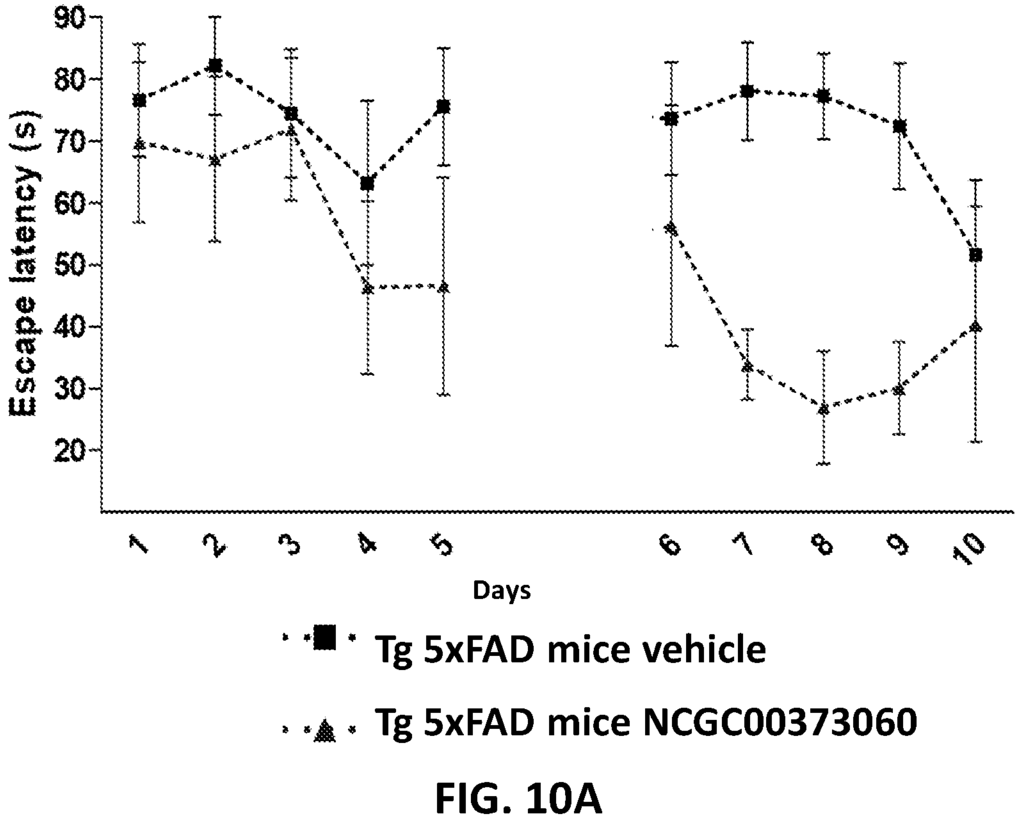
FIGS. 10A and 10B show that compound embodiments NCGC00373060 (FIG. 10A) and NCGC00373056 (FIG. 10B) protect AD mice (5×FAD) against cognitive decline.
Figure 10B:
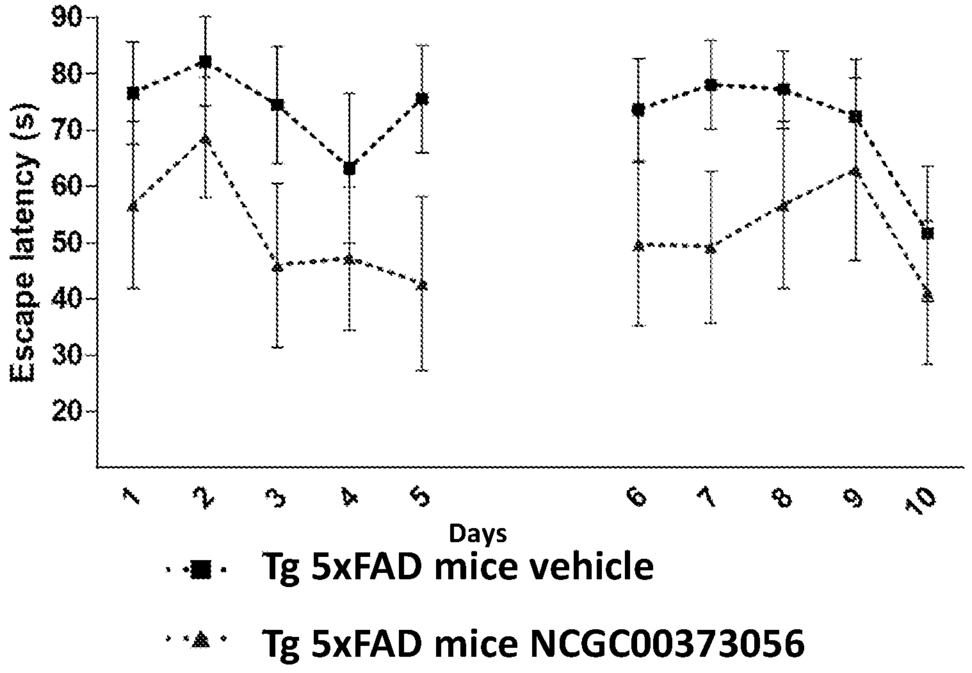
Figure 11A:
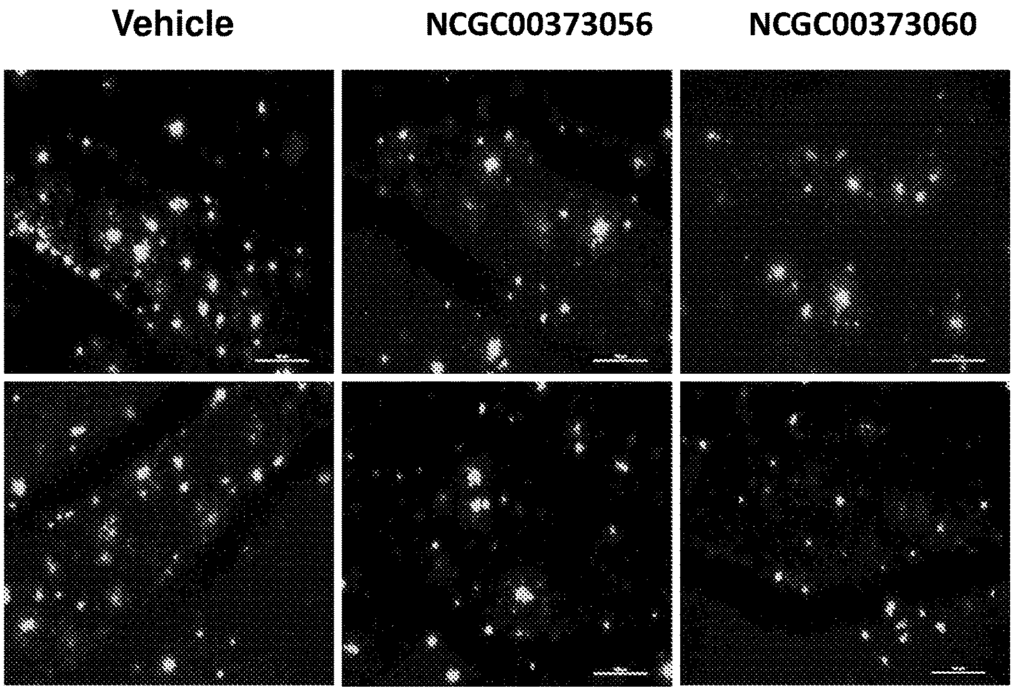
FIGS. 11A-11C show results obtained from analyzing compound performance in the hippocampus.
Figure 11B:
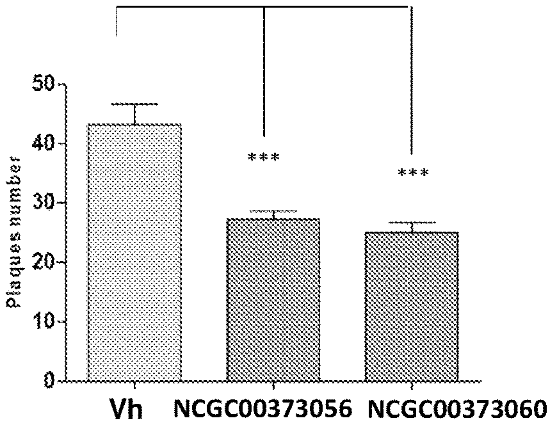
Figure 11C:
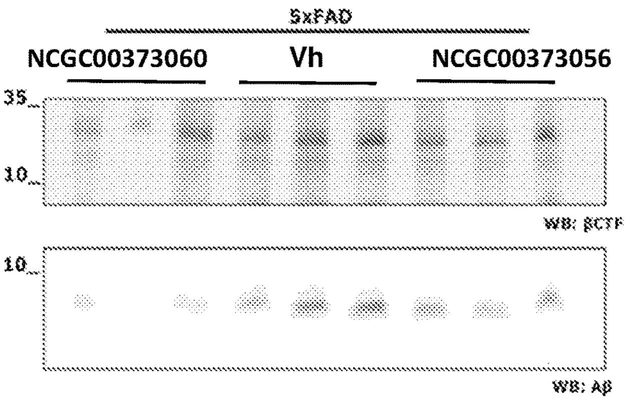

The activity of NCGC00373060 and NCGC00373056 in vivo in AD mice models also was examined. First, the 5×FAD mice was used as the AD model. The NCGC00373060 and NCGC00373056 compound embodiments protected 5×FAD mice against the cognitive decline (FIGS. 10A and 10B, respectively). Water maze assays for 9-month-old 5×FAD mice control (vehicle n=4, vh) and treated with NCGC00373060 (n=3, HOl) or NCGC00373056 (n=3, A02) at 12.5 mg/kg daily for 30 days. The compounds were dissolved in polietilenglicol 30% and propilenglicol 30% and administrated by IP. Although the number of animals analyzed was small (3-4), the treated animals clearly showed better cognitive performance, and learnt where the platform was 5 days earlier in average than control 5×FAD mice. Moreover, the treated animals showed a decrease in the number and area of amyloid plates (FIGS. 11A and 11B) and Aβ levels in brain (FIG. 11C).

Example 4

Figure 12A:
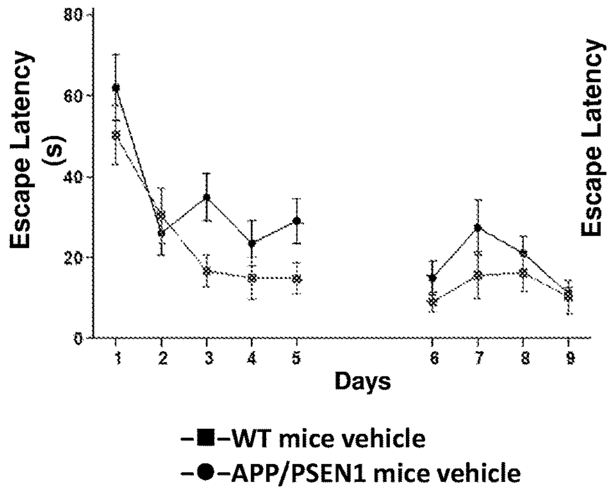
FIGS. 12A-12C provide results showing that NCGC00373060 and NCGC00355551 protects APP/PSEN1 mice against cognitive decline.
Figure 12B:
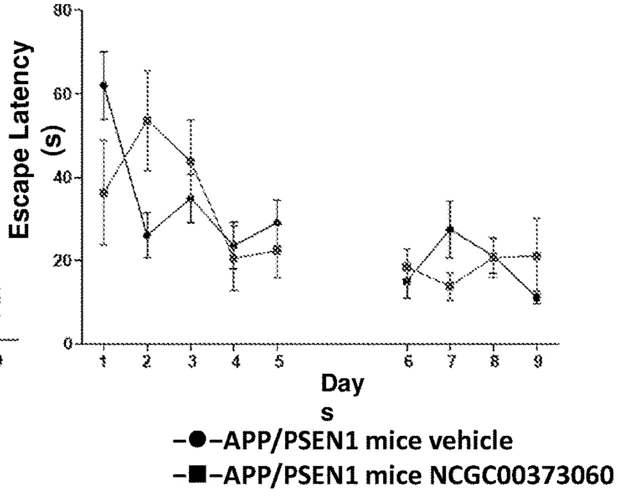
Figure 12C:
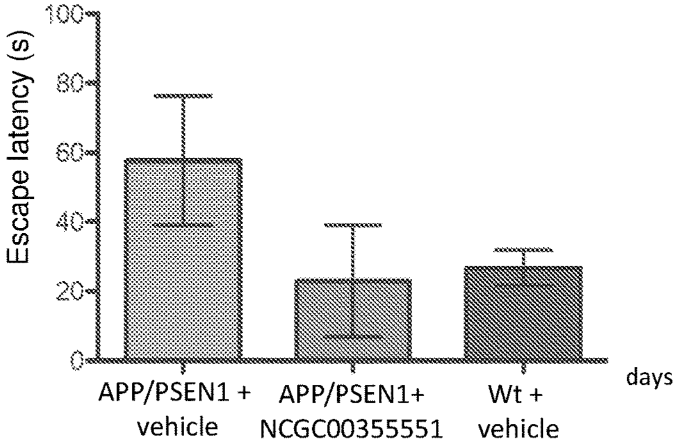
Figure 13A:
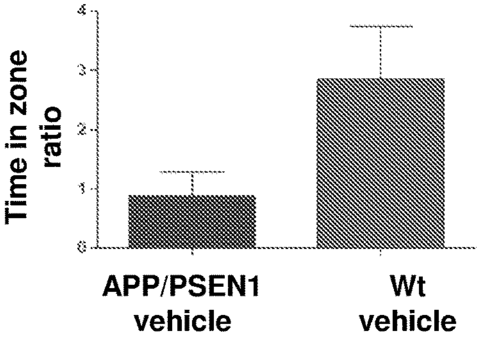
FIGS. 13A and 13B provide results showing that NCGC00373060 protects APP/PSEN1 mice against cognitive decline.
Figure 13B:
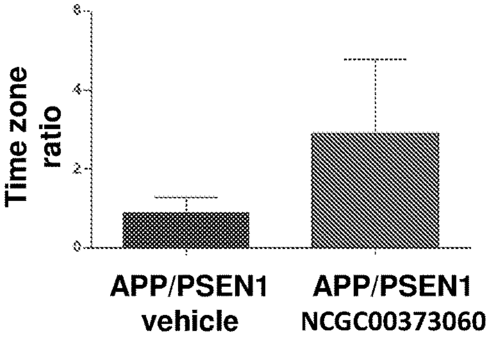
Figure 14A:
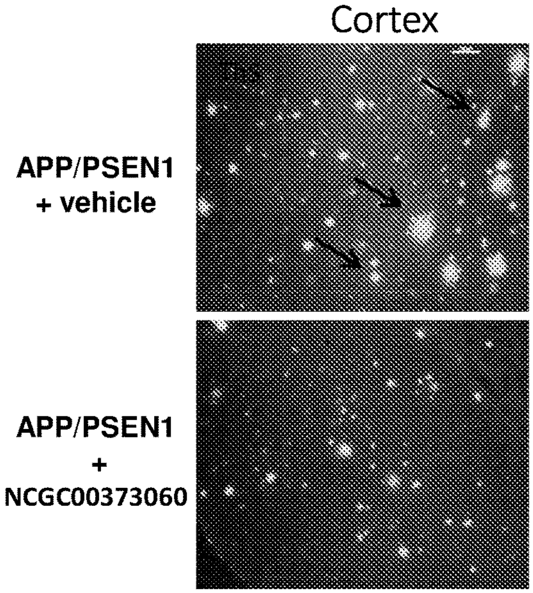
FIGS. 14A-14E show results obtained from analyzing hippocampus slices from control APP/PSEN1 mice and APP/PSEN1 mice treated with NCGC00373060 and NCGC00355551.
Figure 14B:
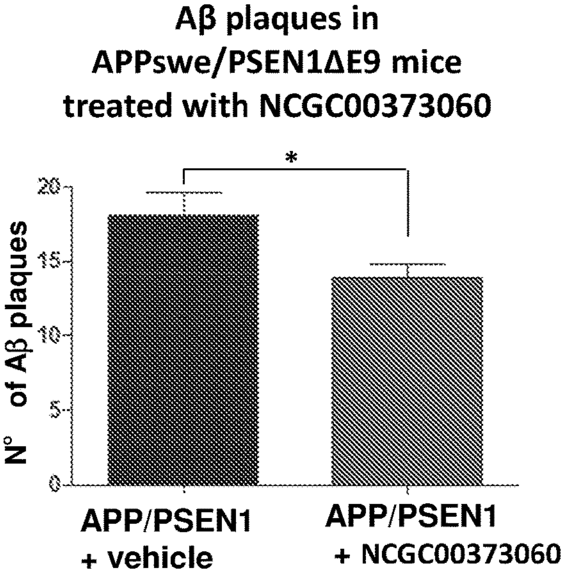
Figure 14C:
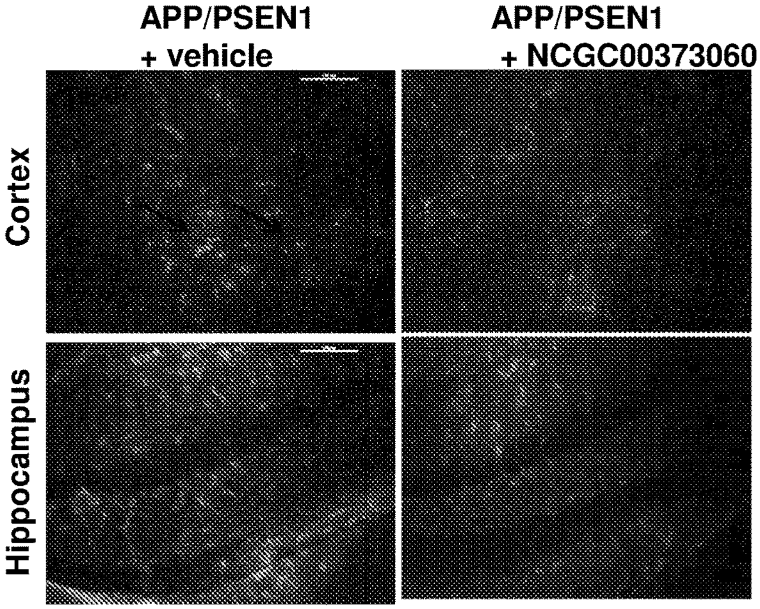
Figure 14D:
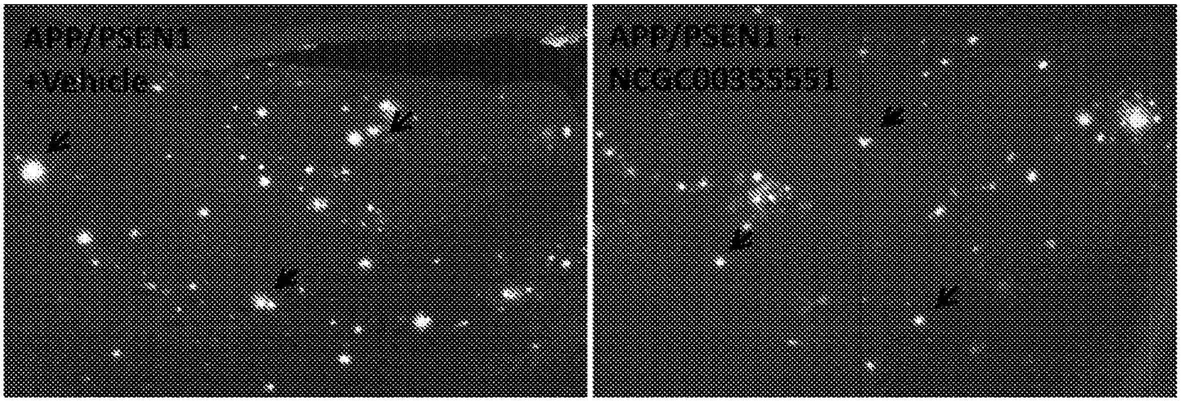
Figure 14E:
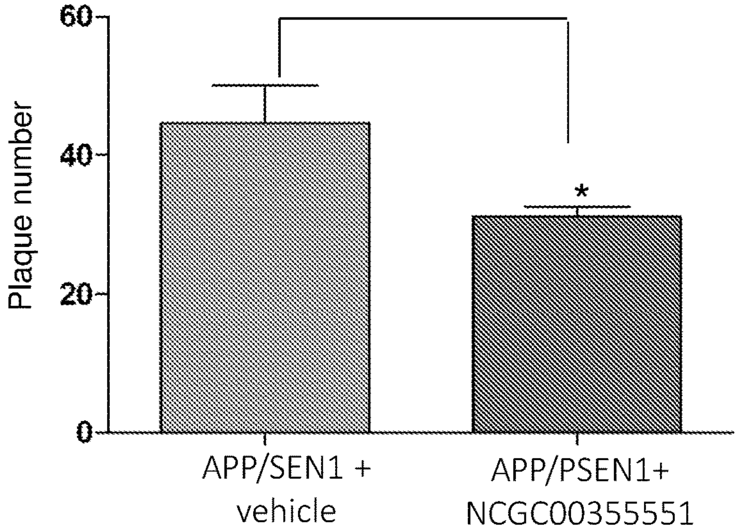

In this example, the APP/PSEN1 mice were used to repeat the cognitive studies with NCGC00373060. 9-month-old APP/PSEN1 mice and their control WT siblings were treated with vehicle (control n=3 vh) or with NCGC00373060 at 12.5 mg/kg daily for 60 days. The compound was dissolved in polietilenglicol 30% and propilenglicol 30% and administrated by IP. Although the APP/PSEN1 mice treated with NCGC00373060 did not shown a better performance in the water maze assays (FIGS. 12A and 12B), a significantly better performance was observed using the Barnes test maze (FIGS. 13A and 13B). Additional results from another compound embodiment, NCGC00355551, are provided by FIG. 12C. Without being limited to a single theory, it currently is believed that this difference between the two AD mice models 5×FAD and APP/PSEN1 may be due to the low number of animals analyzed (n=3) and that APP/PSEN1 mice used were not enough old and did not showed a cognitive impairment in a water maze test. Regardless, the NCGC00373060-treated APP/PSEN1 animals showed a tendency to have better cognitive performance than their APP/PSEN1 siblings not administered the compound. The 5×FAD mouse is a more aggressive AD model that shows the cognitive deterioration and AD pathology earlier than other AD mouse models. The Barnes maze test is a more sensible test that detects the earlier and subtle cognitive alterations. Also, as the 5×FAD mice, the APP/PSEN1 treated animals showed a decrease in the number of amyloid Aβ plates and astrogliosis followed by GFAP signal in the brain (FIGS. 14A-14E).

Figure 15:
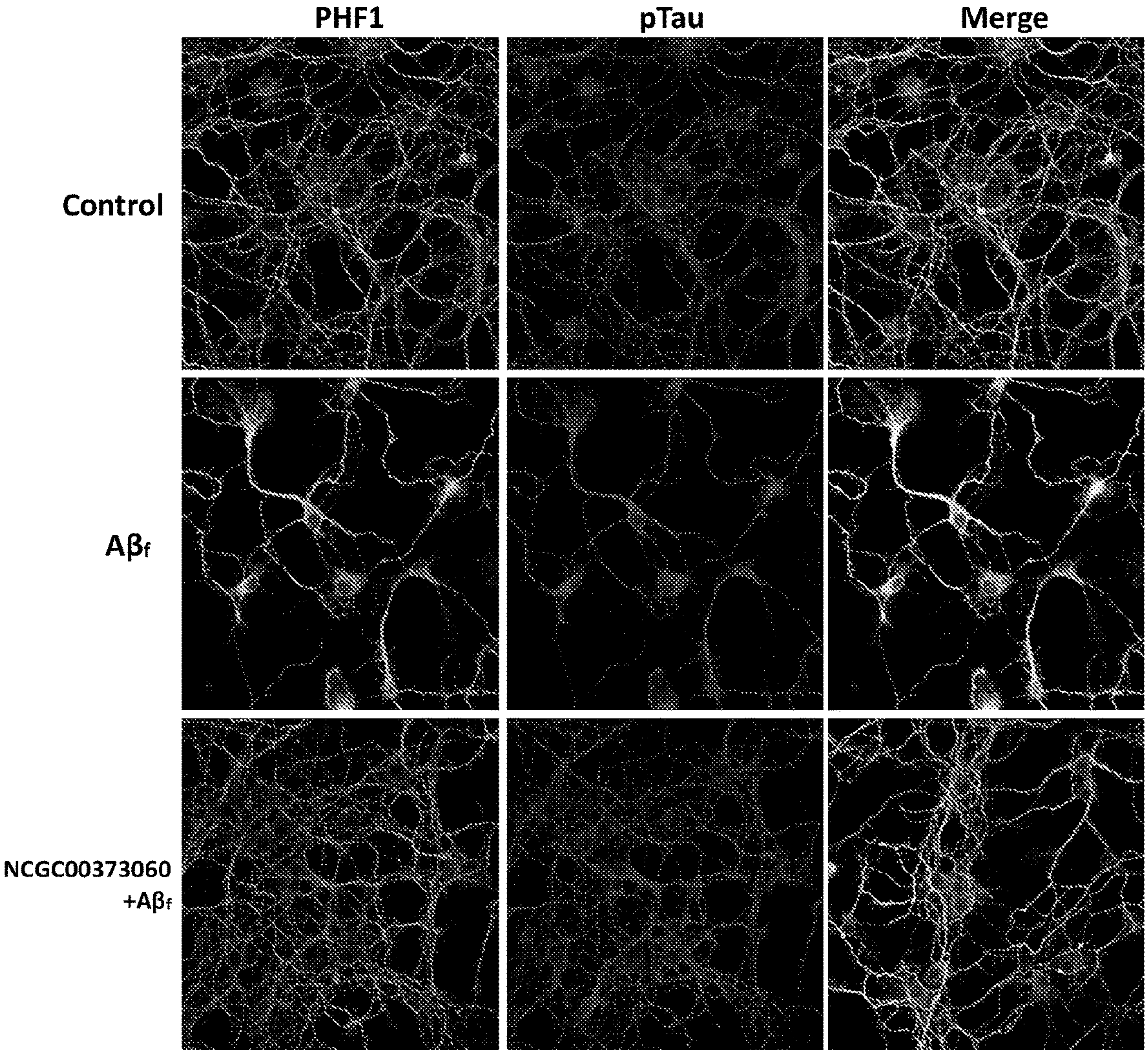
FIG. 15 shows immunofluorescence images of hippocampal neurons treated with $A_f$, 5 μM, and compound embodiment NCGC00373060 and shows that NCGC00373060 prevents the Tau phosphorylation and its relocalization to the somatodendritic compartment induced by $Ap_f$.
Figure 16:
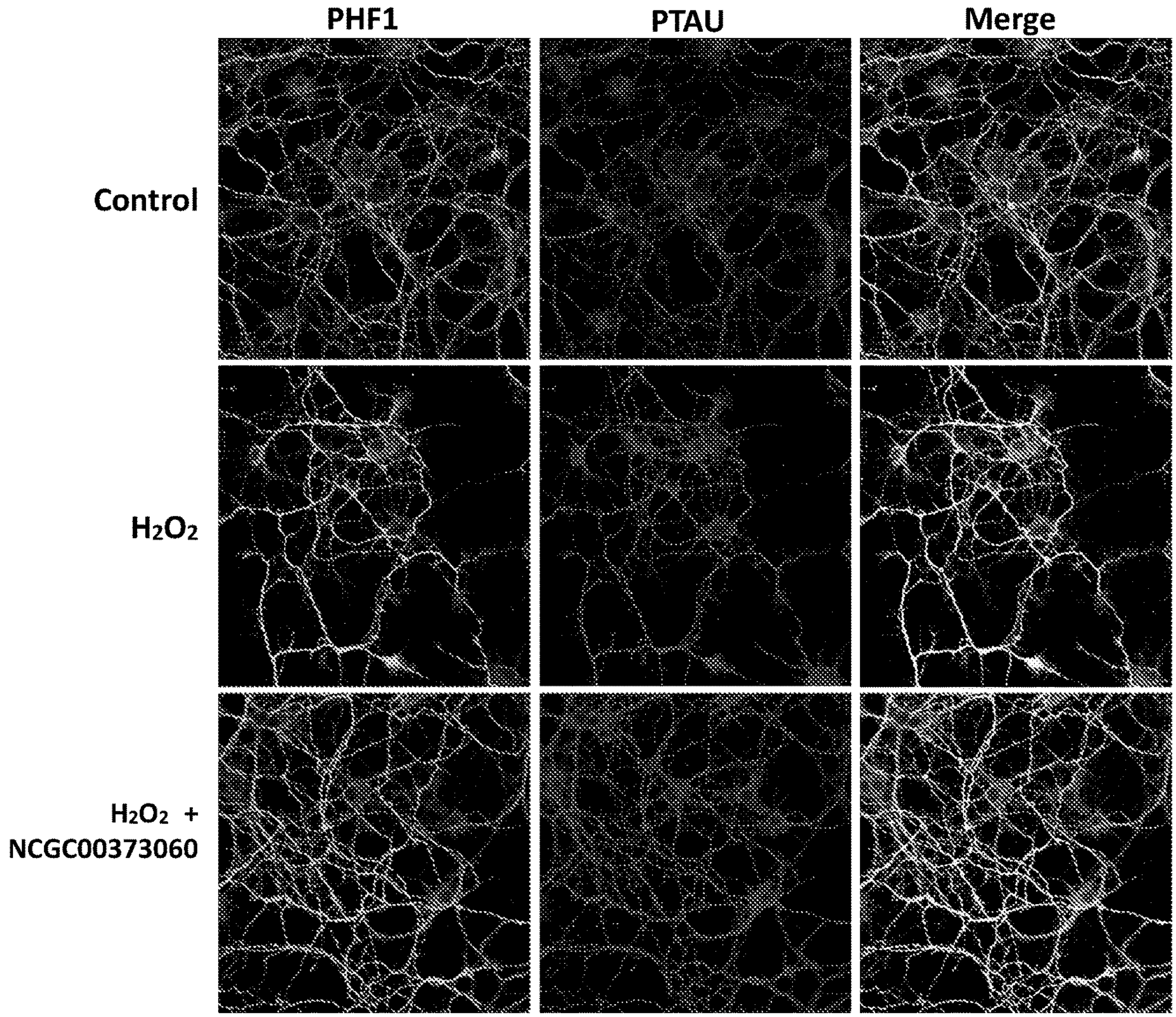
FIG. 16 shows immunofluorescence images of hippocampal neurons treated with $H_2O2$, 25 μM, and compound embodiment NCGC00373060 and shows that NCGC00373060 prevents the Tau phosphorylation and its relocalization to the somatodendritic compartment induced by oxidative stress.
Figure 17A:
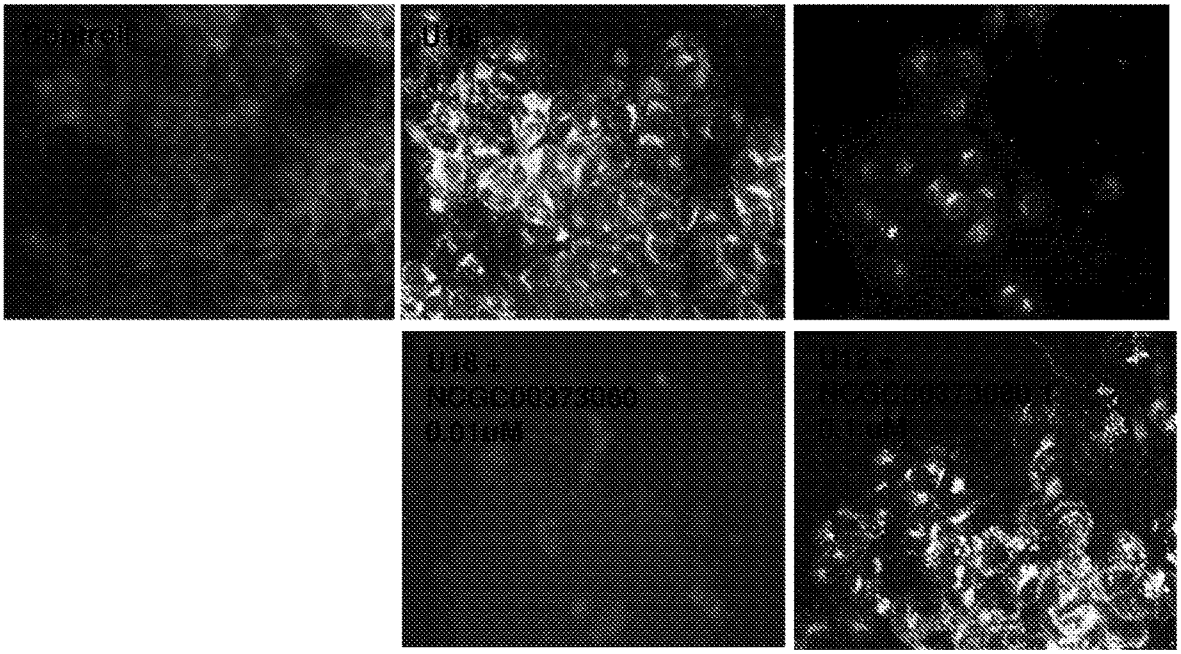
FIGS. 17A and 17B show results comparing activity in ShSySy neuroblastome cells with Imatinib (10 uM) and NCGC00373060 at two concentrations using Filipin staining; these results establish that while both c-Abl inhibitors decreased the cholesterol accumulation, a superior effect was observed with 0.01 M NCGC00373060.
Figure 17B:
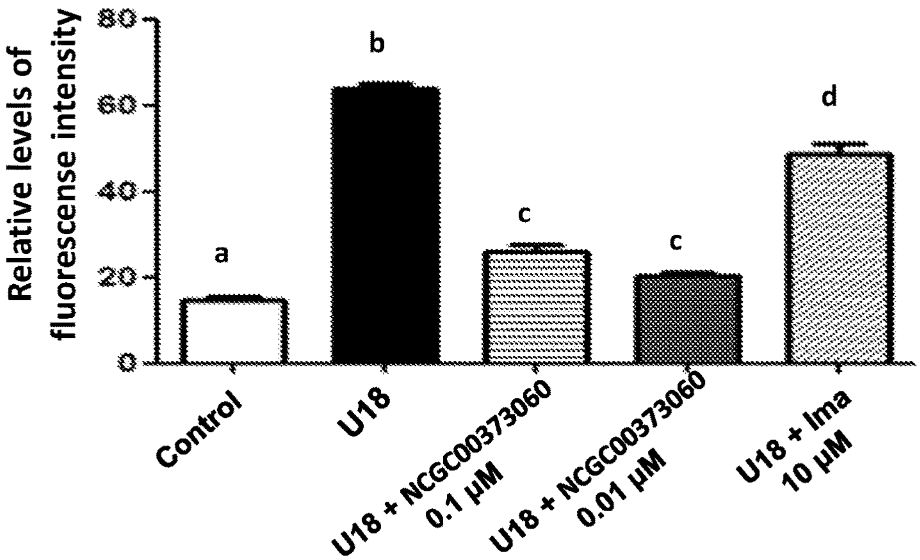
Figure 18A:
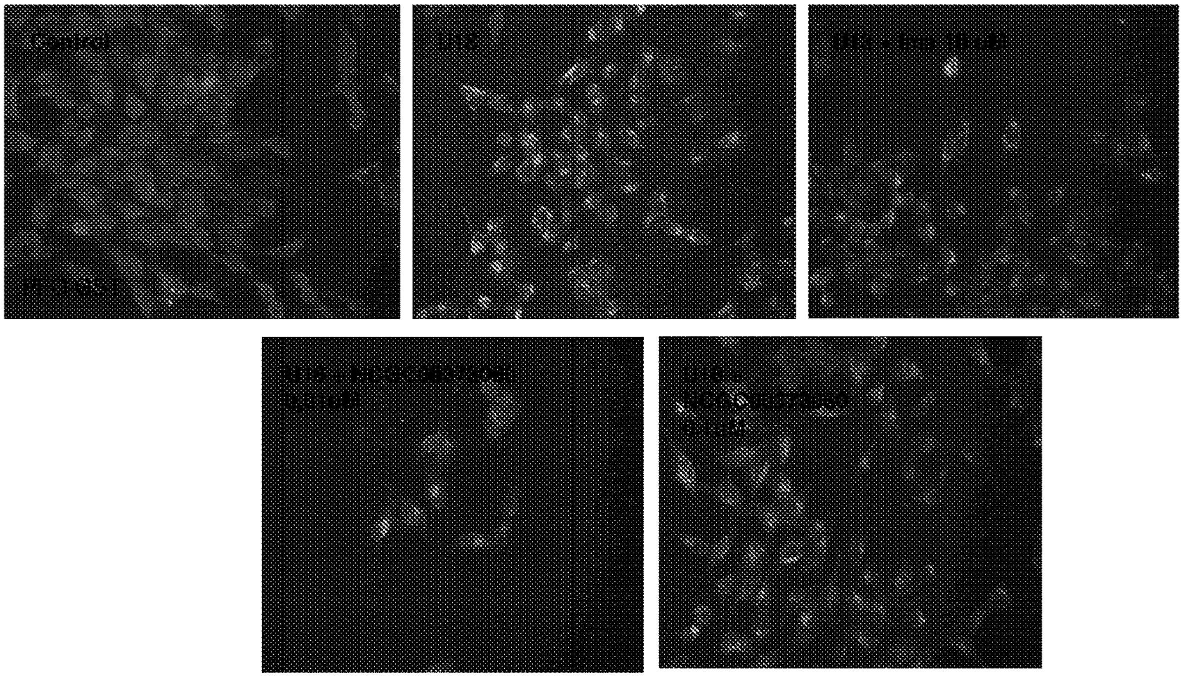
FIGS. 18A and 18B show results comparing activity in ShSy5y neuroblastome cells with Imatinib (10 uM) and NCGC00373060 at two concentrations using PFO-GST immunofluorescence; these results establish that while both c-Abl inhibitors decreased the cholesterol accumulation, a superior effect was observed with 0.01 M NCGC00373060.
Figure 18B:
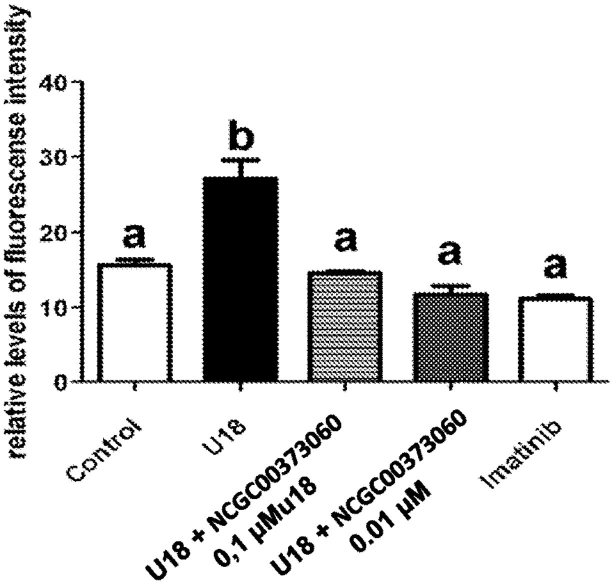

Furthermore, it was observed that NCGC00373060 decreased Tau pathology and the loss of neuritis induced by Aβ fibrils and oxidative stress in culture neurons supporting its ability to protects neurons against different damages, namely $A_f$ and $H_2O_2$(FIGS. 15 and 16, respectively). The data shown in FIG. 15 was obtained as follows: 50.000 neurons per well were maintained by 7 DIV, 1 hour before the A3 treatment and the inhibitor NCGC00373060 (1 μM) was added. Then the cells were treated with Aβf (5 μM) for 6 hours. After the treatment, the neurons were fixed and immunofluorescence was performed. The primary antibodies, PHF1 1: 1000 and anti P-Tau 1: 1000 (Millipore), were incubated in 3% BSA-PBS 1×, anti, overnight at 4° C. Secondary antibodies anti IgG- mouse Alexa 555 and anti IgG rabbit alexa 488 (1: 1000) were incubated for 1 hour at room temperature. Images were obtained with a Zeiss 5.0 LSM Confocal microscope at 60× magnification. Representative image of 3 independent experiments are shown in FIG. 15. The data shown in FIG. 16 was obtained as follows: 50.000 neurons per well were maintained by 7 DIV, 1 hour before $H_2O_2$ treatment and the inhibitor NCGC00373060 (1 μM) was added. Then the cells were treated with $H_2O_2$(25 μM) for 6 hours. After the treatment, the neurons were fixed and immunofluorescence was performed. The primary antibodies, PHF1 1: 1000 and anti P-Tau 1:1000 (Millipore), were incubated in 3% BSA-PBS 1×, anti, overnight at 4° C. Secondary antibodies anti IgG- mouse Alexa 555 and anti IgG rabbit alexa 488 (1:1000) were incubated for 1 hour at room temperature. Images were obtained with a Zeiss 5.0 LSM Confocal microscope at 60× magnification. Representative image of 2 independent experiments are shown in FIG. 16.

These results show that compound embodiment NCGC00373060 protects neurons against A3 toxicity, cross the BBB decrease the amyloid burden and improve cognitive ability of AD mice.

Example 5

As c-Abl inhibition can protect neurons against other damage conditions, such as cholesterol accumulation in NPC models and exitotoxicity in Epilepsy models, the NCGC00373060 compound embodiment was evaluated in these models as well.

Compound embodiments NCGC00373060 reduces intracellular cholesterol levels in several NPC cellular models, which have indicated that Imatinib and GNF-2 reduce cholesterol in NPC1 in vitro and in vivo models.

FIGS. 17A, 17B, and 18A and 18B show that NCGC00373060 decreases cholesterol accumulation induced by U18666 drug (a drug that inhibits NPC1 protein and that is pharmacological inductor of PC phenotype). The results shown in FIGS. 17A and 17B were obtained as follows: ShSy5y neuroblastome cells were treated with Imatinib (10 uM) and NCGC00373060 at two concentrations (0.1 μM and 0.01 μM) 1 hour before treating the cells with U18 (0.5 μg/ml), a pharmacological inductor of cholesterol accumulation, for 24 hours. Cells were fixed and then stained with Filipin Staining. Different letters in FIGS. 17A and 17B mean that the bars significantly different. The results shown in FIGS. 18A and 18B were obtained as follows: ShSy5y neuroblastome cells were treated with Imatinib (10 uM) and NCGC00373060 at two concentrations (0.1 μM and 0.01 μM) 1 hour before treating the cells with U18 (0.5 μg/ml), a pharmacological inductor of cholesterol accumulation, for 24 hours. Cells were fixed and a PFO-GST immunofluorescence was performed. Different letters in FIGS. 18A and 18B mean that the bars significantly different.

A significant cholesterol reduction followed by Filipin (FIGS. 17A and 17B) or PFO (FIGS. 18A and 18B) staining at concentrations of 0.01 and 0.1 M was observed, which are 100 and 1000 fold lower than Imatinib, respectively.

Figure 19A:
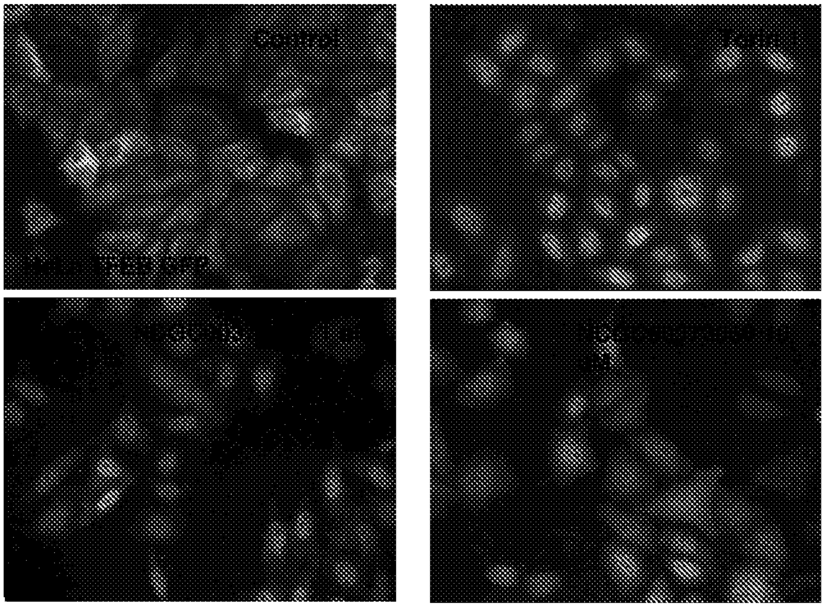
FIGS. 19A-19C show that NCGC00373060 promotes TFEB translocation to the nucleus.
Figure 19B:
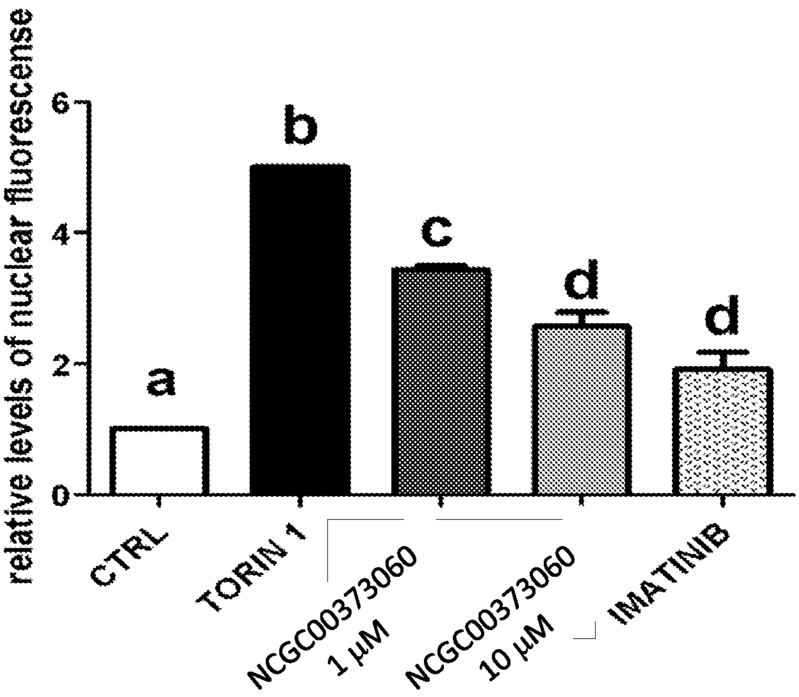
Figure 19C:
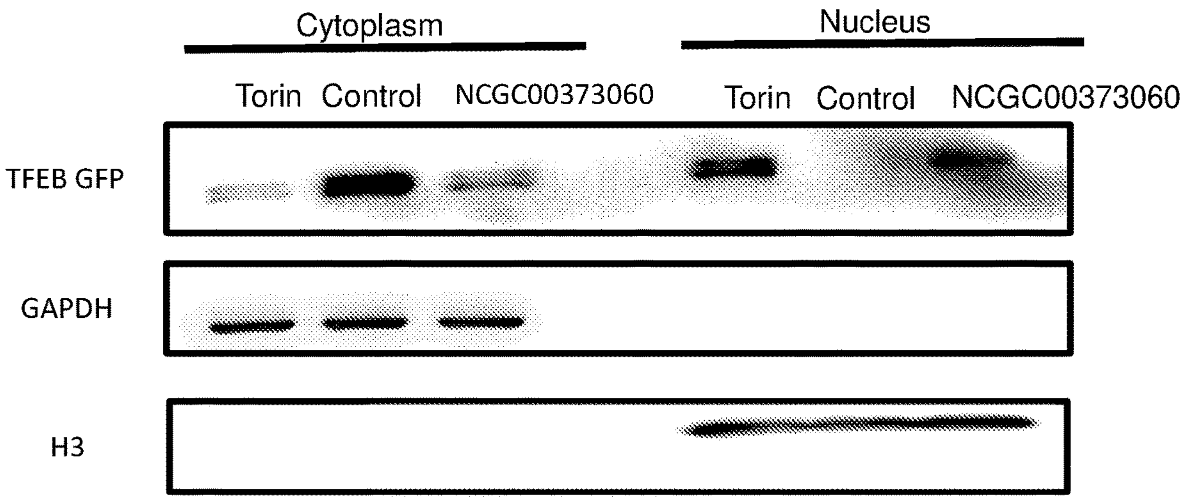

In agreement with the cholesterol reduction, it was observed that NCGC00373060 treatment induced a significant increase in TFEB translocation to the nucleus followed by microscopy and subcellular fractionation (FIGS. 19A-19C). Torin 1, at 0.3 uM, and Imatinib, at 10 uM, were used as controls for this example. For the acquisition of the images in FIG. 19A, 7 images were acquired per well by using microscopy (values are mean±SD). One way ANOVA and Bonferroni's posts were performed to provide the data in FIG. 19B, wherein different letters means bars significantly different. For FIG. 19C, cells were exposed to NCGC00373060 (10 μM) or Torin 1 (0.3 uM) for 24 hours. Cells were harvested, lysed, fractionated for cytoplasmic and nuclear content, and analyzed for TFEB, GAPDH and H3 histone by Western blotting.

Example 6

Figure 20A:
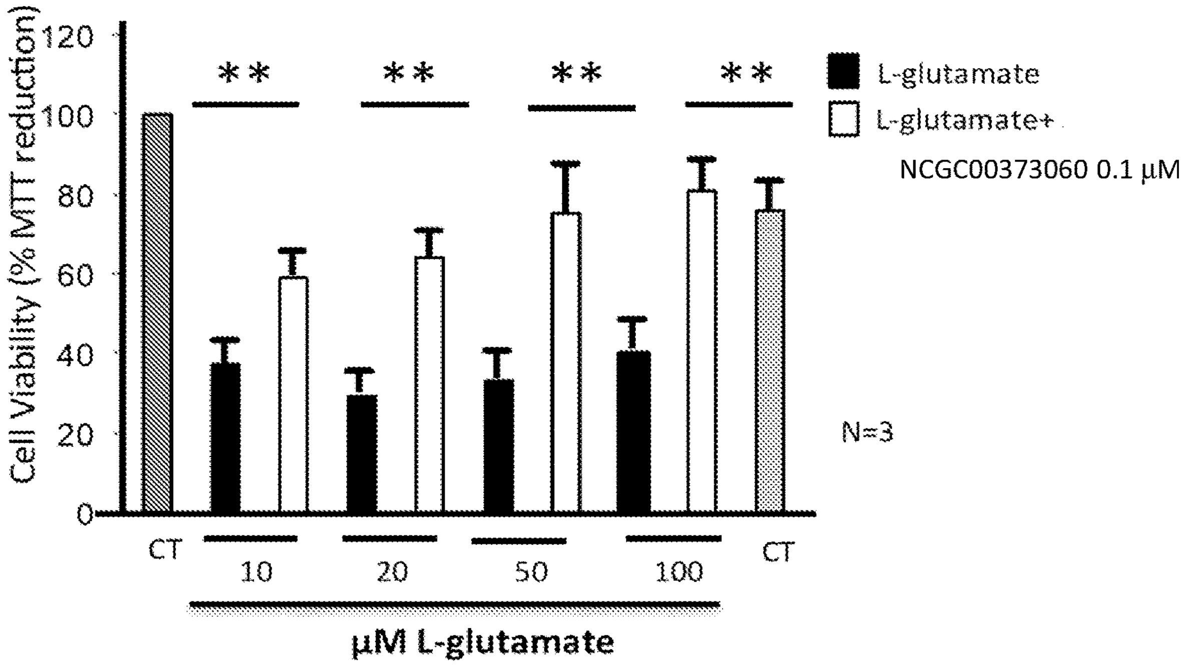
FIGS. 20A and 20B show results from exposing hippocampal neurons 7 DIV to glutamate (50 M) in presence of different concentrations of NCGC00373060; the MTT cell viability test shows the prevention in cell death induced by excitotoxicity by glutamate when the c-Abl is inhibited with NCGC00373060 at 0.1 and 0.01 M.
Figure 20B:
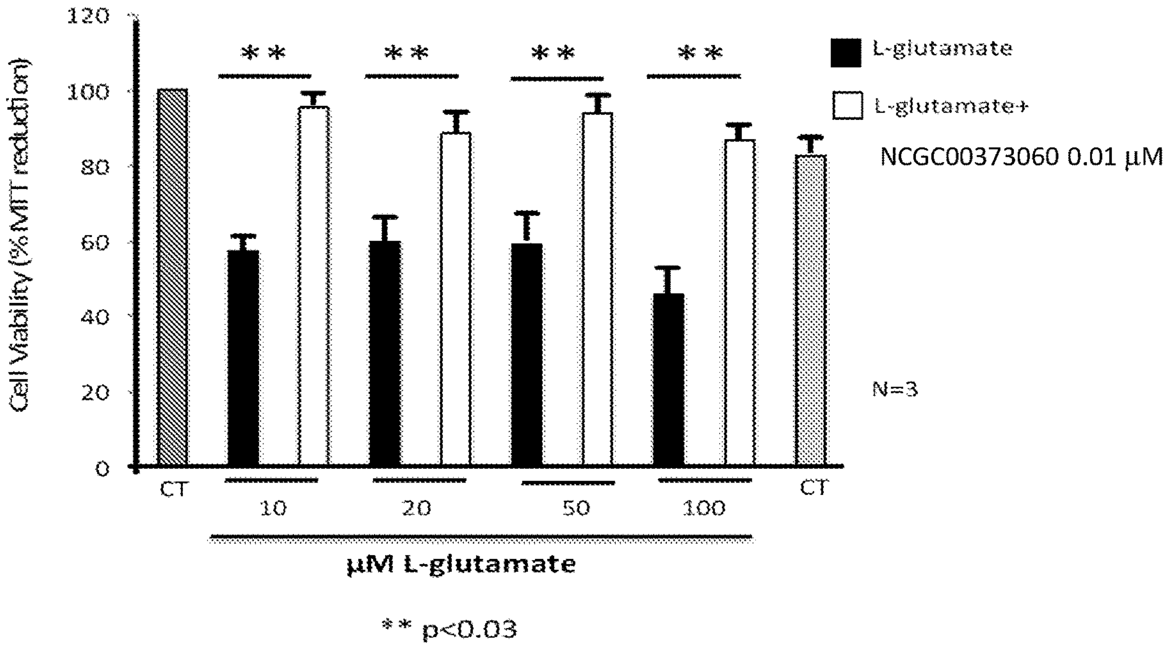
Figure 21:
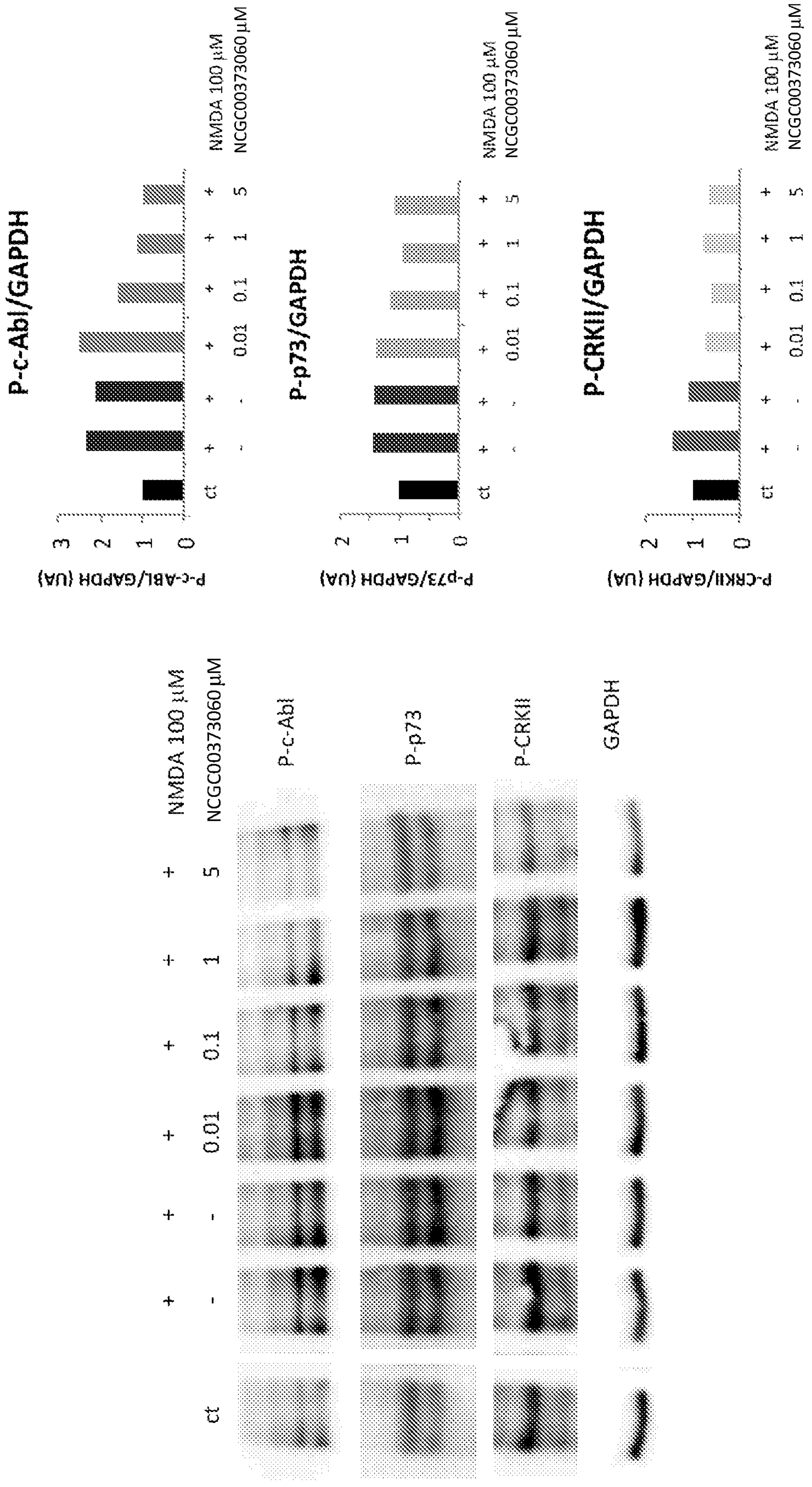
FIG. 21 shows that NCGC00373060 decreases the c-Abl downstream signaling activation induced by exitotoxicity by NMDA and provides a Western blot for c-Abl phosphorylation in tyrosine 412, (p-cAbl), p73 phosphorylation in tyrosine 99 and CRKII phosphorylation in tyrosine and graphs of the ratio value resulting from the average intensity of p-c-Abl, p-p73, and p-CRKII corrected by the GAPDH signal intensity.
Figure 22A:
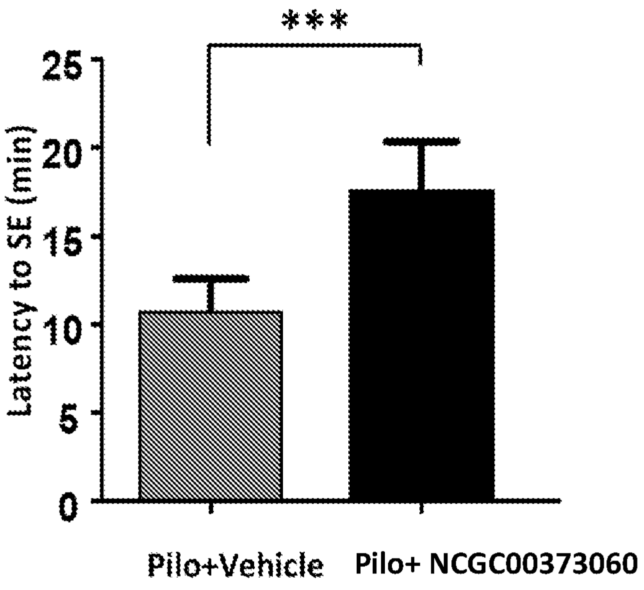
FIGS. 22A and 22B show results obtained from a TLE-mice model.
Figure 22B:
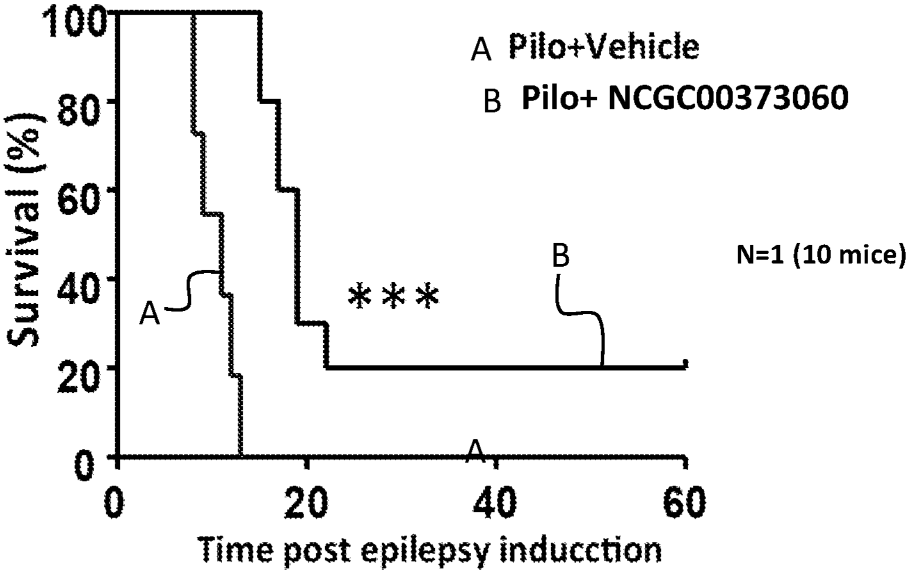

Additionally, the inhibition of c-Abl has other positive effects, besides reducing cholesterol accumulation, decreasing pro-apoptotic signaling in neurons. Compound embodiment NCGC00373060 also prevents neuronal death by exitotoxicity and prevents the mice death in epilepsy model. c-Abl kinase has been shown to have a role in epilepsy as there is a significant increment of activated c-Abl in neurons exposed to glutamate or NMDA and in the Pilocarpine-induced status epilepticus (SE) TLE mouse model. FIGS. 20A and 20B show that NCGC00373060 protects neurons against neuronal death induced by Glutamate in a doses dependent way, wherein results were obtained using an MTT cell viability test. Additionally, compound embodiment NCGC00373060 prevents the downstream signaling associated to c-Abl activation by NMDA (FIG. 21). The results shown in FIG. 21 were obtained as follows: hippocampal neurons (6 DIV) were exposed to NMDA 100 M plus NCGC00373060 at 0.01, 0.1, 1 and 5 μM for 24 h, harvested, lysed, and analyzed for c-Abl phosphorylation, to follow the c-Abl activation, and the phosphorylation downstream targets p73 and CRKII. GAPDH was evaluated as control. Moreover the pre-treatment with NCGC00373060 three days before to induce seizure activity by Pilocarpine (a TLE epilepsy model) prevented the seizures increasing the latency time that the animals takes to reach the seizures and decreases the mortality associated to the epileptic status (FIGS. 22A and 22B). The results shown in FIGS. 22A and 22B were obtained by pretreating mice with NCGC00373060, with 5 mg/Kg IP each day three days before the induction of epileptic status with Pilocarpine. The injected animals were observed by 60 min after the Pilocarpine.

Example 7

Additional efficacy data based on Leukemia K562 cell data for other compound embodiments described herein are provided below in Table 6, along with results obtained from using Nilotinib, Imatinib, GNF-2, and GNF-5 as comparison compounds.

TABLE 6

| Sample ID | Structure | IC50 (uM) | Efficacy |
|---|---|---|---|
| NCGC00483140 | 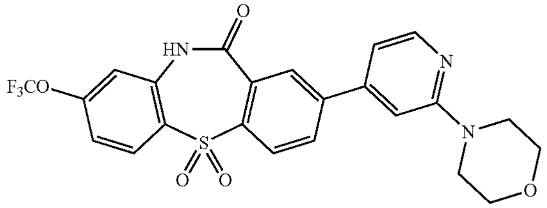 [SMILES: O=C1Nc2cc(OC(F)(F)F)ccc2S(=O)(=O)c2ccc(-c3ccnc(N4CCOCC4)c3)cc21] | 0.105 | −87.2 |
| NCGC00481508 | 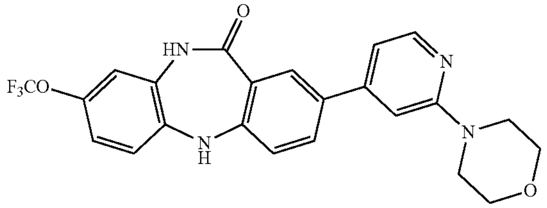 [SMILES: O=C1Nc2cc(OC(F)(F)F)ccc2Nc2ccc(-c3ccnc(N4CCOCC4)c3)cc21] | 0.118 | −80.1 |

TABLE 6-continued
| Sample ID | Structure | IC50 (uM) | Efficacy |
|---|---|---|---|
| NCGC00411866 | 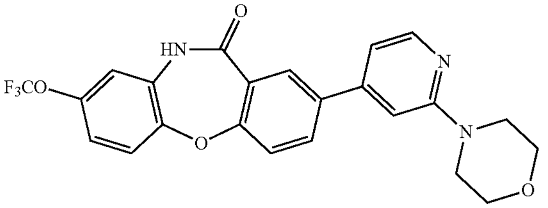 [SMILES: O=C1Nc2cc(OC(F)(F)F)ccc2Oc2ccc(-c3ccnc(N4CCOCC4)c3)cc21] | 0.166 | −90.5 |
| NCGC00355551 | 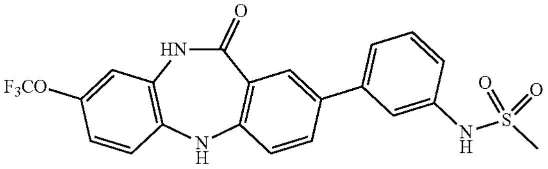 [SMILES: CS(=O)(=O)Nc1cccc(-c2ccc3c(c2)C(=O)Nc2cc(OC(F)(F)F)ccc2N3)c1] | 0.187 | −85.3 |
| NCGC00481504 | 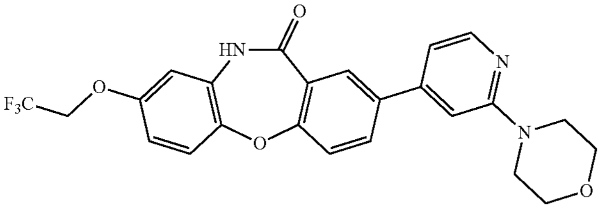 [SMILES: O=C1Nc2cc(OCC(F)(F)F)ccc2Oc2ccc(-c3ccnc(N4CCOCC4)c3)cc21] | 0.235 | −85.1 |
| NCGC00482446 | 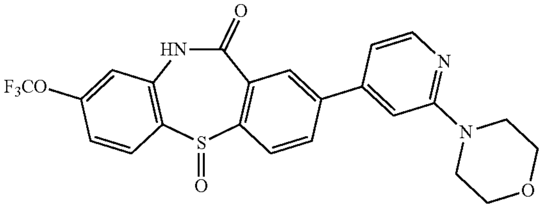 [SMILES: O=C1Nc2cc(OC(F)(F)F)ccc2S(=O)c2ccc(-c3ccnc(N4CCOCC4)c3)cc21] | 0.264 | −83.3 |
| NCGC00356665 | 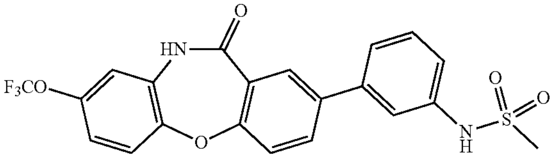 [SMILES: CS(=O)(=O)Nc1cccc(-c2ccc3c(c2)C(=O)Nc2cc(OC(F)(F)F)ccc2O3)c1] | 0.296 | −83.8 |
| NCGC00481503 | 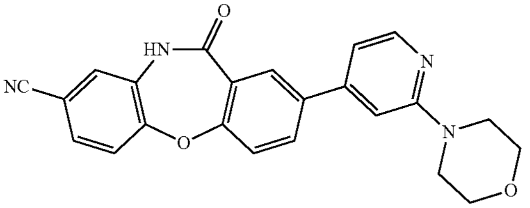 [SMILES: N#Cc1ccc2c(c1)NC(=O)c1cc(-c3ccnc(N4CCOCC4)c3)ccc1O2] | 0.526 | −80.5 |
| NCGC00355558 | 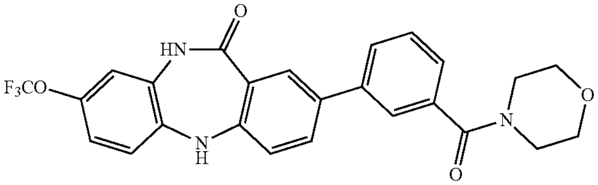 [SMILES: O=C1Nc2cc(OC(F)(F)F)ccc2Nc2ccc(-c3cccc(C(=O)N4CCOCC4)c3)cc21] | 0.743 | −89.5 |

TABLE 6-continued
| Sample ID | Structure | IC50 (uM) | Efficacy |
|---|---|---|---|
| NCGC00373056 | 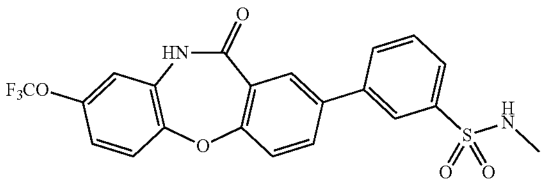 [SMILES: CNS(=O)(=O)c1cccc(-c2ccc3c(c2)C(=O)Nc2cc(OC(F)(F)F)ccc2O3)c1] | 0.833 | −78.5 |
| NCGC00411876 | 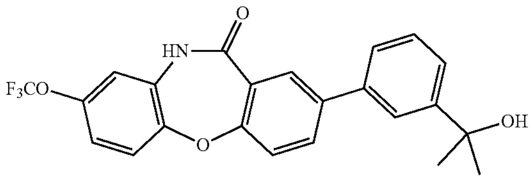 [SMILES: CC(C)(O)c1cccc(-c2ccc3c(c2)C(=O)Nc2cc(OC(F)(F)F)ccc2O3)c1] | 0.833 | −86.3 |
| NCGC00373057 | 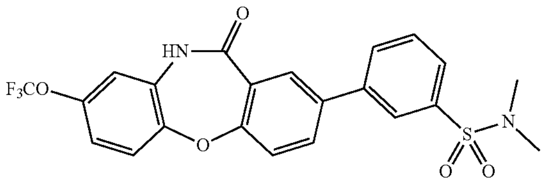 | 0.935 | −85.1 |
| NCGC00356666 | 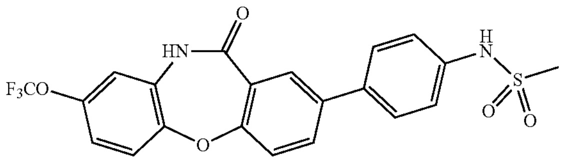 [SMILES: CS(=O)(=O)Nc1ccc(-c2ccc3c(c2)C(=O)Nc2cc(OC(F)(F)F)ccc2O3)cc1] | 0.935 | −79.9 |
| NCGC00355552 | 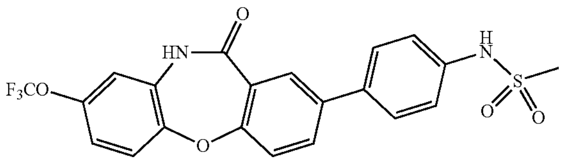 [SMILES: CS(=O)(=O)Nc1ccc(-c2ccc3c(c2)C(=O)Nc2cc(OC(F)(F)F)ccc2O3)cc1] | 1.049 | −86.3 |
| NCGC00388536 | 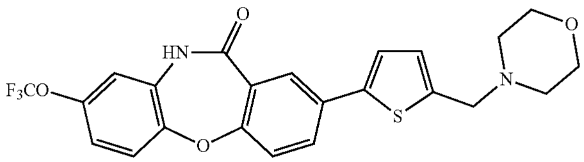 [SMILES: O=C1Nc2cc(OC(F)(F)F)ccc2Oc2ccc(-c3ccc(CN4CCOCC4)s3)cc21] | 1.049 | −83.1 |
| NCGC00373058 | 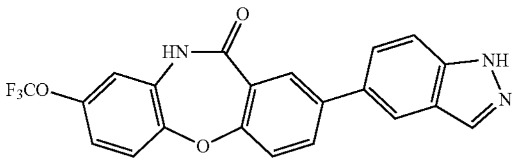 [SMILES: O=C1Nc2cc(OC(F)(F)F)ccc2Oc2ccc(-c3ccc4[nH]ncc4c3)cc21] | 1.177 | −74.3 |
| NCGC00409812 | 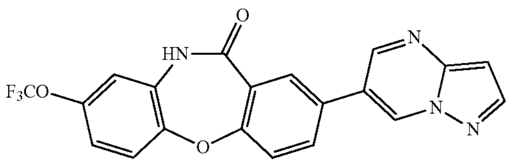 [SMILES: O=C1Nc2cc(OC(F)(F)F)ccc2Oc2ccc(-c3cnc4ccnn4c3)cc21] | 1.177 | −69.0 |

TABLE 6-continued
| Sample ID | Structure | IC50 (uM) | Efficacy |
|---|---|---|---|
| NCGC00411874 | 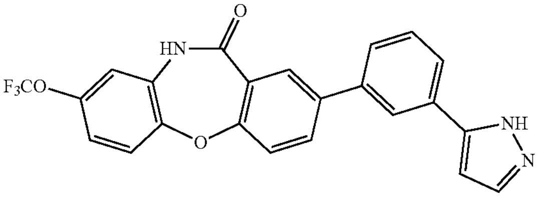 [SMILES: O=C1Nc2cc(OC(F)(F)F)ccc2Oc2ccc(-c3cccc(-c4ccn[nH]4)c3)cc21] | 1.177 | −84.3 |
| NCGC00482456 | 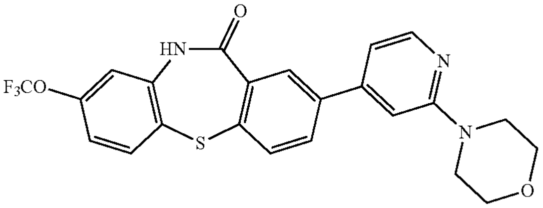 [SMILES: O=C1Nc2cc(OC(F)(F)F)ccc2Sc2ccc(-c3ccnc(N4CCOCC4)c3)cc21] | 1.482 | −85.7 |
| NCGC00481507 | 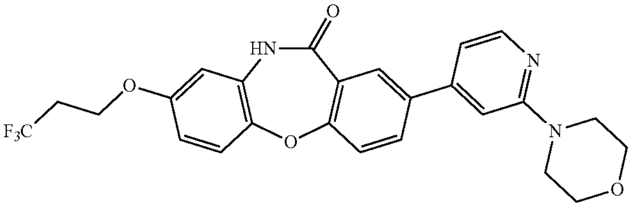 [SMILES: O=C1Nc2cc(OCCC(F)(F)F)ccc2Oc2ccc(-c3ccnc(N4CCOCC4)c3)cc21] | 1.663 | −85.5 |
| NCGC00356745 | 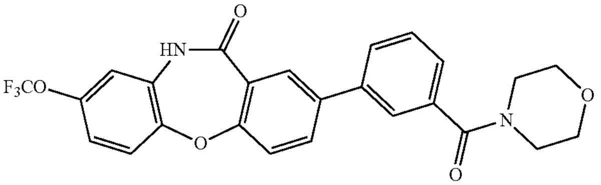 [SMILES: O=C1Nc2cc(OC(F)(F)F)ccc2Oc2ccc(-c3cccc(C(=O)N4CCOCC4)c3)cc21] | 1.865 | −98.3 |
| NCGC00373064 | 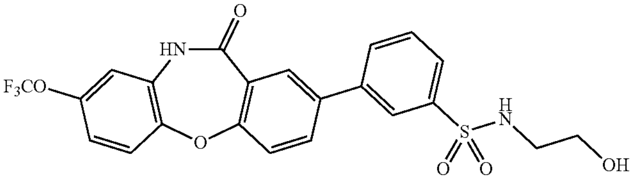 [SMILES: O=C1Nc2cc(OC(F)(F)F)ccc2Oc2ccc(-c3cccc(S(=O)(=O)NCCO)c3)cc21] | 1.865 | −103.3 |
| NCGC00388557 | 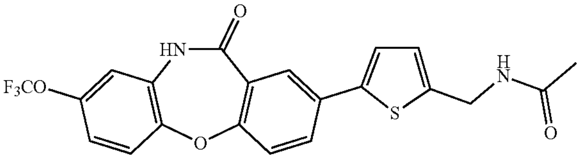 [SMILES: CC(=O)NCc1ccc(-c2ccc3c(c2)C(=O)Nc2cc(OC(F)(F)F)ccc2O3)s1] | 2.093 | −81.9 |
| NCGC00355556 | 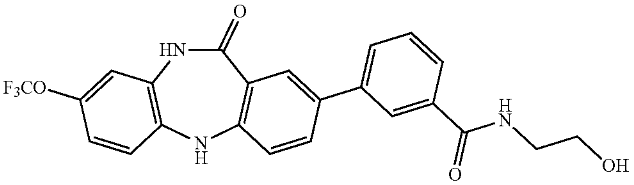 [SMILES: O=C(NCCO)c1cccc(-c2ccc3c(c2)C(=O)Nc2cc(OC(F)(F)F)ccc2N3)c1] | 2.349 | −90.9 |
| NCGC00373062 | 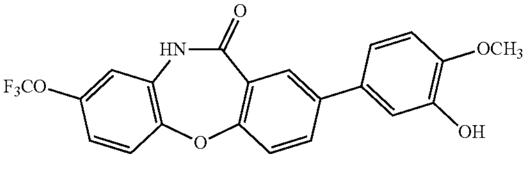 [SMILES: COc1ccc(-c2ccc3c(c2)C(=O)Nc2cc(OC(F)(F)F)ccc2O3)cc1O] | 2.635 | −93.7 |

TABLE 6-continued
| Sample ID | Structure | IC50 (uM) | Efficacy |
|---|---|---|---|
| NCGC00387293 | 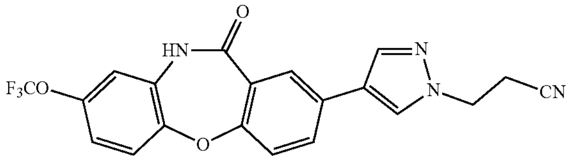 [SMILES: N#CCCn1cc(-c2ccc3c(c2)C(=O)Nc2cc(OC(F)(F)F)ccc2O3)cn1] | 2.957 | −84.4 |
| NCGC00387294 | 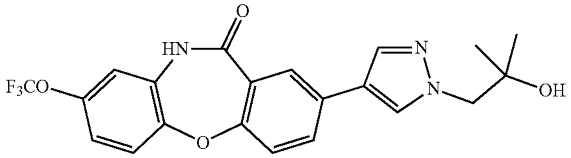 [SMILES: CC(C)(O)Cn1cc(-c2ccc3c(c2)C(=O)Nc2cc(OC(F)(F)F)ccc2O3)cn1] | 2.957 | −82.3 |
| NCGC00415019 | 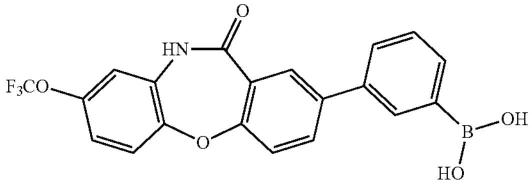 [SMILES: O=C1Nc2cc(OC(F)(F)F)ccc2Oc2ccc(-c3cccc(B(O)O)c3)cc21] | 3.317 | −79.0 |
| NCGC00373060 | 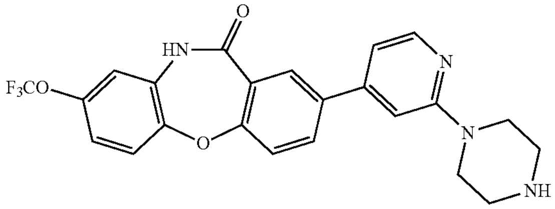 [SMILES: O=C1Nc2cc(OC(F)(F)F)ccc2Oc2ccc(-c3ccnc(N4CCNCC4)c3)cc21] | 3.317 | −99.1 |
| NCGC00388580 | 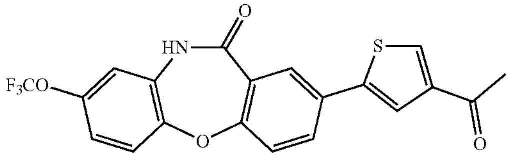 [SMILES: CC(=O)c1csc(-c2ccc3c(c2)C(=O)Nc2cc(OC(F)(F)F)ccc2O3)c1] | 3.317 | −92.6 |
| NCGC00388560 | 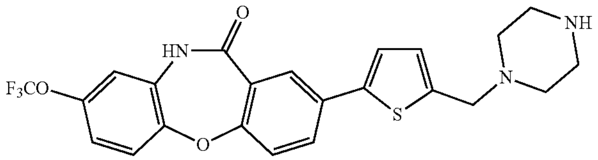 [SMILES: O=C1Nc2cc(OC(F)(F)F)ccc2Oc2ccc(-c3ccc(CN4CCNCC4)s3)cc21] | 3.722 | −95.0 |
| NCGC00371309 | 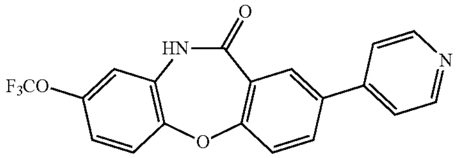 | 3.722 | −77.6 |
| NCGC00371364 | 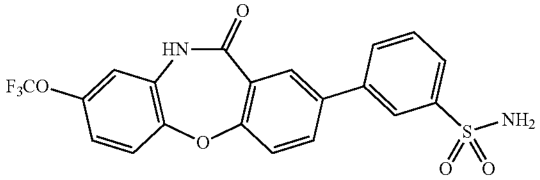 [SMILES: NS(=O)(=O)c1cccc(-c2ccc3c(c2)C(=O)Nc2cc(OC(F)(F)F)ccc2O3)c1] | 4.176 | −94.9 |

TABLE 6-continued
| Sample ID | Structure | IC50 (uM) | Efficacy |
|---|---|---|---|
| NCGC00373061 | 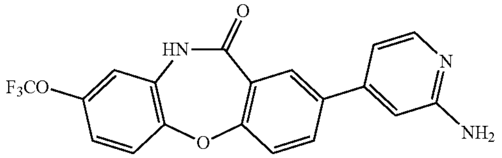 [SMILES: Nc1cc(-c2ccc3c(c2)C(=O)Nc2cc(OC(F)(F)F)ccc2O3)ccn1] | 4.176 | −87.0 |
| NCGC00371644 | 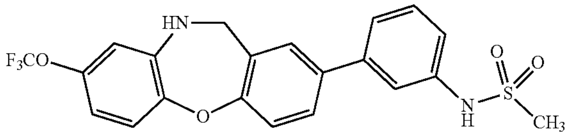 | 4.176 | −90.7 |
| NCGC00355569 | 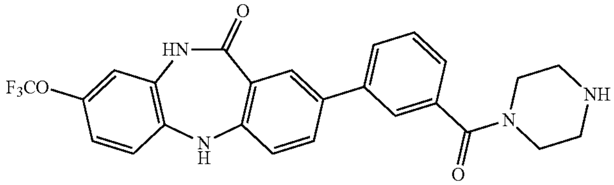 [SMILES: O=C1Nc2cc(OC(F)(F)F)ccc2Nc2ccc(-c3cccc(C(=O)N4CCNCC4)c3)cc21] | 4.686 | −97.3 |
| NCGC00373063 | 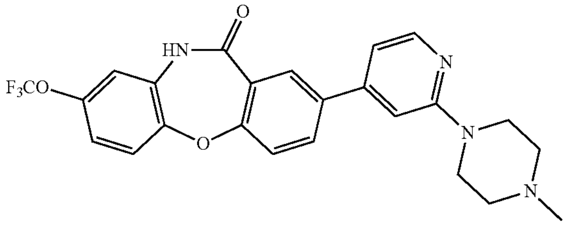 [SMILES: CN1CCN(c2cc(-c3ccc4c(c3)C(=O)Nc3cc(OC(F)(F)F)ccc3O4)ccn2)CC1] | 4.686 | −107.9 |
| NCGC00387298 | 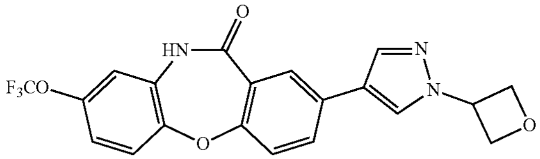 [SMILES: O=C1Nc2cc(OC(F)(F)F)ccc2Oc2ccc(-c3cnn(C4COC4)c3)cc21] | 4.686 | −93.8 |
| NCGC00387295 | 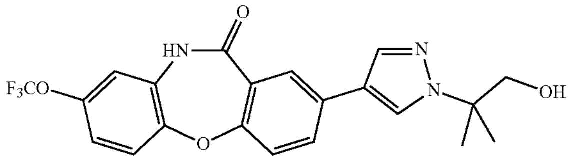 [SMILES: CC(C)(CO)n1cc(-c2ccc3c(c2)C(=O)Nc2cc(OC(F)(F)F)ccc2O3)cn1] | 4.686 | −87.7 |
| NCGC00481506 | 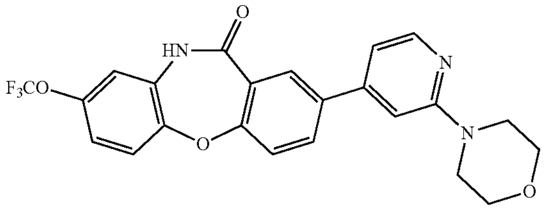 [SMILES: O=C1Nc2cc(OC(F)(F)F)ccc2Oc2ccc(-c3ccnc(N4CCOCC4)c3)cc21] | 5.899 | −87.5 |
| NCGC00355557 | 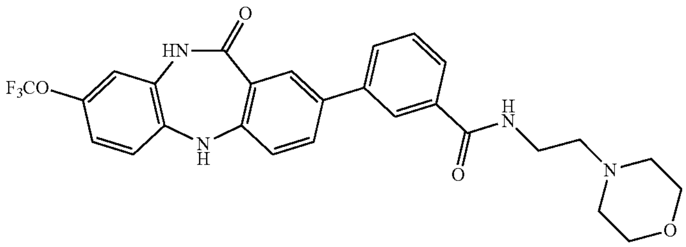 [SMILES: O=C(NCCN1CCOCC1)c1cccc(-c2ccc3c(c2)C(=O)Nc2cc(OC(F)(F)F)ccc2N3)c1] | 6.619 | −91.1 |

TABLE 6-continued
| Sample ID | Structure | IC50 (uM) | Efficacy |
|---|---|---|---|
| NCGC00384235 | 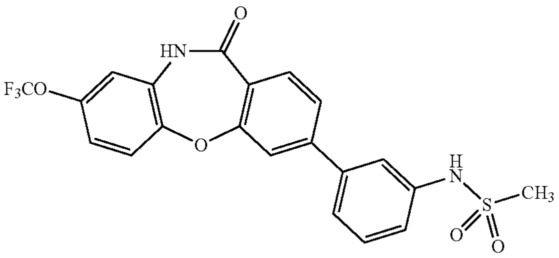 [SMILES: CS(=O)(=O)Nc1cccc(-c2ccc3c(c2)Oc2ccc(OC(F)(F)F)cc2NC3=O)c1] | 7.427 | −99.8 |
| NCGC00356688 | 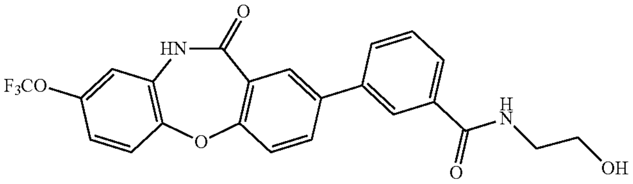 [SMILES: O=C(NCCO)c1cccc(-c2ccc3c(c2)C(=O)Nc2cc(OC(F)(F)F)ccc2O3)c1] | 9.350 | −89.8 |
| NCGC00387297 | 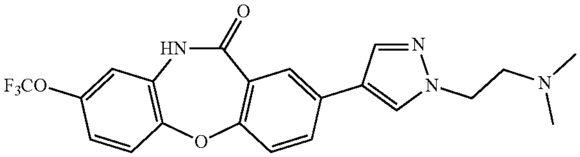 [SMILES: CN(C)CCn1cc(-c2ccc3c(c2)C(=O)Nc2cc(OC(F)(F)F)ccc2O3)cn1] | 9.350 | −115.7 |
| NCGC00387296 | 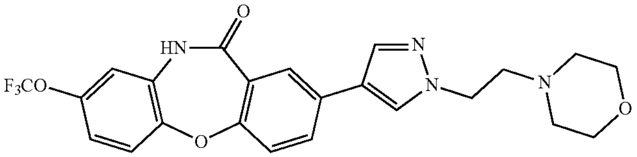 [SMILES: O=C1Nc2cc(OC(F)(F)F)ccc2Oc2ccc(-c3cnn(CCN4CCOCC4)c3)cc21] | 10.490 | −81.7 |
| NCGC00356689 | 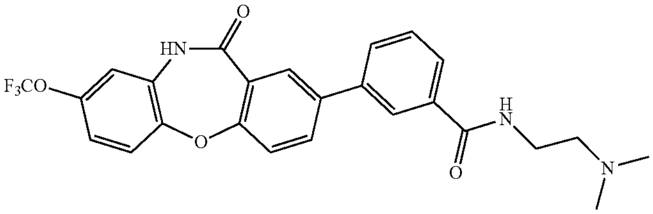 [SMILES: CN(C)CCNC(=O)c1cccc(-c2ccc3c(c2)C(=O)Nc2cc(OC(F)(F)F)ccc2O3)c1] | 10.490 | −102.5 |
| NCGC00390142 | 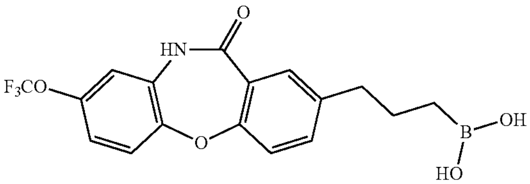 [SMILES: O=C1Nc2cc(OC(F)(F)F)ccc2Oc2ccc(CCCB(O)O)cc21] | 11.770 | −103.4 |
| NCGC00354777 | 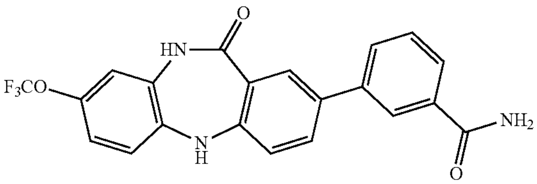 [SMILES: NC(=O)c1cccc(-c2ccc3c(c2)C(=O)Nc2cc(OC(F)(F)F)ccc2N3)c1] | 11.770 | −95.9 |
| NCGC00388626 | 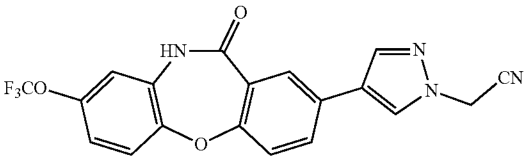 [SMILES: N#CCn1cc(-c2ccc3c(c2)C(=O)Nc2cc(OC(F)(F)F)ccc2O3)cn1] | 11.770 | −34.8 |

TABLE 6-continued
| Sample ID | Structure | IC50 (uM) | Efficacy |
|---|---|---|---|
| NCGC00373124 | 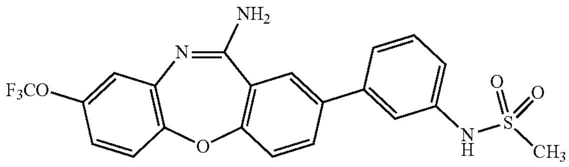 | 14.818 | −87.5 |
| NCGC00355553 | 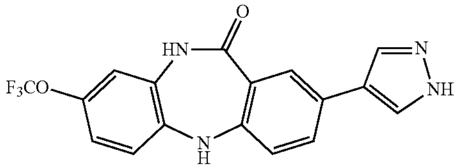 [SMILES: O=C1Nc2cc(OC(F)(F)F)ccc2Nc2ccc(-c3cn[nH]c3)cc21] | 14.818 | −87.6 |
| NCGC00356842 | 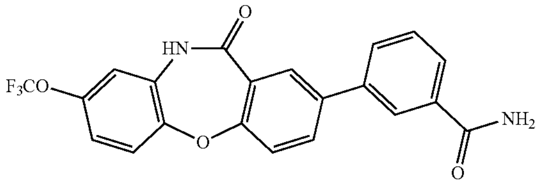 [SMILES: NC(=O)c1cccc(-c2ccc3c(c2)C(=O)Nc2cc(OC(F)(F)F)ccc2O3)c1] | 14.818 | −67.0 |
| NCGC00387437 | 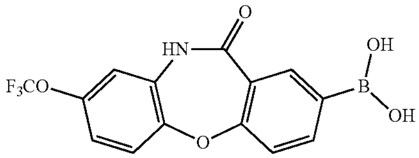 [SMILES: O=C1Nc2cc(OC(F)(F)F)ccc2Oc2ccc(B(O)O)cc21] | 14.818 | −82.6 |
| NCGC00355553 | 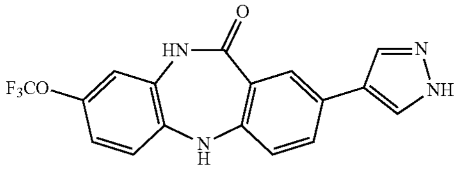 [SMILES: O=C1Nc2cc(OC(F)(F)F)ccc2Nc2ccc(-c3cn[nH]c3)cc21] | 16.626 | −80.4 |
| NCGC00355568 | 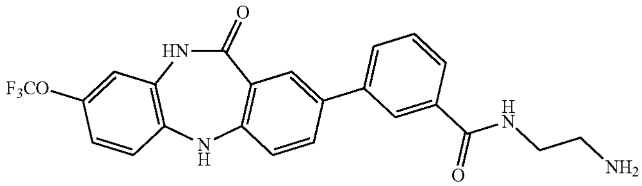 [SMILES: NCCNC(=O)c1cccc(-c2ccc3c(c2)C(=O)Nc2cc(OC(F)(F)F)ccc2N3)c1] | 16.626 | −81.4 |
| NCGC00388547 | 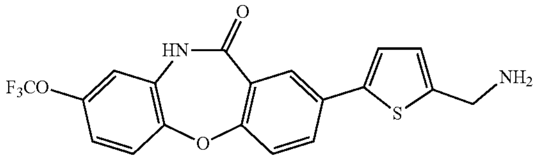 [SMILES: NCc1ccc(-c2ccc3c(c2)C(=O)Nc2cc(OC(F)(F)F)ccc2O3)s1] | 18.655 | −91.7 |
| NCGC00384234 | 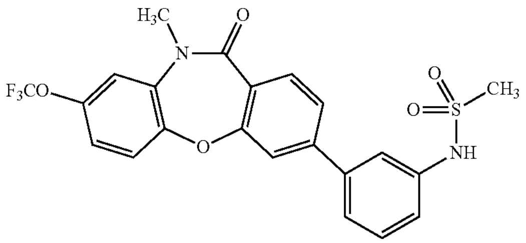 [SMILES: CN1C(=O)c2ccc(-c3cccc(NS(C)(=O)=O)c3)cc2Oc2ccc(OC(F)(F)F)cc21] | 18.655 | −54.1 |

TABLE 6-continued
| Sample ID | Structure | IC50 (uM) | Efficacy |
| --- | --- | --- | --- |
| NCGC00384286 | 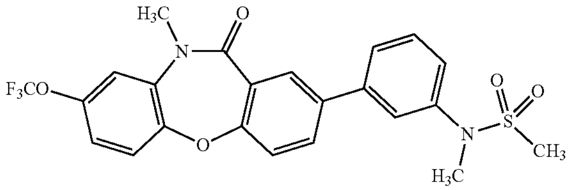 [SMILES: CN1C(=O)c2cc(-c3cccc(N(C)S(C)(=O)=O)c3)ccc2Oc2ccc(OC(F)(F)F)cc21] | 18.655 | −54.6 |
| NCGC00356690 | 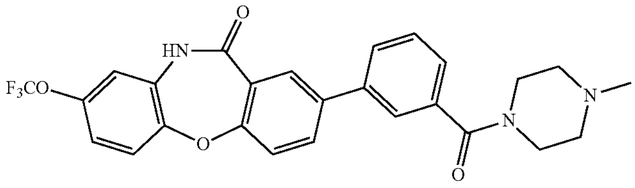 [SMILES: CN1CCN(C(=O)c2cccc(-c3ccc4c(c3)C(=O)Nc3cc(OC(F)(F)F)ccc3O4)c2)CC1] | 18.655 | −121.9 |
| NCGC00415061 | 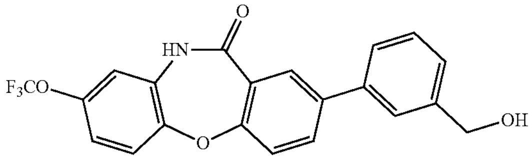 [SMILES: O=C1Nc2cc(OC(F)(F)F)ccc2Oc2ccc(-c3cccc(CO)c3)cc21] | 18.655 | −71.4 |
| NCGC00384303 | 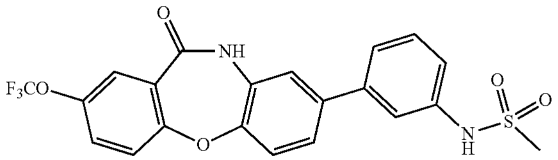 [SMILES: CS(=O)(=O)Nc1cccc(-c2ccc3c(c2)NC(=O)c2cc(OC(F)(F)F)ccc2O3)c1] | 18.655 | −86.6 |
| NCGC00384298 | 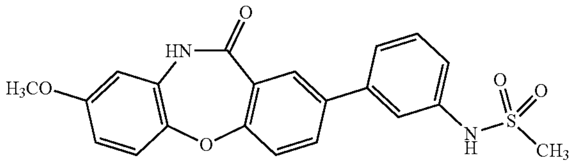 [SMILES: COc1ccc2c(c1)NC(=O)c1cc(-c3cccc(NS(C)(=O)=O)c3)ccc1O2] | 20.931 | −65.5 |
| NCGC00384267 | 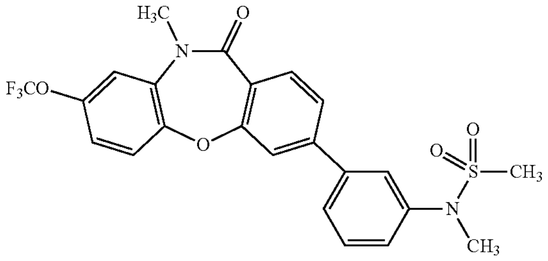 [SMILES: CN1C(=O)c2ccc(-c3cccc(N(C)S(C)(=O)=O)c3)cc2Oc2ccc(OC(F)(F)F)cc21] | 20.931 | −48.4 |
| NCGC00384295 | 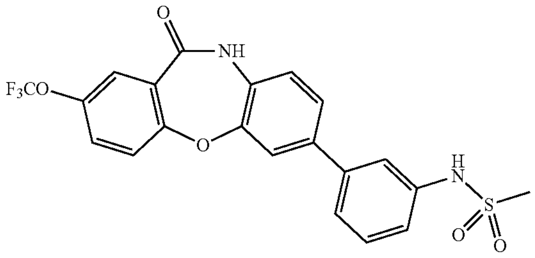 [SMILES: CS(=O)(=O)Nc1cccc(-c2ccc3c(c2)Oc2ccc(OC(F)(F)F)cc2C(=O)N3)c1] | 23.485 | −80.6 |
| NCGC00387403 | 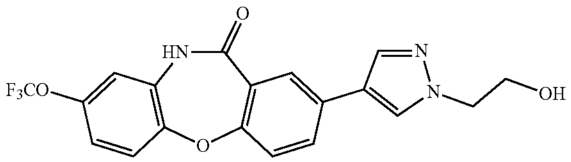 [SMILES: O=C1Nc2cc(OC(F)(F)F)ccc2Oc2ccc(-c3cnn(CCO)c3)cc21] | 23.485 | −37.6 |

TABLE 6-continued
| Sample ID | Structure | IC50 (uM) | Efficacy |
|---|---|---|---|
| NCGC00384296 | 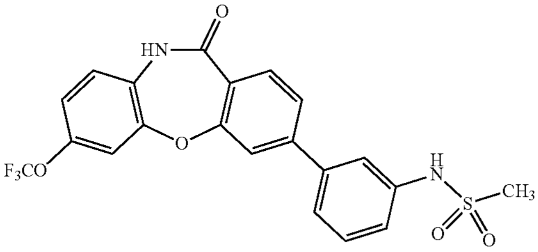 [SMILES: CS(=O)(=O)Nc1cccc(-c2ccc3c(c2)Oc2cc(OC(F)(F)F)ccc2NC3=O)c1] | 26.351 | −73.3 |
| NCGC00390141 | 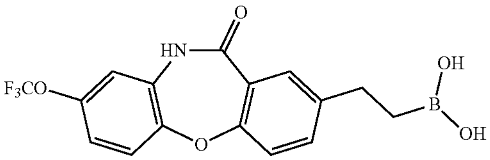 [SMILES: O=C1Nc2cc(OC(F)(F)F)ccc2Oc2ccc(CCB(O)O)cc21] | 26.351 | −45.8 |
| NCGC00384233 | 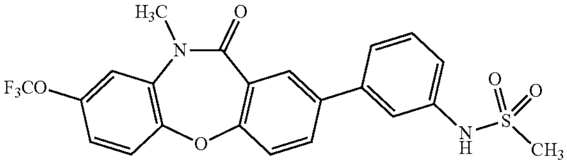 [SMILES: CN1C(=O)c2cc(-c3cccc(NS(C)(=O)=O)c3)ccc2Oc2ccc(OC(F)(F)F)cc21] | 29.566 | −75.1 |
| NCGC00373059 | 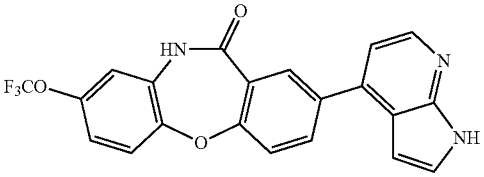 [SMILES: O=C1Nc2cc(OC(F)(F)F)ccc2Oc2ccc(-c3ccnc4[nH]ccc34)cc21] | 29.566 | −52.9 |
| NCGC00371310 | 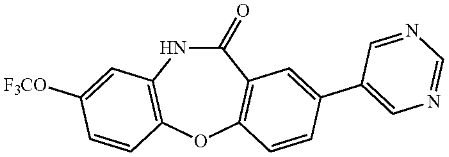 [SMILES: O=C1Nc2cc(OC(F)(F)F)ccc2Oc2ccc(-c3cncnc3)cc21] | null | −15.0 |
| NCGC00387752 | 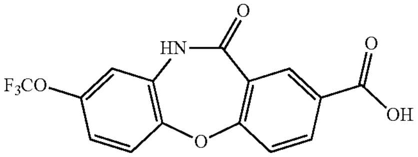 [SMILES: O=C(O)c1ccc2c(c1)C(=O)Nc1cc(OC(F)(F)F)ccc1O2] | null | 0.0 |
| NCGC00371308 | 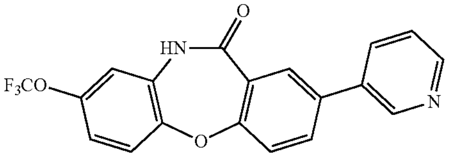 [SMILES: O=C1Nc2cc(OC(F)(F)F)ccc2Oc2ccc(-c3cccnc3)cc21] | null | −7.0 |
| NCGC00387394 | 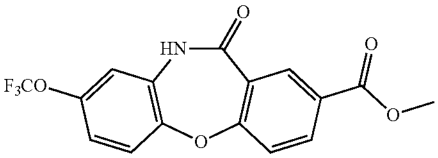 [SMILES: COC(=O)c1ccc2c(c1)C(=O)Nc1cc(OC(F)(F)F)ccc1O2] | null | 0.0 |

TABLE 6-continued
| Sample ID | Structure | IC50 (uM) | Efficacy |
|---|---|---|---|
| NCGC00420743 | 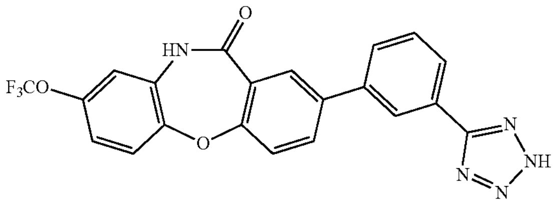 [SMILES: O=C1Nc2cc(OC(F)(F)F)ccc2Oc2ccc(-c3cccc(-c4nn[nH]n4)c3)cc21] | null | 0.0 |
| NCGC00387404 | 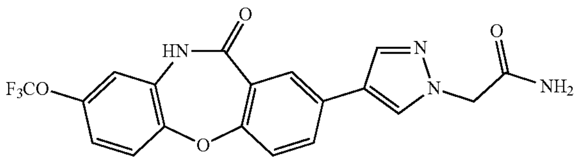 [SMILES: NC(=O)Cn1cc(-c2ccc3c(c2)C(=O)Nc2cc(OC(F)(F)F)ccc2O3)cn1] | null | −8.8 |
| NCGC00532318 | 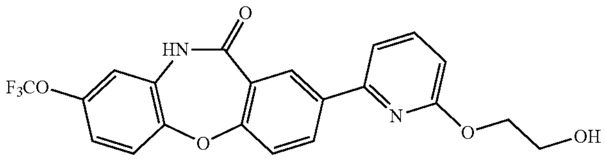 [SMILES: O=C1Nc2cc(OC(F)(F)F)ccc2Oc2ccc(-c3cccc(OCCO)n3)cc21] | 1.28 | |
| NCGC00507969 | 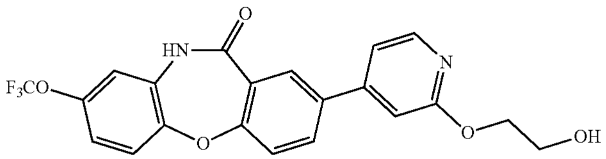 [SMILES: O=C1Nc2cc(OC(F)(F)F)ccc2Oc2ccc(-c3ccnc(OCCO)c3)cc21] | 1.55 | |
| NCGC00508975 | 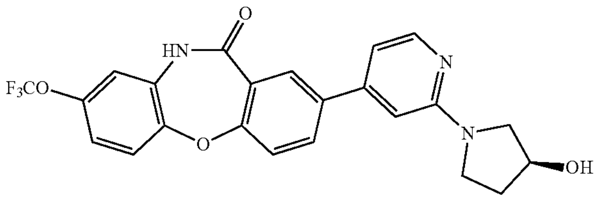 [SMILES: O=C1Nc2cc(OC(F)(F)F)ccc2Oc2ccc(-c3ccnc(N4CC[C@H](O)C4)c3)cc21] | 0.048 | |
| NCGC00508973 | 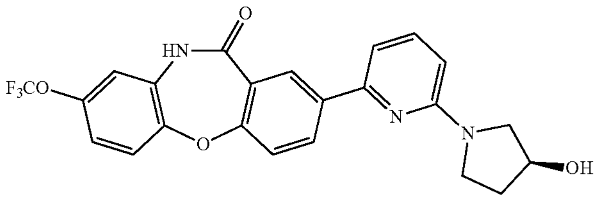 [SMILES: O=C1Nc2cc(OC(F)(F)F)ccc2Oc2ccc(-c3cccc(N4CC[C@H](O)C4)n3)cc21] | 0.398 | |
| NCGC00508838 | 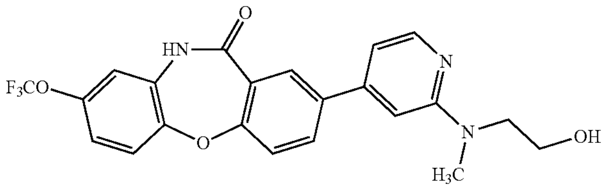 [SMILES: CN(CCO)c1cc(-c2ccc3c(c2)C(=O)Nc2cc(OC(F)(F)F)ccc2O3)ccn1] | 0.105 | |
| NCGC00507975 | 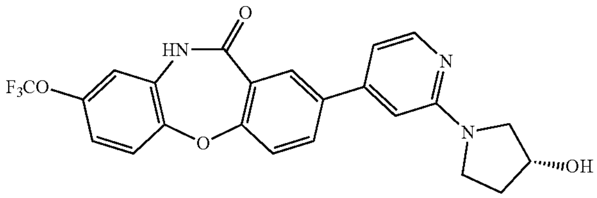 [SMILES: O=C1Nc2cc(OC(F)(F)F)ccc2Oc2ccc(-c3ccnc(N4CC[C@@H](O)C4)c3)cc21] | 0.083 | |

TABLE 6-continued

| Sample ID | Structure | IC50 (uM) | Efficacy |
|---|---|---|---|
| NCGC00532289 | 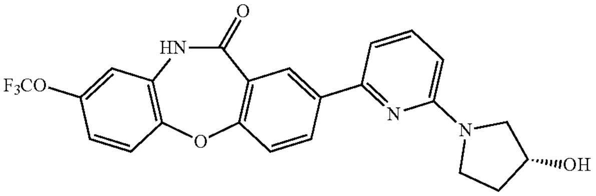 [SMILES: O=C1Nc2cc(OC(F)(F)F)ccc2Oc2ccc(-c3cccc(N4CC[C@@H](O)C4)n3)cc21] | 0.118 | |
| NCGC00508972 | 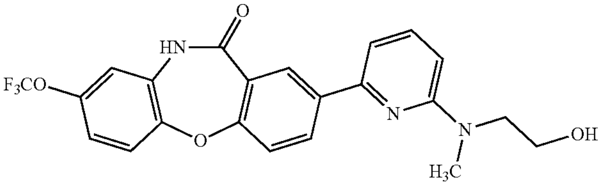 [SMILES: CN(CCO)c1cccc(-c2ccc3c(c2)C(=O)Nc2cc(OC(F)(F)F)ccc2O3)n1] | 0.112 | |
| Nilotinib | 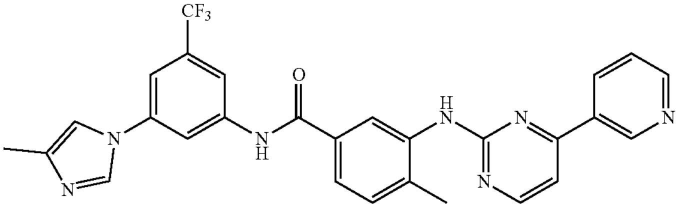 [SMILES: Cc1cn(-c2cc(NC(=O)c3ccc(C)c(Nc4nccc(-c5cccnc5)n4)c3)cc(C(F)(F)F)c2)cn1] | 0.033 | −86.5 |
| Imatinib | 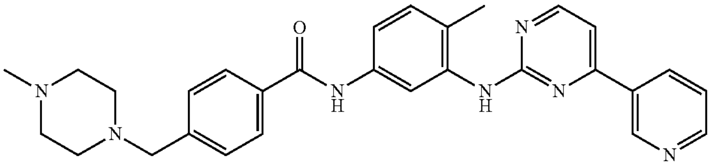 [SMILES: Cc1ccc(NC(=O)c2ccc(CN3CCN(C)CC3)cc2)cc1Nc1nccc(-c2cccnc2)n1] | 0.631 | −105.5 |
| GNF-2 | 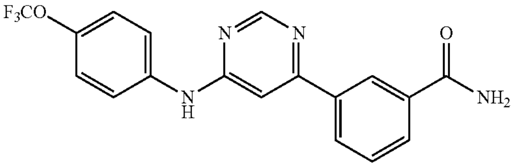 [SMILES: NC(=O)c1cccc(-c2cc(Nc3ccc(OC(F)(F)F)cc3)ncn2)c1] | 0.935 | −85.2 |
| GNF-5 | 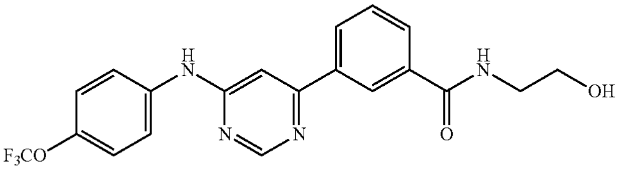 [SMILES: O=C(NCCO)c1cccc(-c2cc(Nc3ccc(OC(F)(F)F)cc3)ncn2)c1] | 0.935 | −85.8 |
| ABL-001 | 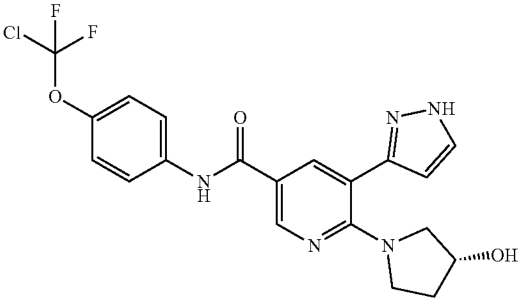 [SMILES: O=C(Nc1ccc(OC(F)(F)Cl)cc1)c1cnc(N2CC[C@@H](O)C2)c(-c2cc[nH]n2)c1] | 0.016 | |

Example 8

In this example, several ofthe c-Abl inhibitors were tested in the asexual NF54 strain of *P. falciparum* parasites for activity against malaria. NCGC00373060 and NCGC00373056 displayed activities in the low single digit uM range. Asexual parasites of *P. falciparum* strain NF54 were cultured as described previously (Sun et al., *Malar. J.*

16:147, 2017). Drug activity in inhibiting growth of asexual stage parasites was tested using a SYBR Green assay as described previously (Eastman et al., *Antimicrob. Agents. Chemother.* 57:425-435, 2013; Smilkstein et al., *Antimicrob. Agents. Chemother.* 48:1803-1806, 2004). Briefly, parasites were diluted to 0.5% parasitemia in complete culture medium with 2% hematocrit and drugs were diluted in DMS0 (<0.5%). The pre-diluted parasites were dispensed into a 1536-well plate (2.5 μL/well). After 72 hours incubation under the standard culture condition, 5 μL/well of lysis buffer containing SYBR Green I was added to the parasite culture and incubated for 30 minutes at room temperature. The fluorescence of each well was measured at 520 nm following excitation at 490 nm using a ViewLux platereader (PerkinElmer). Results are summarized in Table 7 and Table 8 provides a comparison of these compound embodiments to Imatinib, Chloroquine, Nilotinib, and GNF-2.

TABLE 7

| Sample ID | Structure | $IC_{50}$ (uM) | % Killing |
|---|---|---|---|
| NCGC00373056 | 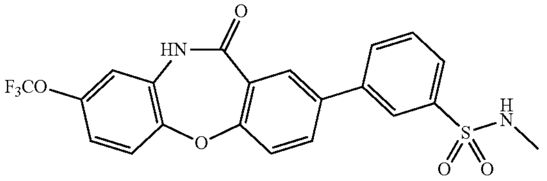 [SMILES: CNS(=O)(=O)c1cccc(-c2ccc3c(c2)C(=O)Nc2cc(OC(F)(F)F)ccc2O3)c1] | 1.362 | 96.5 |
| NCGC00373060 | 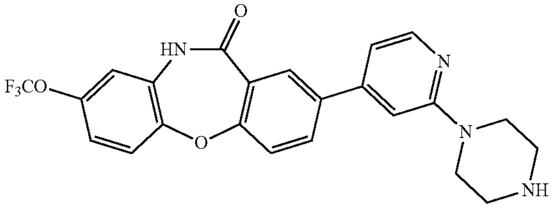 [SMILES: O=C1Nc2cc(OC(F)(F)F)ccc2Oc2ccc(-c3ccnc(N4CCNCC4)c3)cc21] | 1.632 | 89.9 |
| NCGC00411866 | 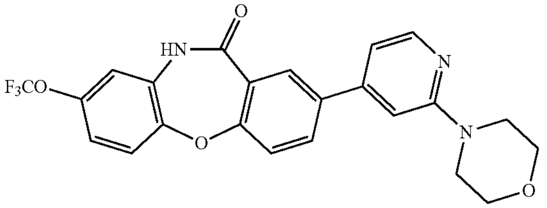 | 9.687 | 92.9 |

TABLE 8

| Sample ID | Structure | $IC_{50}$ (uM) | % Killing |
|---|---|---|---|
| Imatinib | 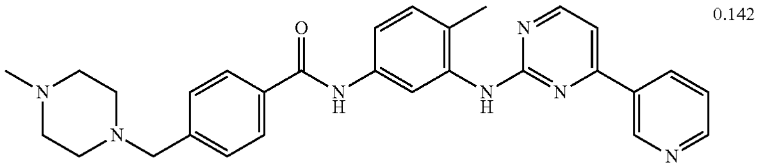 | 0.142 | 111.0 |
| Chloroquine | 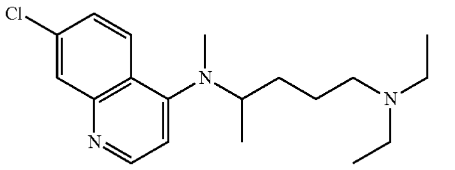 [SMILES: CCN(CC)CCCC(C)N(C)c1ccnc2cc(Cl)ccc12] | 0.244 | 103.0 |
| Nilotinib | 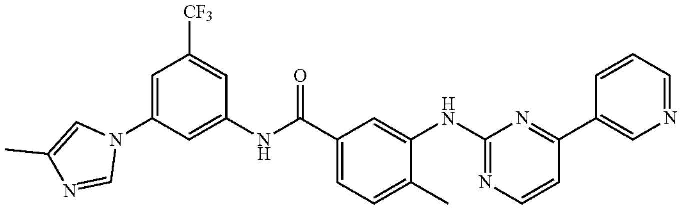 [SMILES: Cc1cn(-c2cc(NC(=O)c3ccc(C)c(Nc4nccc(-c5cccnc5)n4)c3)cc(C(F)(F)F)c2)cn1] | 0.648 | 98.7 |

TABLE 8-continued

| Sample ID | Structure | $IC_{50}$ (uM) | % Killing |
|---|---|---|---|
| GNF-2 | 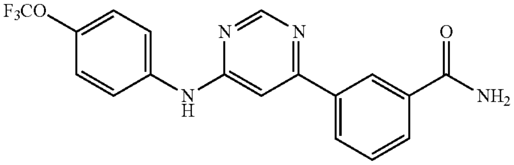 [SMILES: NC(=O)c1cccc(-c2cc(Nc3ccc(OC(F)(F)F)cc3)ncn2)c1] | 1.404 | 86.0 |
| NCGC00373056 | 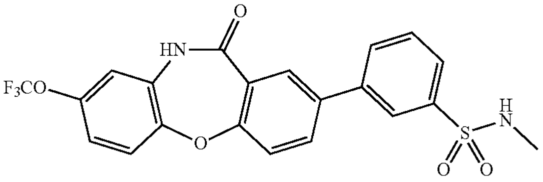 [SMILES: CNS(=O)(=O)c1cccc(-c2ccc3c(c2)C(=O)Nc2cc(OC(F)(F)F)ccc2O3)c1] | 1.362 | 96.5 |
| NCGC00373060 | 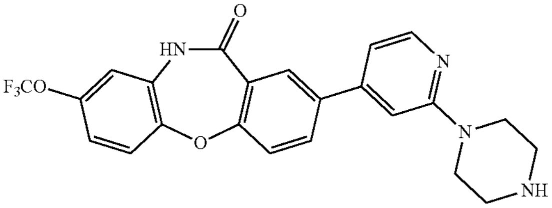 [SMILES: O=C1Nc2cc(OC(F)(F)F)ccc2Oc2ccc(-c3ccnc(N4CCNCC4)c3)cc21] | 1.632 | 89.9 |
| NCGC00411866 | 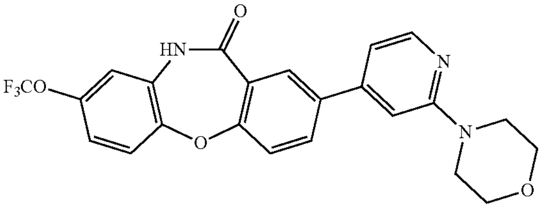 [SMILES: O=C1Nc2cc(OC(F)(F)F)ccc2Oc2ccc(-c3ccnc(N4CCOCC4)c3)cc21] | 9.687 | 92.9 |

Example 9

Figure 23:
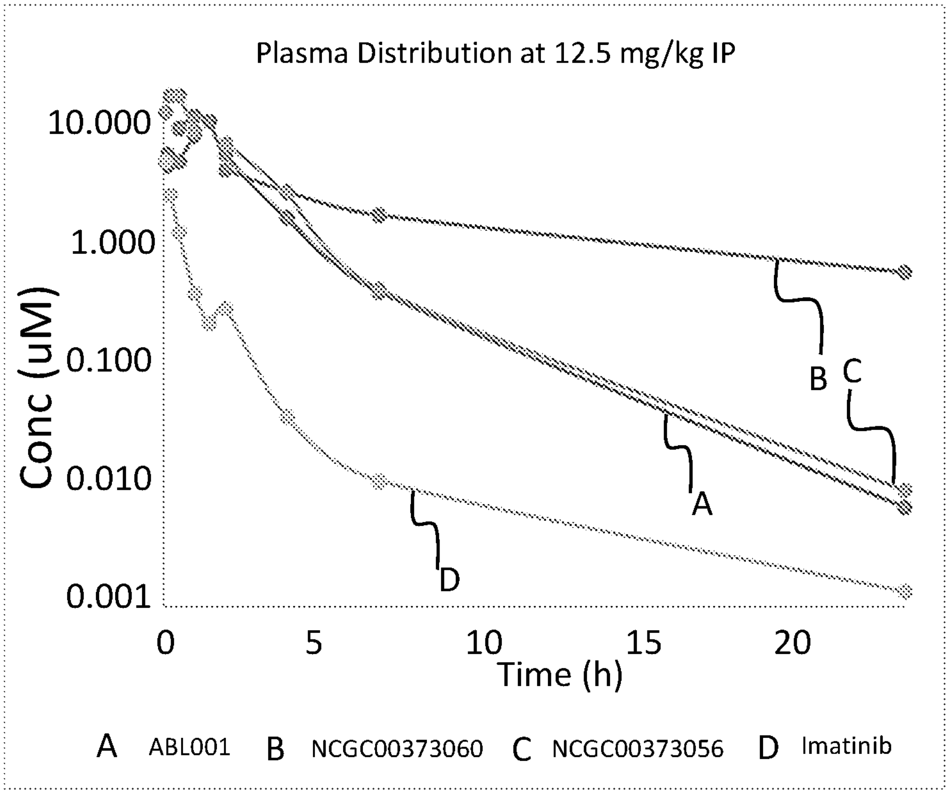
FIG. 23 provides a graph of plasma distribution results obtained in mice using 12.5 mg/kg of NCGC00373060 and NCGC00373056 as compared to comparison compounds ABL001 and Imatinib.
Figure 24:
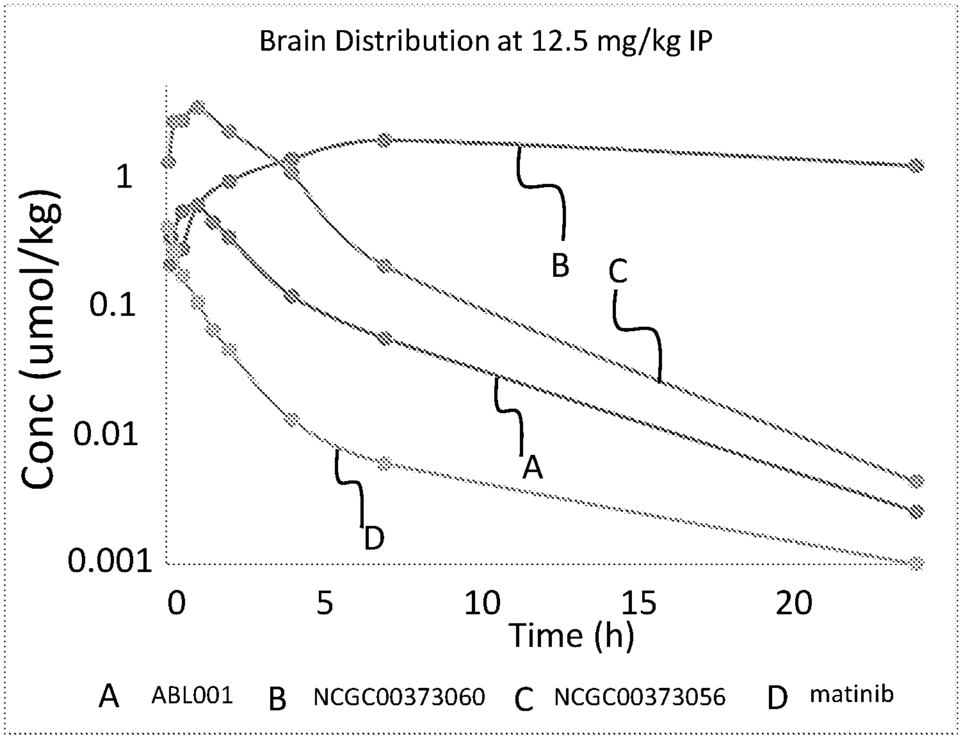
FIG. 24 provides a graph of brain distribution results obtained in mice using 12.5 mg/kg of NCGC00373060 and NCGC00373056 as compared to comparison compounds ABL001 and Imatinib.

In this example, the pharmacokinetic profile in plasma and brain of particular compound embodiments were determined, along with that of Imatinib and the clinical compound ABLOO1. The result for plasma are summarized in Table 9 and the plasma distribution is provided in FIG. 23. The result for brain are summarized in Table 10 and the brain distribution is provided in FIG. 24.

TABLE 9

| | Name | |
|---|---|---|
| | ABL001 | NCGC00373060 |
| Structure | 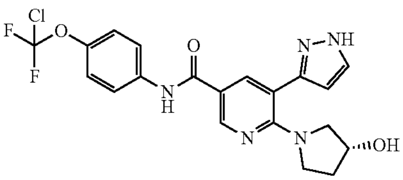 | 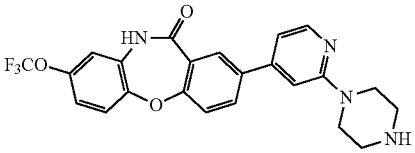 |
| Dose<br>Route<br>Sample | 12.5 mg/kg<br>IP<br>Plasma | |
| Time | uM | uM |
| 0.083 | | |
| 0.167 | 5.454 | 4.440 |
| 0.25 | | |
| 0.5 | 9.137 | 4.784 |
| 1 | 11.174 | 7.844 |

TABLE 9-continued
| | | |
|---|---|---|
| 1.5 | 10.189 | |
| 2 | 5.483 | 4.112 |
| 4 | 1.628 | 2.709 |
| 7 | 0.399 | 1.723 |
| 24 | 0.007 | 0.581 |
| 48 | | 0.138 |
| 72 | | 0.070 |
| 96 | | 0.036 |
| 120 | | 0.011 |
| 168 | | 0.004 |
| | Name | |
| | NCGC00373056 | Imatinib |
| Structure | 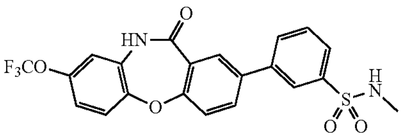 | 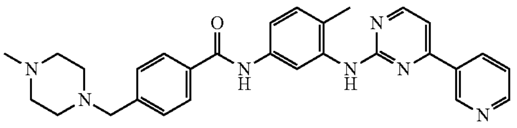 |
| Dose | 12.5 mg/kg | |
| Route | IP | |
| Sample | Plasma | |
| Time | uM | uM |
| 0.083 | 12.080 | 4.754 |
| 0.167 | | |
| 0.25 | 16.961 | 2.519 |
| 0.5 | 16.559 | 1.239 |
| 1 | 8.627 | 0.396 |
| 1.5 | | 0.222 |
| 2 | 6.747 | 0.290 |
| 4 | 2.600 | 0.037 |
| 7 | 0.421 | 0.011 |
| 24 | 0.009 | 0.001 |
| 48 | | |
| 72 | | |
| 96 | | |
| 120 | | |
| 168 | | |
TABLE 10
| | Name | |
|---|---|---|
| | ABL001 | NCGC00373060 |
| Structure | 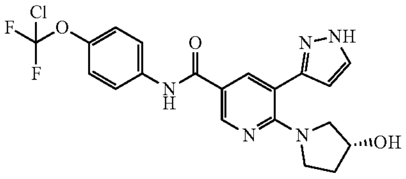 | 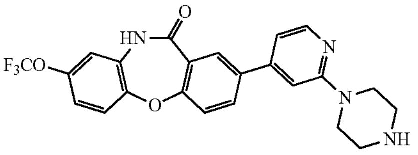 |
| Dose | 12.5 mg/kg | |
| Route | IP | |
| Sample | Brain | |
| Time | umol/kg | umol/kg |
| 0.083 | | |
| 0.167 | 0.330 | 0.208 |
| 0.25 | | |
| 0.5 | 0.534 | 0.275 |
| 1 | 0.597 | 0.595 |
| 1.5 | 0.442 | |
| 2 | 0.336 | 0.912 |
| 4 | 0.119 | 1.351 |
| 7 | 0.056 | 1.887 |
| 24 | 0.003 | 1.198 |

TABLE 10-continued

| | | |
|---|---|---|
| 48 | | 0.493 |
| 72 | | 0.208 |
| 96 | | 0.089 |
| 120 | | 0.044 |
| 168 | | 0.010 |
| | Name | |
| | NCGC00373056 | Imatinib |
| Structure | 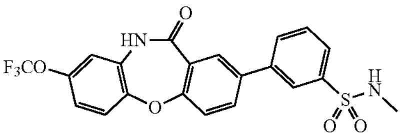 | 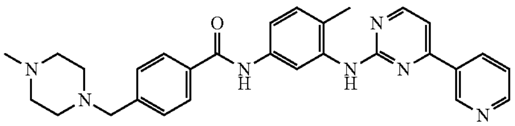 |
| Dose | 12.5 mg/kg | |
| Route | IP | |
| Sample | Brain | |
| Time | umol/kg | umol/kg |
| 0.083 | 1.291 | 0.405 |
| 0.167 | | |
| 0.25 | 2.649 | 0.263 |
| 0.5 | 2.658 | 0.172 |
| 1 | 3.381 | 0.107 |
| 1.5 | | 0.065 |
| 2 | 2.212 | 0.046 |
| 4 | 1.065 | 0.013 |
| 7 | 0.202 | 0.006 |
| 24 | 0.004 | 0.001 |
| 48 | | |
| 72 | | |
| 96 | | |
| 120 | | |
| 168 | | |

Example 10

Figure 25:
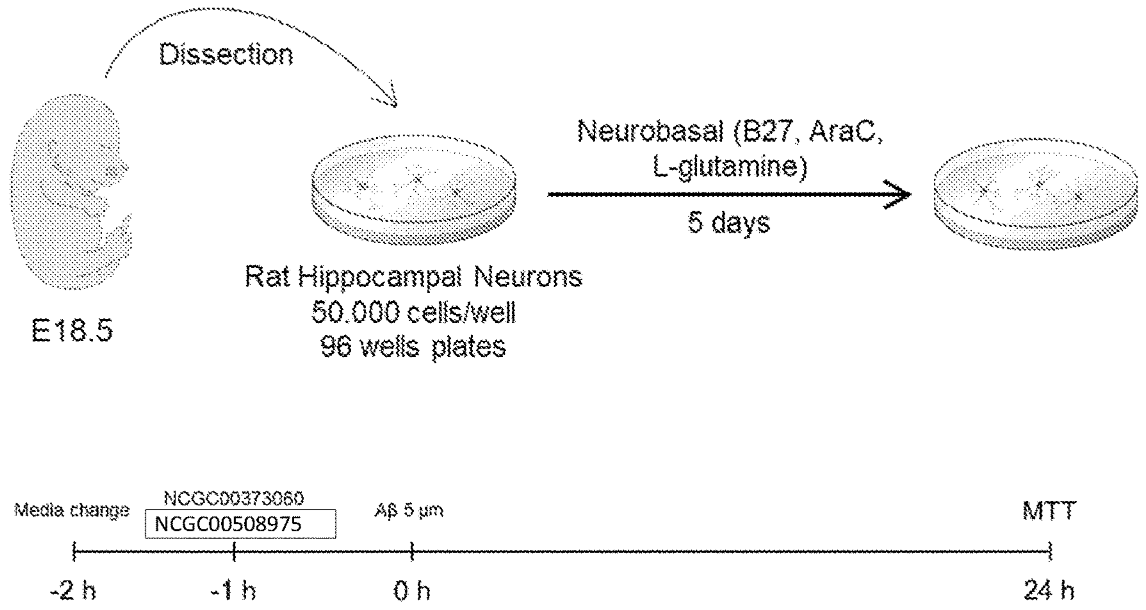
FIG. 25 provides a schematic illustration of the procedure used for the MTT viability assay used in Example 10 of the present disclosure.
Figure 26A:
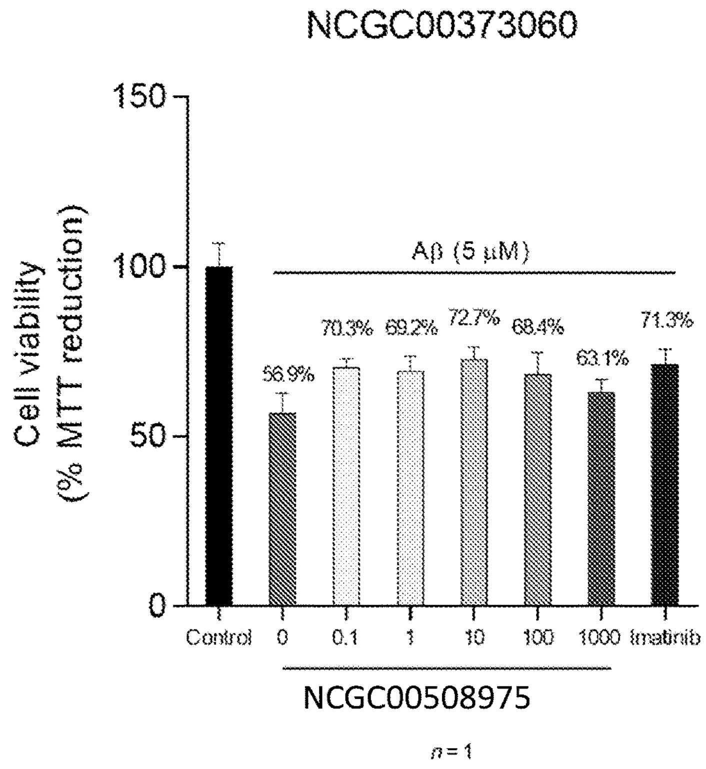
Figure 26B:
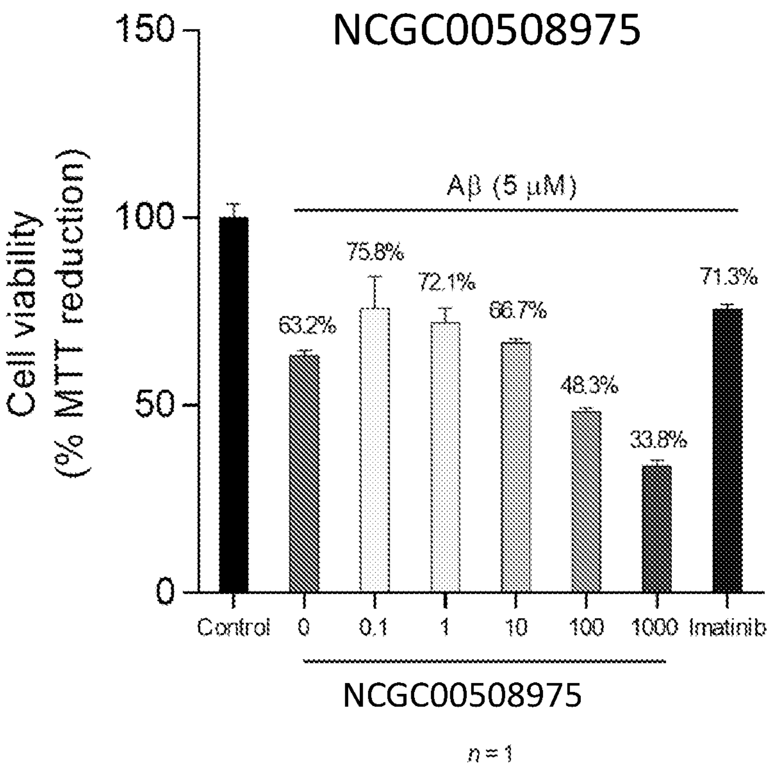
Figure 26C:
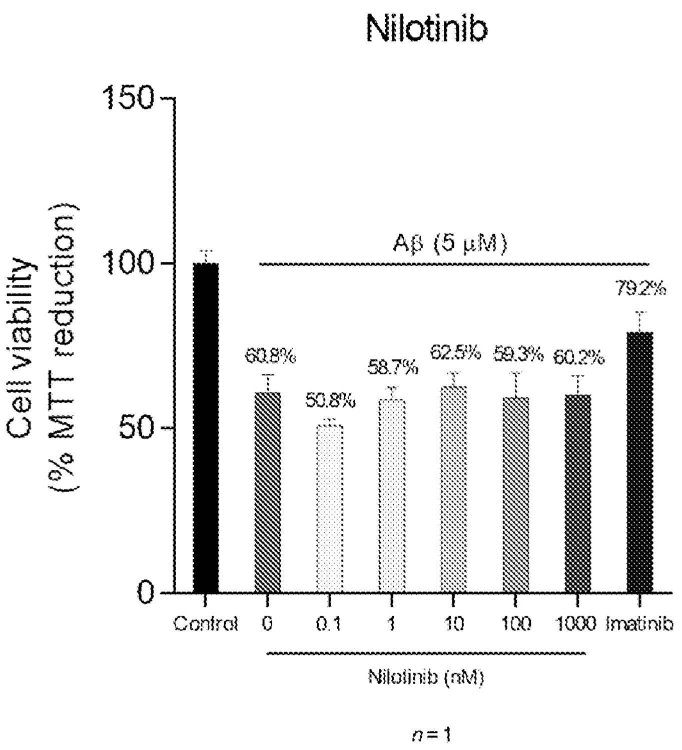

In this example, neuroprotection against Aβ fibrils using an MTT viability assay in primary neuronal cells was evaluated using NCGC00373060, NCGC00508975, and Nilotinib at different concentrations. A schematic illustration of the MTT viability assay procedure is illustrated in FIG. 25. Primary neuronal cells viability was assessed with the MTT assay. Rat hippocampal neurons were exposed to Aβ fibers (5 μM) in the presence and absence of (A) NCGC00373060, (B) NCGC00508975 and (C) Nilotinib at concentrations of 0.1 nM, 1 nM, 10 nM, 100 nM and 1000 nM for 48 hours, using Imatinib as a positive control. Results are illustrated in FIGS. 26A-26C.

Example 11

Figure 27A:
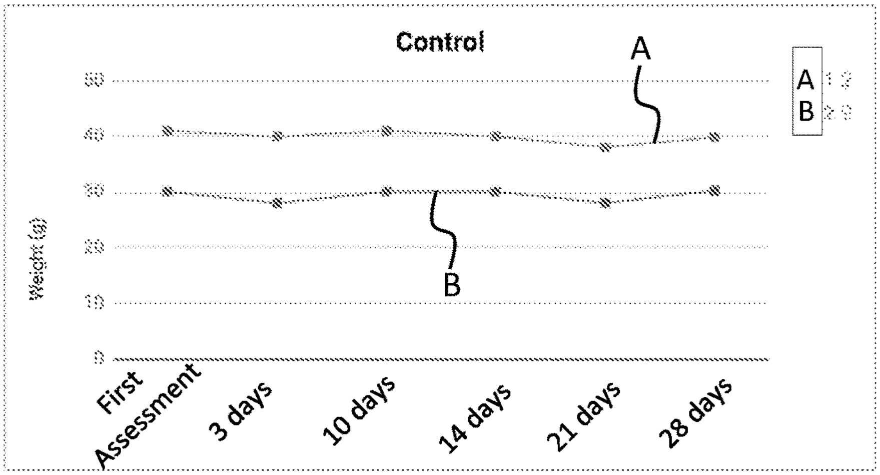
FIGS. 27A-27C are graphs of weight (g) as a function of feeding period (days) for mice fed (i) a control feed with no additive (FIG. 27A), (ii) feed with NCGC00373060 added (FIG. 27B), and (iii) feed with Nilotinib added (FIG. 27C).
Figure 27B:
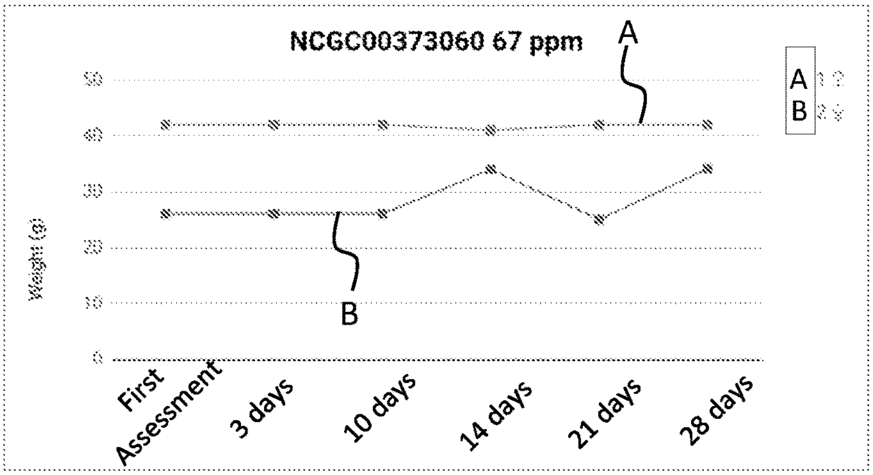
Figure 27C:
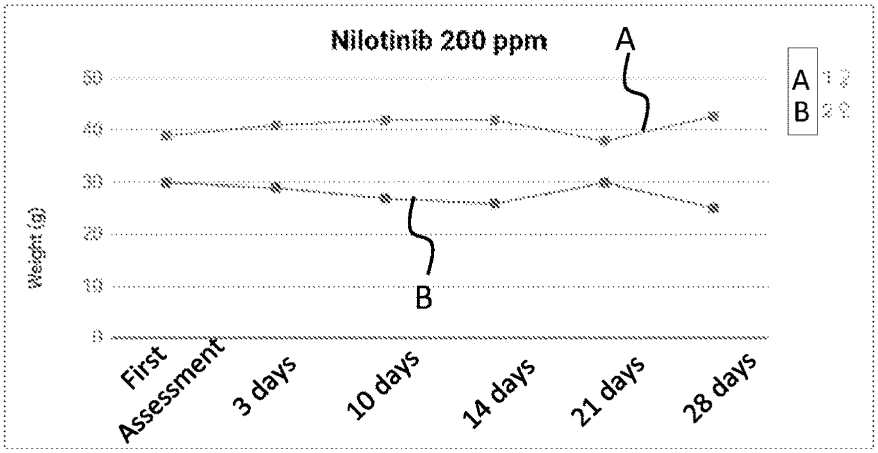

In this example, 10 weeks-old female mice (C57BL/6×C3H) were fed with a control diet (n=2), a diet supplemented with 67 ppm NCGC0037306 (n=2), or a diet with 200 ppm Nilotinib (n=2) for 1 month. After this one-month period, blood and serum was obtained from the mice and analyzed. Results are shown in FIGS. 27A-27C and additional results are provided in Table 11. As can be seen, mice treated with c-Abl inhibitors do not show changes in body weight.

TABLE 11

| | Control | | Nilotinib 200 ppm | | NCGC00373060 (67 ppm) | | Reference |
|---|---|---|---|---|---|---|---|
| Parameter | 1 | 2 | 1 | 2 | 1 | 2 | Values |
| Glucose (without fluoride) (mg/dL) | 130.0 | 98.0 | 84.0 | 56.0 | 152.0 | 42.0 | 57.1-150.1 |
| Total cholesterol (mg/dL) | 106.0 | 110.0 | 114.0 | 84.0 | 92.0 | 107.4 | 51.9-170.3 |
| Total proteins (mg/dL) | 6.22 | 5.8 | 6.4 | 5.6 | 6.4 | 6.2 | 5.57-6.28 |
| Albumin (mg/dL) | 3.4 | 3.2 | 3.6 | 3.4 | 3.2 | 3.4 | 3.17-4.70 |
| Globulin (mg/dL) | | 2.6 | 2.8 | 2.2 | 3.2 | 2.8 | 1.58-2.40 |

TABLE 11-continued

| Parameter | Control 1 | Control 2 | Nilotinib 200 ppm 1 | Nilotinib 200 ppm 2 | NCGC00373060 (67 ppm) 1 | NCGC00373060 (67 ppm) 2 | Reference Values |
|---|---|---|---|---|---|---|---|
| Phosphorus (mg/dL) | 9.6 | — | — | — | — | — | 6.15-9.76 |
| Calcium (mg/dL) | 10.4 | 10.2 | 10.4 | 10.2 | 10.4 | 10.6 | 6.84-11.88 |
| Blood urea nitrogen (mg/dL) | 20.0 | 23.7 | 19.7 | 18.2 | 24.3 | 13.5 | 21.0-50.1 |
| Creatinine (mg/dL) | 0.8 | 0.8 | 1.0 | 0.8 | 0.6 | 1.0 | 0.55-1.55 |
| Total bilirubin (mg/dL) | — | — | — | — | — | — | 0.20-0.85 |
| Alkaline phosphatase (IU/) | 331.6 | 280.0 | 386.4 | 278.2 | 156.8 | 202.4 | 13.3-78.3 |
| ALT (IU/L) | 41.0 | 28.8 | 36.0 | 26.0 | 69.2 | 35.4 | 12.7-71.4 |
| AST (IU/L) | 254.0 | 128.8 | 142.0 | 114.0 | 652.0 | 144.0 | 67.4-328 |
| GGT (IU/L) | — | — | — | — | — | — | S/R |
| Erythrocytes (x$10^6$/μL) | 9.5 | 9.0 | 5.9 | 8.6 | — | 8.3 | 6.51-9.05 |
| Hematocrit (%) | 46.8 | 43.5 | 30.0 | 43.6 | — | 41.8 | 38.5-48.3 |
| Hemoglobin (g/dL) | 14.0 | 13.0 | 8.8 | 12.6 | — | 12.1 | 12.3-15.6 |
| V.C.M. (fL) | 49.4 | 48.4 | 50.8 | 51.0 | — | 50.2 | 43.8-74.8 |
| H.C.M. (pg/cel) | 14.8 | 14.5 | 14.9 | 14.7 | — | 14.5 | 12.0-27.7 |
| C.H.C.M. (g/dL) | 29.9 | 29.9 | 29.3 | 28.9 | — | 29.0 | 27.4-37.0 |
| Reticulocytes (%) | | 0.4 | 0.5 | 0.6 | — | 0.6 | |
| Reticulocytes (x$10^3$/μL) | 0.0 | 36.0 | 29.6 | 51.3 | — | 49.9 | |
| V.H.S. | | 3.0 | 3.0 | 6.0 | — | 5.0 | |
| Leukocytes (/μL) | 2,200 | 1,900 | 3,200 | 3,300 | — | 2,400 | 3100-7700 |
| Eosinophils (/μL) | 22 | 19 | 32 | 0 | — | 0 | 0-240 |
| Blastos (/μL) | 0 | 0 | 0 | 0 | — | 0 | 0-100 |
| Myelocytes (/μL) | 0 | 0 | 0 | 0 | — | 0 | 0-0 |
| Juvenile (/μL) | 0 | 0 | 0 | 0 | — | 0 | 0-0 |
| Bacilliformes (/μL) | 0 | 0 | 0 | 0 | | 0 | S/R |
| Segmented (μL) | 990 | 722 | 1,120 | 759 | — | 744 | 1000-6480 |
| Lymphocytes | 1,144 | 1,064 | 1,920 | 2,046 | — | 1,536 | 1520-7390 |
| Monocytes | 44 | 95 | 128 | 495 | — | 120 | 0-270 |
| Eosinophils (%) | 1 | 1 | 1 | 0 | — | 0 | |
| Youth (%) | 1 | 0 | 0 | 0 | — | 0 | |
| Bacilliformres (%) | 0 | 0 | 0 | 0 | — | 0 | |
| Segmented (%) | 45 | 38 | 35 | 23 | — | 31 | |
| Lymphocytes (%) | 52 | 56 | 60 | 62 | — | 64 | |
| Monocytes (%) | 2 | 5 | 4 | 15 | — | 5 | |
| Morphology leukocytes | Normal | Normal | Normal | Normal | — | Normal | |
| Thrombocytes (/μL) | 611,000 | 668,000 | 780,000 | 689,000 | — | 707,000 | S/R |
| Mean platelet vol. (fL) | 6.0 | 6.0 | 6.9 | 6.1 | — | 6.4 | |
| Thrombocyte morphology | Normal | Normal | Normal | Normal | — | Normal | |
| Conclusions | Leukopenia, Normal morph. | Leukopenia, Normal morph. | Normochromic, non-regenerative normochromic anemia | Moderate neutropenia (normal morph.) | | Moderate neutropenia (normal morph.) | |
| Weight (g) | 39.8 | 30.2 | 42.7 | 25.2 | 42.0 | 34.1 | |

Example 12

Figure 28:
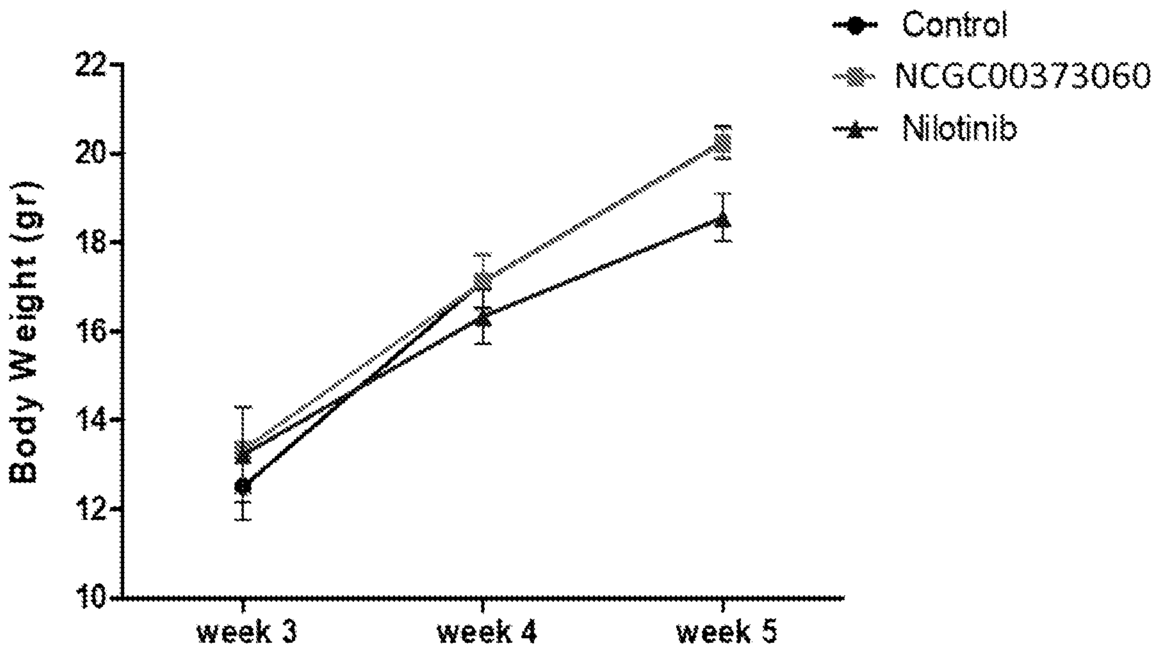
FIG. 28 is a graph of body weight (gr) as a function of time for mice fed (i) a control feed with no additive (line labeled with a "●" symbol), (ii) feed with NCGC00373060 added (line labeled with a "■" symbol), and (iii) feed with Nilotinib added (line labeled with a "▲" symbol).
Figure 29A:
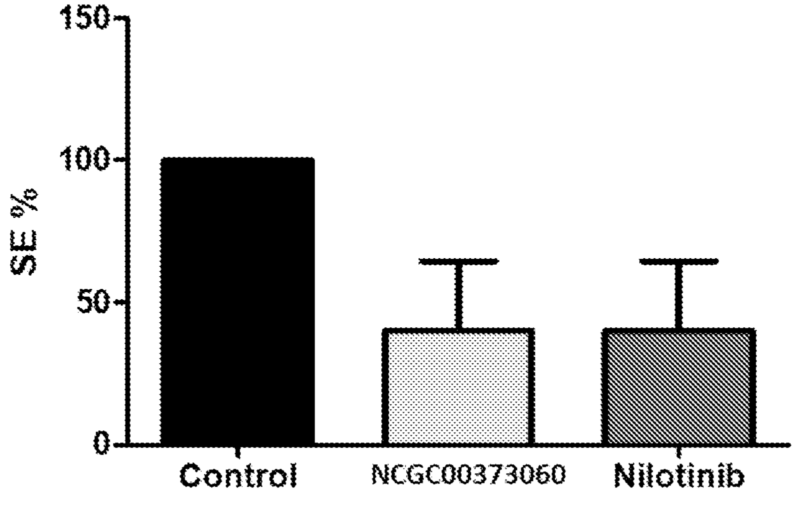
FIGS. 29A-29D provide results obtained from analyzing mice administered a control, NCGC00373060, and Nilotinib for latency Status Epilepticus (SE) (FIG. 29A), percentage SE (FIG. 29B), and survival (FIGS. 29C and 29D).
Figure 29B:
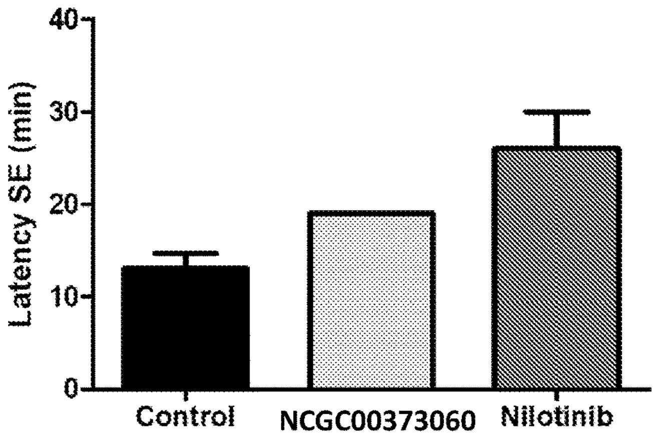
Figure 29C:
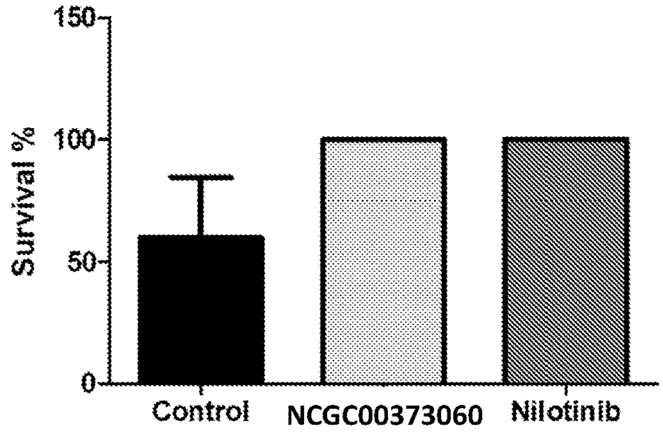
Figure 29D:
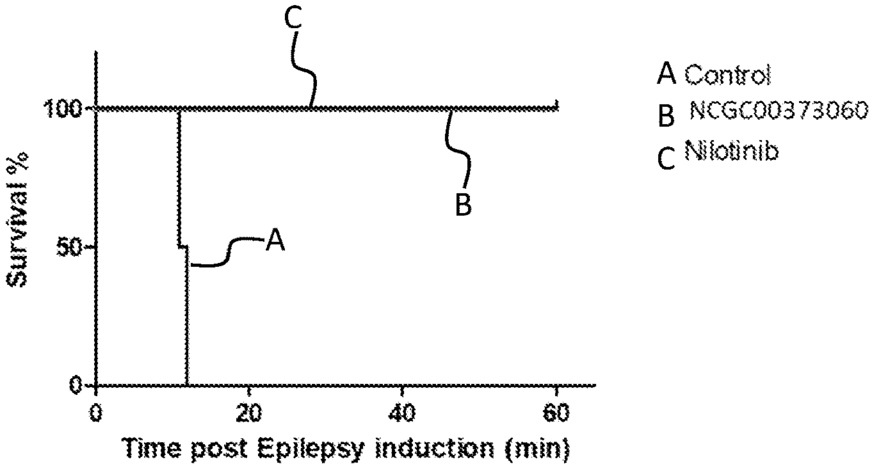

In this example, the ability of compound embodiments of the present disclosure to increase survival and diminish seizure symptoms in a TLE mice model was evaluated. Three weeks-old mice (C57BL/6) were fed with a control diet (n=8), a diet supplemented with 67 ppm NCGC0037306 (n=9), or a diet with 200 ppm Nilotinib (n=9). The animals' weights were determined the week before and during the two weeks of c-Abl inhibitors treatment (results are provided in Table 12 and are illustrated graphically in FIG. 28). After 15 days of feeding, status epilepticus (SE) induction was evaluated. The mice were IP injected with Scopolamine (1.5 mg/Kg) and after 15 minutes, the SE was induced by IP injection of Pilocarpine (420 mg/Kg). The animals' behavior and the seizures induction was evaluated according to Racine's scale and the survival was determined during 60 minutes post-SE induction. Some mice did not developed seizures in registered time. Latency of the SE was significantly increased when mice were pretreated with diets comprising NCGC0037306. Results are tabulated in Table 13, below and also are illustrated graphically in FIGS. 29A-29D. FIG. 29A shows a decrease in the percentage of mice that reach the SE when fed food containing NCGC0037306 as compared to the control diet. FIG. 29B shows that the latency to reach the SE was significantly increased in mice fed food containing NCGC0037306 and FIGS. 29C and 29D show that mice survival also was significantly increased in mice fed food containing NCGC0037306.

TABLE 12

| Controls | | | | NCGC00373060 | | | | Nilotinib | | | |
|---|---|---|---|---|---|---|---|---|---|---|---|
| Mice | week 3 (gr) | week 4 (gr) | week 5 (gr) | Mice | week 3 (gr) | week 4 (gr) | week 5 (gr) | Mice | week 3 (gr) | week 4 (gr) | week 5 (gr) |
| n1 | 13 | 17 | 19 | n1 | 14 | 17 | 19 | n1 | 12 | 14 | 16 |
| n2 | 14 | 19 | 20 | n2 | 13 | 17 | 20 | n2 | 14 | 17 | 18 |
| n3 | 15 | 19 | 22 | n3 | 14 | 18 | 20 | n3 | 15 | 18 | 20 |
| n4 | 12 | 15 | 19 | n4 | 16 | 18 | 20 | n4 | 16 | 18 | 20 |
| n5 | 15 | 19 | 21 | n5 | 15 | 16 | 19 | n5 | 15 | 17 | 18 |
| n6 | 11 | 16 | 20 | n6 | 17 | 19 | 21 | n6 | 18 | 19 | 21 |
| n7 | 10 | 16 | 21 | n7 | 7 | 14 | 20 | n7 | 11 | 15 | 18 |
| n8 | 10 | 16 | 20 | n8 | 11 | 15 | 22 | n8 | 9 | 14 | 17 |
| | | | | n9 | 13 | 20 | 21 | n9 | 9 | 15 | 19 |
| mean | 13 | 17 | 20 | mean | 13 | 17 | 20 | mean | 13 | 16 | 19 |

TABLE 13

| Controls Pilocarpine | | | | NCGC00373060 Pilocarpine | | | | Nilotinib Pilocarpine | | | |
|---|---|---|---|---|---|---|---|---|---|---|---|
| Mice | Latency SE (min) | SE % | Survival % | Mice | Latency SE (min) | SE % | Survival % | Mice | Latency SE (min) | SE % | Survival % |
| n1 | 11 | 100 | 100 | n1 | 19 | 100 | 100 | n1 | — | 0 | 100 |
| n2 | 17 | 100 | 100 | n2 | 19 | 100 | 100 | n2 | 22 | 100 | 100 |
| n3 | 17 | 100 | 100 | n3 | — | 0 | 100 | n3 | — | 0 | 100 |
| n4 | 10 | 100 | 0 | n4 | — | 0 | 100 | n4 | — | 0 | 100 |
| n5 | 10 | 100 | 0 | n5 | — | 0 | 100 | n5 | 30 | 100 | 100 |
| mean | 13 | 100 | 60 | mean | 19 | 40 | 100 | mean | 26 | 40 | 100 |
| error | 1.6 | 0.0 | 24.5 | error | 0.0 | 24.5 | 0.0 | error | 6.9 | 24.5 | 0.0 |

VII. Overview of Several Embodiments

Disclosed herein are embodiments of compounds having a structure satisfying Formula I Formula I

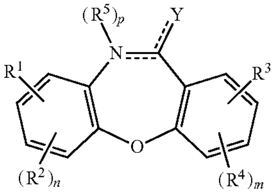

or a stereoisomer, tautomer, pharmaceutically acceptable salt, solvate, or prodrug thereof, wherein X is oxygen, NR', CR'R", S, SO, or $SO_2$ wherein each R' and R" independently is selected from hydrogen, aliphatic, heteroaliphatic, haloaliphatic, haloheteroaliphatic, aromatic, aliphatic-aromatic, or heteroaliphatic-aromatic;

Y is hydrogen, oxygen, NR', NR'R", or CR'R" wherein each R' and R" independently is selected from hydrogen, aliphatic, heteroaliphatic, haloaliphatic, haloheteroaliphatic, aromatic, aliphatic-aromatic, or heteroaliphatic-aromatic;

$R^1$ and $R^3$ independently are heteroaliphatic, haloaliphatic, haloheteroaliphatic, aromatic, or boronic acid;

$R^2$ and $R^4$, if present, independently are aliphatic, heteroaliphatic, or halogen;

$R^5$, when present, is selected from hydrogen, aliphatic, heteroaliphatic, aromatic, aliphatic-aromatic, heteroaliphatic-aromatic, or heteroaliphatic-aromatic;

each of n and m independently is an integer selected from 0 to 3; and p is 0 or 1, wherein when p is 0, then no $R^5$ group is present and therefore the nitrogen atom of Formula I forms a double bond with the carbon atom attached to Y of Formula I and wherein when p is one, $R^5$ is present and thus the nitrogen atom of Formula I forms a single bond with the carbon atom attached to Y of Formula I; and provided that $R^1$ and $R^3$ are not both —$OCH_3$ when $R^5$ is H and when both Y and X are oxygen.

In some embodiments, each R' and R" independently is hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl.

In any or all of the above embodiments, each R' and R" independently is hydrogen, lower alkyl, or lower heteroalkyl.

In any or all of the above embodiments, p is 1 and $R^5$ is hydrogen, alkyl, or heteroalkyl.

In any or all of the above embodiments, p is 1 and $R^5$ is hydrogen, $CH_3$, or $-(CH_2)_qO(CH_2)_qSi(CH_3)_3$, wherein each q independently is an integer ranging from 0 to 50.

In any or all of the above embodiments, n is 1 and m is 1.

In any or all of the above embodiments, n is 0 and m is 1.

In any or all of the above embodiments, n is 1 and m is 0.

In any or all of the above embodiments, Y is oxygen, NH, $NCH_3$, $CH_2$, or $C(CH_3)_2$ and Y is bound via a double bond.

In any or all of the above embodiments, Y is oxygen and is bound via a double bond.

In any or all of the above embodiments, Y is hydrogen, $NH_2$, $NHCH_3$, or $N(CH_3)_2$ and Y is bound via a single bond.

In any or all of the above embodiments, $R^1$ and $R^3$ independently are alkoxy, thioether, haloalkoxy, haloalkyl, haloalkenyl, haloalkynyl, cyano, aryl, heteroaryl, alkyl-B$(OH)_2$, heteroalkyl-B$(OH)_2$, —B$(OH)_2$, aryl-$(R'''')_{n'}$, heteroaryl-$(R''')_{n'}$", wherein each R" independently is heteroaliphatic, sulfonamide, amine, boronic acid, or hydroxyl, and n' is an integer ranging from 0 to 5.

In any or all of the above embodiments, each $R^2$ and $R^4$, if present, independently is alkyl, alkenyl, alkynyl, heteroalkyl, chloro, fluoro, bromo, iodo, or cyano.

In any or all of the above embodiments, the compound (or a stereoisomer, tautomer, pharmaceutically acceptable salt, solvate, or prodrug thereof) has a structure satisfying any one or more of Formulas IIA-IIF:

Formula IIA

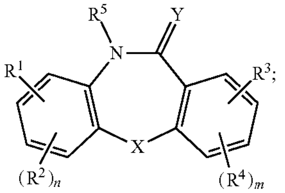

Formula IIB

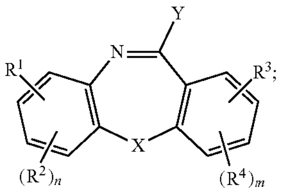

-continued

Formula IIC

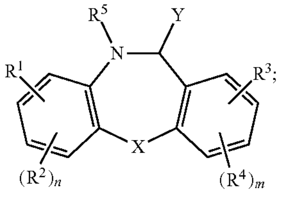

Y = H

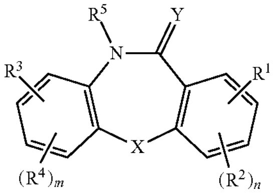

Formula IIE

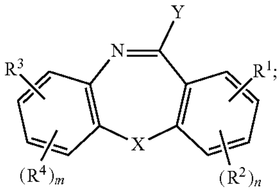

or

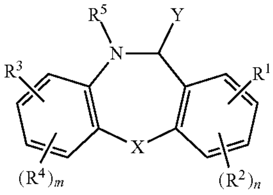

Y = H

Formula IID; Formula IIE.

In any or all of the above embodiments, the compound (or a stereoisomer, tautomer, pharmaceutically acceptable salt, solvate, or prodrug thereof) has a structure satisfying any one or more of Formulas IIIA-IIIH Formula IIIA

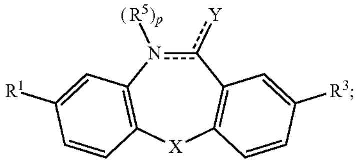

Formula IIIB

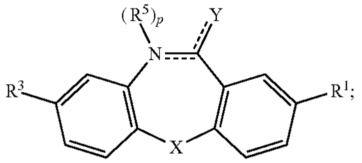

Formula IIIC

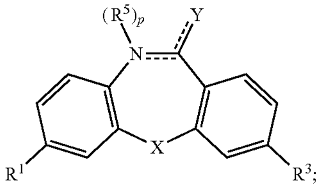

-continued

Formula IIID

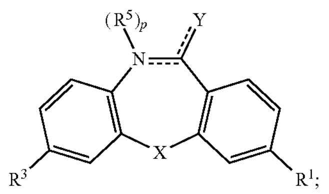

Formula IIIE

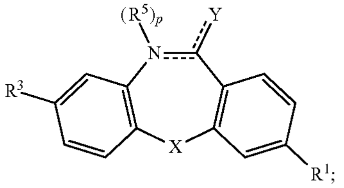

Formula IIIF

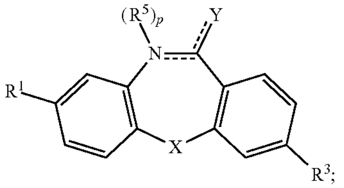

Formula IIIG

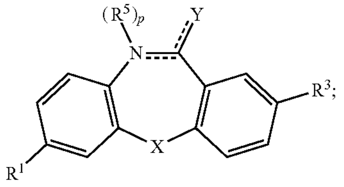

or

Formula IIIH

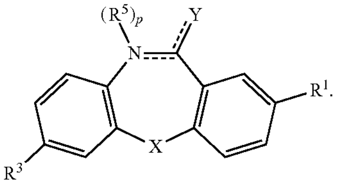

In any or all of the above embodiments, the compound (or a stereoisomer, tautomer, pharmaceutically acceptable salt, solvate, or prodrug thereof) compound has a structure satisfying any one or more of Formulas IVA-IVF Formula IVA

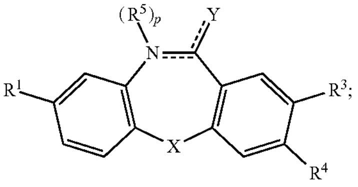

Formula IVB

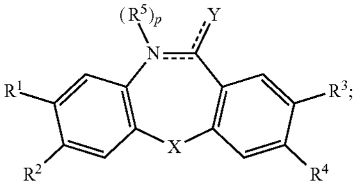

-continued

Formula IVC

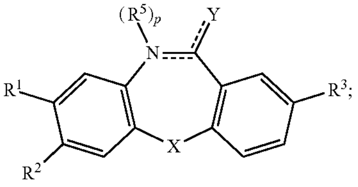

Formula IVD

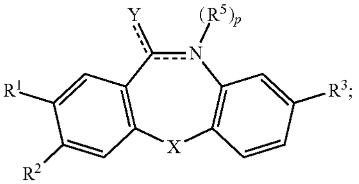

Formula IVE

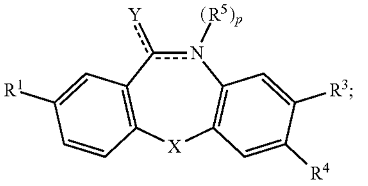

or

Formula IVF

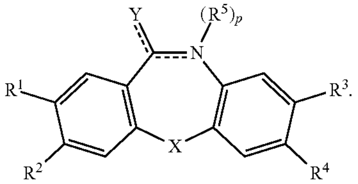

Also disclosed herein are embodiments of a precursor compound having a structure satisfying Formula I Formula I

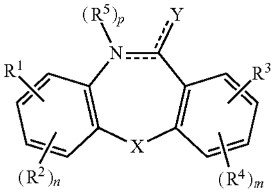

wherein

X is oxygen, NR', CR'R", S, SO, or $SO_2$ wherein each R' and R" independently is selected from hydrogen, aliphatic, heteroaliphatic, haloaliphatic, haloheteroaliphatic, aromatic, aliphatic-aromatic, or heteroaliphatic-aromatic;

Y is hydrogen, oxygen, NR', NR'R", or CR'R" wherein each R' and R" independently is selected from hydrogen, aliphatic, heteroaliphatic, haloaliphatic, haloheteroaliphatic, aromatic, aliphatic-aromatic, or heteroaliphatic-aromatic;

at least one of $R^1$ and $R^3$ is halogen or a boronic ester and the other of $R^1$ or $R^3$ is heteroaliphatic, haloaliphatic, haloheteroaliphatic, aromatic, or boronic acid;

$R^2$ and $R^4$, if present, independently are aliphatic, heteroaliphatic, or halogen;

$R^5$, when present, is selected from hydrogen, aliphatic, heteroaliphatic, aromatic, aliphatic-aromatic, heteroaliphatic-aromatic, or heteroaliphatic-aromatic;

each of n and m independently is an integer selected from 0 to 3; and p is 0 or 1, wherein when p is 0, then no $R^5$ group is present and therefore the nitrogen atom of Formula I forms a double bond with the carbon atom attached to Y of Formula I and wherein when p is one, $R^5$ is present and thus the nitrogen atom of Formula I forms a single bond with the carbon atom attached to Y of Formula I.

Also disclosed herein are embodiments of a method for making any or all of the above compound embodiments, wherein the method comprise:

coupling a compound having a structure satisfying a formula

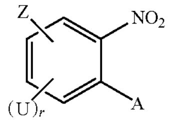

with a compound having a structure satisfying a formula

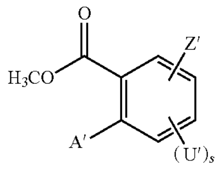

to provide a coupled compound having a structure satisfying a formula

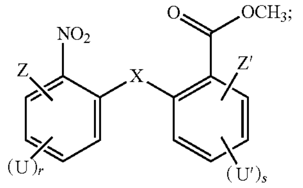

cyclizing the coupled compound to provide a precursor compound having a structure satisfying a formula

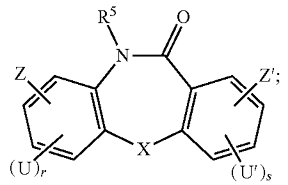

coupling the precursor compound with a coupling partner group to provide the compound; wherein X and $R^5$ are as defined herein;

each of Z and Z' independently is $R^1$ or $R^3$ wherein $R^3$ is halogen or boronic ester, provided that when Z is $R^1$ then Z' is $R^3$ and when Z is $R^3$ then Z' is $R^1$;

each of U and U' independently is $R^2$ or $R^4$, provided that when U is $R^2$, then U' is $R^4$, Z is $R^1$, and Z' is $R^3$; and provided that when U' is $R^2$, then U is $R^4$, Z' is $R^1$, and Z is $R^3$; and A and A' independently are halogen, OH, SH, or $NH_2$; and each of r and s independently is an integer selected from 0 to 3.

In some embodiments, the method further comprises exposing the precursor compound to a post-cyclization step.

In any or all of the above method embodiments, variable X of the precursor compound is sulfur and the post-cyclization step comprises oxidizing variable X to an SO or $SO_2$ group.

In any or all of the above method embodiments, variable X of the precursor compound is NH and the post-cyclization step comprises functionalizing the NH group to provide an NR' group, wherein R' is aliphatic, heteroaliphatic, haloaliphatic, haloheteroaliphatic, aromatic, aliphatic-aromatic, or heteroaliphatic-aromatic.

In any or all of the above method embodiments, coupling the precursor compound with a coupling partner group comprises exposing the precursor compound to a transition metal-containing catalyst, a base, a solvent, and the coupling partner group.

In any or all of the above method embodiments, the transition metal-containing catalyst is $CuBr(PPh_3)_3$, $Pd(PPh_3)_4$, $Pd(OAc)_2$, Pd(crotyl)Cl, or $Pd(dppf)Cl_2$; the base is $Cs_2CO_3$, $Na_2CO_3$, or KOAc; and the solvent is toluene, dimethoxyethane, dimethylformamide, or any combination thereof.

In any or all of the above method embodiments, the method further comprises a reduction step or a dehydration step.

In any or all of the above method embodiments, the reduction step comprises exposing the precursor compound or the compound embodiment disclosed herein to a reducing agent capable of reducing an amide group of the precursor compound or the compound.

In any or all of the above method embodiments, the dehydration step comprises exposing the precursor compound or the compound embodiment disclosed herein a dehydration reagent and an amine reagent capable of converting an amide group of the precursor compound or the compound to an amine group.

Also disclosed herein are embodiments of a pharmaceutical composition, comprising: a compound according to any or all of the above compound embodiments, or a stereoisomer, tautomer, pharmaceutically acceptable salt, solvate, or prodrug thereof; and a pharmaceutically acceptable excipient, an adjuvant, a therapeutically active compound, or any combination thereof.

In some embodiments, the composition is formulated for topical, parenteral, or oral administration.

In any or all of the above composition embodiments, the compound is

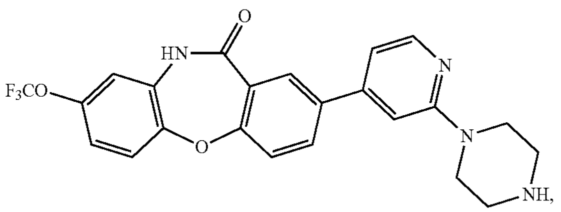

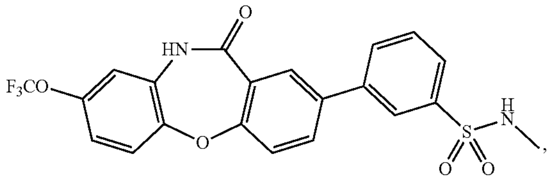

-continued

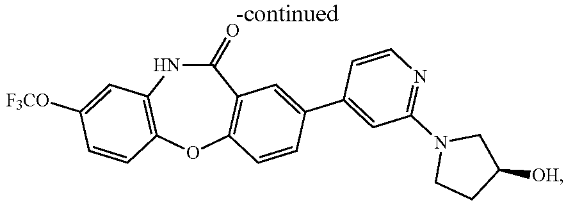

or a stereoisomer, tautomer, pharmaceutically acceptable salt, solvate, or prodrug thereof.

Also disclosed herein are embodiments of a method for treating a disease in a subject, comprising:

administering (i) a therapeutically effective amount of the compound of according to claims of the present disclosure, or a stereoisomer, tautomer, pharmaceutically acceptable salt, solvate, or prodrug thereof; or (ii) a therapeutically effective amount of the pharmaceutical composition of according to claims of the present disclosure to a subject having, or suspected of having, the disease, wherein the disease is a disease involving c-Abl tyrosine kinase.

In some embodiments, the disease is Farber disease, Krabbe disease, Fabry disease, Schindler disease, Sandhoff disease, Tay-Sachs disease, Gaucher disease, Niemann-Pick A disease, Niemann-Pick B disease, Hunter disease, Sanfilippo syndrome, Sly syndrome, Niemann-Pick C disease. Niemann-Pick D disease, bacterial pathogenesis resulting from *Shigella flexneri, Escherichia coli, Helicobacter pylori, Anaplasma phagocytophilum, Salmonella enterica*, or *Plasmodium falciparum* (malaria), viral pathogenesis resulting from HIV, or any combinations thereof.

In some embodiments, disease is a cancer or a neurodegenerative disease.

In any or all of the above method embodiments, the neurodegenerative disease is Alzheimer's disease, Parkinson's disease, epilepsy, amyotrophic lateral sclerosis, primary lateral sclerosis, Kennedy's syndrome, frontal temporal dementia associated with ALS, spinal muscular atrophy, and any combinations thereof.

In any or all of the above method embodiments, the cancer is leukemia, glioma, glioblastoma and neuroblastoma.

In any or all of the above method embodiments, the disease results from overexpression of c-Abl tyrosine kinase.

In any or all of the above method embodiments, the compound

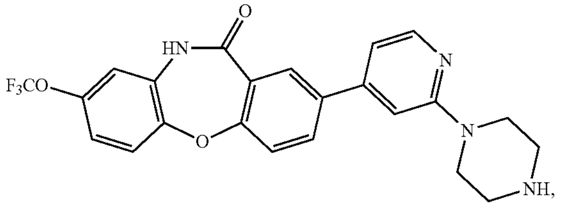

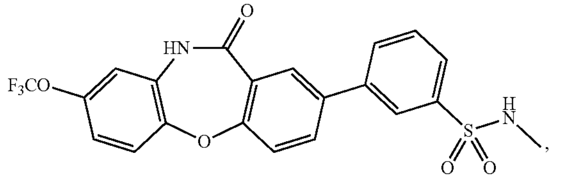

-continued

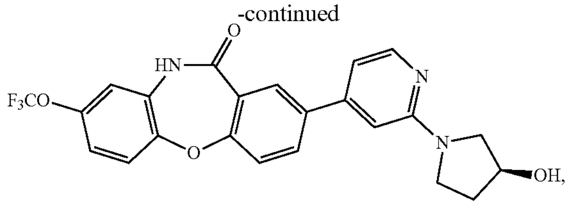

or a stereoisomer, tautomer, pharmaceutically acceptable salt, solvate, or prodrug thereof.

In some embodiments, any or all of the above compounds can be used to inhibiting c-Abl tyrosine kinase.

In some embodiments, the compound inhibits c-Abl tyrosine kinase by binding to an allosteric site of the c-Abl tyrosine kinase.

In any of the above use embodiments, the compound binds to a myristate pocket of the c-Abl tyrosine kinase.

In any or all of the above use embodiments, the compound is capable of passing through a blood brain barrier of a subject.

In any or all of the above use embodiments, the compound is

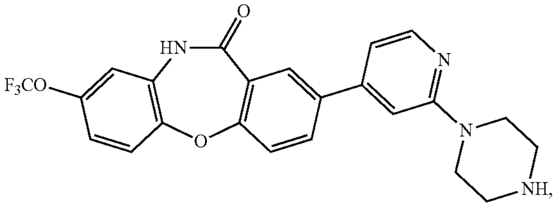

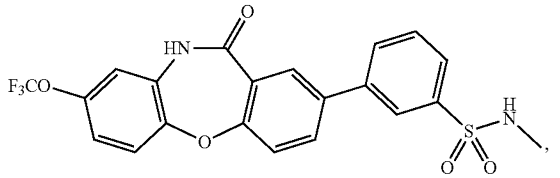

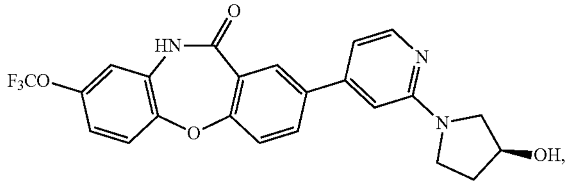

or a stereoisomer, tautomer, pharmaceutically acceptable salt, solvate, or prodrug thereof.

In some embodiments, any or all of the above compounds can be used for treating a disease involving c-Abl tyrosine kinase activity or c-Abl tyrosine kinase overexpression.

In some embodiments, the disease is Farber disease, Krabbe disease, Fabry disease, Schindler disease, Sandhoff disease, Tay-Sachs disease, Gaucher disease, Niemann-Pick A disease, Niemann-Pick B disease, Hunter disease, Sanfilippo syndrome, Sly syndrome, Niemann-Pick C disease. Niemann-Pick D disease, bacterial pathogenesis resulting from *Shigella flexneri, Escherichia coli, Helicobacter pylori, Anaplasma phagocytophilum, Salmonella enterica*, or *Plasmodium falciparum* (malaria), viral pathogenesis resulting from HIV, or any combinations thereof.

In some embodiments, disease is cancer, a neurodegenerative disease, or malaria.

In any or all of the above use embodiments, the neurodegenerative disease is Alzheimer's disease, Parkinson's disease, amyotrophic lateral sclerosis, epilepsy, primary lateral sclerosis, Kennedy's syndrome, frontal temporal dementia associated with ALS, spinal muscular atrophy, and any combinations thereof.

In any or all of the above use embodiments, the cancer is leukemia, glioma, glioblastoma and neuroblastoma.

In view of the many possible embodiments to which the principles of the present disclosure may be applied, it should be recognized that the illustrated embodiments are only preferred examples and should not be taken as limiting in scope. Rather, the scope is defined by the following claims. We therefore claim as our invention all that comes within the scope and spirit of these claims.

We claim:

1. A compound, having a structure satisfying any of Formulas IIA-IIF

Formula IIA

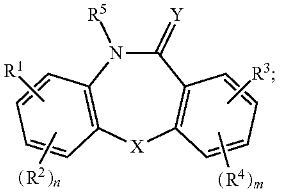

Formula IIB

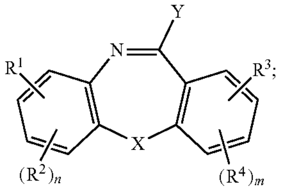

Formula IIC

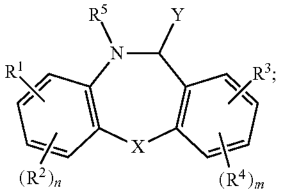

Y = H

Formula IID

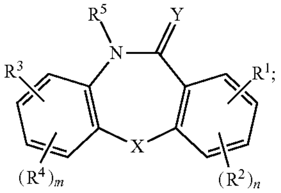

Formula IIE

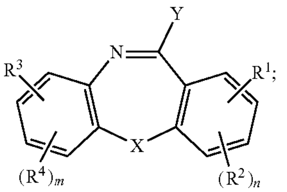

or

-continued

Formula IIF

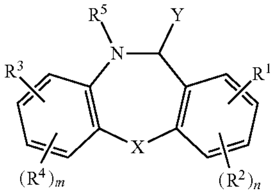

Y = H or a stereoisomer, tautomer, or pharmaceutically acceptable salt thereof, wherein X is NR', wherein R' is selected from hydrogen, aliphatic, heteroaliphatic, haloaliphatic, haloheteroaliphatic, aromatic, aliphatic-aromatic, or heteroaliphatic-aromatic;

for Formulas IIA and IID, Y is oxygen, NR', or CR'R" wherein each R' and R" independently is selected from hydrogen, aliphatic, heteroaliphatic, haloaliphatic, haloheteroaliphatic, aromatic, aliphatic-aromatic, or heteroaliphatic-aromatic;

for Formulas IIB and IIE, Y is hydrogen or NR'R" wherein each R' and R" independently is selected from hydrogen, aliphatic, heteroaliphatic, haloaliphatic, haloheteroaliphatic, aromatic, aliphatic-aromatic, or heteroaliphatic-aromatic;

for Formulas IIC and IIF, Y is hydrogen;

at least one of $R^1$ and $R^3$ is trifluoroalkoxy and the other of $R^1$ and $R^3$ is heteroaliphatic, haloaliphatic, haloheteroaliphatic, aromatic, or boronic acid, and provided that (a) $R^1$ and $R^3$ are each positioned para relative to X of Formulas IIA-IIF; or (b)(i) for Formulas IIA and IIC, $R^1$ is para relative to the nitrogen atom bound to $R^5$ and $R^3$ is para relative to the carbon atom bound to Y; (b)(ii) for Formula IIB, $R^1$ is para relative to the imine nitrogen atom and $R^3$ is para relative to the carbon atom bound to Y; (b)(iii) for Formulas IID and IIF, $R^1$ is para relative to the carbon atom bound to Y and $R^3$ is para relative to the nitrogen atom bound to $R^5$; or (b)(iv) for Formula IIE, $R^1$ is para relative to the carbon atom bound to Y and $R^3$ is para relative to the imine nitrogen atom;

$R^2$ and $R^4$, if present, independently are aliphatic, heteroaliphatic, or halogen;

$R^5$ is selected from hydrogen, aliphatic, heteroaliphatic, aromatic, aliphatic-aromatic, or heteroaliphatic-aromatic; and each of n and m independently is an integer selected from 0 to 3.

2. The compound of claim 1, wherein each R' and R" independently is hydrogen, alkyl, alkenyl, alkynyl, aryl, heteroalkyl, heteroalkenyl, heteroalkynyl, heteroaryl, alkyl-aryl, alkenyl-aryl, alkynyl-aryl, alkyl-heteroaryl, alkenyl-heteroaryl, or alkynyl-heteroaryl.

3. The compound of claim 1, wherein each R' and R" independently is hydrogen, lower alkyl, or lower heteroalkyl.

4. The compound of claim 1, wherein $R^5$ is hydrogen, alkyl, or heteroalkyl.

5. The compound of claim 1, wherein $R^5$ is hydrogen, $CH_3$, or $—(CH_2)_qO(CH_2)_qSi(CH_3)_3$, wherein each q independently is an integer ranging from 0 to 50.

6. The compound of claim 1, wherein n is 1 and m is 1; or n is 0 and m is 1; or n is 1 and m is 0.

7. The compound of claim 1, wherein for Formulas IIA and ID, Y is oxygen, NH, $NCH_3$, $CH_2$, or $C(CH_3)_2$; or wherein for Formulas IIB and IIE, Y is hydrogen, NH2, $NHCH_3$, or $N(CH_3)_2$; or wherein for Formulas IIC and IIF, Y is hydrogen.

8. The compound of claim 1, wherein at least one of $R^1$ and $R^3$ is fluoroalkoxy and the other of $R^1$ and $R^3$ is alkoxy, thioether, haloalkoxy, haloalkyl, haloalkenyl, haloalkynyl, cyano, aryl, heteroaryl, alkyl-$B(OH)_2$, heteroalkyl-$B(OH)_2$, —$B(OH)_2$, aryl-$(R''')_{n'}$, or heteroaryl-$(R''')_{n'}$, wherein each R''' independently is heteroaliphatic, sulfonamide, amine, boronic acid, or hydroxyl, and n' is an integer ranging from 0 to 5.

9. The compound of claim 1, wherein each $R^2$ and $R^4$, if present, independently is alkyl, alkenyl, alkynyl, heteroalkyl, chloro, fluoro, bromo, iodo, or cyano.

10. The compound of claim 1, or a stereoisomer, tautomer, or pharmaceutically acceptable salt thereof, wherein each of $R^1$ and $R^3$ is positioned para relative to X.

11. The compound of claim 1, or a stereoisomer, tautomer, or pharmaceutically acceptable salt thereof, wherein each of $R^1$ and $R^3$ is positioned para relative to X and (i) $R^4$ is present and is positioned meta relative to X; (ii) $R^2$ is present and is positioned meta relative to X; or (iii) both $R^2$ and $R^4$ are present and each of $R^2$ and $R^4$ is positioned meta relative to X.

12. The compound of claim 1, wherein the compound is 3-(11-oxo-8-(trifluoromethoxy)-10,11-dihydro-5H-dibenzo[b,e][1,4]diazepin-2-yl)benzoic acid;

3-(11-Oxo-8-(trifluoromethoxy)-10,11-dihydro-5H-dibenzo[b,e][1,4]diazepin-2-yl)benzamide;

N-(2-Hydroxyethyl)-3-(11-oxo-8-(trifluoromethoxy)-10,11-dihydro-5H-dibenzo[b,e][1,4]diazepin-2-yl)benzamide;

N-(2-Aminoethyl)-3-(11-oxo-8-(trifluoromethoxy)-10,11-dihydro-5H-dibenzo[b,e][1,4]diazepin-2-yl)benzamide;

N-(2-Morpholinoethyl)-3-(11-oxo-8-(trifluoromethoxy)-10,11-dihydro-5H-dibenzo[b,e][1,4]diazepin-2-yl)benzamide;

2-(3-(Morpholine-4-carbonyl)phenyl)-8-(trifluoromethoxy)-5,1 0-dihydro-11H-dibenzo[b,e][1,4]diazepin-11-one;

2-(3-(Piperazine-1-carbonyl)phenyl)-8-(trifluoromethoxy)-5,1 0-dihydro-11H-dibenzo[b,e][1,4]diazepin-11-one;

N-(3-(11-Oxo-8-(trifluoromethoxy)-10,11-dihydro-5H-dibenzo[b,e][1,4]diazepin-2-yl)phenyl)methanesulfonamide;

N-(4-(11-oxo-8-(trifluoromethoxy)-10,11-dihydro-5H-dibenzo[b,e][1,4]diazepin-2-yl)phenyl)methanesulfonamide;

2-(2-Morpholinopyridin-4-yl)-8-(trifluoromethoxy)-5,1 0-dihydro-11H-dibenzo[b,e][1,4]diazepin-11-one;

2-(1 H-Pyrazol-4-yl)-8-(trifluoromethoxy)-5,1 0-dihydro-11H-dibenzo[b,e][1,4]diazepin-11-one;

5-Methyl-2-(2-morpholinopyridin-4-yl)-8-(trifluoromethoxy)-5,1 0-dihydro-11H dibenzo[b,e][1,4]diazepin-11-one;

5-Ethyl-2-(2-morpholinopyridin-4-yl)-8-(trifluoromethoxy)-5,1 0-dihydro-11H-dibenzo[b,e][1,4]diazepin-11-one;

2-(2-Morpholinopyridin-4-yl)-5-propyl-8-(trifluoromethoxy)-5,1 0-dihydro-11H-dibenzo[b,e][1,4]diazepin-11-one;

5-(2-Methoxyethyl)-2-(2-morpholinopyridin-4-yl)-8-(trifluoromethoxy)-5,10-dihydro-11H-dibenzo[b,e][1,4]diazepin-11-one;

or a stereoisomer, tautomer, or pharmaceutically acceptable salt thereof.

13. A method for making the compound of claim 1 according to Formulas IIA or ID, comprising:

coupling a compound having a structure satisfying a formula

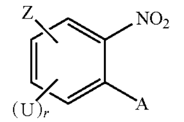

with a compound having a structure satisfying a formula

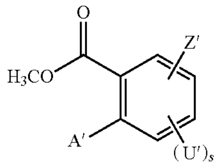

to provide a coupled compound having a structure satisfying a formula

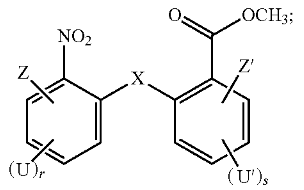

cyclizing the coupled compound to provide a precursor compound having a structure satisfying a formula

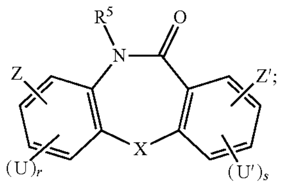

coupling the precursor compound with a coupling partner group to provide the compound of claim 1; wherein X and $R^5$ are as defined in claim 1;

at least one of Z and Z'fluoroalkoxy and the other of Z and Z' is halogen or boronic ester, provided that if Z is fluoroalkoxy then Z' is halogen or boronic ester and if Z is halogen or boronic ester then Z' is trifluoroalkoxy;

each of U and U' independently is $R^2$ or $R^4$, provided that when U is $R^2$, then U' is $R^4$, Z is fluoroalkoxy, and Z' is halogen or boronic ester; and provided that when U' is $R^2$, then U is $R^4$, Z' is trifluoroalkoxy, and Z is halogen or boronic ester; and A and A' independently are halogen, OH, SH, or $NH_2$; and each of r and s independently is an integer selected from 0 to 3.

14. The method of claim 13, wherein coupling the precursor compound with a coupling partner group comprises exposing the precursor compound to a transition metal-containing catalyst, a base, a solvent, and the coupling partner group and wherein the transition metal-containing catalyst is $CuBr(PPh_3)_3$, $Pd(PPh_3)_4$, $Pd(OAc)_2$, Pd(crotyl) Cl, or $Pd(dppf)Cl_2$; the base is $Cs_2CO_3$, $Na_2CO_3$, or KOAc; and the solvent is toluene, dimethoxyethane, dimethylformamide, or any combination thereof.

15. The method of claim 1 wherein the method further comprises a reduction step comprising exposing the precursor compound or the compound to a reducing agent capable of reducing an amide group of the precursor compound or the compound; or a dehydration step comprising exposing the precursor compound or the compound to a dehydration reagent and an amine reagent capable of converting an amide group of the precursor compound or the compound of to an amine group.

16. A pharmaceutical composition, comprising:

a compound of claim 1, or a stereoisomer, tautomer, or pharmaceutically acceptable salt thereof; and a pharmaceutically acceptable excipient, an adjuvant, a therapeutically active compound, or any combination thereof.

17. The pharmaceutical composition of claim 16, formulated for topical, parenteral, or oral administration and wherein the compound is selected from 3-(11-oxo-8-(trifluoromethoxy)-10,11-dihydro-5H-dibenzo[b,e][1,4]diazepin-2-yl)benzoic acid;

3-(11-Oxo-8-(trifluoromethoxy)-10,11-dihydro-5H-dibenzo[b,e][1,4]diazepin-2-yl)benzamide;

N-(2-Hydroxyethyl)-3-(11-oxo-8-(trifluoromethoxy)-10,11-dihydro-5H-dibenzo[b,e][1,4]diazepin-2-yl)benzamide;

N-(2-Aminoethyl)-3-(11-oxo-8-(trifluoromethoxy)-10,11-dihydro-5H-dibenzo[b,e][1,4]diazepin-2-yl)benzamide;

N-(2-Morpholinoethyl)-3-(11-oxo-8-(trifluoromethoxy)-10,11-dihydro-5H-dibenzo[b,e][1,4]diazepin-2-yl)benzamide;

2-(3-(Morpholine-4-carbonyl)phenyl)-8-(trifluoromethoxy)-5,1 0-dihydro-11H-dibenzo[b,e][1,4]diazepin-11-one;

2-(3-(Piperazine-1-carbonyl)phenyl)-8-(trifluoromethoxy)-5,1 0-dihydro-11H-dibenzo[b,e][1,4]diazepin-11-one;

N-(3-(11-Oxo-8-(trifluoromethoxy)-10,11-dihydro-5H-dibenzo[b,e][1,4]diazepin-2-yl)phenyl)methanesulfonamide;

N-(4-(11-oxo-8-(trifluoromethoxy)-10,11-dihydro-5H-dibenzo[b,e][1,4]diazepin-2-yl)phenyl)methanesulfonamide;

2-(2-Morpholinopyridin-4-yl)-8-(trifluoromethoxy)-5,1 0-dihydro-11H-dibenzo[b,e][1,4]diazepin-11-one;

2-(1 H-Pyrazol-4-yl)-8-(trifluoromethoxy)-5,1 0-dihydro-11H-dibenzo[b,e][1,4]diazepin-11-one;

5-Methyl-2-(2-morpholinopyridin-4-yl)-8-(trifluoromethoxy)-5,1 0-dihydro-11H dibenzo[b,e][1,4]diazepin-11-one;

5-Ethyl-2-(2-morpholinopyridin-4-yl)-8-(trifluoromethoxy)-5,1 0-dihydro-11H-dibenzo[b,e][1,4]diazepin-11-one;

2-(2-Morpholinopyridin-4-yl)-5-propyl-8-(trifluoromethoxy)-5,1 0-dihydro-11H-dibenzo[b,e][1,4]diazepin-11-one;

5-(2-Methoxyethyl)-2-(2-morpholinopyridin-4-yl)-8-(trifluoromethoxy)-5,10-dihydro-11H-dibenzo[b,e][1,4]diazepin-11-one;

or a stereoisomer, tautomer, or pharmaceutically acceptable salt thereof.

18. A method for treating a disease in a subject, comprising:

administering a therapeutically effective amount of the compound of claim 1, or a stereoisomer, tautomer, or pharmaceutically acceptable salt thereof, or a therapeutically effective amount of a pharmaceutical composition thereof to a subject having, or suspected of having, the disease, wherein the disease is selected from (i) Alzheimer's disease, Parkinson's disease, epilepsy, amyotrophic lateral sclerosis, primary lateral sclerosis, Kennedy's syndrome, frontal temporal dementia associated with ALS, spinal muscular atrophy, and any combinations thereof; (ii) Farber disease, Krabbe disease, Fabry disease, Schindler disease, Sandhoff disease, Tay-Sachs disease, Gaucher disease, Niemann-Pick A disease, or Niemann-Pick B disease; (iii) Hunter disease, Sanfilippo syndrome, or Sly syndrome; (iv) Niemann-Pick C disease, or Niemann-Pick D disease; (v) bacterial pathogensis resulting from *Shigella flexneri, Escherichia coli, Helicobacter pylon, Anaplasma phagocytophilum, Salmonella enterica*, or *Plasmodium falciparum* (malaria); and/or (vi) viral pathogenesis resulting from HIV.

19. The method of claim 18, wherein the compound is selected from 3-(11-oxo-8-(trifluoromethoxy)-10,11-dihydro-5H-dibenzo[b,e][1,4]diazepin-2-yl)benzoic acid;

3-(11-Oxo-8-(trifluoromethoxy)-10,11-dihydro-5H-dibenzo[b,e][1,4]diazepin-2-yl)benzamide;

N-(2-Hydroxyethyl)-3-(11-oxo-8-(trifluoromethoxy)-10,11-dihydro-5H-dibenzo[b,e][1,4]diazepin-2-yl)benzamide;

N-(2-Aminoethyl)-3-(11-oxo-8-(trifluoromethoxy)-10,11-dihydro-5H-dibenzo[b,e][1,4]diazepin-2-yl)benzamide;

N-(2-Morpholinoethyl)-3-(11-oxo-8-(trifluoromethoxy)-10,11-dihydro-5H-dibenzo[b,e][1,4]diazepin-2-yl)benzamide;

2-(3-(Morpholine-4-carbonyl)phenyl)-8-(trifluoromethoxy)-5,1 0-dihydro-11H-dibenzo[b,e][1,4]diazepin-11-one;

2-(3-(Piperazine-1-carbonyl)phenyl)-8-(trifluoromethoxy)-5,10-dihydro-11H-dibenzo[b,e][1,4]diazepin-11-one;

N-(3-(11-Oxo-8-(trifluoromethoxy)-10,11-dihydro-5H-dibenzo[b,e][1,4]diazepin-2-yl)phenyl)methanesulfonamide;

N-(4-(11-oxo-8-(trifluoromethoxy)-10,11-dihydro-5H-dibenzo[b,e][1,4]diazepin-2-yl)phenyl)methanesulfonamide;

2-(2-Morpholinopyridin-4-yl)-8-(trifluoromethoxy)-5,1 0-dihydro-11H-dibenzo[b,e][1,4]diazepin-11-one;

2-(1 H-Pyrazol-4-yl)-8-(trifluoromethoxy)-5,1 0-dihydro-11H-dibenzo[b,e][1,4]diazepin-11-one;

5-Methyl-2-(2-morpholinopyridin-4-yl)-8-(trifluoromethoxy)-5,1 0-dihydro-11H dibenzo[b,e][1,4]diazepin-11-one;

5-Ethyl-2-(2-morpholinopyridin-4-yl)-8-(trifluoromethoxy)-5,1 0-dihydro-11H-dibenzo[b,e][1,4]diazepin-11-one;

2-(2-Morpholinopyridin-4-yl)-5-propyl-8-(trifluoromethoxy)-5,1 0-dihydro-11H-dibenzo[b,e][1,4]diazepin-11-one;

5-(2-Methoxyethyl)-2-(2-morpholinopyridin-4-yl)-8-(trifluoromethoxy)-5,10-dihydro-11H-dibenzo[b,e][1,4] diazepin-11-one;

or a stereoisomer, tautomer, or pharmaceutically acceptable salt thereof.

* * * * *